US010752953B2

(12) United States Patent
Feinberg et al.

(10) Patent No.: US 10,752,953 B2
(45) Date of Patent: Aug. 25, 2020

(54) METHOD OF DETECTING CANCER THROUGH GENERALIZED LOSS OF STABILITY OF EPIGENETIC DOMAINS, AND COMPOSITIONS THEREOF

(75) Inventors: Andrew P. Feinberg, Lutherville, MD (US); Rafael I. Irizarry, Brookline, MA (US)

(73) Assignee: The Johns Hopkins University, Baltimore, MD (US)

( * ) Notice: Subject to any disclaimer, the term of this patent is extended or adjusted under 35 U.S.C. 154(b) by 294 days.

(21) Appl. No.: 14/115,617

(22) PCT Filed: May 10, 2012

(86) PCT No.: PCT/US2012/037362
§ 371 (c)(1),
(2), (4) Date: Jan. 23, 2014

(87) PCT Pub. No.: WO2012/154979
PCT Pub. Date: Nov. 15, 2012

(65) Prior Publication Data

US 2014/0128283 A1 May 8, 2014

Related U.S. Application Data

(60) Provisional application No. 61/518,892, filed on May 12, 2011.

(51) Int. Cl.
*C12Q 1/68* (2018.01)
*C12P 19/34* (2006.01)
*C12Q 1/6886* (2018.01)

(52) U.S. Cl.
CPC ..... *C12Q 1/6886* (2013.01); *C12Q 2600/154* (2013.01)

(58) Field of Classification Search
CPC ........................ C12Q 1/6886; C12Q 2600/154
See application file for complete search history.

(56) References Cited

U.S. PATENT DOCUMENTS

| | | | | |
|---|---|---|---|---|
| 2001/0053519 | A1* | 12/2001 | Fodor .................. | B01J 19/0046 435/6.11 |
| 2003/0190616 | A1 | 10/2003 | Goggins et al. | |
| 2004/0248171 | A1 | 12/2004 | Palmisano et al. | |
| 2005/0064401 | A1 | 3/2005 | Olek et al. | |
| 2009/0305256 | A1 | 12/2009 | Pfeifer et al. | |
| 2010/0167940 | A1 | 7/2010 | Feinberg | |

FOREIGN PATENT DOCUMENTS

| | | |
|---|---|---|
| EP | 2253714 | 11/2010 |
| WO | WO 2005/059172 A2 | 6/2005 |
| WO | WO 2009/021141 A1 | 2/2009 |
| WO | WO 2010/062914 A1 | 6/2010 |

OTHER PUBLICATIONS

Irizarry R.A. Nature Genetics (2009) col. 41, No. 2, pp. 178-186.*
Feinberg, A.P. et al. “Stochastic epigenetic variation as a driving force of development, evolutionary adaptation, and disease” PNAS (Jan. 26, 2010), vol. 107, suppl. 1, p. 1757-1764, with supporting information.*
Bell, J. T. et al.: DNA methylation patterns associate with genetic and gene expression variation in HapMap cell lines. Genome Biology 2011 12:R10. (Year: 2011).*
Irizarry R.A. et al. Comprehensive high-throughput arrays for relative methylation (CHARM). Genome Research (2008) 18:780-790. (Year: 2008).*
Minna, J.D. et al. Tumor mRNA Expression Profiles Predict Responses to Chemotherapy, Journal of Clinical Oncology, vol. 25, No. 28 (Oct. 1): pp. 4329-4336. (Year: 2007).*
Affymetrix Expression Probeset Details for HT_HG-U133A:205680_AT (MMP10), from www.affymetrix.com/analysis/netaffx, printed on Nov. 14, 2018, pp. 1-3.*
Affymetrix Expression Probeset Details for HT_HG-U133A:204259_AT (MMP7), from www.affymetrix.com/analysis/netaffx, printed on Nov. 14, 2018, pp. 1-4.*
Affymetrix Expression Probeset Details for HT HG-U133A:205828 AT (MMP3), from www.affymetrix.com/analysis/netaffx, printed on Nov. 14, 2018, pp. 1-4.*
Hansen, K. D. et al.: “*Increased methylation variation in epigenetic domains across cancer types*”, Nature Genetics; Jun. 2011, vol. 43, No. 8, pp. 768-775.
International Search Report Regarding PCT/US2012 /037362.
Maradeo, Marie E. et al: “*Translational application of epigenetic alterations: Ovarian cancer as a model*”; FEBS Letters; Elsevier, Amsterdam; NL, 585:13, Mar. 7, 2011, pp. 2112-2120.
Chari, Raj et al.: “*Integrating the multiple dimensions of genomic and epigenomic landscapes of cancer*”; Cancer and Metastasis Reviews, Kluwer Academic Publishers, DO, 29:1, Jan. 29, 2010, pp. 73-93.
Ananiev, Gene E. et al.: “*Optical mapping discerns genome wide DNA methylation profiles*”; BMC Molecular Biology, Biomed Central Ltd, GB, 9:1, Jul. 30, 2008, p. 68.
Costello, J. F. et al.: “*Methylation Matters*”; Journal of Medical Genetics, BMJ Publishing Group, London, GB, 38:5, May 1, 2001, pp. 285-303.
Baylin, Stephen B. et al.: “*A decade of exploring the cancer epigenome—biological and translational implications*”; Nature Reviews Cancer, 11:10, Jan. 1, 2011, pp. 726-734.

(Continued)

*Primary Examiner* — Stephen T Kapushoc
(74) *Attorney, Agent, or Firm* — DLA Piper LLP (US)

(57) ABSTRACT

Provided herein is a method of detecting cancer through generalized loss of stability of epigenetic domains as well as compositions useful therein. The present invention is based on the discovery that generalized loss of stability of epigenetic domains was determined to be a characteristic across various cancer types. Genome-scale bisulfite sequencing of cancers revealed a surprising loss of methylation stability in the cancer methylome, involving both CpG islands and shores, as well as large (up to several megabases) blocks of hypomethylation affecting more than half of the genome, with concomitant stochastic variability in gene expression.

10 Claims, 21 Drawing Sheets

(56) References Cited

OTHER PUBLICATIONS

European Search Report Regarding EP 12 78 1728.
Abratani , Hideyuki: "*Global mapping of epigenetic marks*"; Experimental Medicine, (2007), vol. 25, No. 17, p. 88-95 (English Abstract).
Okochi-Takada, Eriko et al.: "*Epigenetic abnormalities in cancers*"; Experimental Medicine, (2006), vol. 24, No. 8, p. 171-178 (English Abstract).
Takeshima et al.: "*Aberrant epigenetic modifications in cancer*"; Experimental Medicine, (Feb. 1, 2011), vol. 29, No. 2, p. 50-55. (English Abstract).
Ushijima,Toshikazu: "*Diagnostic application of cancer epigenetics*"; Journal of Clinical and Experimental Medicine, (2008), vol. 225, No. 7, p. 559-564 (English Abstract).
Japanese Office Action dated Mar. 23, 2016, regarding JP 2014-510472.
Bolstad, B.M. et al.: "*A comparison of normalization methods for high density oligonucleotide array data based on variance and bias*"; Bioinformatics, 2003, vol. 19, No. 2, pp. 185-193.
Irizarry, Rafael A. et al.: "*Exploration, normalization, and summaries of high density oligonucleotide array probe level data*"; Biostatistics, 2003, vol. 4:2, pp. 249-264.
Japanese Office Action dated Jan. 31, 2018, regarding JP 2014-510472.

* cited by examiner b

METHOD OF DETECTING CANCER THROUGH GENERALIZED LOSS OF STABILITY OF EPIGENETIC DOMAINS, AND COMPOSITIONS THEREOF

CROSS-REFERENCE TO RELATED APPLICATIONS

This application is a 35 USC § 371 National Stage application of International Application No. PCT/US2012/037362 filed May 10, 2012; which claims the benefit under 35 USC § 119(e) to U.S. Application Ser. No. 61/518,892 filed May 12, 2011. The disclosure of each of the prior applications is considered part of and is incorporated by reference in the disclosure of this application.

GRANT INFORMATION

This invention was made with government support under Grant Nos. R37CA054358, R01HG005220, 5P50HG003233 and 5R01GM083084 awarded by the National Institutes of Health. The government has certain rights in the invention.

This invention was made with government support under grant numbers CA054358, HG005220, HG003233, and GM083084 awarded by the National Institutes of Health. The government has certain rights in the invention.

BACKGROUND OF THE INVENTION

Field of the Invention

The present invention relates generally to methylome analysis, and more specifically to a method for detecting cancer through generalized loss of stability of epigenetic domains of the genome.

Background Information

Epigenetics is the study of non-sequence information of chromosome DNA during cell division and differentiation. The molecular basis of epigenetics is complex and involves modifications of the activation or inactivation of certain genes. Additionally, the chromatin proteins associated with DNA may be activated or silenced. Epigenetic changes are preserved when cells divide. Most epigenetic changes only occur within the course of one individual organism's lifetime, but some epigenetic changes are inherited from one generation to the next.

One example of an epigenetic mechanism is DNA methylation (DNAm), a covalent modification of the nucleotide cytosine. In particular, it involves the addition of methyl groups to cytosine nucleotides in the DNA, to convert cytosine to 5-methylcytosine. DNA methylation plays an important role in determining whether some genes are expressed or not. Abnormal DNA methylation is one of the mechanisms known to underlie the changes observed with aging and development of many cancers.

Cancers have historically been linked to genetic changes such as DNA sequence mutations. Evidence now supports that a relatively large number of cancers originate, not from mutations, but from epigenetic changes such as inappropriate DNA methylation. In some cases, hypermethylation of DNA results the an inhibition of expression of critical genes, such as tumor suppressor genes or DNA repair genes, allowing cancers to develop. In other cases, hypomethylation of genes modulates expression, which contributes to the development of cancer.

Cancer is generally viewed as over 200 separate organ-specific diseases of abnormal cell growth, largely controlled by a series of mutations, but also involving epigenetic, i.e. non-sequence based, changes that might involve the same sets of genes'. DNA methylation at CpG dinucleotides in particular has been studied extensively in cancer, with hypomethylation reported at some genes, hypermethylation at others, and a global loss of DNA methylation ascribed to repetitive DNA elements that are normally methylated.

Since the discovery of altered DNA methylation in human cancer, the focus of cancer epigenetics has been on candidate regions of the genome, either high-density CpG islands, gene promoters, or dispersed repetitive elements[2,3], and there has not been a comprehensive genome-scale understanding of the relationship between DNA methylation loss and gain in cancer and in normal differentiation.

SUMMARY OF THE INVENTION

The present invention is based on the discovery that generalized loss of stability of epigenetic domains was determined to be characteristic across various cancer types. Genome-scale bisulfite sequencing of cancers revealed a surprising loss of methylation stability in the cancer methylome, involving both CpG islands and shores, as well as large (up to several megabases) blocks of hypomethylation affecting more than half of the genome, with concomitant stochastic variability in gene expression.

As such, in one aspect, a method of diagnosing cancer or a risk of cancer in a subject is provided. The method includes identifying an anti-profile in a sample from a subject including: i) determining the methylation status of a plurality of genomic nucleic acid sequences from a non-cancerous biological sample and corresponding plurality of genomic nucleic acid sequences in a test sample from the subject; ii) detecting a deviation in the methylation status from the test sample from the methylation status of the non-cancerous sample; iii) detecting an increased methylation variance in the test sample as compared to the non-cancerous sample; and iv) determining a methylation variance score by performing statistical analysis, thereby diagnosing cancer in the subject. In one embodiment, the method includes detecting the methylation status of one or more nucleic acid sequences selected from those set forth in Table 6, Table 7, Table 16 or Table 17. In one embodiment, the method further includes detecting expression of one or more genes as set forth in FIG. 16A, FIG. 16B, Table 3 or Table 5.

In another aspect, a method for providing a prognosis for cancer is provided. The method includes: a) comparing the methylation status of one or more nucleic acid sequences in a sample from a subject diagnosed with, or being treated for cancer, to a methylation status of the one or more nucleic acid sequences of a cancer cell; b) identifying a methylation anti-profile using the methylation status of (a) including: i) detecting a deviation in the methylation status of (a) from a methylation status of a corresponding plurality of nucleic acid sequences of a genome from a sample known to be non-cancerous; ii) detecting an increased methylation variance in the sample as compared to the non-cancerous sample; and iii) determining a methylation variance score by performing statistical analysis, wherein at least 25 nucleic acids are analyzed; and c) correlating the anti-profile of (b) with a prognosis, thereby providing a prognosis for cancer in the subject. In one embodiment the one or more nucleic acid sequences are selected from the group consisting of a nucleic acid sequence as set forth in Table 6, Table 7, Table 16 or Table 17, thereby providing a prognosis for the cancer. In one embodiment, the method further includes detecting expression of one or more genes as set forth in FIG. 16A, FIG. 16B, Table 3 or Table 5.

In another aspect, a method of diagnosing cancer in a subject is provided utilizing detection of a shift or loss of methylation boundary. The method includes: i) determining the methylation status of a plurality of genomic nucleic acid sequences from a non-cancerous biological sample and corresponding plurality of genomic nucleic acid sequences in a test sample from the subject; and ii) detecting a deviation in the methylation status from the test sample from the methylation status of the non-cancerous sample, wherein the deviation in the methylation status comprises a shift or loss of methylation boundary in one or more of the plurality of nucleic acid sequences in the test sample as compared to that of the corresponding plurality of nucleic acid sequences from the non-cancerous biological sample, thereby diagnosing cancer in the subject. In one embodiment, the plurality of nucleic acid sequences are selected from those set forth in Table 6, Table 7, Table 16 or Table 17. In various embodiment, a deviation is detected in at least about 10, 15, 25, 50, 100 or 1000 nucleic acids sequences.

In another aspect, a method for providing a prognosis for cancer in a subject utilizing detection of a shift or loss of methylation boundary. The method includes: a) detecting the methylation status of a plurality of nucleic acid sequences in a sample from a subject diagnosed with, or being treated for cancer; b) detecting a deviation in the methylation status from (a) as compared to a corresponding plurality of nucleic acid sequences of a genome from a sample known to be non-cancerous, wherein the deviation in the methylation status comprises a shift or loss of methylation boundary in the plurality of nucleic acid sequences in the sample from the subject diagnosed with, or being treated for cancer as compared to that of the corresponding plurality of nucleic acid sequences from the sample known to be non-cancerous; and c) correlating the deviation of (b) with a prognosis, thereby providing a prognosis for cancer in the subject. In one embodiment, the plurality of nucleic acid sequences are selected from those set forth in Table 6, Table 7, Table 16 or Table 17. In various embodiment, a deviation is detected in at least about 10, 15, 25, 50, 100 or 1000 nucleic acids sequences.

In another aspect, a method of diagnosing cancer in a subject is provided utilizing detection of hypomethylated genomic block regions. The method includes: i) determining the methylation status of a plurality of genomic nucleic acid sequences from a non-cancerous biological sample and corresponding plurality of genomic nucleic acid sequences in a test sample from the subject; and ii) detecting a deviation in the methylation status from the test sample from the methylation status of the non-cancerous sample, wherein the deviation in the methylation status comprises an increase in hypomethylation in the plurality of nucleic acid sequences in the test sample as compared to that of the corresponding plurality of nucleic acid sequences from the non-cancerous biological sample, and wherein the plurality of nucleic acid sequences is selected from those set forth in Table 6 [genomic block sequences], thereby diagnosing cancer in the subject. In various embodiment, a deviation is detected in at least about 10, 15, 25, 50, 100 or 1000 nucleic acids sequences.

In another aspect, a method for providing a prognosis for cancer in a subject utilizing detection of hypomethylated genomic block regions. The method includes: a) detecting the methylation status of a plurality of nucleic acid sequences in a sample from a subject diagnosed with, or being treated for cancer; b) detecting a deviation in the methylation status from (a) as compared to a corresponding plurality of nucleic acid sequences of a genome from a sample known to be non-cancerous, wherein the deviation in the methylation status comprises an increase in hypomethylation in the plurality of nucleic acid sequences in the sample from the subject as compared to that of the corresponding plurality of nucleic acid sequences from the sample known to be non-cancerous, and wherein the plurality of nucleic acid sequences is selected from those set forth in Table 6 [genomic block sequences]; and c) correlating the deviation of (b) with a prognosis, thereby providing a prognosis for cancer in the subject. In various embodiment, a deviation is detected in at least about 10, 15, 25, 50, 100 or 1000 nucleic acids sequences.

In another aspect, a plurality of nucleic acid sequences is provided. The nucleic acid sequences are capable of selectively hybridizing to a nucleic acid sequence selected from cancer-specific differentially methylated regions (cDMRs) as set forth in Table 17, wherein the cDMRs are stochastically methylated in cancer. In one embodiment, each nucleic acid sequence is about 10-55 base pairs in length.

In another aspect, a microarray is provided which includes the plurality of nucleic acid sequences as described herein.

In another aspect, a method of performing methylation analysis of genomic DNA isolated from a cell. The method includes performing comprehensive high-throughput array for relative methylation (CHARM) analysis on a sample of labeled, digested genomic DNA isolated from the cell using the microarray described herein, thereby performing methylation analysis.

In another aspect, a method of determining a therapeutic regimen for a subject is provided. The method includes a) analyzing a determined methylation profile; and b) determining an appropriate therapeutic regimen based on the analysis, thereby determining a therapeutic regime for the subject.

BRIEF DESCRIPTION OF THE DRAWINGS

FIG. 5(*a*) presents analysis of three normal samples (three top lines of center box) and matched cancers (three bottom lines of center box).

FIG. 6(*a*) plots methylation variance of common CpG sites in colon cancer. FIG. 6(*b*) plots methylation variance of common CpG sites in colon cancer. FIG. 6(*b*) plots methylation variance of common CpG sites in lung cancer. FIG. 6(*c*) plots methylation variance of common CpG sites in breast cancer. FIG. 6(*d*) plots methylation variance of common CpG sites in thyroid cancer. FIG. 6(*e*) plots methylation variance of common CpG sites in kidney (Wilms) cancer. FIG. 6(*f*) is a heatmap of the methylation values for CpGs clearly distinguishing the tissue types.

FIG. 7(*a*) is a praphical plot of a methylation boundary shift outward (normal-top lines in shaded area; cancer-bottom lines in shaded area). FIG. 7(*b*) is a praphical plot of a methylation boundary shift inward (cancer-top lines in shaded area; normal-bottom lines in shaded area). FIG. 7(*c*) is a praphical plot of a loss of methylation boundary (cancer-top lines in shaded area normal-bottom lines in shaded area). FIG. 7(*d*) is a praphical plot of a novel hypomethylation DMR (normal-top lines in shaded area; cancer-bottom lines in shaded area).

FIG. 9(*a*) is clustering of normal and colon tissues. FIG. 9(*b*) is clustering of normal and lung tissues. FIG. 9(*c*) is clustering of normal and breast tissues. FIG. 9(*d*) is clustering of normal and thyroid tissues. FIG. 9(*e*) is clustering of normal and kidney (Wilms) tissues.

FIG. 10(*a*) is a plot of smoothed methylation values from bisulfite sequencing data for cancer samples and normal samples. FIG. 10(*b*) are smoothed methylation values from bisulfite sequencing data for cancer samples and normal samples. FIG. 10(*c*) is a plot of the distribution of methylation values for the normal samples versus the cancer samples. FIG. 10(*d*) is a plot of the distribution of methylation values in the blocks (solid lines) and outside the blocks (dashed lines) for normal samples and cancer samples. FIG. 10(*e*) is a plot of the distribution of methylation differences between cancer and normal samples stratified by inclusion in repetitive DNA and blocks.

FIG. 12(*a*) is a multidimensional scaling of pairwise distances derived from methylation levels assayed on a custom array. FIG. 13(*b*) is a multidimensional scaling of pairwise distances derived from average methylation values in blocks identified via bisulfite sequencing. FIG. 13(*c*) is a plot of methylation values for normal, cancer and two adenoma samples.

FIG. 16(*a*) is a plot of methylation values for cancer samples and normal samples with hypomethylated block locations highlighted (shading) plotted against genomic location. FIG. 16(*b*) plots standardized log expression values for 26 hypervariable genes in cancer located within hypomethylated block regions.

DETAILED DESCRIPTION OF THE INVENTION

Figure 1:
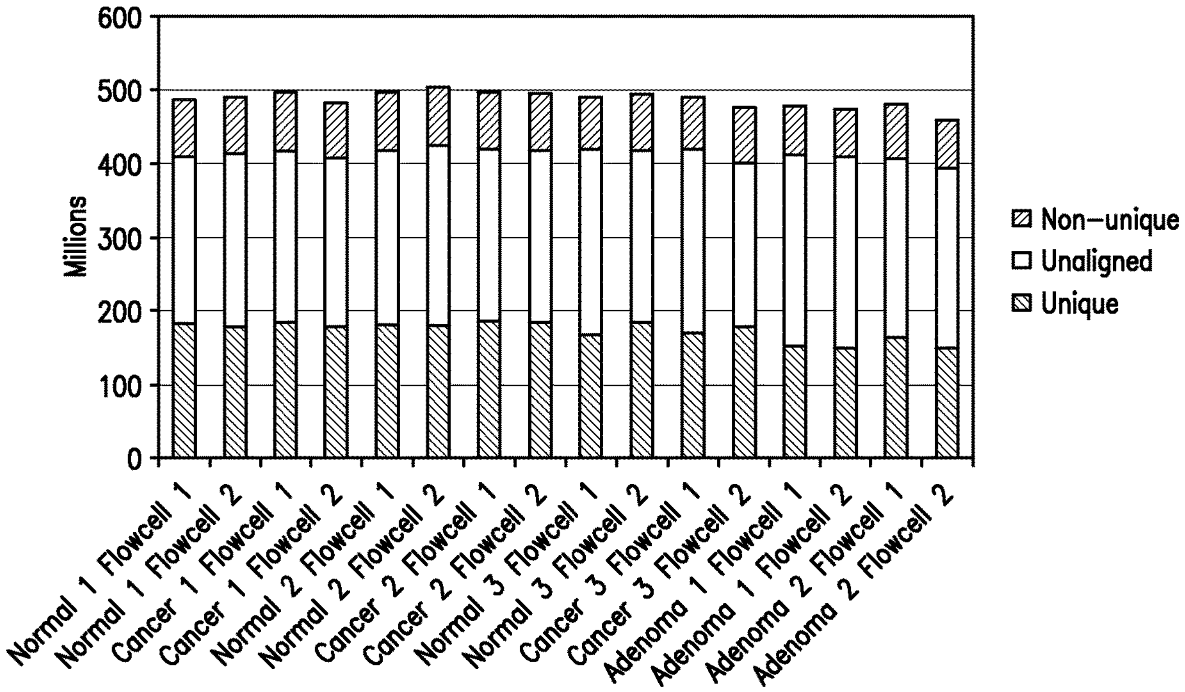
FIG. 1 is a graphical plot of number of reads and alignments obtained from bisulfite sequencing.

The present invention is based on the discovery that generalized loss of stability of epigenetic domains was determined to be a characteristic across various cancer types. A different and more general approach to cancer epigenetics is discussed herein based, in part on the recent observation of frequent methylation alterations in colon cancer of lower cytosine-density CpG regions near islands, termed shores; as well as the observation that these cancer-specific differentially methylated regions (cDMRs), correspond largely to the same regions that show DNA methylation variation among normal spleen, liver, and brain, or tissue-specific DMRs (tDMRs)[4]. Furthermore, these same cDMRs are highly enriched among regions differentially methylated during stem cell reprogramming of induced pluripotent stem (iPS) cells[5]. Thus it was reasoned that the very same sites might be generalized cDMRs, since they are involved in normal tissue differentiation but show aberrant methylation in at least one cancer type (colon).

Before the present compositions and methods are described, it is to be understood that this invention is not limited to the particular composition, method, and experimental conditions described, as such composition, method, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The hypothesis was tested by designing a semi-quantitative custom array for methylation analysis of cDMRs consistently altered across colon cancer, and analyzing these sites in 290 samples, including matched normal and cancer from colon, breast, lung, thyroid, and Wilms' tumor. As described below, it was surprisingly discovered that almost all of the cDMRs were altered across all cancers tested. Specifically, the cDMRs appeared to display an increased stochastic variation in methylation level, suggesting a generalized disruption of the integrity of the cancer epigenome. To investigate this idea further, genome-scale bisulfite sequencing of 3 colorectal cancers, the matched normal colonic mucosa, and two adenomatous polyps was performed. These experiments revealed a surprising loss of methylation stability in colon cancer, involving both CpG islands and shores, as well as large (up to several megabases) blocks of hypomethylation affecting more than half of the genome, with concomitant stochastic variability in gene expression.

As such, in one aspect, a method for detecting cancer or a risk of cancer in a subject is provided. The method includes detecting the methylation status of a genome from a nucleic acid containing sample from the subject, wherein hypomethylation or hypermethylation of at least 50% or more of the genome is indicative of cancer or a risk of cancer, thereby detecting cancer or a risk thereof.

In one embodiment, hypomethylation of at least 50% or more of the genome is indicative of cancer. For example, hypomethylation of at least 50, 55, 60, 65, 70, 75, 80, 85, 90, 95 or more of the genome is indicative of cancer.

In various embodiments, the methylation status is determined of one or more nucleic acid sequences selected from a differentially methylated region (DMR) as set forth in Table 16 or Table 17, wherein the one or more nucleic acid sequences are stochastically methylated in cancer. In another embodiment, the method includes detecting the methylation status of one or more nucleic acid sequences selected from a differentially methylated region (DMR) as set forth in Table 10, wherein the one or more nucleic acid sequences are stochastically methylated in cancer. In one embodiment, the method includes detecting the methylation status of one or more nucleic acid sequences selected from a genomic block region as set forth in Table 4, wherein the one or more nucleic acid sequences are stochastically methylated in cancer.

Hypomethylation is present when there is a measurable decrease in methylation. In some embodiments, a DMR or block can be determined to be hypomethylated when less than 50% of the methylation sites analyzed are not methylated. Hypermethylation is present when there is a measurable increase in methylation. In some embodiments, a DMR or block can be determined to be hypermethylated when more than 50% of the methylation sites analyzed are methylated. Methods for determining methylation states are provided herein and are known in the art. In some embodiments methylation status is converted to an M value. As used herein an M value, can be a log ratio of intensities from total (Cy3) and McrBC-fractionated DNA (Cy5): positive and negative M values are quantitatively associated with methylated and unmethylated sites, respectively. M values are calculated as described in the Examples. In some embodiments, M values which range from −0.5 to 0.5 represent unmethylated sites as defined by the control probes, and values from 0.5 to 1.5 represent baseline levels of methylation.

In various embodiments, a genome is present in a biological sample taken from a subject. The biological sample can be virtually any biological sample, particularly a sample that contains RNA or DNA from the subject. The biological sample can be a tissue sample which contains about 1 to about 10,000,000, about 1000 to about 10,000,000, or about 1,000,000 to about 10,000,000 somatic cells. However, it is possible to obtain samples that contain smaller numbers of cells, even a single cell in embodiments that utilize an amplification protocol such as PCR. The sample need not contain any intact cells, so long as it contains sufficient biological material (e.g., protein or genetic material, such as RNA or DNA) to assess methylation status of the one or more DMRs.

In some embodiments, a biological or tissue sample can be drawn from any tissue that is susceptible to cancer. A biological or tissue sample may be obtained by surgery, biopsy, swab, stool, or other collection method. In some embodiments, the sample is derived from blood, plasma, serum, lymph, nerve-cell containing tissue, cerebrospinal fluid, biopsy material, tumor tissue, bone marrow, nervous tissue, skin, hair, tears, fetal material, amniocentesis material, uterine tissue, saliva, feces, or sperm. In particular embodiments, the biological sample for methods of the present invention can be, for example, a sample from colorectal tissue, or in certain embodiments, can be a blood sample, or a fraction of a blood sample such as a peripheral blood lymphocyte (PBL) fraction. Methods for isolating PBLs from whole blood are well known in the art. In addition, it is possible to use a blood sample and enrich the small amount of circulating cells from a tissue of interest, e.g., colon, breast, lung, prostate, head and neck, etc. using a method known in the art.

As disclosed above, the biological sample can be a blood sample. The blood sample can be obtained using methods known in the art, such as finger prick or phlebotomy. Suitably, the blood sample is approximately 0.1 to 20 ml, or alternatively approximately 1 to 15 ml with the volume of blood being approximately 10 ml.

In one embodiment, the identified cancer risk is for colorectal cancer, and the biological sample is a tissue sample obtained from the colon, blood, or a stool sample. In another embodiment, the identified cancer risk is for stomach cancer or esophageal cancer, and the tissue may be obtained by endoscopic biopsy or aspiration, or stool sample or saliva sample. In another embodiment, the identified cancer risk is esophageal cancer, and the tissue is obtained by endoscopic biopsy, aspiration, or oral or saliva sample. In another embodiment, the identified cancer risk is leukemia/lymphoma and the tissue sample is blood. In another embodiment, the identified cancer risk is breast cancer, and the tissue is obtained by breast, blood, or nipple aspiration sample. In another embodiment, the identified cancer risk is breast cancer, and the tissue is obtained by breast, blood, or nipple fluid or aspiration sample. In another embodiment, the identified cancer risk is lung cancer, and the tissue is obtained by lung, blood, endoscopic biopsy or aspirate sample. In another embodiment, the identified cancer risk is thyroid cancer, and the tissue is obtained by thyroid, blood, or endoscopic biopsy sample. In another embodiment, the identified cancer risk is kidney cancer, and the tissue is obtained by thyroid, blood, or endoscopic biopsy sample.

In the present invention, the subject is typically a human but also can be any mammal, including, but not limited to, a dog, cat, rabbit, cow, bird, rat, horse, pig, or monkey.

As mentioned above, for certain embodiments of the present invention, the method is performed as part of a regular checkup. Therefore, for these methods the subject has not been diagnosed with cancer, and typically for these present embodiments it is not known that a subject has a hyperproliferative disorder, such as a cancer.

Methods of the present invention identify a risk of developing cancer for a subject. A cancer can include, but is not limited to, colorectal cancer, esophageal cancer, stomach cancer, leukemia/lymphoma, lung cancer, prostate cancer, uterine cancer, breast cancer, skin cancer, endocrine cancer, urinary cancer, liver cancer, thyroid cancer, kidney cancer (Wilms), pancreas cancer, other gastrointestinal cancer, ovarian cancer, cervical cancer, head cancer, neck cancer, and adenomas.

A hyperproliferative disorder includes, but is not limited to, neoplasms located in the following: abdomen, bone, breast, digestive system, liver, kidney, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital. In certain embodiments, the hyperproliferative disorder is a cancer.

In another embodiment, the present invention provides a method for managing health of a subject. The method includes performing the method for identifying an increased risk of developing cancer discussed above and performing a traditional cancer detection method. For example a traditional cancer detection method can be performed if the method for identifying cancer risk indicates that the subject is at an increased risk for developing cancer. Many traditional cancer detection methods are known and can be included in this aspect of the invention. The traditional cancer detection method can include, for example, one or more of chest X-ray, carcinoembryonic antigen (CEA) level determination, colorectal examination, endoscopic examination, MRI, CAT scanning, or other imaging such as gallium scanning, and barium imaging, and sigmoidoscopy/colonoscopy, a breast exam, or a prostate specific antigen (PSA) assay.

In another embodiment, a method for providing a prognosis for cancer is provided. The method includes a) comparing the methylation status of one or more nucleic acid sequences in a sample from a subject diagnosed with, or being treated for cancer, to a methylation status of the one or more nucleic acid sequences of a cancer cell; and b) determining a prognosis based on the comparison of (a), wherein the one or more nucleic acid sequences are selected from the group consisting of a nucleic acid sequence as set forth in Table 4, Table 10, Table 16 and Table 17, thereby providing a prognosis for the cancer. In one embodiment, the method further includes detecting expression of one or more genes as set forth in FIG. 16A, FIG. 16B, Table 3 or Table 5.

In another aspect, a method for providing a profile of cancer is provided. The method includes a) comparing the methylation status of one or more nucleic acid sequences in a putative cancer cell from a subject, to a known methylation status of the one or more nucleic acid sequences of a cancer cell; and b) determining a methylation profile for the putative cancer cell based on the comparison of (a), wherein a stochastic variation in methylation status is indicative of the putative cancer cell being cancerous, and wherein further the one or more nucleic acid sequences are selected from a nucleic acid sequence as set forth in Table 4, Table 10, Table 16 and Table 17. In one embodiment, the method further includes detecting expression of one or more genes as set forth in FIG. 16A, FIG. 16B, Table 3 or Table 5.

Numerous methods for analyzing methylation status of a gene are known in the art and can be used in the methods of the present invention to identify either hypomethylation or hypermethylation of a genomic region. In some embodiments, the determining of methylation status is performed by one or more techniques selected from the group consisting of a nucleic acid amplification, polymerase chain reaction (PCR), methylation specific PCR, bisulfite pyrosequenceing, single-strand conformation polymorphism (SSCP) analysis, restriction analysis, and microarray technology. As illustrated in the Examples herein, analysis of methylation can be performed by bisulfite genomic sequencing. Bisulfite treatment modifies DNA converting unmethylated, but not methylated, cytosines to uracil. Bisulfite treatment can be carried out using the METHYLEASY bisulfite modification kit (Human Genetic Signatures).

In some embodiments, bisulfite pyrosequencing, which is a sequencing-based analysis of DNA methylation that quantitatively measures multiple, consecutive CpG sites individually with high accuracy and reproducibility, may be used. Nucleic acid primers or probes for such analysis may be derived from any of the Tables included herein or any other known genomic sequence.

It will be recognized that depending on the site bound by the primer and the direction of extension from a primer, that the primers listed above can be used in different pairs. Furthermore, it will be recognized that additional primers can be identified within the genomic regions identified in the Tables, especially primers that allow analysis of the same methylation sites as those analyzed with primers that correspond to the primers disclosed herein or any other known genomic sequence.

Altered methylation can be identified by identifying a detectable difference in methylation. For example, hypomethylation can be determined by identifying whether after bisulfite treatment a uracil or a cytosine is present a particular location. If uracil is present after bisulfite treatment, then the residue is unmethylated. Hypomethylation is present when there is a measurable decrease in methylation.

In an alternative embodiment, the method for analyzing methylation can include amplification using a primer pair specific for methylated residues within a genomic region, such as a DMR or block. In these embodiments, selective hybridization or binding of at least one of the primers is dependent on the methylation state of the target DNA sequence (Herman et al., *Proc. Natl. Acad. Sci. USA,* 93:9821 (1996)). For example, the amplification reaction can be preceded by bisulfite treatment, and the primers can selectively hybridize to target sequences in a manner that is dependent on bisulfite treatment. For example, one primer can selectively bind to a target sequence only when one or more base of the target sequence is altered by bisulfite treatment, thereby being specific for a methylated target sequence.

Other methods are known in the art for determining methylation status, including, but not limited to, array-based methylation analysis and Southern blot analysis.

Methods using an amplification reaction, for example methods above for detecting hypomethylation or hyprmethylation, can utilize a real-time detection amplification procedure. For example, the method can utilize molecular beacon technology (Tyagi S., et al., *Nature Biotechnology,* 14: 303 (1996)) or Taqman™ technology (Holland, P. M., et al., *Proc. Natl. Acad. Sci. USA,* 88:7276 (1991)).

Also methyl light (Trinh B N, Long T I, Laird P W. DNA methylation analysis by MethyLight technology, Methods, 25(4):456-62 (2001), incorporated herein in its entirety by reference), Methyl Heavy (Epigenomics, Berlin, Germany), or SNuPE (single nucleotide primer extension) (See e.g., Watson D., et al., *Genet Res.* 75(3):269-74 (2000)). Can be used in the methods of the present invention related to identifying altered methylation of DMRs.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The degree of methylation in the DNA being assessed, may be measured by fluorescent in situ hybridization (FISH) by means of probes which identify and differentiate between genomic DNAs, associated regions being assessed, which exhibit different degrees of DNA methylation. FISH is described in the Human chromosomes: principles and techniques (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Giancotti P., Marotta, M. R., Spano A., Rocchi M., Archidiacono N., Niveleau A. Computer-assisted analysis of methylation status of individual interphase nuclei in human cultured cells. *Cytometry.* 31:85-92, 1998 which is incorporated herein by reference. In this case, the biological sample will typically be any which contains sufficient whole cells or nuclei to perform short term culture. Usually, the sample will be a tissue sample that contains 10 to 10,000, or, for example, 100 to 10,000, whole somatic cells.

Additionally, as mentioned above, methyl light, methyl heavy, and array-based methylation analysis can be performed, by using bisulfite treated DNA that is then PCR-amplified, against microarrays of oligonucleotide target sequences with the various forms corresponding to unmethylated and methylated DNA.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

In another aspect, the present invention includes kits that are useful for carrying out the methods of the present invention. The components contained in the kit depend on a number of factors, including: the particular analytical technique used to detect methylation or measure the degree of methylation or a change in methylation, and the one or more genomic regions being assayed for methylation status.

In another aspect, a plurality of nucleic acid sequences is provided, useful as primers or probes. The nucleic acid sequences are capable of selectively hybridizing to a nucleic acid sequence selected from cancer-specific differentially methylated regions (cDMRs) as set forth in Table 17, wherein the cDMRs are stochastically methylated in cancer. In one embodiment, each nucleic acid sequence is about 10-55 base pairs in length.

To examine DNAm on a genome-wide scale, comprehensive high-throughput array-based relative methylation (CHARM) analysis, which is a microarray-based method agnostic to preconceptions about DNAm, including location relative to genes and CpG content was carried out. cDMRs identified in Irizarry et al.[1], and shown in Tables 14 and 15, including regions consistently differentially methylated in colon cancers were studied by comprehensive high-throughput array based methylation (CHARM) analysis. Probes were designed around CpGs that showed consistent differences in CHARM, while passing quality control metrics. The resulting probes covered 139 regions, with 1-7 probes per region. The majority of the probes were in CpG island shores (66%), defined as less than 2 kb away from the edge of a canonically defined high-CpG density island[1]. The remainder of the probes were either inside CpG islands (11%) or >2 kb distant (23%). The resulting quantitative measurements of DNAm, denoted with M, are log ratios of intensities from total (Cy3) and McrBC-fractionated DNA (Cy5): positive and negative M values are quantitatively associated with methylated and unmethylated sites, respectively. The CHARM results were also extensively corroborated by quantitative bisulfite pyrosequencing analysis.

As such, in another aspect, a microarray is provided which includes the plurality of nucleic acid sequences as described herein. Further, in another aspect, a method of performing methylation analysis of genomic DNA isolated from a cell. The method includes performing comprehensive high-throughput array for relative methylation (CHARM) analysis an a sample of labeled, digested genomic DNA isolated from the cell using the microarray described herein, thereby performing methylation analysis.

Provided herein is a genome-wide analysis of DNA methylation of various cancer cells, revealing several surprising epigenomic observations. Surprisingly, two thirds of all methylation changes in colon cancer involve hypomethylation of large blocks comprising more than half of the genome. The most variably expressed genes in cancer are extraordinarily enriched in the blocks, and they involve genes associated with tumor heterogeneity and progression, including three matrix metalloproteinase genes, MMP3, MMP7, and MMP10, and a fourth, SIM2, which acts through metalloproteinases to promote tumor invasion. Another, STCI1, helps mediate the Warburg effect of reprogramming tumor metabolism. CHI3L1 encodes a secreted glycoprotein associated with inflammatory responses and poor prognosis in multiple tumor types including the colon. WISP genes are targets of Wnt-1 and are thought to contribute to tissue invasion in breast and colon cancer. One cautionary note raised by these findings is that treatment of cancer patients with nonspecific DNA methylation inhibitors could have unintended consequences in the activation of tumor-promoting genes in hypomethylated blocks.

The following example is provided to further illustrate the advantages and features of the present invention, but are not intended to limit the scope of the invention. While they are typical of those that might be used, other procedures, methodologies, or techniques known to those skilled in the art may alternatively be used.

Example 1

Generalized Loss of Stability of Epigenetic Domains Across Cancer Types

The following experimental protocols and materials were utilized.

Custom Array Design.

Custom bead arrays were created based on the 151 most statistically significant cDMRs identified in Irizarry et al.[4] for which successful design probes using the Illumina protocol[7] could be designed. Cryogenically stored freshly frozen samples were obtained from the Cooperative Human Tissue Network (NCI, Bethesda, Md.), the National Wilms Tumor Study tissue bank (Edmonton, Alberta, Canada) and the Johns Hopkins Hospital, under an IRB-approved waiver of consent. A pathologist validated classification of all samples independently and blindly. Samples were used for DNA purification, the resulting DNA bisulfite treated, and the custom GoldenGate assay performed. The raw intensity data was processed using quantile normalization[28] and ruled out batch effects following the procedures described by Leek et al.[29]. Differences in variance were tested using a standard F-test.

Custom Methylation Array Processing and Analysis.

The raw intensity data from the Cy5 and Cy3 channels representing methylated and umethylated DNA was quantile normalized[2] separately, and methylation level was calculated as the ratio of the Cy5 intensity over the sum of the intensities from both channels. To control for array quality, arrays for which the average of the median log intensities from the two channels was small (<7), or for which the median absolute deviation of the overall methylation signal was small (<1.9) were removed from the dataset. Differences in methylation variability were measured and tested using an F-test. Differences in mean methylation levels were measured and tested using a t-test. Significance was taken as 0.01.

Illumina HumanMethylation27k™ Array Analysis.

A publicly available dataset was downloaded of methylation levels of 22 matched colon normal/tumor samples assayed using Illumina's HumanMethylation27 K™ array (Gene Expression Omnibus accession number GSE17648). The methylation measurements were used with no further preprocessing. Differences in methylation variability were measured and tested using an F-test. Differences in mean methylation levels were measured and tested using a t-test. Significance was taken as 0.01.

Whole Genome Bisulfite Sequencing.

Bisulfite sequencing libraries were prepared using the approach previously described by Bormann Chung et al[30], with some modifications so the entire protocol is provided in detail here. 5 ug of genomic DNA was sheared using a Covaris E2 sonicator. 40 ng of Alul-digested unmethylated A DNA was added to each sample in order to monitor the efficiency of bisulfite conversion. Sample DNA ends were then repaired using 1× End Polish Buffer, 400 nM each of dATP, dGTP and dTTP (leaving out dCTP), 40 U of End Polishing Enzyme 1 (Life Tech) and 80 U of End Polishing Enzyme 2 (Life Tech). Adaptor sequences, as detailed by Bormann Chung et al.[3], were then ligated onto the samples, using 1×T4 ligase buffer, 4.5 uM of methyl-protect PI adaptor, 4.5 uM of P2 adaptor and 50 U of T4 ligase. Nick translation was performed in IX Exo-Klenow buffer, 0.5 mM dNTPs containing methyl dCTP and 20 units of Exo-Klenow-Fragment (Ambion) for 1 hour at 16° C. 500 ng aliquots of the resulting product was then bisulfite converted using formamide as an additional denaturant[4]. 24 uL of formamide was added to an equal volume of DNA and incubated at 95° C. for 5 minutes. Subsequently, 100 uL of Zymo Gold bisulfite conversion reagent (Zymo) was added, and the mixture was incubated for 8 hours in 50° C. Samples were then desulphonated and purified using spin columns following the EZ-DNA Zymo Methylation-Gold protocol. 5 uL of the bisulfite converted library was amplified in 1×PCR buffer, 0.2 mM dNTP, 1 mM each of the standard SOLiD™ fragment library primers, 5 U of Taq (Denville), and 0.25 U of Pfu Turbo Taq (Stratagene). The DNA was subjected to 8 cycles of PCR and the resulting product was purified using AMpure™ SPRI beads (Beckman Genomics). The libraries were then sequenced on the SOLiD™ 3+ platform yielding 50 base pair reads. Corresponding colon cancer and normal mucosa samples were sequenced simultaneously in adjacent flow cells.

Alignment of SOLiD™ Sequencing Reads from Bisulfite-Treated DNA.

A custom alignment tool for SOLiD™ reads was developed from bisulfite-treated DNA. Reads were aligned with the aid of a spaced-seed index of the genome while biasing neither toward nor against methylated cytosines in CpGs described previously[31] to work with reads from SOLiD™ 3 Plus instruments. Note that aligners can introduce a bias when an unmethylated C (which becomes a T) is penalized for aligning to a C in the genome, but a methylated C (which remains a C) is not. The opposite bias can also occur, e.g., if all CpGs are converted to TpGs in the reference prior to alignment. Other projects address this in part by additionally converting Cs to Ts in the reads. But this approach is not applicable to the colorspace reads generated by the SOLiD™, for which nucleotide positions encoding Cs cannot be accurately determined prior to alignment. The aligner used here leaves each read as-is but penalizes neither C-to-C norT-to-C partial alignments in CpGs.

For alignment the approach taken by the BSMAP tool was extended. The approach used supports a broad range of spaced-seed designs and extends the BSMAP approach to additionally allow alignment of SOLiD™ colorspace reads. C/T bias is avoided by creating and storing multiple copies (potentially) of each reference subsequence indexed, one copy for each distinct assignment of Cs and Ts to genomic Cs or CpGs present in the subsequence. For colorspace reads, the algorithm extracts subsequences of colors (rather than nucleotides), and a copy it created for every distinct assignment of Cs and Ts to genomic Cs present in any nucleotide overlapped by any color in the extracted subsequence.

For these experiments, the alignment algorithm is configured to remove the penalty associated with either a C or a T aligning to a C in a CpG, and to treat non-CpG Cs in the genome as Ts. This policy removes bias from CpG methylation measurements, but assumes that there is little or no non-CpG cytosine methylation. Where non-CpG cytosine methylation occurs, this approach is more likely to fail to find alignments overlapping the methylated cytosine, and the resulting consensus will contain an anti-methylation bias at the methylated cytosine.

The algorithm was used to align a total of 7.79 billion reads obtained from 8 runs of a SOLiD™ 3 Plus instrument against a reference sequence collection consisting of the GRCh37 human genome assembly (including mitochondrial DNA and "unplaced" contigs) plus the sequence of the spiked-in phage genome. Each read obtained from the SOLiD™ 3 Plus instrument consists of a primer nucleotide followed by a string of 50 "colors," where each color encodes a class of dinucleotides according to the SOLiD™ colorspace encoding scheme. Prior to alignment, the initial primer base and 5'-most color were trimmed from all input reads, yielding a string of 49 colors. The alignment policy was selected to guarantee that all alignments with up to 3 color mismatches would be found, and some but not all alignments with 4-6 color mismatches would be found. The alignment of a T or C to a C in a CpG does not incur a mismatch penalty (except in some cases where a sequencing error is also present). The policy was also set to distinguish between reads that align uniquely and those that align non-uniquely.

Color-to-color alignments are decoded into nucleotide alignments with a Viterbi-like algorithm. The final alignment, when expressed in nucleotides, is one character shorter than the input read, i.e. 48 nucleotides long. Alignments for reads aligning non-uniquely are ignored in subsequent stages. Alignment results are summarized in Table 1 and FIG. 1.

For the data of Table 1, alignment was performed against a collection of reference sequences consisting of the GRCh37 human genome assembly, including mitochondrial DNA and "unplaced" contigs, plus the sequence of the spiked-in A DNA. A read is said to align "uniquely" if it has exactly one valid alignment to the reference according to the alignment policy. A read is said to align "non-uniquely" if it has more than one valid alignment according to the alignment policy. A read "fails" to align if it has zero valid alignments. Cytosine conversion percentage is estimated as the fraction of high-quality evidence from unique A phage alignments indicating lack of methylation.

FIG. 1 shows the number of reads and alignments obtained from SOLiD™ 3+ bisulfite sequencing. The stacked bar chart illustrates the number of reads sequenced per flowcell, with the colors indicating uniquely reads, unaligned reads and non-uniquely aligned reads. A total of 7.79 billion reads were obtained from 8 runs (16 flowcells) of a SOLiD™ 3+ instrument.

After alignment, a series of scripts extract and summarize CpG methylation evidence present in the unique alignments. The evidence is compiled into a set of per-sample, per-chromosome evidence tables. Alignments to the A phage genome are also compiled into a separate table. A piece of CpG "evidence" is created when an alignment overlaps the cytosine position of a CpG in the reference and the overlapping nucleotide in the alignment is either a T (indicating a lack of methylation) or a C (indicating presence of methylation). Once a piece of evidence is extracted from a unique alignment, it is subjected to a filter. The filter removes evidence that is either refuted by one or both of the overlapping colors from the original read, or is within 4 positions of either end of the nucleotide alignment. All evidence that passes the filter is added to the CpG summary table. A record in the table summarizes, for a given CpG: the filtered evidence nucleotides that aligned to it, the filtered quality values (i.e. of the two colors overlapping the evidence nucleotide) that aligned to it, the number of distinct alignment positions from which filtered evidence was taken, the "mapability" of the CpG and surrounding bases (i.e. the number of 50-mers overlapping the CpG that are unique up to 3 mismatches), (e) the local CG content of the bases surrounded the CpG. The mapability measure for each genome position is pre-calculated using Bowtie[8].

Table 2 summarizes the amount and type of evidence extracted at each stage. For Table 2, a piece of CpG evidence occurs when an alignment overlaps the cytosine position of a CpG in the reference sequence and the overlapping alignment nucleotide is either a T (indicating a lack of methylation) or a C (indicating presence of methylation). A filter is applied to remove nucleotide evidence that (a) is refuted by one or both of the overlapping colors from the original read, or (b) is within 4 positions of either end of the nucleotide alignment.

Table 3 summarizes the resulting CpG evidence coverage with respect to the GRCh37 human genome assembly for each sample. For Table 3, each sample is sequenced on two flowcells of a SOLiD™ 3+ instrument; here, results are calculated after pooling evidence from the two flowcells.

Finally, Table 4 summarizes per-sample average coverage both genome-wide and for CpG cytosines. For Table 4, average coverage of mappable CpG cytosines (column 3) is calculated by dividing the total number of pieces of C and T nucleotide evidence aligning to CpG cytosines after filtering (column 2) by the total number of CpG dinucleotides in GRCh37 that are "mappable" in the experiment: 20.9 million. A CpG is considered "mappable" if it is overlapped by at least one non-ambiguous reference 50 bp substring; non-ambiguous substrings are those for which no other 50 bp reference substring exists within 3 mismatches.

Figure 2:
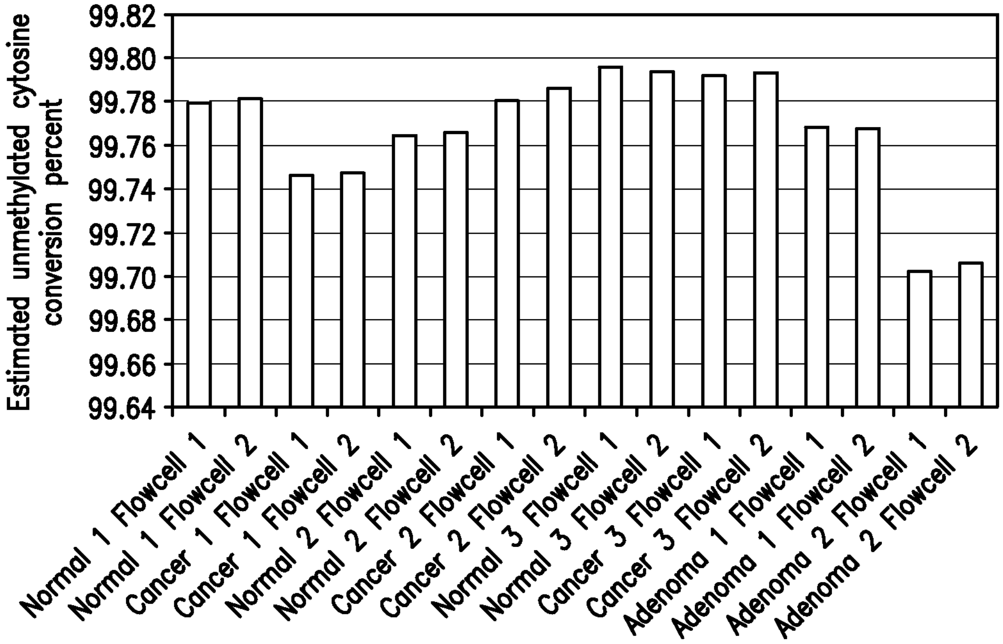
FIG. 2 is a graphical plot of estimated unmethylated cytosine conversion rate.

Evidence from reads that aligned uniquely to the λ genome were used to estimate the bisulfite conversion rate for unmethylated cytosines. The conversion rate is estimated as the fraction of high-quality evidence from reads aligning uniquely to the λ phage genome that indicates lack of methylation. FIG. 2 and the final column of Table 2 show the estimates, which all lie between 99.7% and 99.8%.

FIG. 2 shows the estimated unmethylated cytosine conversion rate per sample. Bisulfite conversion efficiency is plotted per SOLiD™ 3+ flowcell. Conversion efficiency is estimated as the fraction of high-quality evidence aligning to CpG cytosines in the unmethylated λ phage genome that indicates lack of methylation.

To measure global prevalence of non-CpG cytosine methylation, all filtered nucleotide evidence overlapping non-CpG cytosine positions in the human reference genome were examined. Filtered nucleotide evidence consists of evidence (a) from reads that aligned uniquely, (b) where both overlapping colors from the original read agree with the decoded nucleotide and, (c) where nucleotides within 4 positions of either end of the alignment are excluded. For each subject the overall fraction of evidence at CpG cytosine positions where the overlapping nucleotide is a T or a C. The same was done for non-CpG cytosine positions were measured. Table 5 summarizes the results, comparing them with the rate of cytosine non-conversion estimated from filtered evidence aligning to the λ phage genome.

For Table 5, the differentially expressed genes comparing colon cancer samples to normal samples were divided into two groups: those associated hypomethyiated boundary shifts and the rest. The table shows the five categories that with statistically significant enrichment (FDRO.01). It was observed that for all subjects, the fraction of Cs observed overlapping non-CpG cytosines does not rise above the approximate fraction expected from unconverted cytosines.

Figure 3:
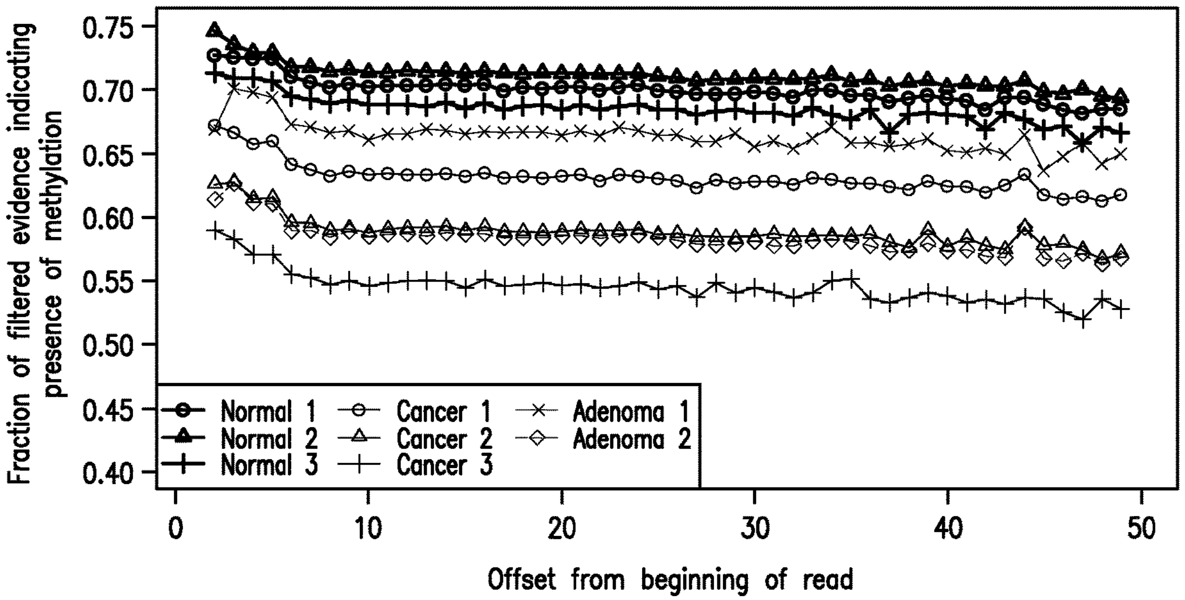
FIG. 3 is a graphical representation of bisulfite read position bias in evidence for methylation.

FIG. 3 shows the results of a simple diagnostic to assess the basic accuracy of the filtered evidence from the reads that aligned uniquely to the human genome. FIG. 3 shows SOLiD™ 3+ read position bias in evidence for methylation. The horizontal axis represents an offset into the nucleotide alignment from the 5' end. The vertical axis represents the fraction of filtered CpG methylation evidence from that offset that indicates that methylation is present. Only reads aligning uniquely to the GRCh37 human genome assembly are considered.

The diagnostic is to calculate, for each alignment position (1 through 48), the proportion of filtered evidence taken from that position that indicates that methylation is present. In a perfect assay, this proportion should be independent of position, and the plot should trace a straight horizontal line. In practice, the lines are not flat due to sequencing error and other noise arising from sample preparation and alignment. The relative flatness of the lines obtained for the samples gives us some assurance that the signal obtained is not substantially affected by noise such as sequencing error. Note that, while this plot shows the proportion in all alignment positions, evidence from the first four and last four positions of the alignment was additionally filtered.

After alignment, reads with a quality score of 10 or less filtered out before smoothing the methylation data (next section).

Reads were mapped to CpGs and determined if they were evidence for methylated or unmethylated cytosines. These data were then processed with the local likelihood approach, which resulted in pair-wise correlations between methylation estimates for the three normal samples of 0.97, 0.96, and 0.96.

DMR Detection.

A smoothing approach was developed, based on local likelihood estimation[33], which leveraged the fact that the methylation status of neighboring CpG is highly correlated[34] to greatly improve precision of methylation measurements. Two related approaches; one for blocks and one for small DMRs was developed.

The alignment algorithm described in the previous section provided two counts for each CpG: number of pieces of filtered evidence indicating presence of methylation (M) and number of pieces of filtered evidence indicating unmethylation (U). The sum of these two counts was the coverage N. It was assumed that for each CpG, M followed a binomial distribution with success probability p, equal to the true methylation level, and N trials. Thus, M/N provided a naive estimate of p with standard error $(M/N)\times(1-M/N)/\sqrt{N}$. Note that N, the coverage, ranged from 0 to 18,090 with a sample mean of 5.8-6.2 (after excluding CpGs with no coverage in all samples). Precision was greatly improved by leveraging the fact that proximal CpG have similar methylation levels and using a smoothing technique similar to that used in CHARM.

Because the data was binomially distributed, local likelihood estimation was used. This approach assumes that the p(L), the methylation level at genomic location L, is a smooth function of L; in other words, that CpGs that are close have similar methylation levels. The local likelihood approach uses data within windows of predefined sizes to estimates p(L) and weighing data based on distance to L (based on a tricube kernel). In addition, the binomial model ensures that data points with high coverage receive greater weight. Two window sizes were defined to detect the two different types of DMRs; for the blocks, a large window to detect low frequency differences, and a smaller window to detect high frequency differences, the small DMRs.

For each sample, the smoothed data was evaluated on the same grid of data points termed "covered CpGs", consisting of those CpGs where at least two normals samples had a coverage of at least 2.

Figure 4:
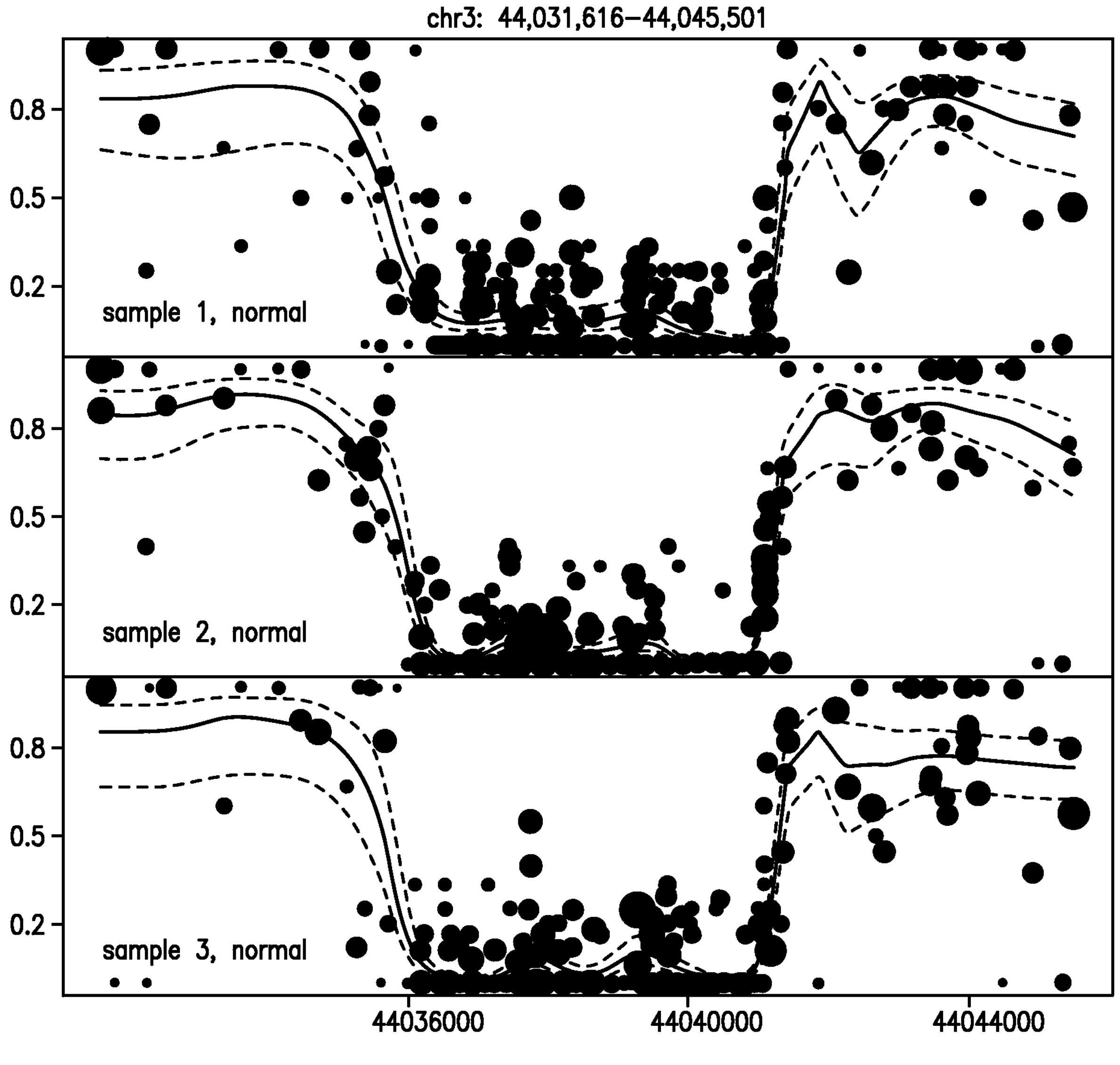
FIG. 4 is a graphical representation of methylation estimates obtained by high-frequency smoothing.

For the small DMRs, the high-frequency analysis used a window size of 70 CpG or 1,000 bps; whichever generated a larger region. For the blocks, the low-frequency analysis used a window size of 500 CpGs or 2,000 basepairs; again whichever was larger. Note that the use of a tricube kernel ensures that data points far from the center of the window receive a smaller weight. This approach provided highly precise estimates of CpG methylation levels p(L) for each sample. The standard errors ranged from 0-0.11 (mean of 0.04) for the high frequency smoothing and 0.01-0.04 (mean 0.02) for low frequency. An example of the results from the high-frequency smoothing is provided as FIG. 4. FIG. 4 shows precise methylation estimates obtained by high-frequency smoothing. The circles represent the single CpG estimates of methylation, which are plotted against the CpG location. The areas of the circles are proportional to the coverage. The high-frequency smoothed values (described in detail in the Methods) are plotted as solid lines. Dashed lines represent 95% pointwise confidence intervals. The region shown in the bottom panel illustrates the statistical approach.

A method for finding differences based on t-statistics that take into account biological variability was then developed. The highly precise estimates of pi(L) for each sample i at each CpG location L was started with. The average difference between the three tumor samples and the three normal samples referred to as d(L) was obtained. To properly account for biological variability (FIG. 5) the standard error of d(L) using the normal samples was estimated.

Figure 5:
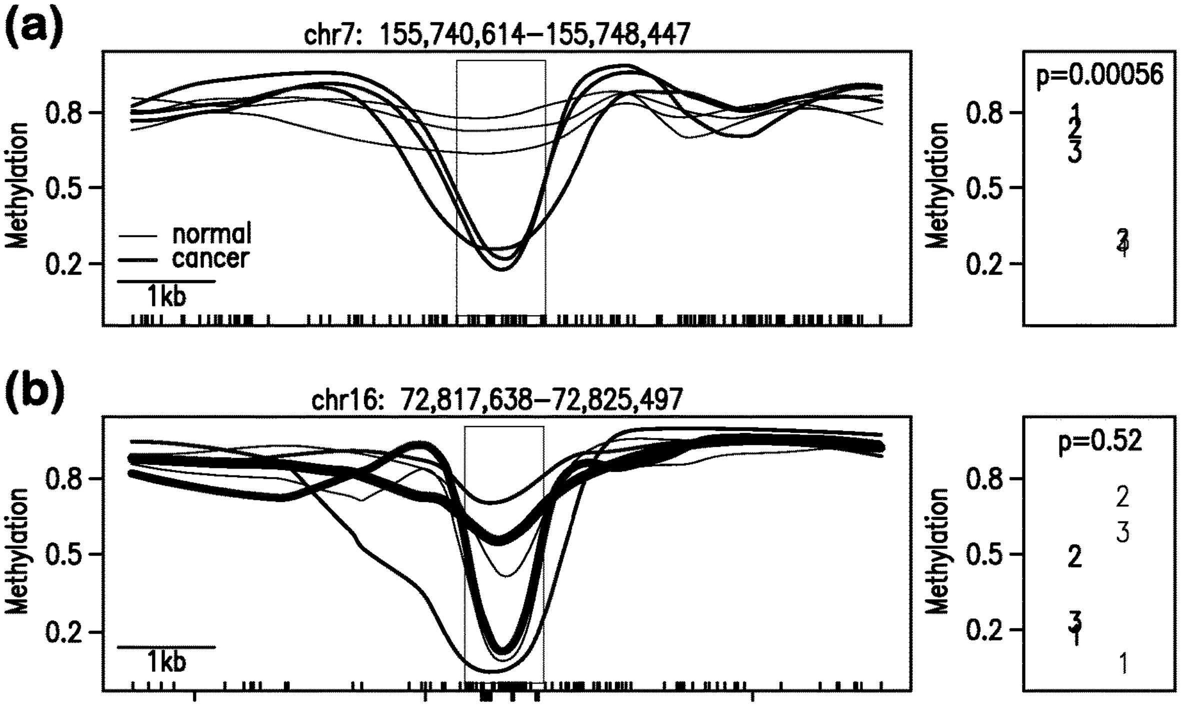
FIG. 5 is series of graphical representations of methylation patterns.

FIG. 5 illustrates the need for biological replication for detecting DMRs. FIG. 5(*a*), in the left panel, methylation patterns for three normal samples (top lines) and matched cancers (bottom) are shown. The detected DMR is shaded in pink. In the right panel, the average methylation values within the DMR for the three paired samples is shown (normal in blue, cancer in red, the matched sample pairs indicated by numbers). A t-test for the difference between normal and cancer and obtained a p value of 0.0056 was performed. FIG. 5(*b*) shows the same analysis as (a) for a region in which if only normal-cancer pair 3 (thick lines) were analyzed, there would appear to be a methylation difference between cancer and normal. However, the p value when all three samples are compared is 0.52. Notice that the methylation estimates are very precise (standard error for points in right panel are <0.02). Therefore the differences seen are biological not technical, and will be seen regardless of the measurement technology.

Figure 6:
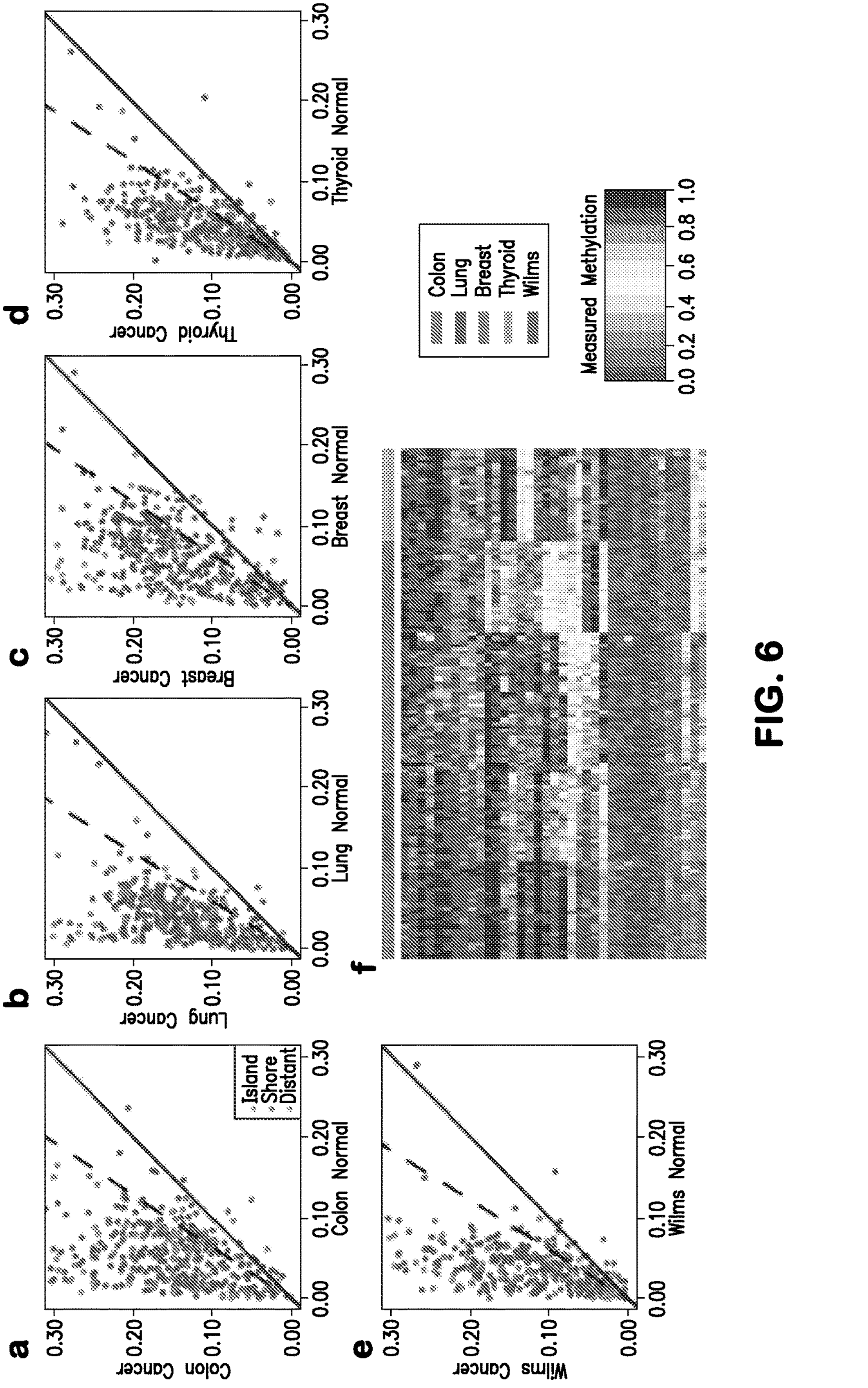
FIG. 6 is a series of graphical plots of methylation variance of common CpG sites across human cancer types.

Only the normal samples were used because as demonstrated, cancer samples are prone to high variability (FIG. 6). FIG. 6 shows the increased methylation variance of common CpG sites across human cancer types. Methylation levels measured at 384 CpG sites using a custom Illumina array exhibit an increase in across-sample variability in (a) colon, (b) lung, (c) breast, (d) thyroid, and (e) kidney (Wilms tumor) cancers. Each panel shows the across-sample standard deviation of methylation level for each CpG in normal and matched cancer samples. The solid line is the identity line; CpGs above this line have greater variability in cancer. The dashed line indicates the threshold at which differences in methylation variance become significant (F-test at 99% level). In all five tissue types, the vast majority of CpGs are above the solid line, indicating that variability is larger in cancer samples than in normal. Colors indicate the location of each CpG with respect to canonical annotated CpG islands. (f) Using the CpGs that showed the largest increase in variability hierarchical clustering was performed on the normal samples. The heatmap of the methylation values for these CpGs clearly distinguishes the tissue types, indicating that these sites of increased methylation heterogeneity in cancer are tissue-specific DMRs.

The standard error se[d(L)] was therefore estimated as σ(L)*V(2/3) with σ(L) the standard deviation of the Pi(L) for the three normal samples. To improve standard error estimates, these were smoothed using a running mean with a window size of 101 observations. To avoid inflated t-statistics as a result of artificially low variance, a threshold for the standard deviation of its 75th percentile was set, before computing the smoothed result. With the standard deviation in place the t-statistic t(L)=d(L)/se[d(L)] was constructed.

For the high frequency analysis the t-statistic was further corrected for low frequency changes. This allowed discovery of local features, such as a hypermethylated small DMR, inside global features, i.e. hypo- or hypermethylated block. This correction factor was calculated by forming a fixed grid of positions 2,000 bp apart in the genome, linearly interpolating the neighboring t-statistics to obtain measurements at these positions and then smoothing this dataset with a robust smoother based on the Huber family[10] and a bandwidth of 25,000 bp. Small DMRs were then defined as contiguous CpGs within 300 bp of each other, with the t-statistics above 4.6 or below −4.6 (corresponding to the 95th quantile of the empirical distribution of the t-statistics) and all differences in the same direction. For the low frequency analysis the t-statistics cutoff was 2 and contiguous CpG were defined as within 10,000 bps from each other.

These sets of regions formed the small DMRs and blocks that were subsequently filtered and processed according to the following criteria. 1) A small DMR needed to contain at least 3 covered CpGs and have at least 1 covered CpG per 300 bp. Furthermore, the mean difference in methylation percentages between tumors and normals across the small DMR had to be greater than 0.1. 2) A block needed to be longer than 5 kb. Blocks containing CpG Islands with a mean methylation of less than 0.25 in the normal samples were separated into two. Putative blocks that were shorter than 5 kb were included as small DMRs provided they satisfied the small DMR filters above.

After filtering, pairs of small DMRs were merged if they were less than 1 kb apart, changed in the same direction (both hypermethylated or both hypomethylated), and had no covered CpGs in the area separating them. A partial list of blocks is shown as Table 6, and of small DMRs as Table 7. Additional blocks and small DMRs were determined which are not shown in Tables 6 and 7.

The data from the adenoma samples were smoothed in the same way.

DMR Classification.

Figure 7:
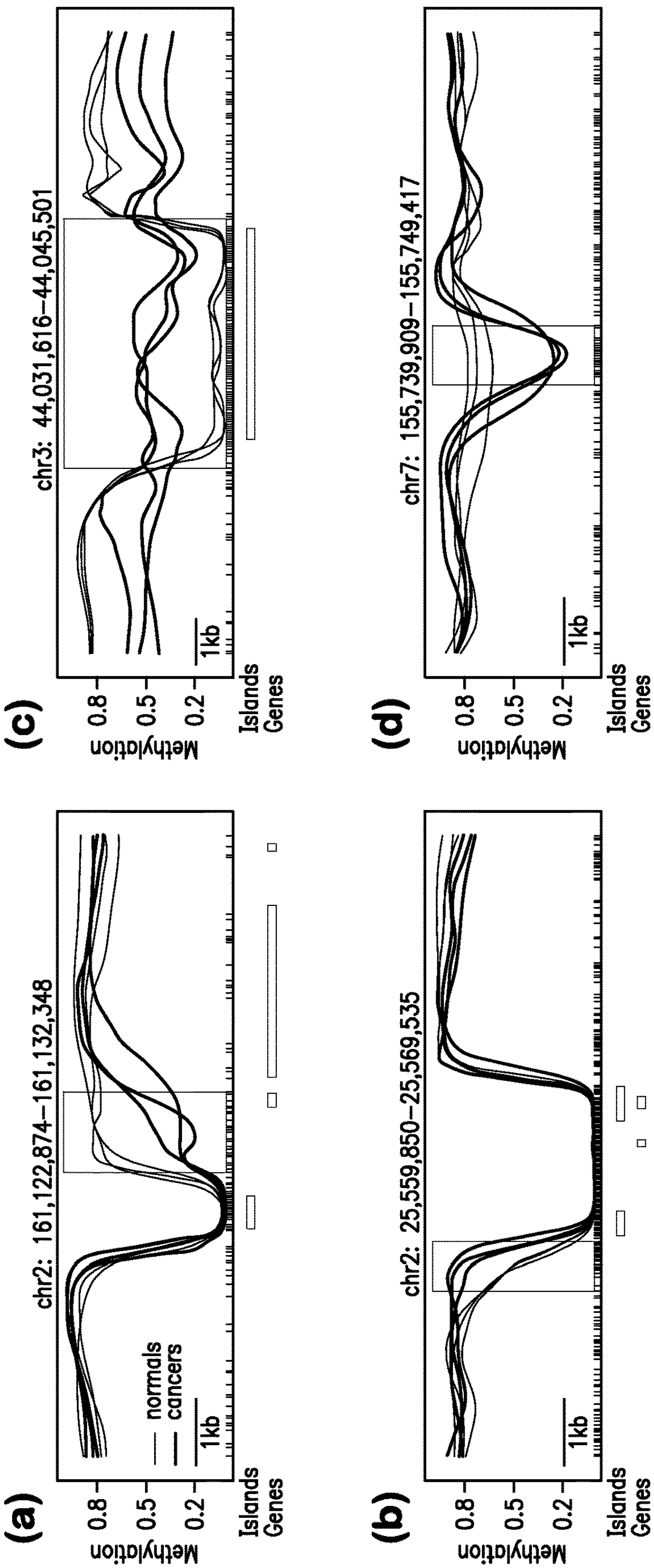
FIG. 7 is a series of graphical plots of methylation estimates plotted against genomic location for normal samples and cancer samples. The small DMR locations are shaded. Grey bars indicate the location of blocks, CpG islands, and gene exons. Tick marks along the bottom axis indicate the location of CpGs.

Small DMRs were classified into categories based methylation profiles of the tumor and normal samples within the DMR and the two flanking regions (within 800 bp). Based on these results, the DMRs that were discovered from data exploration could be classified into three types termed loss of methylation boundaries, shifting of methylation boundaries, and novel hypomethylation (FIG. 7). FIG. 7 shows loss of epigenetic stability at small DMRs. Methylation estimates are plotted against genomic location for normal samples and cancer samples. The small DMR locations are shaded. Grey bars indicate the location of blocks, CpG islands, and gene exons. Tick marks along the bottom axis indicate the location of CpGs. Pictured are examples of (a) a methylation boundary shift outward (normal-top lines in shaded area; cancer-bottom lines in shaded area), (b) a methylation boundary shift inward (cancer-top lines in shaded area; normal-bottom lines in shaded area), (c) a loss of methylation boundary (cancer-top lines in shaded area; normal-bottom lines in shaded area), and (d) a novel hypomethylation DMR (normal-top lines in shaded area; cancer-bottom lines in shaded area).

A mathematical algorithm was used to automatically classify DMRs. Briefly, mean methylation was computed for both tumor and normal samples within the DMR and in the flanking the DMR both upstream and downstream. This provided three numbers for each of the six samples. If all the normal samples showed high methylation values (>50%) in the flanking regions and low methylation values (<0.25%) and the tumor samples all showed intermediate values across DMR and flanking regions, the DMR was classified as loss of methylation boundary. If one of the flanking regions had low methylation values in both the normal and the tumor samples, the region was classified as a shift of methylation boundary. Finally, if all the normal samples showed high methylation values in the DMR and flanking regions while the tumor samples were lower in the DMR, the region was classified as novel hypomethylation. The details of the algorithm are best understood by viewing the computer code (made available upon request).

Hypomethylation in Blocks and Repeat Regions.

Repeat regions were identified based on the UCSC repeat-Masker track[11]. Based on the repeats and/or blocks, the genome was segmented into regions both repeats and blocks, repeats but not blocks, not repeats but blocks, and neither repeats nor blocks. The methylation levels were computed as the average of the high-frequency smoothed methylation levels of all CpGs in the 4 different regions. Density estimates were computed from the same distribution.

Enrichment of Overlap Between Different Genomic Domains.

For each pair of different genomic domains (like blocks and LOCKs) a 2×2 table is formed containing the number of CpGs inside and outside the two genomic domains (like inside blocks and inside LOCKS, inside blocks and outside LOCKs, etc). Odds ratios and p-values were calculated using Fisher's exact text.

Copy Number Analysis.

Estimates of copy number were based on the per-base coverage obtained after alignment. The filters developed were not applied specifically for methylation measurements (described in the Bisulfite alignment Section). Note that the coverage considered here is not specific to CpGs: every genomic position is assigned a coverage value. For each sample, the average coverage in non-overlapping 10,000 bp windows was then computed, yielding two coverage vectors for each tumor-normal pair denoted cov(T) and cov(N). For each tumor-normal pair the corrected log-ratio: log 2(CN) =log 2(cov(T))−log 2(cov(N))+c was defined. Here c is a correction factor to account for different yields in each sequencing run; c is defined as the log of total sequencing yield of the normal sample divide by total yield of the tumor sample. The copy number log-ratios were segmented using circular binary segmentation (CBS)[12]. For illustrative purposes, copy number log-ratios and the associated segmentation on chromosome 20 were depicted (FIG. 8*a*).

To determine if copy number had an effect on methylation estimates, each segment provided by CBS was divided into 100 kb regions. For each of these regions average copy number ratios as well as average methylation ratios was computed. These were then plotted (FIG. 8*b*) and no relationship between CNV and methylation blocks was observed.

Figure 8:
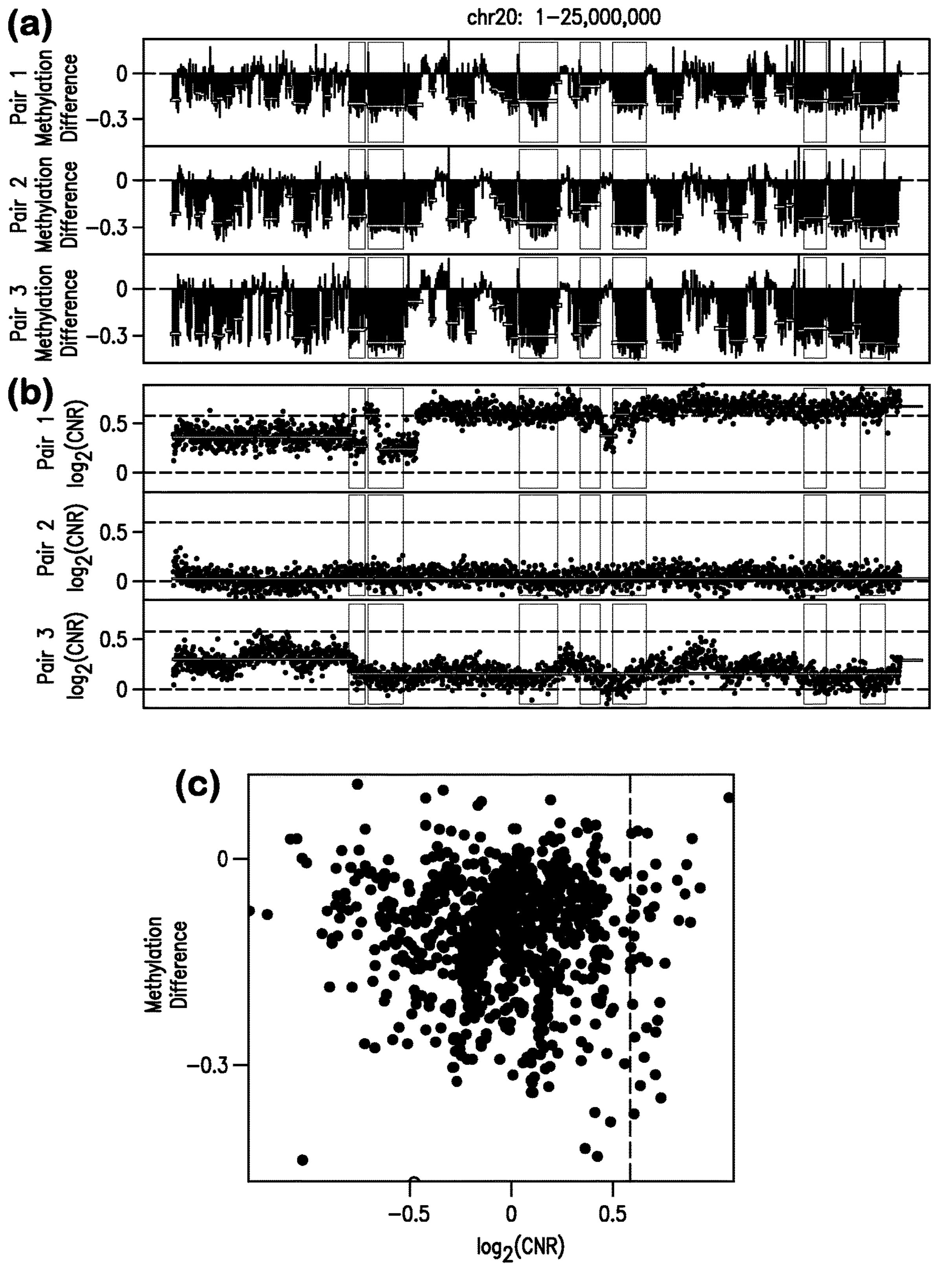
FIG. 8 is a series of graphical plots of: (a) methylation differences; (b) copy number alterations; and (c) differences in methylation plotted against difference in copy number.

FIG. 8 shows that block and small DMR detection not affected by copy number variation. For FIG. 8(*a*) for a 25 megabase region of chromosome 20 (1-25 MB), the methylation differences between all three normal-cancer pairs plotted along the chromosome, with red lines representing the average values in blocks are shown. Notice that the location of blocks is consistent across all three normal-cancer pairs. For illustrative purposed, highlighted (shade) are the seven largest blocks. For FIG. 8(*b*) for each normal-cancer pair, copy number alterations is shown, quantified by log ratios (base 2) of coverage in cancer sample to coverage in normal sample, for the same region as in (a). Log-ratios of 0 are associated with lack of copy number alternations in cancer, while values larger or equal to $\log_2(3/2)$ (dashed line) are associated with gain of copy number in cancer. The red lines represent segments obtained with the CBS algorithm (described in the Methods). Notice that each sample shows different copy number alterations. For FIG. 8(*c*) differences in methylation are plotted against differences in copy number (log-ratios) for the entire genome. Specifically, for each of the segments detected by CBS, the average difference in methylation and the average log-ratio associated with copy number alteration was computed. This was done for each sample and all the points combined in one scatter-plot.

Capture Bisulfite Sequencing.

Bisulfite Padlock Probes (BSPP) were used to capture bisulfite converted gDNA using a previously described method[32]. Sequencing libraries were generated from the captured DNA, and sequenced on an Illumina™ GA II instrument, generating 79.3 million reads. Capture reads were aligned using the same methodology as the whole genome bisulfite reads, but adapted to work in nucleotide space instead of color space.

Assays for Large Organized Chromatin K9-Modifications (LOCKs).

Primary human pulmonary fibroblasts (HPF) were purchased from ScienCell Research Laboratories (San Diego, Calif.). Cell culture was conducted using the media and protocols recommended by ScienCell. Primary cells at the second passage were used for H3K9Me2 LOCK analysis. ChIP-on-chip experiments and microarray data analysis were performed as described earlier[12].

Gene Expression Analysis.

Expression data was obtained from the gene expression barcode (rafalab.jhsph.edu/barcode). This resource combines all the expression data from the public repositories purportedly to standardize data in a way that allows one to call a gene expressed or not expressed. From this source, two independent colon cancer datasets (GSE8671[35] and GSE4183[36,37]) were used. To define hypervariable genes an F-test using a across sample variance in tumor and normal samples computed from the original log expression was performed. A gene was defined as expressed if it had a gene expression barcode standardized value above 2.54 (p=0.01). For the fibroblast analysis datasets (GSE7890[38], GSE11418[39], GSE11919[40]) were downloaded. These expression values from these datasets were also standardized using the gene expression barcode. The standardized values were used to determine if genes were expressed or not each sample.

To determine the correlation between small DMRs and expression, a gene and a small DMR were considered associated if the DMR was within 2,000 bps from the transcription start site of the gene; 6,869 genes mapped to a DMR in this way.

Data Annotation.

Annotation was obtained from the UCSC genome browser based on hgl9. In the cases where a data track was only available for hgl8 or hgl7, the UCSC liftOver tool was used to map between builds of the human genome. Specifically the repeatMasker track, the RefSeq mRNA track, and the UCSC known genes track were used.

Laminin Associated Domain (LAD) coordinates were obtained from the NKI LADs track from UCSC, generated from microarrays in fibroblast cells. PMDs were obtained from Lister et al., generated from bisulfite sequencing in fibroblast cells[11]. DNase I hypersensitive sites were obtained from the UCSC ENCODE track, using the Hies, Caco2rep1, and Caco2rep2, both the narrow and broad peak.

Results

Stochastic variation in DNA methylation as a defining feature across cancer types.

It was desired to increase the precision of DNA over the previous tiling array-based approach, termed CHARM (Comprehensive High-throughput Array for Relative Methylation)[6], analyzing 151 colon cDMRs from Irizarry et al.[4]. A custom nucleotide-specific bead array (see Methods) was designed on the type of Illumina GoldenGate™ platform previously shown to be quantitative within 6% of DNA methylation[7]. The resulting 384 probes covered 139 regions, with 1-7 probes per region. To test the generality of DNA methylation alterations across tumor types, 290 samples were studied, including cancers from colon (10), lung (24), breast (27), thyroid (36), and kidney (Wilms') (25), with matched normal tissues to 111 of these 122 cancers, as well as 30 colon premalignant adenomas, and an additional 18 normal colon and 9 normal breast samples. To minimize the risk of genetic heterogeneity arising from sampling multiple clones DNA from small (0.5 cm×0.2 cm) sections verified by histopathologic examination were purified.

Figure 9:
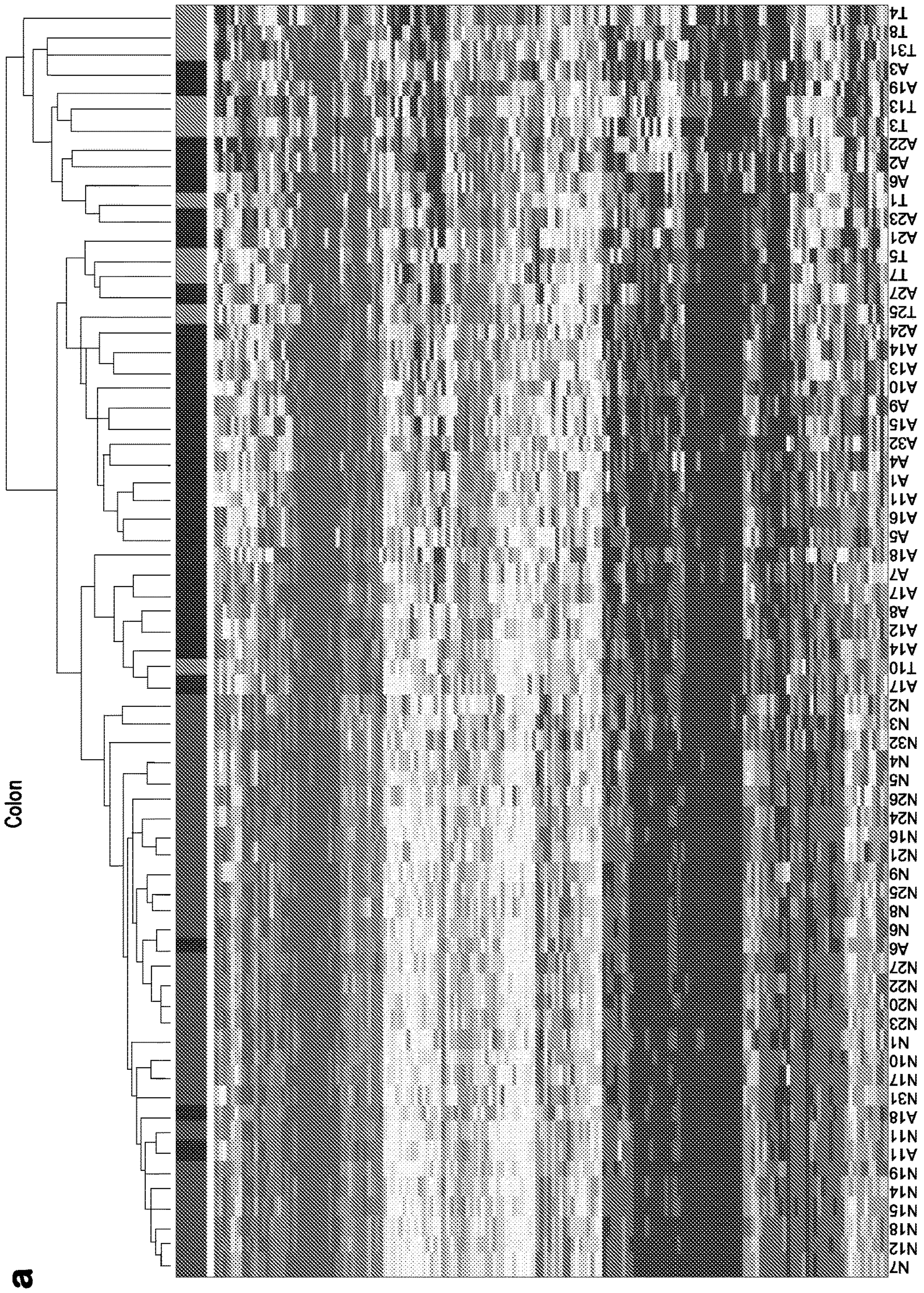
FIG. 9 is a series of clusters of methylation profiles using Euclidean distance.
Figure 9:
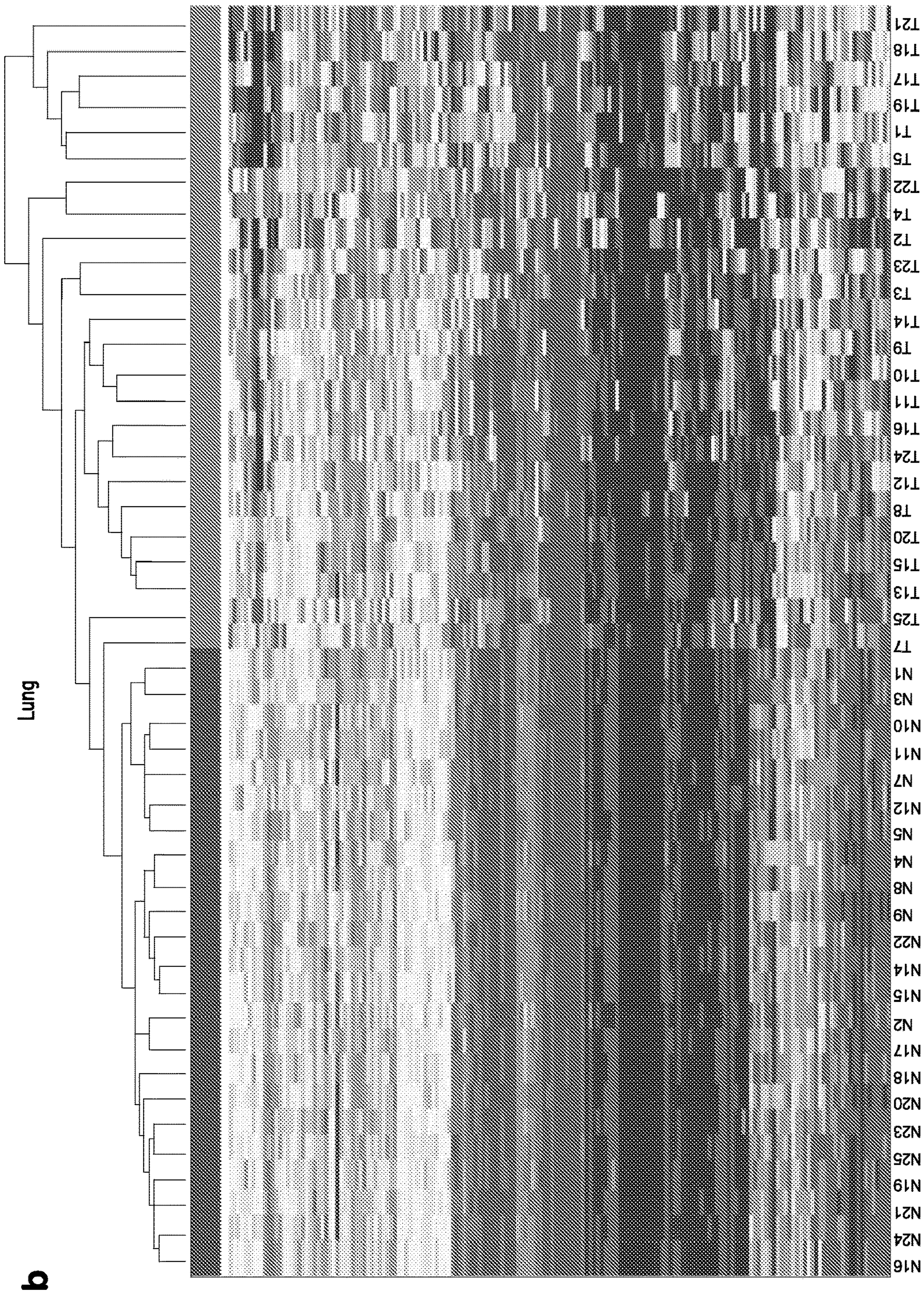
Figure 9:
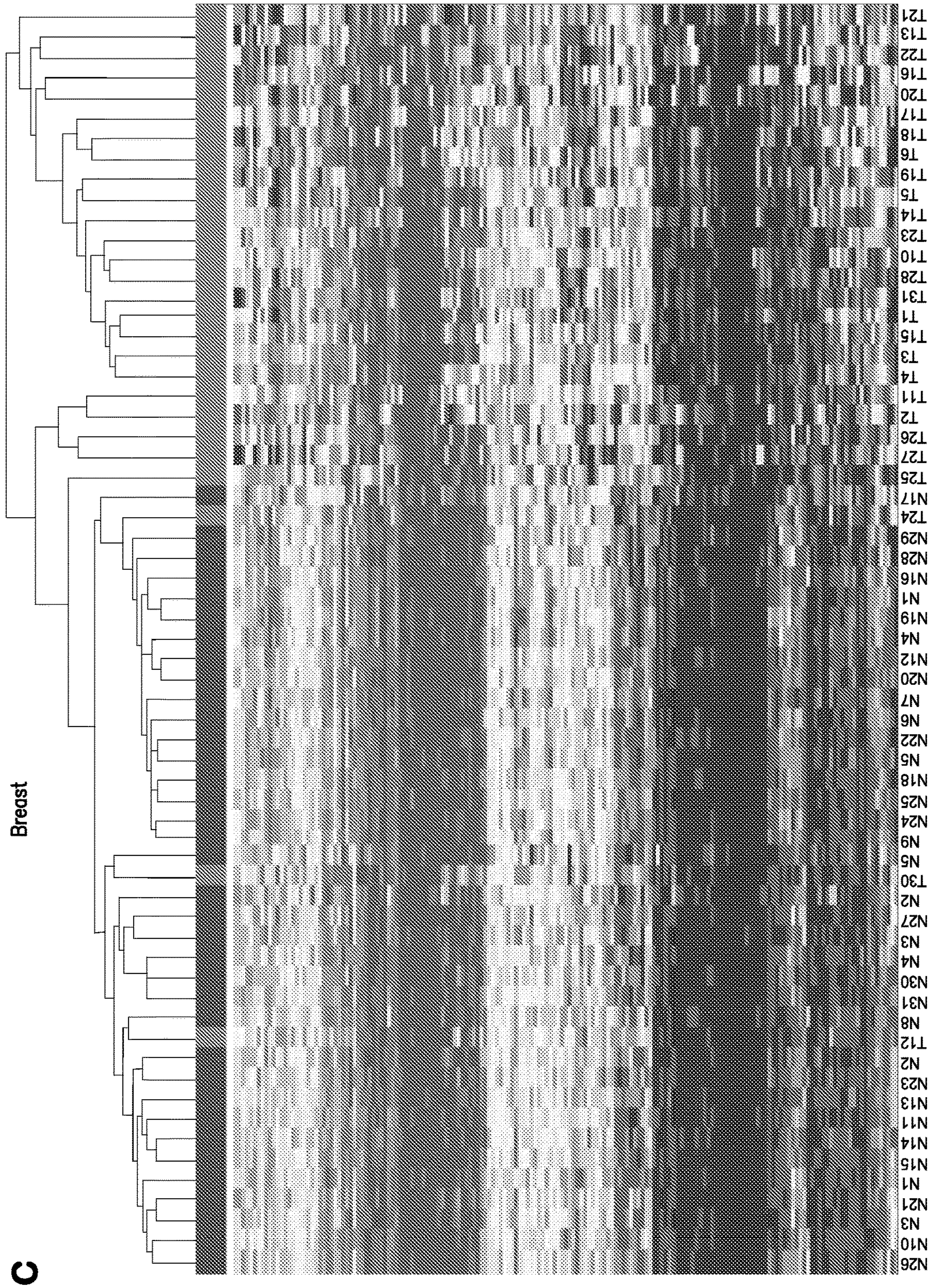
Figure 9:
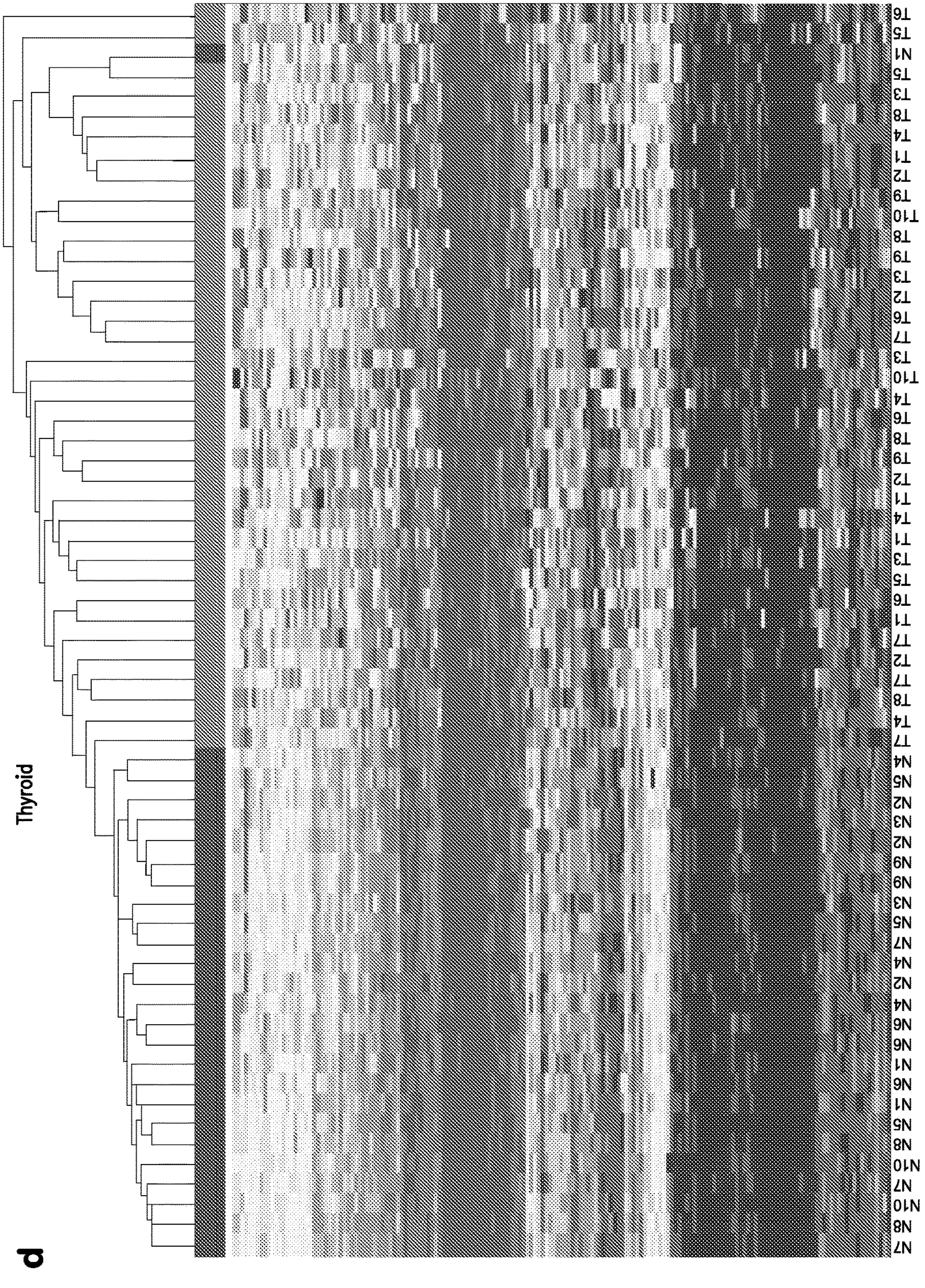
Figure 9:
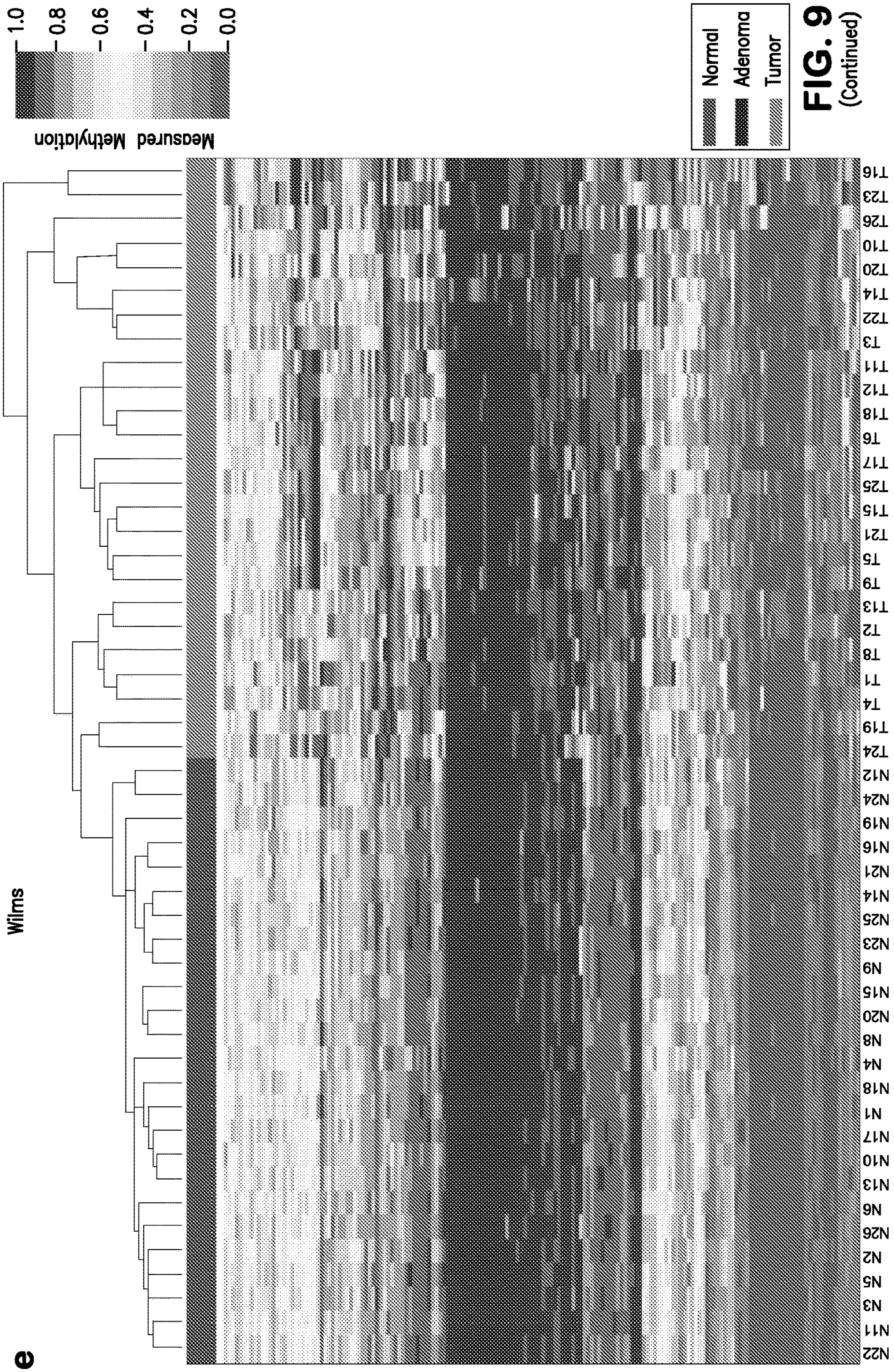

Cluster analysis of the DNA methylation values revealed that the colon cancer cDMRs largely distinguished cancer from normal across tumor types (FIG. 9).

FIG. 9 shows that methylation levels of differentially methylated CpGs in colon cancer largely differentiate cancer from normal in colon(a), lung(b), breast(c), thyroid(d) and kidney(e)(Wilms) tissues. Columns and rows in each panel are ordered by a hierearchical clustering of methylation profiles using Euclidean distance. The heights of dendrogram branches, larger between tumor samples than between normal samples, illustrate the increased across-sample variability in cancer seen in a majority of CpGs in all tissues.

Even more striking than the differences in mean methylation between cancer and normal was the increased across-sample methylation variability in the cancer samples compared to normal, within each type, but occurring generally across all cancer types (FIG. 9). Therefore the across-sample variance within normal and cancer samples in all five tumor/normal tissue types at each CpG site was computed. For each tissue type, the great majority of CpGs exhibited greater variance in cancer than normal (FIG. 6(*a*)-(*e*)), even though these sites had been selected for differences in mean values in colon cancer. This increase was statistically significant ($p<0.01$, using an F-test) for 81%, 92%, 81%, 70%, and 80% of the CpG sites in colon, lung, breast, thyroid, and Wilms' tumor, respectively. Furthermore, 157 CpG sites had statistically significant increased variability in all cancer types tested. This increased stochastic variation was found in CpG islands, CpG island shores, and regions distant from islands (FIG. 6(*a*)-(*e*)). This increased methylation variability in cancer are not themselves due to mean differences because the cancers show marked departure in variation from the expected binomial distribution that is followed in the normal samples. These data suggest a potential mechanism of tumor heterogeneity, namely increased stochastic variation of DNA methylation in cancers compared to normal, within each tumor type tested (see Discussion).

To rule out artifactual methylation heterogeneity caused by a greater degree of cell type heterogeneity in cancers compared to normal, a careful histological analysis for cellular subtypes within all of the colon and kidney tumor and normal samples was performed by a board-certified oncology pathologist. The normal samples were on average much more heterogeneous than the tumor samples in cellular composition. Thus, the data showing greater methylation variability in cancers cannot be due to increased cellular heterogeneity in the cancers compared to normal. This increased variation was not due to patient age, as the great majority of the samples were normal/tumor matched, and an age-corrected analysis did not change the result.

To address a potential connection between genetic and epigenetic heterogeneity that might underlie the data two experiments were performed. First, five Wilms tumor samples were selected which showed little to no intertumoral genetic variation by microarray-based copy number analysis and compared them to five colon cancers which showed relatively high amounts of copy number variation. Similar levels of methylation hypervariability were present in both types of cancers despite the differences in copy number variation. Second, immunohistochemical staining was performed for aberrant p53 expression on sections taken from Wilms tumor and colon cancers (7 samples of each), since p53 expression is a marker of chromosomal instability in both of these types of cancer. All seven colon samples tested positive for aberrant p53 whereas none of the Wilms tumors were positive. Analysis of these same samples by a custom GoldenGate™ arrays showed similar levels of methylation hypervariability in both of these cancer types, despite differential expression of p53.

These same loci which show increased variability in cancer are also able to distinguish the normal tissues from each other, but this is a mean shift rather than a variation shift, apparent from cluster analysis. Interestingly, even using a reduced set of the 25 sites which are most variable in cancer the five normal tissue types are clearly discriminated from each other (FIG. 6(*f*)). This result reinforces the concept of a biological relationship between normal tissue differentiation and stochastic variation in cancer DNA methylation.

To determine if the increased variability is a general property of cytosine methylation in cancer or a specific property of the CpGs selected for the custom array, as a control a publicly available methylation dataset comparing colorectal cancer to matched normal mucosa on the Illumina HumanMethylation™ 27 k beadchip array was used. In this dataset it was found that only 42% of the sites showed a statistically significant increase in methylation variability, compared to 81% in the custom array ($p<0.01$), confirming the specificity of the cancer DMRs included in the custom array. Examining variability with respect to location relative to CpG islands, it was noted that increased stochastic variation was more common in CpGs far from islands (57%) than in shores (44%) or islands (31%), contrasting the relative representation of these locations on the 27 k array which breaks down as: distal to islands (26.4%), shores (31.6%) and islands (42%) (see Methods). This was an intriguing result as it suggested that something other than relationship to CpG islands might be defining the largest fraction of sites of altered DNA methylation in cancer.

Hypomethylation of Large DNA Methylation Blocks in Colon Cancer.

The methylation stochasticity described above appears to be a general property of cancer, affecting cDMRs in both island and non-island regions, in all five cancer types tested. To further investigate this apparent universal loss of DNA methylation pattern integrity in cancer, and to analyze the lower CpG abundance regions not previously examined by array-based methods, shotgun bisulfite genome sequencing on 3 colorectal cancers and the matched normal colonic mucosa from these three patients using the ABI SOLiD™ platform was performed. Methylation estimates with enough precision to detect differences as small as 10% methylation were desired. Because a local likelihood approach was used, which aggregated information from neighboring CpGs, and combined data from 3 biological replicates, it was determined that 4× coverage would suffice to estimate methylation values at the desired precision with a standard error of at most 3% (See Methods for details). Between 12.5 and 13.5 gigabases of data for each sample was therefore obtained, which after quality control filtering (see Methods) provided ~5× coverage for each CpG after aligning the bisulfite converted read (Table 4). After statistical processing, pair-wise correlations were obtained between methylation estimates for the three normal samples of 0.97, 0.96, and 0.96, confirming the adequacy of sequencing coverage. Details on the mapping and statistical algorithms are available in the Methods Section.

To verify the accuracy of the methylation values obtained via the local likelihood approach, capture bisulfite sequencing was performed on the same 6 samples that were sequenced, for 39,262 regions which yielded 39.3 k-125.6 k CpG with >30× coverage. These results showed a correlation of 0.82-0.91 between the local likelihood approach and the capture bisulfite sequencing, a remarkable agreement given that the experiments were performed in different laboratories using different sequencing platforms and different protocols. Close examination of individual loci demonstrated that the methylation estimates closely track the high-coverage capture data. While capture bisulfite sequencing is far more exhaustive and CpG inclusive, traditional bisulfite pyrosequencing was further performed, which also confirmed the accuracy of the approach.

Figure 10:
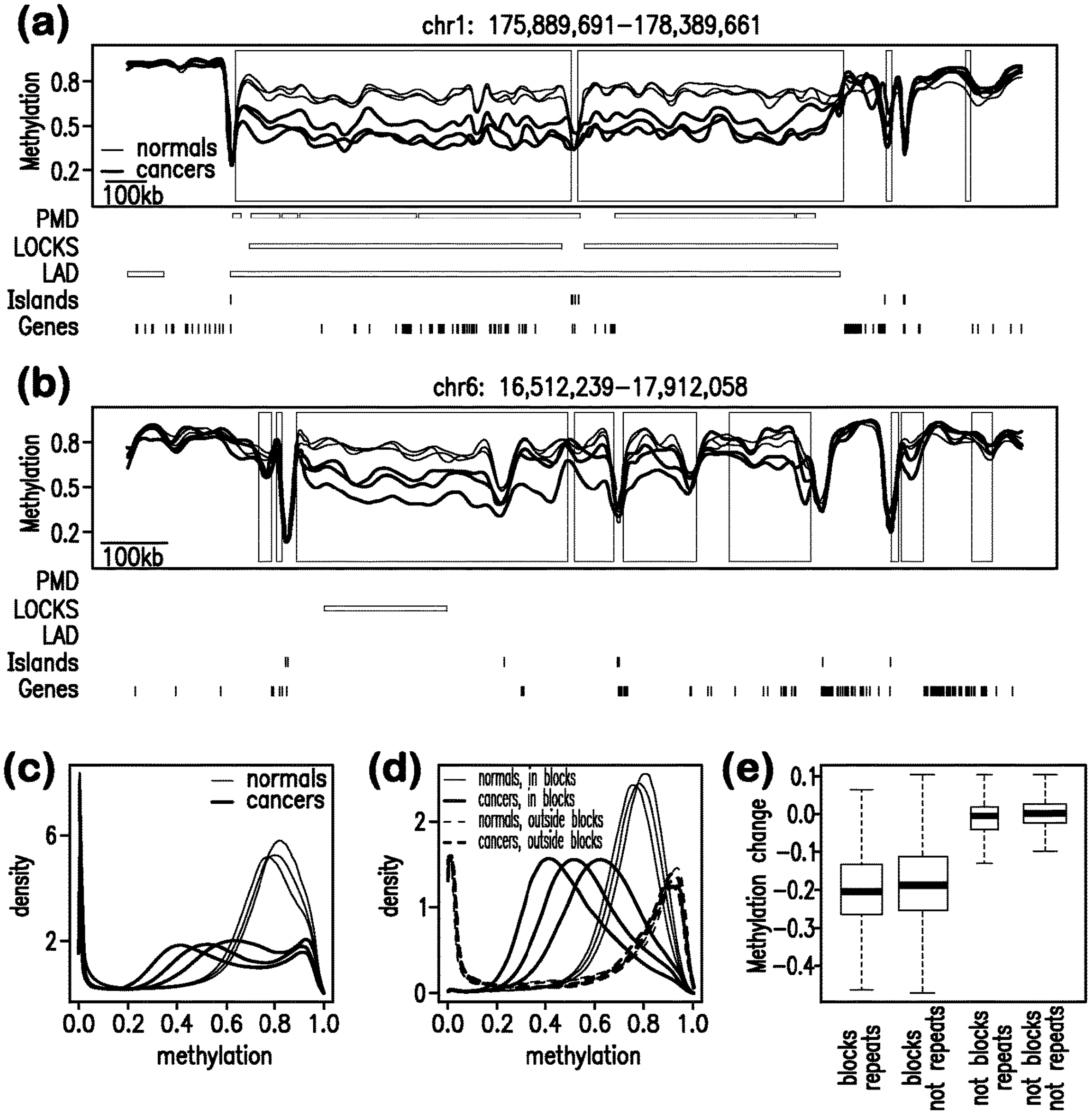
FIG. 10 is a series of graphical representations.

The bisulfite sequencing analysis revealed the surprising presence of large blocks of contiguous relative hypomethylation in cancer compared to normal (FIGS. 10(*a*)-(*b*)). FIG. 10 shows the existence of large hypomethylated genomic blocks in human colon cancer. Shown in (a) and (b) are smoothed methylation values from bisulfite sequencing data for cancer samples (red) and normal samples (blue) in two genomic regions. The hypomethylated blocks are shown with pink shading. Grey bars indicate the location of PMDs, LOCKs, LADs, CpG Islands, and gene exons. Note that the blocks coincide with the PMD, LOCKS, and LADs in panel (a) but not in (b). (c) The distribution of methylation values for the normal samples (blue) versus the cancer samples (red) demonstrates global hypomethylation of cancer compared to normal. (d) The distribution of methylation values in the blocks (solid lines) and outside the block (dashed lines) for normal samples (blue) and cancer samples (red). Note that while the normal and cancer distributions are similar outside the blocks, within the blocks methylation values for cancer exhibit a general shift. (e) Distribution of methylation differences between cancer and normal samples stratified by inclusion in repetitive DNA and blocks. Inside the blocks, the average difference was ~20% in both in repeat and non-repeat areas. Outside the blocks, the average difference was ~0% in repeat and non-repeat areas, indicating that blocks rather than repeats account for the observed differences in DNA methylation.

13,540 such regions of median size 39 kb, varying from 5 kb-10 MB were identified (partial listing in Tables 6 and 8). The across-cancer average loss of mean DNA methylation throughout all the blocks was 12%-23% (partial listing shown in Table 6). Remarkably, these hypomethylated blocks in cancer corresponded to more than half of the genome, even when accounting for the number of CpG sites within the blocks (Table 8). Analysis shows that these blocks are common across all three cancers; an analysis of the tumors individually versus a normal profile shows consistent block boundary locations (see FIG. 10, FIG. 2, and Methods). The existence of a small fraction of hypermethylated blocks (3% of all differentially methylated blocks) in cancer was also noted, with examples visible on the far right edge of FIG. 10(*a*) and FIG. 10(*b*) (Table 8). A histogram of smoothed methylation values shows the shift in distribution of global DNA methylation (FIG. 10(*c*)). The relatively small compartments of fully unmethylated or fully methylated changed little in the aggregate between normal and cancer. Instead, the predominant change in block methylation in cancer was a loss in the more abundant compartment of intermediate methylation levels (mean 73% for all samples) to a significantly less methylated level (50-61%). Examining methylation density distributions stratified by block and non-block regions supported this finding (FIG. 10(*d*)). It is important to note that copy number variation does not drive the results presented here. First, the locations of copy number variation changes in cancer, observed in the data, were not consistent across subjects, in contrast to the consistent locations of methylation changes in the blocks identified above. Second, the methylation difference estimates provided by the statistical approach did not correlate with copy number values.

Global quantitative hypomethylation in cancer[8] is widely attributed to the presence of normally methylated repetitive elements[9] and may be relevant to colon cancer as UNE-1 element hypomethylation is associated with worse prognosis in colon cancer[10]. It was observed that in normal tissues, repetitive elements were more methylated than non-repetitive regions (76% vs. 66%). To determine whether such repetitive elements were responsible for the block hypomethylation, differences in methylation levels inside and outside repeat elements (see Methods), both inside and outside the blocks were compared. It was clear from this analysis that most of the global hypomethylation was due to hypomethylated blocks (FIG. 10(*e*)) and not to the presence of repetitive elements. As repetitive elements are slightly enriched in blocks (odds ratio 1.4), much of the apparent repeat-associated methylation may in fact be due to blocks. This result does not exclude repeat-associated hypomethylation, since not all repeats were mappable. However, 57% of L1 elements, 94% of L2 elements, 95% of MIR sequences, and 18% of Alu elements were covered by the data (FIG. 11) and did not show repeat-specific hypomethylation (FIG. 4). It is important to note it is possible that Alu sequences not covered by the data are somehow more hypomethylated than covered Alu sequences, and thus would contribute to global hypomethylation.

Figure 11:
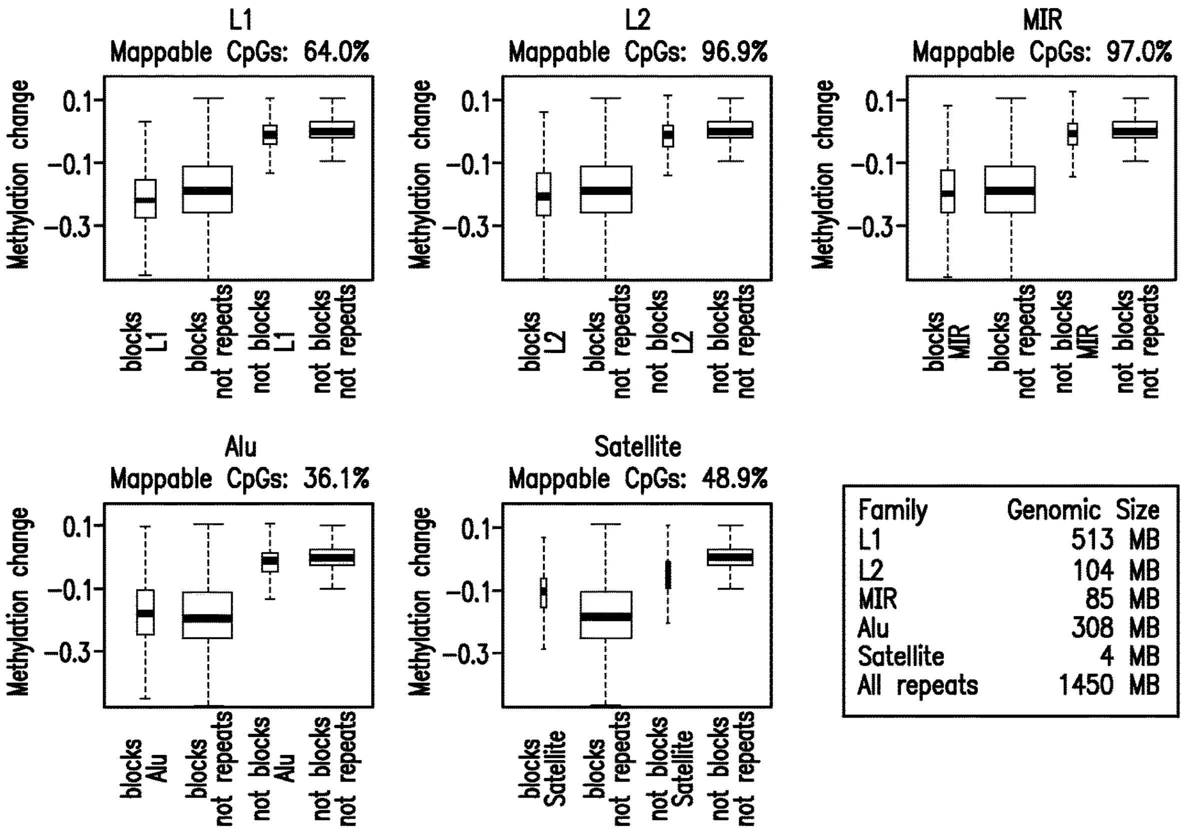
FIG. 11 is a series of graphical plots of the distribution of methylation differences between cancer and normal samples stratified by repeat family and inclusion in blocks.

FIG. 11 shows the methylation changes of selected repetitive DNA families. Distribution of methylation differences between cancer and normal samples stratified by repeat family and inclusion in blocks. CpGs outside all repetitive elements were used as controls. Each graph is the percentage of mappable CpGs in each repeat family.

Lister et al. recently performed bisulfite sequencing analysis of the H1 human embryonic stem cell line compared to the IMR90 fibroblast line, identifying large regions of the genome that are less methylated in fibroblast cells than ES cells, referred to as partially methylated domains (PMDs)[11]. The intermediate-methylation level regions identified above largely coincided with the PMDs, containing 85% of CpGs inside PMDs (odds ratio 6.5, $R<2\times10^{-16}$, Table 9). Large organized chromatin lysine (K) modifications, or LOCKs, genome-wide in normal mouse cells, that are associated with both constitutive and tissue-specific gene silencing were previously described that [12]. Therefore LOCKs in primary human cells (see Methods) mapped and whether the LOCKs also correspond to the hypomethylated blocks was determined. Remarkably, 89% of the LOCKs were contained within the blocks (odds ratio 6.8, $P<2\times10^{-16}$). LOCKs are also known to overlap with nuclear lamina-associated domains or LADs[12]. Approximately 83% of the LADs were also contained within the blocks, similar to the LOCKs (odds ratio 4.9, $P<2\times10^{-16}$). In addition, DNase I hypersensitive sites, a structural signal for regulatory regions[13] were enriched within 1 kb of block boundaries and small DMRs ($p<2\times10^{-16}$ for both). Thus the large hypomethylated blocks identified in cancer correspond to a genomic organization identified in normal cells by several complementary methods. Note that although the PMDs and the hypomethylated blocks largely overlap, significant differences in gene expression in cancer between non-overlapping blocks and PMDs is demonstrated later.

Furthermore, a relationship between the hypervariable CpGs across all cancer types, from the custom Illumina™ array described above, and the hypomethylated blocks identified by whole genome bisulfite sequencing was observed. Because the custom array was designed to contain both hypomethylated and hypermethylated CpG sites tested for enrichment of these hypervariable 157 CpG sites in hypomethylated blocks and in the small number of hypermethylated blocks. It was found that 63% of the hypomethylated hypervariable CpGs were indeed within hypomethylated blocks, and 37% of the hypermethylated hypervariable CpGs were within the hypermethylated blocks. To test for statistical significance, these percentages were compared to those found for the CpGs in the HumanMethylation27K array CpGs that did not vary differently in cancer and normal. These percentages were 13% and 1.5% for the hypomethylated and hypermethylated blocks, respectively, demonstrating high statistical significance for enrichment of hypervariably methylated CpGs in blocks ($p<2\times10^{-16}$; Table 10).

Small DMRs in Cancer Involve Loss of Stability of DNA Methylation Boundaries.

A statistical algorithm (see Methods) was then developed for detecting consistent DNA methylation changes in regions smaller than the blocks (≤5 kb). Critical for this algorithm was the analysis of biological replicates, as it was found that regions showing across-subject variability in normal samples would otherwise be easily confused with DMRs if only one cancer-normal pair were available (FIG.

5). Methylation measurements in these smaller regions exhibited good agreement with methylation measurements in the previous CHARM-based microarray analysis[4] (FIG. 12).

Figure 12:
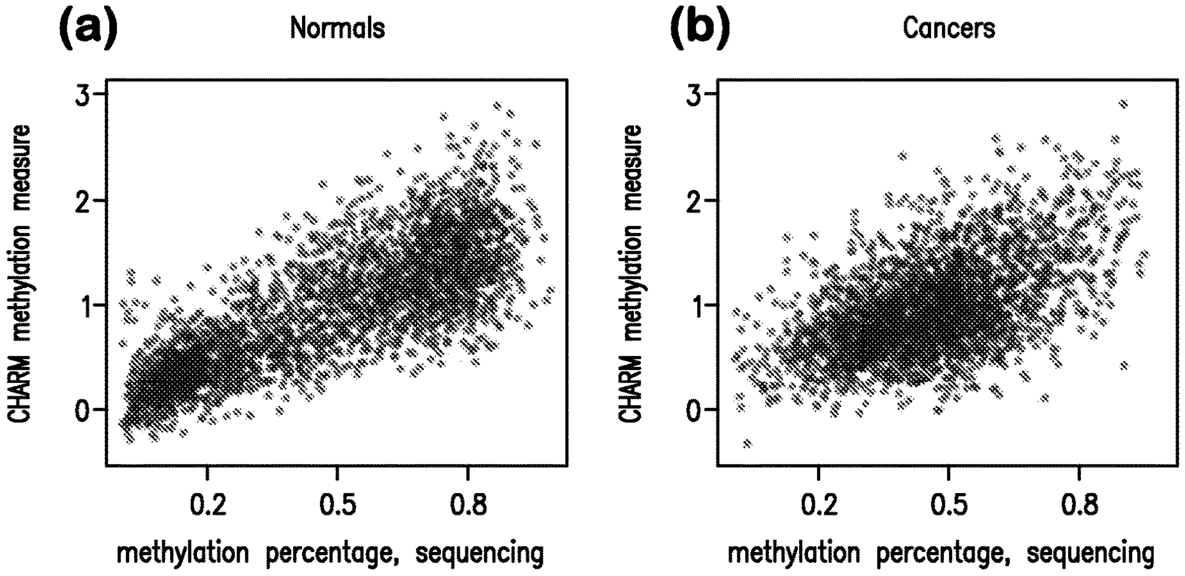
FIG. 12 is a series of graphical plots comparing CHARM microarray data and bisulfite sequencing for measuring methylation in (a) normal and (b) cancer samples.

FIG. 12 shows a comparison of CHARM microarray data and bisulfite sequencing for measuring methylation in (a) normal and (b) cancer samples. Average methylation level from previously published CHARM microarray data (Irizarry et al. (2009)) (y-axis) is plotted versus the average methylation obtained from high-frequency smoothed bisulfite sequencing data. Each point represents one of the cDMR regions originally identified in (Irizarry et al. (2009)). Note the high degree of correlation between CHARM and sequencing.

These are referred to as small DMRs to distinguish them from the large (>5 kb) differentially methylated blocks described above. The increased comprehensiveness of sequencing over CHARM and other published array-based analyses allowed us to detect many more small DMRs than previously reported, 5,810 hypermethylated and 4,315 hypomethylated small DMRs (partial listing of DMRs shown in Table 7). Previous findings[4] that hypermethylated cDMRs are enriched in CpG islands while hypomethylated cDMRs are enriched in CpG island shores were also confirmed (Table 8).

The increased comprehensiveness of sequencing also allowed us to quantify the different types of methylation changes at CpG Islands specifically (Table 11). It was found that: (1) 61% of islands were unmethylated in normal colon, and of these 17% showed a >10% absolute increase in methylation in cancer; (2) 20% of islands were found to be fully methylated in the normal colon, and of these 24% showed a >10% decrease in absolute methylation in cancer; and (3) 18% of islands show partial methylation in normal colon, and of these 17% showed increased and 36% decreased methylation in cancer. Of the 3907 hypermethylated small DMRs overlapping CpG Islands, 63.7% involved changes in either shift or loss boundary. Additionally, to determine if the same pattern held true for promoter, genic, intergenic, and repeat CpG islands analysis in Table 11 was stratified. It was found that in the normal samples promoter CpG Islands are largely unmethylated but that the findings above still hold. In contrast a balanced proportion of methylated and unmethylated (35% versus 26%) intergenic CpG islands with 45% hypomethylated in cancer was observed (Table 1).

When the architecture of the small DMRs was examined, the most common characteristic was a shift in one or both of the DNA methylation boundaries of a CpG island out of the island into the adjacent region (FIG. 7(*a*)) or into the interior of the island (FIG. 7(*b*)). Where the boundary shifts are observed, the same regions would appear on array-based data as hypermethylated islands, if the boundary is shifting into the island, or to hypomethylated shores, if the boundary is shifting outside the island.

The second most frequent category of small DMRs involved loss of methylation boundaries at CpG islands. For example, the architecture of many hypermethylated cDMRs were defined in normal samples by unmethylated regions (<10% methylation) surrounded by highly methylated regions (75-95% methylation), with boundaries ~100 bp wide. In cancer, these regions exhibited an approximately constant methylation level of approximately 40-60% throughout (Table 8, FIG. 7(*c*)). These regions with loss of methylation boundaries largely correspond to what are typically classified as hypermethylated islands in cancer.

Hypomethylated cDMRs were also found that arose de novo in highly methylated regions outside of blocks. In these cases, regions in which normal colon tissue was 75-95% methylated dropped to lower levels (20-40%) in cancer (FIG. 7(*d*)). These regions are referred to as novel hypomethylated DMRs, and they usually corresponded to CpG-rich regions that were not conventional islands (Table 8). In summary, in addition to the hypomethylated blocks, 10,125 small DMRs were found, 5,494 of which clearly fell in three categories: shifts of methylation boundaries, loss of methylation boundaries, and novel hypomethylation. Note that not all small DMRs followed a consistent pattern across all three sample pairs and therefore did not permit their classification (Table 8).

Methylation-Based Euclidean Distances Show Colon Adenomas Intermediate Between Normals and Cancers.

Figure 13:
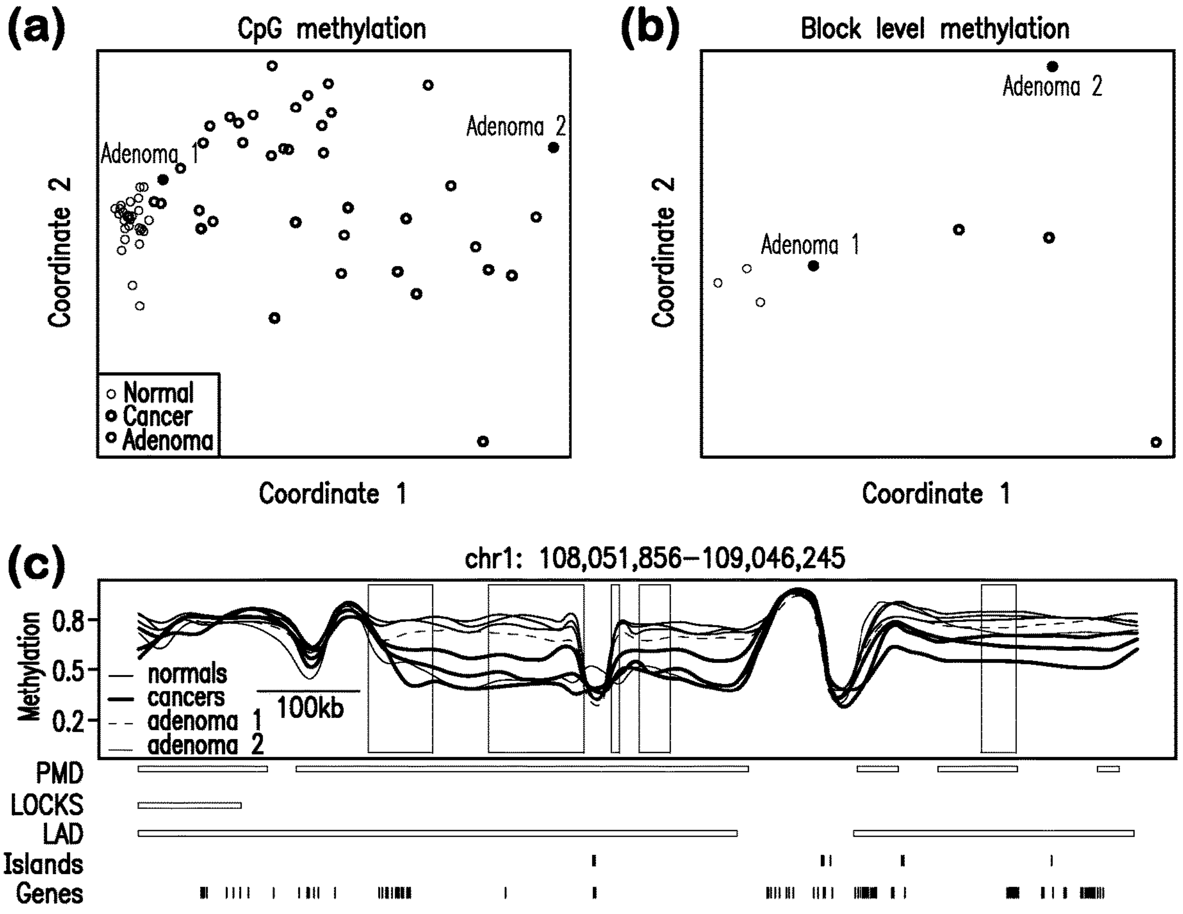
FIG. 13 is a series of graphical plots.

By performing a multidimensional scaling of the methylation values measured via the custom array in each colon sample, it was observed that the normal samples clustered tightly together in contrast to the dispersed methylation values measured in the cancer samples (FIG. 13(*a*)). This is consistent with the observed increase in methylation variability found in cancer that was described earlier. 30 colon adenomas were also analyzed for methylation on the custom array, and found that the adenomas were intermediate in both variability within samples and distance to the cluster of normal samples (FIG. 13(*a*)).

FIG. 13 shows that adenomas show intermediate methylation variability. (a) Multidimensional scaling of pairwise distances derived from methylation levels assayed on a custom array. Note that cancer samples (red) are largely far from the tight cluster of normal samples (blue), while adenoma samples (black) exhibit a range of distances: some are as close as other normal samples, others are as far as cancer samples, and many are at intermediate distances. (b) Multidimensional scaling of pairwise distances derived from average methylation values in blocks identified via bisulfite sequencing. Matching sequenced adenoma samples (labeled 1 and 2) appear in the same locations relative to the cluster of normal samples in both (a) and (b). (c) Methylation values for normal (blue), cancer (red) and two adenoma samples (black). Adenoma 1, which appeared closer to normal samples in the multidimensional scaling analysis (a), follows a similar methylation pattern to the normal samples. However, in some regions (shaded with pink) differences between Adenoma 1 and the normal samples are observed. Adenoma 2 shows a similar pattern to cancers.

Whole genome bisulfite sequencing was then performed on two of these adenomas, a premalignant colon adenoma with relatively small methylation-based distance to the normal colons and an adenoma with a large methylation-based distance to the normal colons, similar to the cancer samples. For each adenoma, the average methylation levels in each block and used these values to compute pairwise Euclidean distances were then computed. These results, based on measurements from the hypomethylated blocks, confirm the characteristic described above for the bead array data: genome-wide increased variability in cancers compared to normals with adenomas exhibiting intermediate values (FIG. 13).

Expression of Cell Cycle Genes Associated with Hypomethylated Shores in Cancer.

Whole genome methylation analysis has shown an inverse relationship between gene expression and methylation, especially at transcriptional start sites[14]. To study the relationship between methylation and gene expression in small DMRs, public microarray gene expression data was obtained from cancer and normal colon samples (see Methods Section) and compared to results from the sequencing data. Each gene represented in the expression microarrays was mapped to the closest DMR. A gene and DMR were considered associated if the DMR was within 2 kb of the transcription start site of the gene; 6,869 genes mapped to a DMR in this way. The expected inverse relationship between DNA methylation and gene expression was observed ($r=-0.27$, $p<2\times10^{-16}$, FIG. 14).

Figure 14:
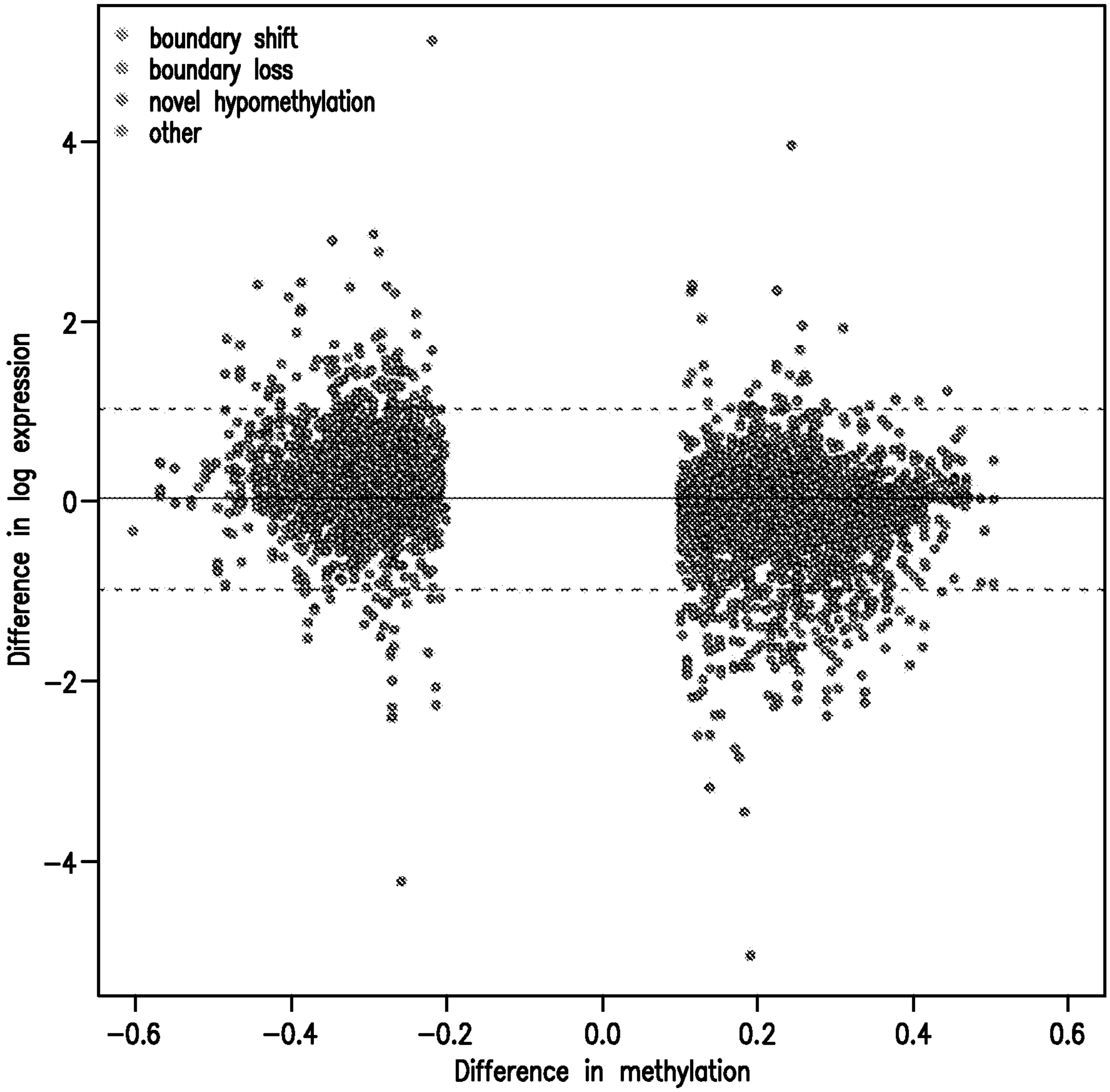
FIG. 14 is a graphical plot of average log gene expression values, obtained from GEO dataset GSE8671, plotted versus the average difference in methylation of a nearby small DMR.

FIG. 14 shows an inverse correlation of gene expression with methylation at small DMRs. Average log gene expression values, obtained from GEO dataset GSE8671, plotted versus the average difference in methylation of a nearby small DMR. A gene and a small DMR were considered associated if the DMR was within 2,000 bp of the transcription start site of the gene; 6,869 genes mapped to a DMR in this way. Different types of small DMRs are indicated by color, boundary shift (green), boundary loss (orange), novel hypomethylation (purple) and other (pink). The dashed lines represent a fold change of 2 in the gene expression comparison.

By examining the inverse relationship between methylation and gene expression for each category of small DMRs separately, the strongest relationship for hypomethylated shores due to methylation boundary shifts (Table 12) was noticed. Gene ontology enrichment analysis was performed for differentially expressed genes (FDR<0.05), comparing those associated with hypomethylated boundary shifts to the other categories. These categories (Table 13) were strongly enriched for cell-cycle related genes CEP55, CCNB1, CDCA2, PRC1, CDC2, FBXO5, AURKA, CDK1, CDKN3, CDK7, and CDC20B, among others (Table 14).

Increased Variation in Gene Expression in Hypomethylated Blocks and DMRs.

Given the increased DNA methylation variability in cancer found with the custom bead arrays (FIG. 6(*a*)-(*e*)), the methylation patterns in the blocks was examined and found increased variability in cancer as well. Specifically, across-subject methylation variability levels within the blocks in cancer and normal were compared, and found a striking similarity to the results found with the Illumina custom bead array as described above (FIG. 6(*a*)-(*e*) compared to FIG. 15).

Figure 15:
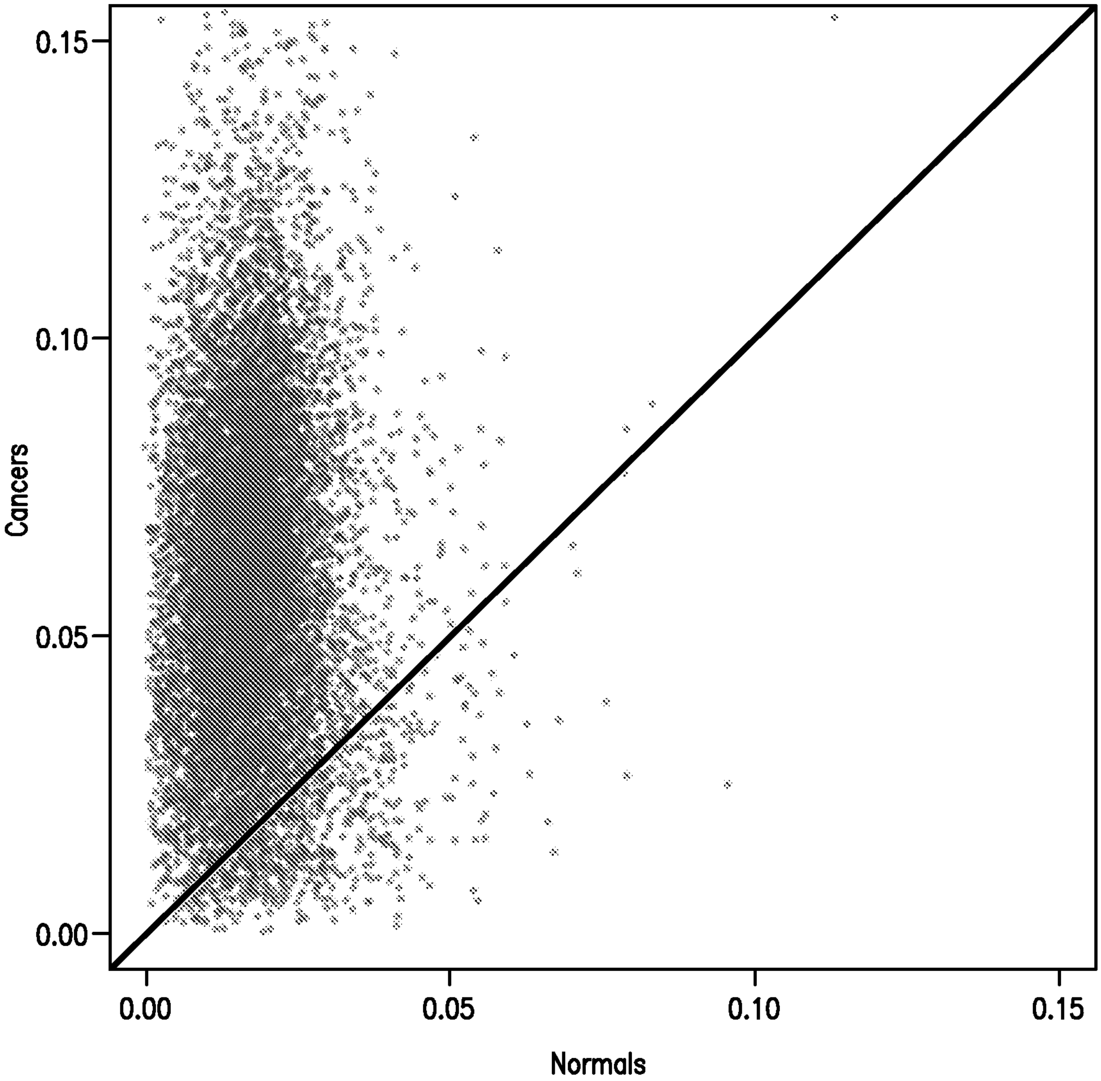
FIG. 15 is a graphical plot of across-sample standard deviation of methylation level for each block of normal versus cancer samples. Average methylation levels were computed for each block using high frequency smoothed SOLiD™ bisulfite sequencing data. The solid line is the identity line; CpGs above this line have greater variability in cancer.

FIG. 15 shows increased variation in methylation between normal and cancer samples in blocks. Across-sample standard deviation of methylation level for each block of normal versus cancer samples. Average methylation levels were computed for each block using high frequency smoothed SOLiD™ bisulfite sequencing data. The solid line is the identity line; CpGs above this line have greater variability in cancer. As in FIG. 6, the vast majority of blocks show an increased variation in cancer compared to normal samples.

To study the relationship to gene expression in colon cancer, public gene expression data was obtained from cancer and normal samples (see Methods Section). The expression data was processed with the gene expression barcode[16], a statistical algorithm that leverages information from thousands of publicly available datasets to standardized expression measurements in a way that expression values for silenced genes follow a standard normal distribution (mean 0 and standard deviation 1). Note that while expression values reported in the public databases cannot be used to call genes silenced or expressed, the barcode approach permits the construction of statistical tests for silencing. Genes in the blocks were generally silenced (80% genes silenced in all samples) both in normal and cancer samples. Of the genes consistently transcribed in normal tissue, albeit at low levels, 36% are silenced in blocks in cancers, compared to 15% expected by chance. This is consistent with other reports in the literature, e.g. Frigola et al[17].

Figure 16:
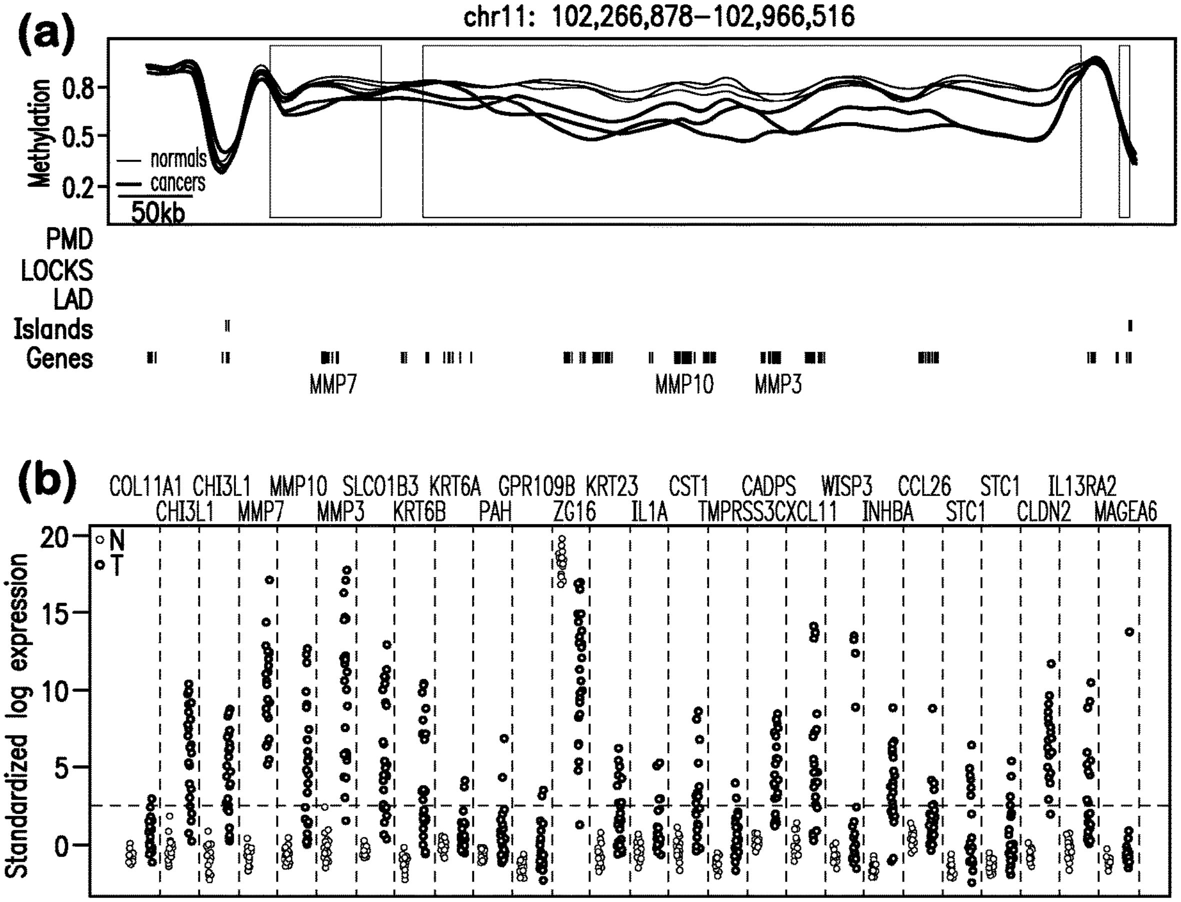
FIG. 16 is a series of graphical plots.
Figure 17:
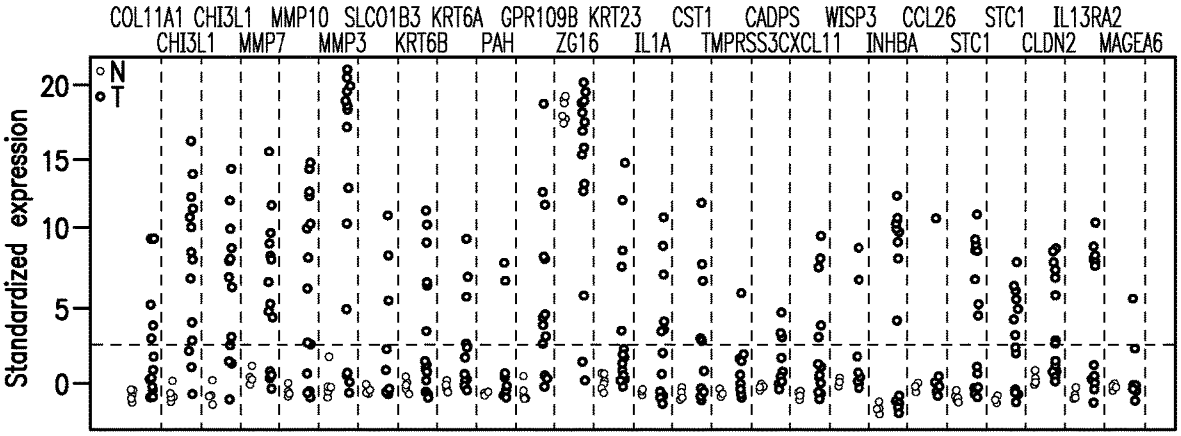
FIG. 17 is a graphical plot of standardized log expression values for 26 hypervariable genes in cancer located within hypomethylated block regions.

More strikingly than subtle differences in gene silencing, substantial enrichment of genes exhibiting increased expression variability in cancer compared to normal samples in the hypomethylated blocks was found. First, the possibility that this observed increased variability was due to tissue-specific genes being over-represented in blocks and the potential high cellular heterogeneity of cancer by noting the lack of association between tissue-specific genes and cancer variability outside of the blocks was ruled out. A clear association between increased variability in expression of a gene and its location within a hypomethylated block was then noticed. For example, 26 of the 50 genes exhibiting the largest increase in expression variability were inside the blocks; 52% compared to the 17% expected by chance ($p=3\times10^{-9}$); and there is significant enrichment at P=0.01 up to as many as 1,000 genes of the 4,940 genes on the array and within the blocks. Expression levels for 25 of these 26 most hypervariable genes exhibited an interesting pattern: while never expressed in normal samples, they exhibited stochastic expression in cancer (FIGS. 16 and 17). For example the genes MMP3, MMP7, MMP10, SIM2, CHI3L1, STC1, and WISP (described in the Discussion) were expressed in 96%, 100%, 67%, 8%, 79%, 50%, and 17% of the cancer samples, respectively, but never expressed in normal samples (Table 14).

FIG. 16 shows high variability of gene expression associated with blocks. (a) An example of hypervariably expressed genes contained within a block, MMP7, MMP10, and MMP3 (red). Methylation values for cancer samples (red) and normal samples (blue) with hypomethylated block locations highlighted (pink shading) are plotted against genomic location. Grey bars are as in FIG. 8. (b) Standardized log expression values for 26 hypervariable genes in cancer located within hypomethylated block regions (normal samples in blue, cancer samples in red). Standardization was performed using the gene expression barcode. Genes with standardized expression values below 2.54, or the 99.5th percentile of a normal distribution (horizontal dashed line) are determined to be silenced by the barcode method[15]. Vertical dashed lines separate the values for the different genes. Note there is consistent expression silencing in normal samples compared to hypervariable expression in cancer samples.

FIG. 17 shows hypervariable gene expression in cancer in hypomethylated blocks. Standardized (using gene expression barcode) expression values for the 26 of the 50 most hypervariable genes in cancer which are within hypomethylated block regions. Genes with standardized expression values below 2.54 (dotted horizontal line) are determined to be silenced by the barcode method (Zilliox and Irizarry, 2007). Expression values for each gene, separated by vertical dotted lines, from dataset GSE4183 are plotted for normal (blue) and cancer (red) samples. Note there is consistent expression silencing in normal samples compared to variable expression in cancer samples.

Functional Differences Between Hypomethylated Blocks and PMDs.

As noted above, the hypomethylated blocks observed, substantially overlapped the PMDs previously reported in a fibroblast cell line by Lister et al.[11]. The genomic regions that did not overlap between blocks and PMDs were therefore examined, in order to identify potential functional differences between them. They were grouped into two sets:

1) regions within the hypomethylated blocks not in the PMDs (B+P−) and 2) the counterpart regions within the PMDs but not in the hypomethylated blocks (B−P+). To examine the expression of genes within these regions, public microarray gene expression data from fibroblast samples was obtained (see Methods Section). As expected, the genes in the fibroblast PMDs were relatively silenced in the fibroblast samples; 79% of genes were silenced in all samples within the PMD compared to 49% outside, $p<2\times10^{-16}$). Furthermore, genes that were silenced in fibroblast samples and consistently expressed in colon were enriched in the B−P+ regions (odds ratio of 3.2, $p<2\times10^{-16}$), while genes consistently silenced in colon and consistently expressed in fibroblast samples were enriched in the B+P− regions (odds ratio 2.8, p=0.0004). B+P− and B−P+ genes were then examined with respect to expression variability in cancer, focusing on the 50 hypervariable genes described above. These genes were markedly enriched in the B+P− regions (p=0.00013), yet showed no enrichment in the B−P+ regions. These results suggest that hypervariable gene expression in colon cancer is related specifically to their presence in hypomethylated blocks.

Discussion

In summary, it is shown that colon cancer cDMRs are generally involved in the common solid tumors of adulthood, lung, breast, thyroid, and colon cancer, and the most common solid tumor of childhood, Wilms tumor, with tight clustering of methylation levels in normal tissues, and marked stochastic variation in cancers. Current efforts to exploit DNA methylation for cancer screening are focused on identifying a cancer-specific profile[18], but the data shown here suggest that epigenetic variability per se may be pathognomonic for cancer. Future efforts might be directed at defining the cancer epigenome as the departure from a narrowly defined normal profile rather identifying a specific narrowly defined cancer profile.

Surprisingly, two-thirds of all methylation changes in colon cancer involve hypomethylation of large blocks, with consistent locations across samples, comprising more than half of the genome. The most variably expressed genes in cancer are extraordinarily enriched in the blocks, and they involve genes associated with tumor heterogeneity and progression, including three matrix metalloproteinase genes, MMP3, MMP7, and MMP10[19], and a fourth, SIM2, which acts through metalloproteinases to promote tumor invasion[20]. Another, STC1, helps mediate the Warburg effect of reprogramming tumor metabolism[21]. CHI3L1 encodes a secreted glycoprotein associated with inflammatory responses and poor prognosis in multiple tumor types including the colon[22]. WISP genes are targets of Wnt-1 and are thought to contribute to tissue invasion in breast and colon cancer[23]. Gene ontology enrichment analysis[15] was performed for genes associated with hypervariable expression in blocks (FDR<0.05), which showed substantial enrichment for categories including extracellular matrix remodeling genes (Table 13). One cautionary note raised by these findings is that treatment of cancer patients with nonspecific DNA methylation inhibitors could have unintended consequences in the activation of tumor-promoting genes in hypomethylated blocks. It is also important to note that previous studies[24,25] have shown large-region hypermethylation or no regional methylation change, although the present study is based on whole-genome bisulfite sequencing.

The small DMRs, which while representing a relatively small fraction of the genome (0.3%), are numerous (10,125), and frequently involve loss of boundaries of DNA methylation at the edge of CpG islands, shifting of the DNA methylation boundaries, or the creation of novel hypomethylated regions in CG-dense regions that are not canonical islands. These data underscore the importance of hypomethylated CpG island shores in cancer. In particular, the large number of shores associated with hypomethylation and gene overexpression in cancer are enriched for cell cycle related genes, suggesting a role in the unregulated growth that characterizes cancer.

A model it proposed that might help to explain the relationship between tissue-specific DMRs and the sites of extreme methylation variability in cancer. Pluripotency itself might require a certain degree of stochastic gene expression at some loci, allowing for differentiation along alternative pathways in response to external stimuli, or even in part randomly. The epigenome could collaborate by changing its physical configuration to relax the stringency of epigenetic marks away from extremes near 100% and 0%, since variance increases away from the extremes. One potential way the epigenome may do this is by reducing the methylation of large blocks in cancer, which overlap with known functionally important domains, LOCKs and LADs, and thus could involve a change in the chromatin packing density or proximity to the nuclear lamina. Similarly, subtle shifts in DNA methylation boundaries near CpG islands may drive chromatin organization and normal tissue-specific and aberrant cancer-specific gene expression. Consistent with this idea, a shift in methylation boundary was shown to differentially regulate genes escaping X-inactivation[26]. It will therefore be important in the future to relate the data presented here to large-scale chromatin organization, and to normal developmental changes in DNA methylation and chromatin, as well as to expand future epigenetic investigations on the boundaries of blocks and CpG island shores.

It is not argued that epigenetic changes in cancer arise independently of genetic changes; both are clearly important and they are highly inter-related. However, the increased methylation and expression variability in each cancer type, compared to the normal samples, is consistent with the potential selective value of increased epigenetic plasticity in a varying environment first suggested for evolution but equally applicable to the strong but variable selective forces under which a cancer grows, such as varying oxygen tension or metastasis to a distant site[27]. Thus, increased epigenetic heterogeneity in cancer at cDMRs (which are shown also as tDMRs) could underlie the ability of cancer cells to adapt rapidly to changing environments, such as increased oxygen with neovascularization, then decreased oxygen with necrosis; or metastasis to a new intercellular milieu.

REFERENCES

1. Jones, P. A. & Baylin, S. B. The fundamental role of epigenetic events in cancer. *Nat Rev Genet* 3, 415-28 (2002).
2. Feinberg, A. P. & Tycko, B. The history of cancer epigenetics. *Nat Rev Cancer* 4, 143-53 (2004).
3. Esteller, M. Epigenetics in cancer. *N Engl J Med* 358, 1148-59 (2008).
4. Irizarry, R. A. et al. The human colon cancer methylome shows similar hypo- and hypermethylation at conserved tissue-specific CpG island shores. *Nat Genet* 41, 178-86 (2009).
5. Doi, A. et al. Differential methylation of tissue- and cancer-specific CpG island shores distinguishes human induced pluripotent stem cells, embryonic stem cells and fibroblasts. *Nat Genet* 41, 1350-3 (2009).

6. Irizarry, R. A. et al. Comprehensive high-throughput arrays for relative methylation (CHARM). *Genome Res* 18, 780-90 (2008).
7. Bibikova, M. et al. High-throughput DNA methylation profiling using universal bead arrays. *Genome Res* 16, 383-93 (2006).
8. Feinberg, A. P., Gehrke, C. W., Kuo, K. C. & Ehrlich, M. Reduced genomic 5-methylcytosine content in human colonic neoplasia. *Cancer Res* 48, 1159-61 (1988).
9. Ehrlich, M. DNA methylation in cancer: too much, but also too little. *Oncogene* 21, 5400-13 (2002).
10. Ogino, S. et al. A cohort study of tumoral LINE-1 hypomethylation and prognosis in colon cancer. *J Natl Cancer Inst* 100, 1734-8 (2008).
11. Lister, R. et al. Human DNA methylomes at base resolution show widespread epigenomic differences. *Nature* 462, 315-22 (2009).
12. Wen, B., Wu, H., Shinkai, Y., Irizarry, R. A. & Feinberg, A. P. Large histone H3 lysine 9 dimethylated chromatin blocks distinguish differentiated from embryonic stem cells. *Nat Genet* 41, 246-50 (2009).
13. Hesselberth, J. R. et al. Global mapping of protein-DNA interactions in vivo by digital genomic footprinting. *Nat Methods* 6, 283-9 (2009).
14. Li, Y. et al. The DNA Methylome of Human Peripheral Blood Mononuclear Cells. *PLoS Biol* 8, e1000533 (2010).
15. Falcon, S. & Gentleman, R. Using GOstats to test gene lists for GO term association. *Bioinformatics* 23, 257-8 (2007).
16. Zilliox, M. J. & Irizarry, R. A. A gene expression bar code for microarray data. *Nat Methods* 4, 911-3 (2007).
17. Frigola, J. et al. Epigenetic remodeling in colorectal cancer results in coordinate gene suppression across an entire chromosome band. *Nat Genet* 38, 540-9 (2006).
18. Gal-Yam, E. N., Saito, Y., Egger, G. & Jones, P. A. Cancer epigenetics: modifications, screening, and therapy. *Annu Rev Med* 59, 267-80 (2008).
19. Yu, A. E., Hewitt, R. E., Connor, E. W. & Stetler-Stevenson, W. G. Matrix metalloproteinases. Novel targets for directed cancer therapy. *Drugs Aging* 11, 229-44 (1997).
20. Aleman, M. J. et al. Inhibition of Single Minded 2 gene expression mediates tumor-selective apoptosis and differentiation in human colon cancer cells. *Proc Natl Acad Sci USA* 102, 12765-70 (2005).
21. Yeung, H. Y. et al. Hypoxia-inducible factor-1-mediated activation of stanniocalcin-1 in human cancer cells. *Endocrinology* 146, 4951-60 (2005).
22. Eurich, K., Segawa, M., Toei-Shimizu, S. & Mizoguchi, E. Potential role of chitinase 3-like-1 in inflammation-associated carcinogenic changes of epithelial cells. *World J Gastroenterol* 15, 5249-59 (2009).
23. Fischer, H. et al. COL11A1 in FAP polyps and in sporadic colorectal tumors. *BMC Cancer* 1, 17 (2001).
24. Clark, S. J. Action at a distance: epigenetic silencing of large chromosomal regions in carcinogenesis. *Human Molecular Genetics* 16, R88-R95 (2007).
25. Feber, A. et al. Comparative methylome analysis of benign and malignant peripheral nerve sheath tumours. *Genome Research* (2011).
26. Goto, Y. & Kimura, H. Inactive X chromosome-specific histone H3 modifications and CpG hypomethylation flank a chromatin boundary between an X-inactivated and an escape gene. *Nucleic Acids Res* 37, 7416-28 (2009).
27. Feinberg, A. & Irizarry, R. Stochastic epigenetic variation as a driving force of development, evolutionary adaptation, and disease. *Proceedings of the National Academy of Sciences* 107, 1757 (2010).
28. Bolstad, B. M., Irizarry, R. A., Astrand, M. & Speed, T. P. A comparison of normalization methods for high density oligonucleotide array data based on variance and bias. *Bioinformatics* 19, 185-93 (2003).
29. Leek, J. T. et al. Tackling the widespread and critical impact of batch effects in high-throughput data. *Nat Rev Genet* 11, 733-9 (2010).
30. Bormann Chung, C. A. et al. Whole methylome analysis by ultra-deep sequencing using two-base encoding. *PLoS One* 5, e9320 (2010).
31. Xi, Y. & Li, W. BSMAP: whole genome bisulfite sequence MAPping program. *BMC Bioinformatics* 10, 232 (2009).
32. Deng, J. et al. Targeted bisulfite sequencing reveals changes in DNA methylation associated with nuclear reprogramming. *Nat Biotechnol* 27, 353-60 (2009).
33. Loader, C. *Local regression and likelihood*, (Springer Verlag, 1999).
34. Eckhardt, F. et al. DNA methylation profiling of human chromosomes 6, 20 and 22. *Nat Genet* 38, 1378-85 (2006).
35. Sabates-Bellver, J. et al. Transcriptome profile of human colorectal adenomas. *Mol Cancer Res* 5, 1263-75 (2007).
36. Gyorffy, B., Molnar, B., Lage, H., Szallasi, Z. & Eklund, A. C. Evaluation of microarray preprocessing algorithms based on concordance with RT-PCR in clinical samples. *PLoS One* 4, e5645 (2009).
37. Galamb, O. et al. Reversal of gene expression changes in the colorectal normal-adenoma pathway by NS398 selective COX2 inhibitor. *Br J Cancer* 102, 765-73 (2010).
38. Smith, J. C., Boone, B. E., Opalenik, S. R., Williams, S. M. & Russell, S. B. Gene profiling of keloid fibroblasts shows altered expression in multiple fibrosis-associated pathways. *J Invest Dermatol* 128, 1298-310 (2008).
39. Chen, Y. et al. Developing and applying a gene functional association network for anti-angiogenic kinase inhibitor activity assessment in an angiogenesis co-culture model. *BMC Genomics* 9, 264 (2008).
40. Duarte, T. L., Cooke, M. S. & Jones, G. D. Gene expression profiling reveals new protective roles for vitamin C in human skin cells. *Free Radic Biol Med* 46, 78-87 (2009).

Tables

The following is a listing of the Tables which form part of this specification.

TABLE 1

Sequencing and alignment results for the 7.79 billion bisulfite reads obtained from 8 runs (16 flowcells) of a SOLiD ™ 3+ instrument.

| | Reads | Unique | Unaligned | Non-unique | Uniquely aligned to A phagze | Conversion percent (A estimate) |
|---|---|---|---|---|---|---|
| Normal 1 Flowcell 1 | 485,990,920 | 183,844,653 | 226,160,599 | 75,985,667 | 6,762,031 | 99.7789 |
| Normal 1 Flowcell 2 | 491,108,959 | 180,074,869 | 235,598,979 | 75,435,110 | 6,974,109 | 99.7807 |
| Tumor 1 Flowcell 1 | 495,809,693 | 185,828,257 | 233,836,993 | 76,144,442 | 8,526,067 | 99.7456 |
| Tumor 1 Flowcell 2 | 482,952,465 | 178,456,624 | 230,494,869 | 74,000,971 | 8,122,750 | 99.7472 |
| Normal 2 Flowcell 1 | 496,397,317 | 180,791,619 | 237,818,636 | 77,787,061 | 7,270,350 | 99.7646 |
| Normal 2 Flowcell 2 | 503,561,286 | 182,437,294 | 242,263,685 | 78,860,306 | 7,538,526 | 99.7657 |
| Tumor 2 Flowcell 1 | 497,625,604 | 187,406,059 | 232,909,571 | 77,309,973 | 8,251,881 | 99.7804 |
| Tumor 2 Flowcell 2 | 494,805,108 | 184,876,404 | 233,935,851 | 75,992,852 | 8,261,281 | 99.7860 |
| Normal 3 Flowcell 1 | 489,558,995 | 168,584,119 | 251,409,912 | 69,564,963 | 8,817,079 | 99.7953 |
| Normal 3 Flowcell 2 | 495,129,950 | 185,140,655 | 234,292,582 | 75,696,712 | 9,550,241 | 99.7937 |
| Tumor 3 Flowcell 1 | 491,209,978 | 170,520,921 | 249,977,651 | 70,711,405 | 7,104,618 | 99.7919 |
| Tumor 3 Flowcell 2 | 475,735,953 | 179,289,913 | 222,767,391 | 73,678,648 | 7,295,636 | 99.7930 |
| Adenoma 1 Flowcell 1 | 477,819,340 | 153,546,992 | 259,594,989 | 64,677,358 | 3,457,741 | 99.7684 |
| Adenoma 1 Flowcell 2 | 474,211,342 | 149,570,667 | 260,639,196 | 64,001,478 | 3,337,933 | 99.7678 |
| Adenoma 2 Flowcell 1 | 479,069,565 | 165,738,601 | 242,575,131 | 70,755,832 | 12,991,935 | 99.7021 |
| Adenoma 2 Flowcell 2 | 458,864,972 | 150,866,083 | 244,060,513 | 63,938,375 | 10,969,639 | 99.7055 |
| Total | 7,789,851,447 | 2,786,973,730 | 3,838,336,548 | 1,164,541,153 | 125,231,817 | N/A |
| Average | 486,865,715 | 174,185,858 | 239,896,034 | 72,783,822 | 7,826,989 | 99.7667 |

TABLE 2

Methylation evidence results for the 831 million bisulfite reads that aligned uniquely to the GRCh37 human genome assembly and overlapped at least one CpG cytosine.

| | Reads providing human CpG evidence | Raw pieces of human CpG evidence | Filtered pieces of human CpG evidence | Filtered evidence Indicating presence of methylation | Filtered evidence indicating lack of methylation | % CpGs covered by £1 piece of filtered evidence |
|---|---|---|---|---|---|---|
| Normal 1 Flowcell 1 | 54,178,356 | 74,924,756 | 68,839,724 | 48,253,347 | 20,586,377 | 65.158% |
| Normal 1 Flowcell 2 | 53,689,203 | 74,623,785 | 68,199,772 | 47,773,815 | 20,425,957 | 65.045% |
| Tumor 1 Flowcell 1 | 55,834,653 | 77,831,608 | 71,498,083 | 45,243,596 | 26,254,487 | 65.103% |
| Tumor 1 Flowcell 2 | 53,902,278 | 75,253,470 | 68,697,400 | 43,321,299 | 25,376,101 | 64.479% |
| Normal 2 Flowcell 1 | 54,492,135 | 76,436,939 | 70,022,135 | 49,881,756 | 20,140,379 | 65.797% |
| Normal 2 Flowcell 2 | 55,012,691 | 77,239,693 | 70,641,796 | 50,296,004 | 20,345,792 | 65.978% |
| Tumor 2 Flowcell 1 | 55,815,773 | 77,542,380 | 71,153,086 | 42,104,541 | 29,048,545 | 65.526% |
| Tumor 2 Flowcell 2 | 54,867,691 | 76,121,856 | 69,486,614 | 40,787,828 | 28,698,786 | 65.271% |
| Normal 3 Flowcell 1 | 50,056,580 | 70,114,583 | 63,620,050 | 43,447,381 | 20,172,669 | 64.004% |
| Normal 3 Flowcell 2 | 54,385,230 | 75,777,367 | 69,162,172 | 47,580,371 | 21,581,801 | 65.333% |
| Tumor 3 Flowcell 1 | 51,426,265 | 71,942,006 | 65,509,795 | 35,741,629 | 29,768,166 | 63.954% |
| Tumor 3 Flowcell 2 | 53,527,518 | 74,427,549 | 68,200,974 | 37,298,457 | 30,902,517 | 64.356% |
| Adenoma 1 Flowcell 1 | 47,841,436 | 67,596,302 | 61,069,078 | 40,572,495 | 20,496,583 | 63.580% |
| Adenoma 1 Flowcell 2 | 46,522,581 | 65,753,563 | 59,413,620 | 39,519,156 | 19,894,464 | 63.125% |
| Adenoma 2 Flowcell 1 | 46,102,652 | 63,325,754 | 58,045,004 | 33,949,586 | 24,095,418 | 61.767% |
| Adenoma 2 Flowcell 2 | 43,224,022 | 59,918,936 | 54,862,907 | 32,006,566 | 22,856,341 | 60.444% |
| Total | 830,879,064 | 1,158,830,547 | 1,058,422,210 | 677,777,827 | 380,644,383 | N/A |
| Average | 51,929,942 | 72,426,909 | 66,151,388 | 42,361,114 | 23,790,274 | 64.308% |

TABLE 3

Coverage per sample in terms of fraction of CpGs in the GRCh37 human genome assembly covered by at least one through ten pieces of filtered evidence.

| | Percent of CpGs in human genome covered with filtered evidence at depth > threshold | | | | | | | |
|---|---|---|---|---|---|---|---|---|
| Threshold | Normal 1 | Tumor 1 | Normal 2 | Tumor 2 | Normal 3 | Tumor 3 | Adenoma 1 | Adenoma 2 |
| 1 | 73.395% | 73.279% | 73.934% | 73.636% | 73.555% | 72.994% | 73.062% | 71.459% |
| 2 | 64.399% | 63.918% | 65.169% | 64.567% | 63.869% | 63.247% | 62.381% | 60.906% |
| 3 | 56.813% | 56.119% | 57.880% | 57.091% | 55.734% | 55.099% | 53.244% | 51.613% |
| 4 | 49.137% | 48.461% | 50.469% | 49.640% | 47.684% | 47.116% | 44.372% | 42.406% |
| 5 | 41.348% | 40.917% | 42.832% | 42.148% | 39.706% | 39.335% | 35.876% | 33.569% |
| 6 | 33.796% | 33.753% | 35.286% | 34.872% | 32.115% | 32.000% | 28.103% | 25.573% |
| 7 | 26.804% | 27.219% | 28.188% | 28.088% | 25.232% | 25.391% | 21.338% | 18.770% |

TABLE 3-continued

Coverage per sample in terms of fraction of CpGs in the GRCh37 human genome assembly covered by at least one through ten pieces of filtered evidence.

| | Percent of CpGs in human genome covered with filtered evidence at depth > threshold | | | | | | | |
|---|---|---|---|---|---|---|---|---|
| Threshold | Normal 1 | Tumor 1 | Normal 2 | Tumor 2 | Normal 3 | Tumor 3 | Adenoma 1 | Adenoma 2 |
| 8 | 20.635% | 21.496% | 21.847% | 22.042% | 19.270% | 19.674% | 15.731% | 13.296% |
| 9 | 15.442% | 16.658% | 16.446% | 16.862% | 14.321% | 14.917% | 11.282% | 9.114% |
| 10 | 11.254% | 12.693% | 12.040% | 12.596% | 10.369% | 11.087% | 7.892% | 6.061% |

TABLE 4

Per-sample total coverage both genome-wide and for CpG cytosines.

| | Total genome coverage after filtering | Total # Cs, Ts aligning to CpG cytosines after filtering | Average coverage of mappable CpG cytosines |
|---|---|---|---|
| Normal 1 | 13,213,005,428 | 116,394,219 | 5.578 |
| Tumor 1 | 13,106,826,609 | 118,994,714 | 5.703 |
| Normal 2 | 13,137,358,383 | 119,303,310 | 5.717 |
| Tumor 2 | 13,411,947,895 | 119,273,248 | 5.716 |
| Normal 3 | 12,592,027,592 | 113,220,232 | 5.426 |
| Tumor 3 | 12,593,520,085 | 113,929,959 | 5.460 |
| Adenoma 1 | 10,965,839,892 | 102,341,491 | 4.905 |
| Adenoma 2 | 11,017,476,026 | 95,652,482 | 4.584 |

TABLE 5

Gene ontology enrichment analysis of differentially expressed genes associated with hypomethylated boundary shifts.

| Gene ontology term | Expected count | Count | Size | Odds ratio | P-value | Q-value |
|---|---|---|---|---|---|---|
| Mitotic cell cycle | 11.6 | 31 | 185 | 3.1 | 3.8 × 10''' | 0.00036 |
| Cell cycle process | 18.7 | 42 | 297 | 2.6 | 5.4 × 10''' | 0.00036 |
| Mitosis | 9.9 | 25 | 157 | 2.9 | 1.5 × 10* | 0.006 |
| Positive regulation of ubiquitin-protein ligase activity during mitotic cell cycle | 3.9 | 14 | 61 | 4.5 | 2.0 × 10"$^5$ | 0.0071 |
| Organelle fission | 13.7 | 30 | 216 | 2.5 | 3.6 × 10"$^6$ | 0.0097 |

TABLE 6

Partial listing of all blocks.

| Chromosome | Start | End | Length (bp) | Number of Covered CpGs | Mean Difference in Block (Normal to Cancer) | Mean Normal Methylation in Block | Direction of Methylation Change | Block Identifier # |
|---|---|---|---|---|---|---|---|---|
| chr5 | 21489059 | 31186536 | 9697478 | 37675 | −0.234268134 | 0.734330205 | hypo | Block: 4543 |
| chr11 | 36593009 | 43333410 | 6740402 | 25948 | −0.24463665 | 0.72048786 | hypo | Block: 9693 |
| chr13 | 53781664 | 57714588 | 3932925 | 13954 | −0.305545997 | 0.711763715 | hypo | Block: 11148 |
| chr21 | 22381968 | 26930794 | 4548827 | 18960 | −0.2505675 | 0.756884964 | hypo | Block: 15290 |
| chr2 | 80539743 | 84644887 | 4105145 | 16332 | −0.267703723 | 0.759607379 | hypo | Block: 1907 |
| chr13 | 80942533 | 84441763 | 3499231 | 12625 | −0.298381103 | 0.746321237 | hypo | Block: 11199 |
| chr13 | 64409368 | 67804582 | 3395215 | 13021 | −0.307076261 | 0.738041828 | hypo | Block: 11158 |
| chr4 | 31837743 | 36042235 | 4204493 | 15647 | −0.241796633 | 0.745280322 | hypo | Block: 3920 |
| chr4 | 62080875 | 66522493 | 4441619 | 15678 | −0.215135077 | 0.727287561 | hypo | Block: 4022 |
| chr13 | 88335260 | 91331372 | 2996113 | 11498 | −0.317647884 | 0.746888186 | hypo | Block: 11205 |
| chr14 | 82002535 | 85986581 | 3984047 | 16771 | −0.237315369 | 0.732144115 | hypo | Block: 11690 |
| chr1 | 186650123 | 190431798 | 3781676 | 13581 | −0.239010595 | 0.730909343 | hypo | Block: 1093 |
| chr2 | 139542344 | 142876253 | 3333910 | 13078 | −0.271062506 | 0.730863885 | hypo | Block: 2253 |
| chr13 | 67805561 | 70681708 | 2876148 | 10486 | −0.312824914 | 0.741708123 | hypo | Block: 11159 |
| chr6 | 101857270 | 105211359 | 3354090 | 11778 | −0.265353657 | 0.718599696 | hypo | Block: 5932 |
| chr8 | 110991321 | 114435951 | 3444631 | 12032 | −0.249961594 | 0.726061396 | hypo | Block: 7777 |
| chr4 | 27027813 | 30714427 | 3686615 | 15174 | −0.233244635 | 0.732405787 | hypo | Block: 3918 |
| chr6 | 64781914 | 68135922 | 3354009 | 11651 | −0.254436718 | 0.742306268 | hypo | Block: 5815 |
| chr13 | 103537996 | 106379735 | 2841740 | 14762 | −0.299969882 | 0.75065476 | hypo | Block: 11280 |
| chr4 | 135122912 | 139025858 | 3902947 | 14280 | −0.216279595 | 0.731078219 | hypo | Block: 4261 |

TABLE 6-continued

Partial listing of all blocks.

| Chromosome | Start | End | Length (bp) | Number of Covered CpGs | Mean Difference in Block (Normal to Cancer) | Mean Normal Methylation in Block | Direction of Methylation Change | Block Identifier # |
|---|---|---|---|---|---|---|---|---|
| chr8 | 103515636 | 107003349 | 3487714 | 13016 | −0.241256516 | 0.770620255 | hypo | Block: 4846 |
| chr2 | 145284315 | 148597827 | 3313513 | 13133 | −0.250369967 | 0.768882073 | hypo | Block: 2263 |
| chr5 | 162945693 | 166400217 | 3454525 | 15949 | −0.236434257 | 0.743274302 | hypo | Block: 5162 |
| chr11 | 79160629 | 82433198 | 3272570 | 13761 | −0.249348956 | 0.741907936 | hypo | Block: 9922 |
| chr16 | 58772443 | 62060450 | 3288008 | 13991 | −0.246684267 | 0.718572681 | hypo | Block: 12754 |
| chr7 | 51385467 | 54287005 | 2901539 | 13679 | −0.275190877 | 0.748760802 | hypo | Block: 6651 |
| chr16 | 62080456 | 65149968 | 3069513 | 13481 | −0.256640701 | 0.733695903 | hypo | Block: 12756 |
| chr9 | 29226108 | 32382722 | 3156615 | 11467 | −0.249093612 | 0.731939294 | hypo | Block: 8015 |
| chr3 | 101813882 | 105080396 | 3266515 | 12243 | −0.240181749 | 0.731165345 | hypo | Block: 3257 |
| chr1 | 104303555 | 107593269 | 3289715 | 11541 | −0.23823305 | 0.72189185 | hypo | Block: 707 |
| chr3 | 81815567 | 84995827 | 3180261 | 12053 | −0.245526983 | 0.722332842 | hypo | Block: 3219 |
| chr6 | 91326051 | 94116126 | 2790076 | 10822 | −0.268202124 | 0.718064341 | hypo | Block: 5907 |
| chr1 | 79126358 | 82259961 | 3133604 | 12403 | −0.237925127 | 0.743040164 | hypo | Block: 604 |
| chr2 | 50583698 | 53900730 | 3317033 | 13801 | −0.22375074 | 0.736886578 | hypo | Block: 1751 |
| chr2 | 33830244 | 36578497 | 2748254 | 11175 | −0.267193673 | 0.748361203 | hypo | Block: 1661 |
| chr8 | 136654697 | 139508773 | 2854077 | 14571 | −0.254392188 | 0.728932573 | hypo | Block: 7864 |
| chr13 | 61995910 | 64396288 | 2400379 | 8579 | −0.299834016 | 0.724209953 | hypo | Block: 11157 |
| chrX | 85414815 | 88460052 | 3045238 | 9748 | −0.2314649 | 0.691151077 | hypo | Block: 16142 |
| chr2 | 115926233 | 118572016 | 2645784 | 10906 | −0.265411244 | 0.744511161 | hypo | Block: 2128 |
| chr11 | 24518888 | 27204558 | 2685671 | 9942 | −0.259298873 | 0.719126267 | hypo | Block: 9649 |
| chrX | 92939359 | 95917227 | 2977869 | 9693 | −0.229421228 | 0.715510287 | hypo | Block: 16168 |
| chr12 | 59990530 | 62574045 | 2583516 | 8746 | −0.260909378 | 0.736280652 | hypo | Block: 10512 |
| chr10 | 106407888 | 108914052 | 2506165 | 11609 | −0.267129648 | 0.727394012 | hypo | Block: 9300 |
| chrX | 125623341 | 128646623 | 3023283 | 9673 | −0.220628914 | 0.680113668 | hypo | Block: 16272 |
| chr7 | 8491816 | 10972334 | 2480519 | 9599 | −0.266486025 | 0.731347171 | hypo | Block: 6419 |
| chr3 | 93844458 | 96523914 | 2679457 | 9264 | −0.244848019 | 0.749307746 | hypo | Block: 3231 |
| chr4 | 96481198 | 99064573 | 2583376 | 8631 | −0.253163018 | 0.771246185 | hypo | Block: 4142 |
| chr21 | 19619152 | 22361288 | 2742137 | 11521 | −0.237643624 | 0.735566502 | hypo | Block: 15289 |
| chr11 | 96438151 | 98891492 | 2453342 | 9261 | −0.260094762 | 0.736211041 | hypo | Block: 9971 |
| chr3 | 164922858 | 167395863 | 2473006 | 8723 | −0.25282541 | 0.728991946 | hypo | Block: 3569 |
| chr5 | 83689571 | 86368465 | 2678895 | 9231 | −0.232430302 | 0.734591762 | hypo | Block: 4793 |
| chr13 | 84465407 | 86760270 | 2294864 | 8967 | −0.270969783 | 0.744753069 | hypo | Block: 11201 |
| chr5 | 18724044 | 21326444 | 2602401 | 9227 | −0.236011523 | 0.728125296 | hypo | Block: 4541 |
| chr13 | 58216167 | 60245957 | 2029791 | 8263 | −0.302398366 | 0.736161101 | hypo | Block: 11151 |
| chr11 | 82997567 | 85330225 | 2332659 | 8797 | −0.262715066 | 0.750980029 | hypo | Block: 9926 |
| chrX | 25044753 | 27938276 | 2893524 | 10823 | −0.210432677 | 0.69002005 | hypo | Block: 15922 |
| chr8 | 114455735 | 116660311 | 2204577 | 8460 | −0.275918809 | 0.760219929 | hypo | Block: 7778 |
| chr3 | 162545744 | 164854376 | 2308633 | 7528 | −0.26187185 | 0.751854969 | hypo | Block: 3567 |
| chr8 | 82757802 | 85082598 | 2324797 | 8122 | −0.259271201 | 0.732975303 | hypo | Block: 7663 |
| chrX | 120120740 | 122716511 | 2595772 | 9115 | −0.232007342 | 0.696660353 | hypo | Block: 16266 |
| chr8 | 2075841 | 4842451 | 2766611 | 23658 | −0.217001119 | 0.747948445 | hypo | Block: 7279 |
| chr2 | 21266995 | 23605857 | 2338863 | 11850 | −0.255865544 | 0.744975472 | hypo | Block: 1569 |
| chr7 | 108217612 | 110648801 | 2431190 | 8810 | −0.245305894 | 0.745758531 | hypo | Block: 6973 |
| chrX | 97112870 | 99651996 | 2539127 | 8276 | −0.233209651 | 0.701125869 | hypo | Block: 16172 |
| chr14 | 42090762 | 44858143 | 2767382 | 9153 | −0.213661689 | 0.751157265 | hypo | Block: 11469 |
| chr18 | 25765038 | 28557567 | 2792530 | 10654 | −0.208293299 | 0.732008432 | hypo | Block: 13796 |
| chr4 | 178373228 | 180974533 | 2601306 | 11690 | −0.22356313 | 0.74760807 | hypo | Block: 4408 |
| chr9 | 104504246 | 106855909 | 2351664 | 8348 | −0.246985287 | 0.712364561 | hypo | Block: 8388 |
| chr10 | 54882137 | 57367947 | 2485811 | 9209 | −0.231717077 | 0.726408164 | hypo | Block: 8998 |
| chr2 | 122525765 | 124771883 | 2246119 | 10811 | −0.254626436 | 0.742716913 | hypo | Block: 2167 |
| chr7 | 145833098 | 148036419 | 2203322 | 11206 | −0.257545498 | 0.741253435 | hypo | Block: 7162 |
| chr14 | 45729749 | 48134117 | 2404369 | 8507 | −0.231616334 | 0.743704513 | hypo | Block: 11474 |
| chr12 | 16556035 | 19048774 | 2492740 | 9971 | −0.222688407 | 0.741387585 | hypo | Block: 10279 |
| chrX | 31285029 | 33741131 | 2456103 | 12249 | −0.222790713 | 0.71239725 | hypo | Block: 15929 |
| chr3 | 20235490 | 22413466 | 2177977 | 8565 | −0.25102724 | 0.731377306 | hypo | Block: 2920 |
| chr14 | 27076164 | 29220955 | 2144792 | 7582 | −0.253990664 | 0.745559366 | hypo | Block: 11415 |
| chr4 | 161308668 | 164025969 | 2717302 | 10275 | −0.199998113 | 0.734277673 | hypo | Block: 4363 |
| chr14 | 86008725 | 88447418 | 2438694 | 10658 | −0.222147798 | 0.729272346 | hypo | Block: 11692 |
| chr6 | 139925122 | 142404629 | 2479508 | 9214 | −0.218090162 | 0.773113438 | hypo | Block: 6130 |
| chr10 | 83643326 | 85899009 | 2255684 | 9719 | −0.238429087 | 0.717901237 | hypo | Block: 9135 |
| chr18 | 39683477 | 42254337 | 2570861 | 9558 | −0.208077845 | 0.726480785 | hypo | Block: 13842 |
| chr2 | 211343341 | 213393136 | 2049796 | 8062 | −0.260670698 | 0.715032503 | hypo | Block: 2573 |
| chr1 | 190452410 | 192505179 | 2052770 | 7275 | −0.259681969 | 0.746636933 | hypo | Block: 1094 |
| chr13 | 92051762 | 93866964 | 1815203 | 7386 | −0.293411846 | 0.747627221 | hypo | Block: 11209 |
| chrX | 3855730 | 6130707 | 2274978 | 11389 | −0.232508521 | 0.750302774 | hypo | Block: 15845 |
| chr4 | 115618708 | 118006513 | 2387806 | 8414 | −0.218711272 | 0.73447363 | hypo | Block: 4208 |
| chr7 | 117970353 | 119906785 | 1936433 | 6581 | −0.269548773 | 0.722954824 | hypo | Block: 7008 |
| chr3 | 143720800 | 145789116 | 2068317 | 7390 | −0.252294248 | 0.745173492 | hypo | Block: 3493 |
| chr3 | 85024558 | 87039586 | 2015029 | 8042 | −0.258692117 | 0.715713079 | hypo | Block: 3220 |
| chr5 | 115916225 | 118236347 | 2320123 | 9563 | −0.224129125 | 0.763312656 | hypo | Block: 4883 |
| chr2 | 103457866 | 105456231 | 1998366 | 10688 | −0.259016024 | 0.73603149 | hypo | Block: 2051 |
| chr11 | 54786586 | 57043515 | 2256930 | 8679 | −0.228713765 | 0.724414673 | hypo | Block: 9737 |
| chr12 | 72675647 | 74917679 | 2242033 | 7398 | −0.227951742 | 0.722874947 | hypo | Block: 10574 |
| chr14 | 39911247 | 42065903 | 2154657 | 7118 | −0.236850258 | 0.722983848 | hypo | Block: 11467 |

TABLE 6-continued

Partial listing of all blocks.

| Chromosome | Start | End | Length (bp) | Number of Covered CpGs | Mean Difference in Block (Normal to Cancer) | Mean Normal Methylation in Block | Direction of Methylation Change | Block Identifier # |
|---|---|---|---|---|---|---|---|---|
| chr5 | 11914272 | 14011546 | 2097275 | 9183 | −0.24321052 | 0.72539112 | hypo | Block: 4519 |
| chr7 | 66804283 | 69056971 | 2252689 | 13569 | −0.226275186 | 0.735389169 | hypo | Block: 6745 |
| chr4 | 130273911 | 132671888 | 2397978 | 8289 | −0.212562183 | 0.729529185 | hypo | Block: 4257 |
| chr4 | 59789825 | 62054959 | 2265135 | 7865 | −0.223670844 | 0.731342303 | hypo | Block: 4019 |
| chr6 | 163846971 | 166069139 | 2222169 | 15012 | −0.227916488 | 0.756939791 | hypo | Block: 6273 |
| chr6 | 119675078 | 121601483 | 1926406 | 6466 | −0.2619216 | 0.770046668 | hypo | Block: 6034 |
| chr10 | 8664676 | 10829539 | 2164864 | 10788 | −0.232183905 | 0.742287306 | hypo | Block: 8749 |
| chr9 | 10613402 | 12753819 | 2140418 | 7809 | −0.234322236 | 0.705397233 | hypo | Block: 7967 |
| chr2 | 56412566 | 58264417 | 1851852 | 6609 | −0.270537007 | 0.747124217 | hypo | Block: 1773 |
| chr5 | 151213087 | 153371753 | 2158667 | 8761 | −0.230799856 | 0.68593744 | hypo | Block: 5121 |
| chr12 | 22844481 | 24710052 | 1865572 | 8863 | −0.263910157 | 0.772428572 | hypo | Block: 10298 |
| chr10 | 67427590 | 69523794 | 2096205 | 7535 | −0.234031965 | 0.735648136 | hypo | Block: 9034 |
| chr4 | 18112842 | 20246643 | 2133802 | 8383 | −0.228840198 | 0.737278081 | hypo | Block: 3891 |
| chr9 | 82200245 | 84170920 | 1970676 | 8616 | −0.246448084 | 0.772746707 | hypo | Block: 8220 |
| chr1 | 237213374 | 239373044 | 2159671 | 11319 | −0.224512634 | 0.746604208 | hypo | Block: 1417 |
| chr2 | 220492771 | 222431393 | 1938623 | 10621 | −0.249878344 | 0.760577316 | hypo | Block: 2628 |
| chr3 | 247241 | 2131382 | 1884142 | 8570 | −0.256663703 | 0.729530649 | hypo | Block: 2821 |
| chrX | 80574760 | 82747637 | 2172878 | 6456 | −0.221461745 | 0.681012768 | hypo | Block: 16133 |
| chr12 | 85684351 | 87760343 | 2075993 | 7075 | −0.231147689 | 0.709615032 | hypo | Block: 10605 |
| chr17 | 50912563 | 52975694 | 2063132 | 7791 | −0.23175904 | 0.729709362 | hypo | Block: 13410 |
| chr1 | 101706840 | 103791505 | 2084666 | 7441 | −0.225419163 | 0.705688214 | hypo | Block: 702 |
| chr7 | 84829210 | 86668664 | 1839455 | 6374 | −0.253604714 | 0.719519919 | hypo | Block: 6825 |
| chr8 | 87569653 | 89329302 | 1759650 | 6331 | −0.264384846 | 0.729855941 | hypo | Block: 7674 |
| chr3 | 77099893 | 79060520 | 1960628 | 9088 | −0.23501305 | 0.748066704 | hypo | Block: 3212 |
| chrX | 140673351 | 142709346 | 2035996 | 8688 | −0.224964391 | 0.718227015 | hypo | Block: 16338 |
| chr18 | 37421889 | 39527088 | 2105200 | 8744 | −0.21715724 | 0.72879371 | hypo | Block: 13841 |
| chr8 | 35099728 | 37008164 | 1908437 | 8792 | −0.239074885 | 0.747485005 | hypo | Block: 7455 |
| chr7 | 48151670 | 49806584 | 1654915 | 7293 | −0.275589237 | 0.740896328 | hypo | Block: 6641 |
| chr6 | 114673278 | 116258585 | 1585308 | 5217 | −0.28717817 | 0.727989936 | hypo | Block: 6012 |
| chr8 | 50832509 | 52729648 | 1897140 | 8173 | −0.239482834 | 0.73990847 | hypo | Block: 7518 |
| chr2 | 142895328 | 144684891 | 1789564 | 7883 | −0.253356233 | 0.782007764 | hypo | Block: 2254 |
| chr9 | 8904243 | 10612604 | 1708362 | 6686 | −0.264485217 | 0.714405588 | hypo | Block: 7966 |
| chr7 | 14034513 | 15711130 | 1676618 | 7258 | −0.269219269 | 0.741573121 | hypo | Block: 6432 |
| chr20 | 37679121 | 39307235 | 1628115 | 8231 | −0.276852076 | 0.716679084 | hypo | Block: 15032 |
| chr9 | 23859297 | 25673473 | 1814177 | 6903 | −0.247573439 | 0.72879801 | hypo | Block: 8008 |
| chr8 | 13138348 | 15089789 | 1951442 | 9737 | −0.230004804 | 0.715747814 | hypo | Block: 7345 |
| chr21 | 28350092 | 30235216 | 1885125 | 7571 | −0.230258474 | 0.763656247 | hypo | Block: 15301 |
| chr2 | 58471755 | 60258397 | 1786643 | 8342 | −0.242640081 | 0.753237611 | hypo | Block: 1776 |
| chr4 | 126249810 | 128291775 | 2041966 | 7551 | −0.211995351 | 0.733752185 | hypo | Block: 4243 |
| chr10 | 35937003 | 38054993 | 2117991 | 9999 | −0.204151188 | 0.749059632 | hypo | Block: 8906 |
| chr11 | 28350586 | 30030226 | 1679641 | 5953 | −0.256603521 | 0.719775504 | hypo | Block: 9652 |
| chr5 | 160975421 | 162777424 | 1802004 | 6856 | −0.239137016 | 0.712603694 | hypo | Block: 5160 |
| chr1 | 82624472 | 84326226 | 1701755 | 6058 | −0.250802019 | 0.769499049 | hypo | Block: 606 |
| chr6 | 76641115 | 78160239 | 1519125 | 4988 | −0.280654111 | 0.727810479 | hypo | Block: 5844 |
| chr7 | 124570226 | 126085673 | 1515448 | 5321 | −0.280536317 | 0.720304727 | hypo | Block: 7028 |
| chr4 | 42663673 | 44436120 | 1772448 | 6287 | −0.238243691 | 0.713954643 | hypo | Block: 3958 |
| chr2 | 75941892 | 77569932 | 1628041 | 6129 | −0.259021217 | 0.707693271 | hypo | Block: 1902 |
| chr14 | 48152692 | 49926673 | 1773982 | 6550 | −0.237460844 | 0.717928952 | hypo | Block: 11476 |
| chr13 | 86910546 | 88311528 | 1400983 | 5327 | −0.29873229 | 0.734880464 | hypo | Block: 11202 |
| chr8 | 129123482 | 130853815 | 1730334 | 7713 | −0.241089287 | 0.776941271 | hypo | Block: 7837 |
| chr12 | 83529421 | 85292742 | 1763322 | 5927 | −0.234766091 | 0.724449951 | hypo | Block: 10602 |
| chr18 | 68101304 | 70202653 | 2101350 | 9934 | −0.196574688 | 0.730577276 | hypo | Block: 13959 |
| chr6 | 97734858 | 99267208 | 1532351 | 5760 | −0.269160495 | 0.692041107 | hypo | Block: 5918 |
| chr14 | 97690118 | 99636646 | 1946529 | 14631 | −0.211547479 | 0.734814512 | hypo | Block: 11765 |
| chr20 | 40322080 | 41811961 | 1489882 | 9095 | −0.274813407 | 0.695473352 | hypo | Block: 15039 |
| chr11 | 98891868 | 100548750 | 1656883 | 6826 | −0.246577714 | 0.728993658 | hypo | Block: 9972 |
| chr13 | 93892547 | 95201535 | 1308989 | 6321 | −0.311471316 | 0.744766082 | hypo | Block: 11212 |
| chr6 | 22726078 | 24351923 | 1625846 | 7442 | −0.250470588 | 0.745808527 | hypo | Block: 5475 |
| chr2 | 48762258 | 50569174 | 1806917 | 7647 | −0.224633502 | 0.71126443 | hypo | Block: 1750 |
| chr13 | 70682249 | 72014730 | 1332482 | 5234 | −0.302714603 | 0.739249403 | hypo | Block: 11160 |
| chr3 | 6910616 | 8487122 | 1576507 | 7492 | −0.253860596 | 0.754752162 | hypo | Block: 2841 |
| chr3 | 28624746 | 30079205 | 1454460 | 6263 | −0.271758663 | 0.75420396 | hypo | Block: 2941 |
| chr6 | 94142013 | 95679823 | 1537811 | 5337 | −0.255561492 | 0.74177875 | hypo | Block: 5910 |
| chr6 | 8439673 | 10376290 | 1936618 | 10003 | −0.202614758 | 0.722556323 | hypo | Block: 5388 |
| chr2 | 129080207 | 130691654 | 1611448 | 12656 | −0.243446061 | 0.746175908 | hypo | Block: 2192 |
| chr11 | 20705914 | 22214132 | 1508219 | 5808 | −0.258721505 | 0.698648581 | hypo | Block: 9643 |
| chr1 | 193755648 | 195438826 | 1683179 | 5970 | −0.230828207 | 0.771427154 | hypo | Block: 1103 |
| chr7 | 88403566 | 89735061 | 1331496 | 4385 | −0.291279269 | 0.727433544 | hypo | Block: 6838 |
| chr4 | 58030584 | 59738686 | 1708103 | 6648 | −0.22553832 | 0.728066993 | hypo | Block: 4018 |
| chr4 | 93240715 | 94746219 | 1505505 | 5516 | −0.254451338 | 0.745921883 | hypo | Block: 4135 |
| chr4 | 44728739 | 46391803 | 1663065 | 5801 | −0.229667774 | 0.712030073 | hypo | Block: 3961 |
| chr2 | 187714106 | 189156378 | 1442273 | 5251 | −0.264499548 | 0.730714076 | hypo | Block: 2453 |
| chr5 | 119811542 | 121294721 | 1483180 | 5408 | −0.257161079 | 0.744582137 | hypo | Block: 4890 |
| chr6 | 78187398 | 79568476 | 1381079 | 4221 | −0.274368459 | 0.728012787 | hypo | Block: 5846 |

TABLE 6-continued

Partial listing of all blocks.

| Chromosome | Start | End | Length (bp) | Number of Covered CpGs | Mean Difference in Block (Normal to Cancer) | Mean Normal Methylation in Block | Direction of Methylation Change | Block Identifier # |
|---|---|---|---|---|---|---|---|---|
| chr8 | 77921809 | 79428387 | 1506579 | 5297 | −0.251320973 | 0.723141998 | hypo | Block: 7639 |
| chr2 | 214176718 | 215591780 | 1415063 | 5307 | −0.267192246 | 0.750009157 | hypo | Block: 2580 |
| chr2 | 184076794 | 185451485 | 1374692 | 4597 | −0.274781456 | 0.780321337 | hypo | Block: 2446 |
| chr1 | 198287268 | 199941077 | 1653810 | 6443 | −0.227636679 | 0.794689858 | hypo | Block: 1111 |
| chr11 | 27580543 | 29203705 | 1623163 | 6493 | −0.231106306 | 0.721623728 | hypo | Block: 8014 |
| chr2 | 12867687 | 14424226 | 1556540 | 6925 | −0.240807832 | 0.744141924 | hypo | Block: 1535 |
| chr11 | 89964764 | 91515223 | 1550460 | 5116 | −0.24116847 | 0.724297279 | hypo | Block: 9947 |
| chr2 | 124784013 | 126400383 | 1616371 | 7598 | −0.229715689 | 0.756532055 | hypo | Block: 2168 |
| chr6 | 74406026 | 75794826 | 1388801 | 4534 | −0.266934567 | 0.723551526 | hypo | Block: 5837 |
| chr8 | 33466116 | 35081533 | 1615418 | 6528 | −0.229066059 | 0.721586536 | hypo | Block: 7454 |
| chr9 | 120546862 | 122121597 | 1574736 | 6794 | −0.234491689 | 0.706981142 | hypo | Block: 8486 |
| chr8 | 20162943 | 21624567 | 1461625 | 10615 | −0.251531499 | 0.741397291 | hypo | Block: 7375 |
| chr13 | 74712715 | 75869380 | 1156666 | 4883 | −0.316909942 | 0.74506049 | hypo | Block: 11177 |
| chr15 | 87176508 | 88791183 | 1614676 | 8463 | −0.223785806 | 0.710578762 | hypo | Block: 12306 |
| chr7 | 114573721 | 115845714 | 1271994 | 4929 | −0.283973362 | 0.782961919 | hypo | Block: 6991 |
| chr5 | 88189739 | 89685631 | 1495893 | 5434 | −0.241307876 | 0.80570768 | hypo | Block: 4801 |
| chr16 | 75702950 | 77223364 | 1520415 | 7487 | −0.236769227 | 0.716577522 | hypo | Block: 12828 |
| chr2 | 194699318 | 196179708 | 1480391 | 4836 | −0.242191373 | 0.732560078 | hypo | Block: 2479 |
| chr7 | 40180732 | 41744986 | 1564255 | 8030 | −0.228537758 | 0.783643222 | hypo | Block: 6589 |
| chr11 | 126873864 | 128315423 | 1441560 | 7845 | −0.247780147 | 0.758288043 | hypo | Block: 10115 |
| chr6 | 50824075 | 52126759 | 1302685 | 5380 | −0.271504627 | 0.725747843 | hypo | Block: 5771 |
| chr18 | 35154119 | 36845764 | 1691646 | 7280 | −0.208429428 | 0.723298364 | hypo | Block: 13838 |
| chr11 | 22856353 | 24511189 | 1654837 | 5889 | −0.211766093 | 0.755774402 | hypo | Block: 9648 |
| chr18 | 917709 | 2532121 | 1614413 | 7122 | −0.216918951 | 0.716659448 | hypo | Block: 13675 |
| chr10 | 58121299 | 59599021 | 1477723 | 5166 | −0.236809062 | 0.729097198 | hypo | Block: 9002 |
| chr8 | 15398333 | 16859006 | 1460674 | 7321 | −0.239024415 | 0.738544516 | hypo | Block: 7347 |
| chr2 | 40684246 | 42067848 | 1383603 | 5821 | −0.252203192 | 0.728997493 | hypo | Block: 1691 |
| chr18 | 49874150 | 51672300 | 1798151 | 7648 | −0.193414099 | 0.734548179 | hypo | Block: 13891 |
| chr4 | 66550451 | 68300779 | 1750329 | 6018 | −0.197995245 | 0.711765197 | hypo | Block: 4023 |
| chr1 | 95707004 | 97181978 | 1474975 | 6020 | −0.233117192 | 0.737582486 | hypo | Block: 681 |
| chr13 | 47371514 | 48516729 | 1145216 | 4630 | −0.299846605 | 0.730517233 | hypo | Block: 11098 |
| chr20 | 6765793 | 7965622 | 1199830 | 5247 | −0.284498962 | 0.712902831 | hypo | Block: 14820 |
| chr5 | 3609160 | 5131460 | 1522301 | 11496 | −0.22275921 | 0.730203314 | hypo | Block: 4491 |
| chr12 | 97349023 | 98850648 | 1501626 | 7249 | −0.22551999 | 0.701282026 | hypo | Block: 10659 |
| chr2 | 225916106 | 227254288 | 1338183 | 5535 | −0.251829775 | 0.739055543 | hypo | Block: 2649 |
| chr21 | 31312141 | 32713070 | 1400930 | 7776 | −0.239501687 | 0.756457396 | hypo | Block: 15307 |
| chr1 | 72792500 | 74258302 | 1465803 | 4867 | −0.22859389 | 0.725252494 | hypo | Block: 582 |
| chr8 | 69259542 | 70626285 | 1366744 | 6448 | −0.243931355 | 0.740485822 | hypo | Block: 7595 |
| chr2 | 217565529 | 218843435 | 1277907 | 8780 | −0.260717728 | 0.720842127 | hypo | Block: 2591 |
| chr3 | 161090707 | 162525583 | 1434877 | 5139 | −0.230750808 | 0.722693122 | hypo | Block: 3566 |
| chr15 | 54052067 | 55473630 | 1421564 | 5836 | −0.231961948 | 0.729701526 | hypo | Block: 12063 |
| chr5 | 100254971 | 101631990 | 1377020 | 4561 | −0.238835983 | 0.745636707 | hypo | Block: 4838 |
| chr4 | 11746917 | 13338762 | 1591846 | 6939 | −0.206591491 | 0.751972054 | hypo | Block: 3871 |
| chr6 | 124134391 | 125270552 | 1136162 | 4659 | −0.28843724 | 0.725194748 | hypo | Block: 6043 |
| chrX | 35505927 | 36965324 | 1459398 | 5067 | −0.224002521 | 0.696838165 | hypo | Block: 15933 |
| chr5 | 50699064 | 52001189 | 1302126 | 4772 | −0.250948448 | 0.737463107 | hypo | Block: 4625 |
| chr6 | 161557451 | 163148363 | 1590913 | 12682 | −0.205356408 | 0.810155814 | hypo | Block: 6270 |
| chr1 | 208418037 | 209784286 | 1366250 | 7450 | −0.238988955 | 0.722956528 | hypo | Block: 1204 |
| chr14 | 78447748 | 79745133 | 1297386 | 6769 | −0.250937615 | 0.709453799 | hypo | Block: 11683 |
| chr8 | 4856601 | 6257776 | 1401176 | 9775 | −0.232178512 | 0.744799287 | hypo | Block: 7280 |
| chr16 | 25709981 | 27120960 | 1410980 | 8626 | −0.230410051 | 0.698107555 | hypo | Block: 12592 |
| chr7 | 77649564 | 78813991 | 1164428 | 5192 | −0.278760971 | 0.745969829 | hypo | Block: 6808 |
| chr13 | 76434672 | 77454881 | 1020210 | 4200 | −0.318122833 | 0.741661797 | hypo | Block: 11185 |
| chrX | 77395364 | 78853597 | 1458234 | 4204 | −0.222368015 | 0.708001429 | hypo | Block: 16129 |
| chr12 | 77719476 | 79255946 | 1536471 | 5942 | −0.210301181 | 0.73642391 | hypo | Block: 10590 |
| chr3 | 54163771 | 55509373 | 1345603 | 8571 | −0.239848516 | 0.741897975 | hypo | Block: 3110 |
| chr3 | 5264743 | 6889392 | 1624650 | 7568 | −0.198126346 | 0.76876557 | hypo | Block: 2840 |
| chr2 | 3753297 | 5018638 | 1265342 | 8508 | −0.253111696 | 0.733900207 | hypo | Block: 1485 |
| chr2 | 77611935 | 79220163 | 1608229 | 6136 | −0.198262321 | 0.714095737 | hypo | Block: 1903 |
| chr20 | 11927340 | 13199855 | 1272516 | 5873 | −0.249737937 | 0.762421628 | hypo | Block: 14848 |
| chr2 | 137533207 | 138674387 | 1141181 | 4538 | −0.277925322 | 0.719488261 | hypo | Block: 2249 |
| chr20 | 58534312 | 59823480 | 1289169 | 11831 | −0.245395659 | 0.716517038 | hypo | Block: 15204 |
| chr21 | 17257846 | 18745487 | 1487642 | 5903 | −0.212279235 | 0.726709083 | hypo | Block: 15285 |
| chr8 | 61940753 | 63244925 | 1304173 | 4528 | −0.241971352 | 0.719739741 | hypo | Block: 4669 |
| chr10 | 65471854 | 67036615 | 1564762 | 5935 | −0.20155706 | 0.751873766 | hypo | Block: 9032 |
| chr10 | 82297397 | 83626440 | 1329044 | 5752 | −0.23715787 | 0.738836573 | hypo | Block: 9134 |
| chr2 | 185471093 | 186603335 | 1132243 | 3741 | −0.277775685 | 0.749247067 | hypo | Block: 2447 |
| chr2 | 155577608 | 156999665 | 1422058 | 5030 | −0.220623378 | 0.741125079 | hypo | Block: 2301 |
| chr15 | 95394371 | 96856821 | 1462451 | 8938 | −0.214405225 | 0.734508017 | hypo | Block: 12351 |
| chr9 | 75783567 | 77098048 | 1314482 | 5065 | −0.238073492 | 0.716538644 | hypo | Block: 8192 |
| chr3 | 134523424 | 135675199 | 1151776 | 5663 | −0.271604401 | 0.732421403 | hypo | Block: 3446 |
| chr3 | 69789260 | 71005934 | 1216675 | 6182 | −0.256957849 | 0.753880128 | hypo | Block: 3181 |
| chr4 | 171280907 | 172720786 | 1439880 | 5451 | −0.216057636 | 0.727356933 | hypo | Block: 4387 |
| chr13 | 22252162 | 23486009 | 1233848 | 8429 | −0.251156049 | 0.770108452 | hypo | Block: 10941 |

TABLE 6-continued

Partial listing of all blocks.

| Chromosome | Start | End | Length (bp) | Number of Covered CpGs | Mean Difference in Block (Normal to Cancer) | Mean Normal Methylation in Block | Direction of Methylation Change | Block Identifier # |
|---|---|---|---|---|---|---|---|---|
| chrX | 115732377 | 117092121 | 1359745 | 3819 | −0.22771657 | 0.685556076 | hypo | Block: 16241 |
| chr11 | 102976520 | 104034425 | 1057906 | 4365 | −0.292544215 | 0.786143326 | hypo | Block: 9986 |
| chr1 | 97287913 | 98386078 | 1098166 | 4353 | −0.281665665 | 0.817606228 | hypo | Block: 683 |
| chr18 | 61656186 | 63406057 | 1749872 | 7948 | −0.17626072 | 0.740873861 | hypo | Block: 13946 |
| chr3 | 105601367 | 106959370 | 1358004 | 5402 | −0.226568377 | 0.78727692 | hypo | Block: 3261 |
| chr4 | 13634688 | 14999233 | 1364546 | 5937 | −0.225270155 | 0.72423666 | hypo | Block: 3877 |
| chr5 | 157287525 | 158519271 | 1231747 | 7228 | −0.249188996 | 0.752808055 | hypo | Block: 5140 |
| chr20 | 15151629 | 16249745 | 1098117 | 5773 | −0.279095562 | 0.78127232 | hypo | Block: 14854 |
| chr4 | 166802249 | 168143034 | 1340786 | 5148 | −0.228280259 | 0.725585351 | hypo | Block: 4376 |
| chr6 | 18391480 | 19691827 | 1300348 | 5508 | −0.234711796 | 0.718212239 | hypo | Block: 5460 |
| chr4 | 189208953 | 190846728 | 1637776 | 11198 | −0.186305884 | 0.737049934 | hypo | Block: 4452 |
| chr6 | 68160231 | 69341214 | 1180984 | 3974 | −0.258261242 | 0.732513873 | hypo | Block: 5816 |
| chr9 | 22456999 | 23813897 | 1356899 | 5830 | −0.22366658 | 0.750584087 | hypo | Block: 8006 |
| chr7 | 112580252 | 113721967 | 1141716 | 3972 | −0.265444113 | 0.704554609 | hypo | Block: 6983 |
| chr1 | 49242900 | 50489398 | 1246499 | 3988 | −0.242682446 | 0.731476109 | hypo | Block: 473 |
| chr18 | 63608495 | 65175021 | 1566527 | 6478 | −0.193083409 | 0.733277345 | hypo | Block: 13948 |
| chr6 | 69345612 | 70390745 | 1045134 | 3926 | −0.288638586 | 0.707537161 | hypo | Block: 5817 |
| chr8 | 76478098 | 77581211 | 1103114 | 3886 | −0.273323454 | 0.729248327 | hypo | Block: 7637 |
| chr5 | 91686377 | 92900713 | 1214337 | 4800 | −0.247444329 | 0.738937249 | hypo | Block: 4810 |
| chr4 | 180987041 | 182460679 | 1473639 | 8451 | −0.20347862 | 0.720062145 | hypo | Block: 4409 |
| chr7 | 45971615 | 47293757 | 1322143 | 6862 | −0.226630592 | 0.747938483 | hypo | Block: 6628 |
| chr6 | 48055975 | 49413992 | 1358018 | 4592 | −0.220107401 | 0.740172996 | hypo | Block: 5763 |
| chr6 | 49549528 | 50669262 | 1119735 | 4116 | −0.26555484 | 0.686779168 | hypo | Block: 5765 |
| chrX | 143559043 | 144887228 | 1328186 | 5708 | −0.222827079 | 0.685062008 | hypo | Block: 16343 |
| chr7 | 3346775 | 4622019 | 1275245 | 12889 | −0.232058594 | 0.793717644 | hypo | Block: 6363 |
| chr2 | 1753251 | 3152539 | 1399289 | 16307 | −0.211182731 | 0.755840284 | hypo | Block: 1481 |
| chr10 | 77832723 | 79392471 | 1559749 | 9219 | −0.188894165 | 0.768744068 | hypo | Block: 9105 |
| chr9 | 117659476 | 118913230 | 1253755 | 5491 | −0.233281478 | 0.727641766 | hypo | Block: 8479 |
| chr5 | 135556607 | 136829036 | 1272430 | 6081 | −0.229119579 | 0.697389693 | hypo | Block: 4993 |
| chr1 | 71553512 | 72741744 | 1188233 | 4419 | −0.245170754 | 0.765193428 | hypo | Block: 581 |
| chr3 | 108912208 | 110166286 | 1254079 | 4633 | −0.231499377 | 0.775665349 | hypo | Block: 3272 |
| chr9 | 81031461 | 82181265 | 1149805 | 5632 | −0.252028141 | 0.733765345 | hypo | Block: 8219 |
| chr8 | 139509853 | 140709323 | 1199471 | 9300 | −0.240767632 | 0.706537233 | hypo | Block: 7865 |
| chr2 | 193397551 | 194689205 | 1291655 | 4457 | −0.223181215 | 0.748779108 | hypo | Block: 2478 |
| chr10 | 116863236 | 118024746 | 1161511 | 5656 | −0.247970217 | 0.724722906 | hypo | Block: 9352 |
| chr16 | 65163637 | 66304268 | 1140632 | 6787 | −0.251844686 | 0.705449393 | hypo | Block: 12757 |
| chr9 | 25684961 | 26838633 | 1153673 | 4602 | −0.248318386 | 0.718224692 | hypo | Block: 8009 |
| chr7 | 81084866 | 82065278 | 980413 | 3965 | −0.292115901 | 0.732982135 | hypo | Block: 6819 |
| chr4 | 132685397 | 134059649 | 1374253 | 4018 | −0.206962617 | 0.736168176 | hypo | Block: 4258 |
| chrX | 22037222 | 23343476 | 1306255 | 6708 | −0.217421997 | 0.718886215 | hypo | Block: 15914 |
| chr8 | 23587917 | 24765322 | 1177406 | 5743 | −0.239394919 | 0.727256523 | hypo | Block: 7401 |
| chr6 | 112576997 | 113851523 | 1274527 | 5020 | −0.220813817 | 0.764128331 | hypo | Block: 6003 |
| chr2 | 189175058 | 190303475 | 1128418 | 4061 | −0.24835515 | 0.732364226 | hypo | Block: 2454 |
| chr8 | 64130512 | 65275119 | 1144608 | 4625 | −0.244729283 | 0.717763749 | hypo | Block: 7570 |
| chr4 | 20756867 | 21941305 | 1184439 | 5274 | −0.23617756 | 0.721970711 | hypo | Block: 3893 |
| chr10 | 86301014 | 87384093 | 1083080 | 4864 | −0.257769293 | 0.727259959 | hypo | Block: 9140 |
| chr8 | 89351126 | 90559951 | 1208826 | 3819 | −0.230793622 | 0.744342447 | hypo | Block: 7675 |
| chr3 | 2151792 | 3161986 | 1010195 | 5570 | −0.275800637 | 0.784443858 | hypo | Block: 2824 |
| chr18 | 57576653 | 58987404 | 1410752 | 6335 | −0.196579267 | 0.735813167 | hypo | Block: 13926 |
| chr7 | 18132546 | 19139482 | 1006937 | 4500 | −0.273700965 | 0.787893387 | hypo | Block: 6446 |
| chr8 | 107946258 | 109080743 | 1134486 | 4641 | −0.242333185 | 0.738790447 | hypo | Block: 7766 |
| chr7 | 144605351 | 145794499 | 1189149 | 4859 | −0.230480441 | 0.730514801 | hypo | Block: 7160 |
| chr7 | 70603939 | 71794745 | 1190807 | 8221 | −0.228983407 | 0.757566153 | hypo | Block: 6751 |
| chr5 | 43707653 | 44801662 | 1094010 | 3499 | −0.249233076 | 0.717306161 | hypo | Block: 4612 |
| chr14 | 29258625 | 30392633 | 1134009 | 4674 | −0.239848411 | 0.735097299 | hypo | Block: 11419 |
| chr4 | 72058474 | 73433711 | 1375238 | 5038 | −0.197343774 | 0.739021541 | hypo | Block: 4037 |
| chr6 | 86718798 | 87647154 | 928357 | 2476 | −0.291483087 | 0.692510023 | hypo | Block: 5883 |
| chr12 | 90355184 | 91783891 | 1428708 | 5298 | −0.189047736 | 0.771490518 | hypo | Block: 10619 |
| chr20 | 53098303 | 54238298 | 1139996 | 5683 | −0.236543872 | 0.731937145 | hypo | Block: 15158 |
| chr6 | 153458258 | 154718235 | 1259978 | 5928 | −0.213976753 | 0.72863515 | hypo | Block: 6212 |
| chr6 | 63015380 | 64282114 | 1266735 | 4702 | −0.212737003 | 0.752126004 | hypo | Block: 5811 |
| chr1 | 55685670 | 56897272 | 1211603 | 5636 | −0.22238201 | 0.770802504 | hypo | Block: 512 |
| chr3 | 147148365 | 148240383 | 1092019 | 3809 | −0.246252898 | 0.73097331 | hypo | Block: 3499 |
| chr1 | 68963027 | 70022986 | 1059960 | 3596 | −0.252564575 | 0.707644962 | hypo | Block: 576 |
| chr10 | 91597832 | 92609615 | 1011784 | 3771 | −0.264402156 | 0.724010043 | hypo | Block: 9173 |
| chr2 | 16689858 | 17656303 | 966446 | 4663 | −0.276457392 | 0.713817408 | hypo | Block: 1545 |
| chr16 | 51197459 | 52414402 | 1216944 | 6560 | −0.219146475 | 0.688741631 | hypo | Block: 12699 |
| chr8 | 46838903 | 48099795 | 1260893 | 9887 | −0.211410253 | 0.741274767 | hypo | Block: 7505 |
| chr5 | 166408484 | 167587319 | 1178836 | 7794 | −0.22577032 | 0.737518333 | hypo | Block: 5163 |
| chr8 | 60036941 | 61189713 | 1152773 | 4711 | −0.229483099 | 0.817476517 | hypo | Block: 7557 |
| chr14 | 25600783 | 26674085 | 1073303 | 4216 | −0.245853638 | 0.716710063 | hypo | Block: 11413 |
| chr10 | 18967678 | 20100781 | 1133104 | 5100 | −0.232775998 | 0.755557369 | hypo | Block: 8805 |
| chr10 | 1782851 | 3026903 | 1244053 | 11254 | −0.211783865 | 0.761053162 | hypo | Block: 8707 |
| chrX | 103831927 | 105040920 | 1208994 | 3649 | −0.217376256 | 0.660298472 | hypo | Block: 16204 |

TABLE 6-continued

Partial listing of all blocks.

| Chromosome | Start | End | Length (bp) | Number of Covered CpGs | Mean Difference in Block (Normal to Cancer) | Mean Normal Methylation in Block | Direction of Methylation Change | Block Identifier # |
|---|---|---|---|---|---|---|---|---|
| chr2 | 5843401 | 6995750 | 1152350 | 8185 | −0.22803249 | 0.742090721 | hypo | Block: 1489 |
| chr3 | 173124980 | 174147410 | 1022431 | 4280 | −0.256468744 | 0.726633598 | hypo | Block: 3605 |
| chr12 | 99298164 | 100378195 | 1080032 | 4099 | −0.242429985 | 0.702603798 | hypo | Block: 10666 |
| chr13 | 34427720 | 35506342 | 1078623 | 5211 | −0.24260414 | 0.775831088 | hypo | Block: 11032 |
| chr5 | 17588719 | 18717318 | 1128600 | 4572 | −0.229737539 | 0.730372689 | hypo | Block: 4540 |
| chr4 | 175750609 | 176911745 | 1161137 | 4947 | −0.223093606 | 0.740684266 | hypo | Block: 4399 |
| chr17 | 31625297 | 32899372 | 1274076 | 8121 | −0.20304692 | 0.673594472 | hypo | Block: 13205 |
| chrX | 75408913 | 76653463 | 1244551 | 3084 | −0.206236156 | 0.676995693 | hypo | Block: 16123 |
| chr8 | 49783393 | 50809666 | 1026274 | 4738 | −0.249824224 | 0.723465401 | hypo | Block: 7517 |
| chr4 | 16260058 | 17468256 | 1208199 | 6649 | −0.21131939 | 0.734387295 | hypo | Block: 3884 |
| chr13 | 72444367 | 73298256 | 853890 | 3699 | −0.29894237 | 0.756284524 | hypo | Block: 11167 |
| chr13 | 96751622 | 97580295 | 828674 | 3819 | −0.306869912 | 0.74266103 | hypo | Block: 11228 |
| chr7 | 136566655 | 137526888 | 960234 | 4743 | −0.264784394 | 0.71882949 | hypo | Block: 7106 |
| chr6 | 62179113 | 62986222 | 807110 | 2712 | −0.314048354 | 0.755952587 | hypo | Block: 5810 |
| chrX | 136663678 | 137777263 | 1113586 | 3952 | −0.227109008 | 0.677011104 | hypo | Block: 16324 |
| chr7 | 83823355 | 84799327 | 975973 | 3594 | −0.259063018 | 0.736909325 | hypo | Block: 6822 |
| chr7 | 135665976 | 136544505 | 878530 | 3428 | −0.286833974 | 0.717287089 | hypo | Block: 7104 |
| chr3 | 73680359 | 74663468 | 983110 | 4457 | −0.256160278 | 0.752777193 | hypo | Block: 3203 |
| chr5 | 143585094 | 144711611 | 1126518 | 4044 | −0.22335272 | 0.736403587 | hypo | Block: 5066 |
| chr8 | 106335686 | 107276292 | 940607 | 3944 | −0.267263178 | 0.748115525 | hypo | Block: 7761 |
| chr4 | 30731414 | 31816116 | 1084703 | 4617 | −0.231478943 | 0.765188282 | hypo | Block: 3919 |
| chr2 | 180871900 | 181843440 | 971541 | 3505 | −0.258430594 | 0.739437567 | hypo | Block: 2432 |
| chr3 | 68057267 | 68973357 | 916091 | 3983 | −0.273996436 | 0.72412874 | hypo | Block: 3175 |
| chr3 | 55527657 | 56501406 | 973750 | 5508 | −0.257260805 | 0.754646207 | hypo | Block: 3111 |
| chr9 | 15601090 | 16726776 | 1125687 | 6817 | −0.221468729 | 0.783145714 | hypo | Block: 7980 |
| chr12 | 54982626 | 56039891 | 1057266 | 3957 | −0.235781713 | 0.709892838 | hypo | Block: 10480 |
| chr16 | 82675170 | 83841324 | 1166155 | 9030 | −0.213596239 | 0.755351049 | hypo | Block: 12862 |
| chr13 | 107571048 | 108512130 | 941083 | 5802 | −0.264170673 | 0.720155401 | hypo | Block: 11294 |
| chr22 | 34323251 | 35447616 | 1124366 | 5713 | −0.21960069 | 0.713448838 | hypo | Block: 15633 |
| chr3 | 34731284 | 35680458 | 949175 | 3336 | −0.259793326 | 0.722094444 | hypo | Block: 2966 |
| chr6 | 121762578 | 122715476 | 952899 | 3776 | −0.258585201 | 0.715488464 | hypo | Block: 6037 |
| chr4 | 111839127 | 113005446 | 1166320 | 4248 | −0.211169788 | 0.70980457 | hypo | Block: 4196 |
| chr10 | 112841466 | 113909773 | 1068308 | 5331 | −0.230291455 | 0.723376242 | hypo | Block: 9325 |
| chr2 | 209272057 | 210288391 | 1016335 | 3414 | −0.241217458 | 0.711491672 | hypo | Block: 2567 |

TABLE 7

Partial list of small DMRs. Details, including column descriptions, are included in the Supplementary Methods. -Loss of boundary

| Chromosome | Start | End | Length (bp) | Number of Covered CpGs | Mean Difference in DMR (Normal to Cancer) | Mean Normal Methylation in DMR | Direction of Methylation Change | DMR Identifier # | Type of small DMR |
|---|---|---|---|---|---|---|---|---|---|
| chr16 | 51183143 | 51190667 | 7525 | 474 | 0.336 | 0.203 | hyper | SmallDMR: 8 | other |
| chr11 | 32454875 | 32461307 | 6433 | 400 | 0.343 | 0.131 | hyper | SmallDMR: 45 | lossOfBoundary |
| chr13 | 58203467 | 58209371 | 5905 | 379 | 0.371 | 0.297 | hyper | SmallDMR: 20 | lossOfBoundary |
| chr20 | 37351482 | 37358279 | 6798 | 434 | 0.316 | 0.187 | hyper | SmallDMR: 22 | other |
| chr8 | 54788861 | 54795497 | 6637 | 443 | 0.319 | 0.093 | hyper | SmallDMR: 7 | boundaryShift |
| chr20 | 55200051 | 55206547 | 6497 | 460 | 0.322 | 0.142 | hyper | SmallDMR: 6 | boundaryShift |
| chr13 | 53419184 | 53424656 | 5473 | 382 | 0.37 | 0.264 | hyper | SmallDMR: 16 | boundaryShift |
| chr10 | 7449233 | 7455383 | 6151 | 421 | 0.329 | 0.124 | hyper | SmallDMR: 1 | lossOfBoundary |
| chr3 | 44035725 | 44041323 | 5599 | 355 | 0.356 | 0.061 | hyper | SmallDMR: 2 | lossOfBoundary |
| chr8 | 10586790 | 10592484 | 5695 | 396 | 0.349 | 0.093 | hyper | SmallDMR: 15 | lossOfBoundary |
| chr16 | 54968642 | 54974174 | 5533 | 297 | 0.337 | 0.136 | hyper | SmallDMR: 252 | lossOfBoundary |
| chr7 | 49812207 | 49815938 | 3732 | 306 | 0.488 | 0.05 | hyper | SmallDMR: 3 | lossOfBoundary |
| chr6 | 166073666 | 166078543 | 4878 | 384 | 0.37 | 0.106 | hyper | SmallDMR: 5 | boundaryShift |
| chr13 | 112757596 | 112761523 | 3928 | 243 | 0.458 | 0.157 | hyper | SmallDMR: 46 | lossOfBoundary |
| chr13 | 28365972 | 28371719 | 5748 | 296 | 0.306 | 0.184 | hyper | SmallDMR: 259 | other |
| chr6 | 137813803 | 137819871 | 6069 | 320 | 0.277 | 0.154 | hyper | SmallDMR: 153 | lossOfBoundary |
| chr14 | 85995273 | 86001268 | 5996 | 338 | 0.276 | 0.157 | hyper | SmallDMR: 109 | other |
| chr11 | 79147781 | 79152750 | 4970 | 311 | 0.33 | 0.042 | hyper | SmallDMR: 25 | lossOfBoundary |
| chr6 | 166579057 | 166583822 | 4766 | 309 | 0.344 | 0.109 | hyper | SmallDMR: 64 | lossOfBoundary |
| chr9 | 135458625 | 135464563 | 5939 | 216 | 0.275 | 0.155 | hyper | SmallDMR: 1322 | other |
| chr6 | 73329426 | 73333491 | 4066 | 221 | 0.401 | 0.069 | hyper | SmallDMR: 47 | boundaryShift |
| chr16 | 67198985 | 67204158 | 5174 | 152 | 0.315 | 0.309 | hyper | SmallDMR: 1086 | other |
| chr13 | 88323452 | 88327174 | 3723 | 202 | 0.434 | 0.08 | hyper | SmallDMR: 135 | boundaryShift |
| chr6 | 163833773 | 163838195 | 4423 | 351 | 0.365 | 0.025 | hyper | SmallDMR: 10 | other |
| chr19 | 30015633 | 30020501 | 4869 | 376 | 0.324 | 0.144 | hyper | SmallDMR: 27 | lossOfBoundary |

TABLE 7-continued

Partial list of small DMRs. Details, including column descriptions, are included in the Supplementary Methods. -Loss of boundary

| Chromosome | Start | End | Length (bp) | Number of Covered CpGs | Mean Difference in DMR (Normal to Cancer) | Mean Normal Methylation in DMR | Direction of Methylation Change | DMR Identifier # | Type of small DMR |
|---|---|---|---|---|---|---|---|---|---|
| chr10 | 50816694 | 50822510 | 5817 | 385 | 0.269 | 0.223 | hyper | SmallDMR: 32 | other |
| chr9 | 100613916 | 100618137 | 4222 | 326 | 0.365 | 0.181 | hyper | SmallDMR: 49 | lossOfBoundary |
| chr1 | 217307316 | 217313506 | 6191 | 306 | 0.248 | 0.165 | hyper | SmallDMR: 152 | lossOfBoundary |
| chr6 | 390473 | 394427 | 3955 | 310 | 0.384 | 0.099 | hyper | SmallDMR: 4 | lossOfBoundary |
| chr13 | 102567686 | 102572645 | 4960 | 191 | 0.306 | 0.174 | hyper | SmallDMR: 196 | other |
| chr10 | 118030090 | 118034625 | 4536 | 305 | 0.331 | 0.104 | hyper | SmallDMR: 18 | lossOfBoundary |
| chr7 | 27182482 | 27186676 | 4195 | 215 | 0.357 | 0.45 | hyper | SmallDMR: 1563 | boundaryShift |
| chr7 | 98182674 | 98186076 | 3403 | 39 | −0.44 | 0.709 | hypo | SmallDMR: 2562 | other |
| chr18 | 903631 | 909338 | 5708 | 339 | 0.262 | 0.174 | hyper | SmallDMR: 87 | lossOfBoundary |
| chr2 | 182544890 | 182549928 | 5039 | 250 | 0.296 | 0.136 | hyper | SmallDMR: 222 | other |
| chrX | 113815462 | 113820414 | 4953 | 221 | 0.298 | 0.27 | hyper | SmallDMR: 501 | boundaryShift |
| chr5 | 37836119 | 37841020 | 4902 | 321 | 0.301 | 0.176 | hyper | SmallDMR: 40 | lossOfBoundary |
| chr11 | 69061244 | 69064318 | 3075 | 73 | −0.477 | 0.837 | hypo | SmallDMR: 1491 | boundaryShift |
| chr6 | 127438642 | 127442978 | 4337 | 243 | 0.335 | 0.068 | hyper | SmallDMR: 23 | boundaryShift |
| chr20 | 23028137 | 23032338 | 4202 | 320 | 0.345 | 0.144 | hyper | SmallDMR: 13 | lossOfBoundary |
| chr8 | 145104341 | 145107516 | 3176 | 288 | 0.456 | 0.073 | hyper | SmallDMR: 26 | boundaryShift |
| chr7 | 155164119 | 155167895 | 3777 | 290 | 0.382 | 0.076 | hyper | SmallDMR: 77 | boundaryShift |
| chr13 | 95363007 | 95366074 | 3068 | 299 | 0.469 | 0.062 | hyper | SmallDMR: 30 | other |
| chr20 | 61048542 | 61052696 | 4155 | 290 | 0.337 | 0.18 | hyper | SmallDMR: 55 | other |
| chr10 | 57387143 | 57391537 | 4395 | 171 | 0.317 | 0.107 | hyper | SmallDMR: 326 | lossOfBoundary |
| chr20 | 61806468 | 61810902 | 4435 | 425 | 0.314 | 0.095 | hyper | SmallDMR: 9 | other |
| chr11 | 110581348 | 110584758 | 3411 | 221 | 0.407 | 0.041 | hyper | SmallDMR: 33 | lossOfBoundary |
| chr11 | 91956571 | 91960687 | 4117 | 258 | 0.335 | 0.072 | hyper | SmallDMR: 52 | other |
| chr13 | 93878699 | 93881494 | 2796 | 160 | 0.485 | 0.096 | hyper | SmallDMR: 138 | other |
| chr6 | 133561368 | 133565148 | 3781 | 209 | 0.358 | 0.083 | hyper | SmallDMR: 42 | boundaryShift |
| chr4 | 134067785 | 134073183 | 5399 | 302 | 0.25 | 0.155 | hyper | SmallDMR: 216 | other |
| chr6 | 94125909 | 94130589 | 4681 | 262 | 0.287 | 0.064 | hyper | SmallDMR: 41 | lossOfBoundary |
| chr20 | 61635973 | 61639232 | 3260 | 312 | 0.412 | 0.111 | hyper | SmallDMR: 53 | other |
| chr9 | 77111502 | 77116390 | 4889 | 243 | 0.273 | 0.087 | hyper | SmallDMR: 119 | lossOfBoundary |
| chr8 | 70981474 | 70985230 | 3757 | 284 | 0.354 | 0.138 | hyper | SmallDMR: 58 | boundaryShift |
| chr13 | 52529621 | 52533517 | 3897 | 57 | −0.34 | 0.632 | hypo | SmallDMR: 2390 | novelMethylation |
| chr21 | 28215838 | 28219559 | 3722 | 247 | 0.355 | 0.042 | hyper | SmallDMR: 91 | boundaryShift |
| chr8 | 9760597 | 9765369 | 4773 | 279 | 0.271 | 0.11 | hyper | SmallDMR: 185 | other |
| chr8 | 72753797 | 72757389 | 3593 | 219 | 0.36 | 0.15 | hyper | SmallDMR: 225 | lossOfBoundary |
| chr13 | 110958465 | 110961303 | 2839 | 225 | 0.453 | 0.067 | hyper | SmallDMR: 36 | lossOfBoundary |
| chr10 | 106398343 | 106403103 | 4761 | 324 | 0.269 | 0.145 | hyper | SmallDMR: 24 | lossOfBoundary |
| chr13 | 84452863 | 84457882 | 5020 | 170 | 0.255 | 0.235 | hyper | SmallDMR: 387 | other |
| chr1 | 40150987 | 40156857 | 5871 | 42 | −0.217 | 0.59 | hypo | SmallDMR: 10063 | boundaryShift |
| chr19 | 1465317 | 1468522 | 3206 | 330 | 0.397 | 0.197 | hyper | SmallDMR: 82 | boundaryShift |
| chr7 | 19155806 | 19159074 | 3269 | 218 | 0.388 | 0.104 | hyper | SmallDMR: 233 | lossOfBoundary |
| chr3 | 142837464 | 142840517 | 3054 | 296 | 0.414 | 0.086 | hyper | SmallDMR: 11 | lossOfBoundary |
| chr1 | 50880917 | 50884889 | 3973 | 247 | 0.318 | 0.122 | hyper | SmallDMR: 338 | boundaryShift |
| chr13 | 26623378 | 26626614 | 3237 | 238 | 0.39 | 0.127 | hyper | SmallDMR: 38 | lossOfBoundary |
| chr4 | 30721103 | 30725148 | 4046 | 338 | 0.311 | 0.121 | hyper | SmallDMR: 37 | boundaryShift |
| chr6 | 125282748 | 125285778 | 3031 | 172 | 0.413 | 0.056 | hyper | SmallDMR: 199 | lossOfBoundary |
| chr8 | 53850933 | 53854633 | 3701 | 262 | 0.337 | 0.137 | hyper | SmallDMR: 66 | lossOfBoundary |
| chr11 | 20180295 | 20185737 | 5443 | 260 | 0.228 | 0.177 | hyper | SmallDMR: 331 | other |
| chr20 | 59826523 | 59829497 | 2975 | 278 | 0.417 | 0.085 | hyper | SmallDMR: 14 | lossOfBoundary |
| chr10 | 134597791 | 134602559 | 4769 | 569 | 0.26 | 0.12 | hyper | SmallDMR: 17 | lossOfBoundary |
| chr2 | 1746207 | 1749394 | 3188 | 220 | 0.387 | 0.096 | hyper | SmallDMR: 59 | lossOfBoundary |
| chr13 | 73939583 | 73943635 | 4053 | 39 | −0.303 | 0.652 | hypo | SmallDMR: 3146 | other |
| chr5 | 82766752 | 82770976 | 4225 | 201 | 0.289 | 0.044 | hyper | SmallDMR: 197 | other |
| chr9 | 101469049 | 101472291 | 3243 | 256 | 0.376 | 0.088 | hyper | SmallDMR: 19 | lossOfBoundary |
| chr2 | 115918267 | 115921372 | 3106 | 207 | 0.392 | 0.085 | hyper | SmallDMR: 48 | lossOfBoundary |
| chr6 | 6002294 | 6005227 | 2934 | 197 | 0.414 | 0.124 | hyper | SmallDMR: 549 | other |
| chr17 | 1959436 | 1962815 | 3380 | 333 | 0.359 | 0.109 | hyper | SmallDMR: 137 | boundaryShift |
| chr2 | 5830537 | 5834912 | 4376 | 324 | 0.277 | 0.221 | hyper | SmallDMR: 61 | lossOfBoundary |
| chr2 | 193058020 | 193061739 | 3720 | 190 | 0.324 | 0.101 | hyper | SmallDMR: 166 | lossOfBoundary |
| chr2 | 119913025 | 119916999 | 3975 | 272 | 0.303 | 0.164 | hyper | SmallDMR: 114 | boundaryShift |
| chr10 | 129533359 | 129537556 | 4198 | 279 | 0.284 | 0.22 | hyper | SmallDMR: 157 | boundaryShift |
| chr12 | 111470562 | 111474977 | 4416 | 272 | 0.263 | 0.089 | hyper | SmallDMR: 69 | lossOfBoundary |
| chr16 | 56224046 | 56228744 | 4699 | 252 | 0.247 | 0.096 | hyper | SmallDMR: 96 | other |
| chr7 | 136552959 | 136556557 | 3599 | 191 | 0.321 | 0.209 | hyper | SmallDMR: 398 | other |
| chr16 | 86598833 | 86602750 | 3918 | 324 | 0.294 | 0.15 | hyper | SmallDMR: 122 | other |
| chr8 | 77593058 | 77596382 | 3325 | 146 | 0.346 | 0.111 | hyper | SmallDMR: 702 | other |
| chr2 | 213400355 | 213404526 | 4172 | 228 | 0.275 | 0.087 | hyper | SmallDMR: 117 | lossOfBoundary |
| chr20 | 54577883 | 54581285 | 3403 | 213 | 0.335 | 0.261 | hyper | SmallDMR: 200 | lossOfBoundary |
| chr1 | 119548395 | 119551319 | 2925 | 199 | 0.389 | 0.122 | hyper | SmallDMR: 330 | other |
| chr2 | 154727485 | 154730720 | 3236 | 146 | 0.351 | 0.178 | hyper | SmallDMR: 267 | lossOfBoundary |
| chr7 | 15724433 | 15728177 | 3745 | 154 | 0.302 | 0.111 | hyper | SmallDMR: 382 | boundaryShift |
| chr3 | 192125431 | 192128625 | 3195 | 208 | 0.353 | 0.105 | hyper | SmallDMR: 70 | lossOfBoundary |

TABLE 7-continued

Partial list of small DMRs. Details, including column descriptions, are included in the Supplementary Methods. -Loss of boundary

| Chromosome | Start | End | Length (bp) | Number of Covered CpGs | Mean Difference in DMR (Normal to Cancer) | Mean Normal Methylation in DMR | Direction of Methylation Change | DMR Identifier # | Type of small DMR |
|---|---|---|---|---|---|---|---|---|---|
| chr7 | 155255369 | 155259176 | 3808 | 98 | 0.295 | 0.2 | hyper | SmallDMR: 3031 | other |
| chr1 | 114694766 | 114698574 | 3809 | 244 | 0.294 | 0.13 | hyper | SmallDMR: 54 | lossOfBoundary |
| chr13 | 109147076 | 109149637 | 2562 | 151 | 0.435 | 0.183 | hyper | SmallDMR: 167 | lossOfBoundary |
| chr16 | 69105495 | 69108076 | 2582 | 24 | −0.431 | 0.815 | hypo | SmallDMR: 3410 | novelMethylation |
| chr1 | 57887008 | 57890941 | 3934 | 231 | 0.282 | 0.104 | hyper | SmallDMR: 192 | lossOfBoundary |
| chr8 | 128752277 | 128754623 | 2347 | 37 | −0.47 | 0.769 | hypo | SmallDMR: 2746 | other |
| chr3 | 184628231 | 184630670 | 2440 | 26 | −0.451 | 0.806 | hypo | SmallDMR: 3211 | novelMethylation |
| chr3 | 6901652 | 6905259 | 3608 | 170 | 0.304 | 0.178 | hyper | SmallDMR: 414 | lossOfBoundary |
| chr2 | 239754875 | 239758481 | 3607 | 317 | 0.304 | 0.165 | hyper | SmallDMR: 28 | lossOfBoundary |
| chr13 | 37004036 | 37007372 | 3337 | 186 | 0.326 | 0.241 | hyper | SmallDMR: 187 | lossOfBoundary |
| chr10 | 125851090 | 125854029 | 2940 | 252 | 0.37 | 0.054 | hyper | SmallDMR: 60 | boundaryShift |
| chr11 | 17740109 | 17743884 | 3776 | 271 | 0.287 | 0.178 | hyper | SmallDMR: 94 | lossOfBoundary |
| chr10 | 83633120 | 83636930 | 3811 | 245 | 0.284 | 0.14 | hyper | SmallDMR: 86 | other |
| chr5 | 127871927 | 127875163 | 3237 | 218 | 0.334 | 0.189 | hyper | SmallDMR: 72 | lossOfBoundary |
| chr20 | 25063432 | 25065910 | 2479 | 142 | 0.436 | 0.166 | hyper | SmallDMR: 911 | other |
| chr7 | 24322944 | 24325427 | 2484 | 150 | 0.435 | 0.149 | hyper | SmallDMR: 274 | lossOfBoundary |
| chr13 | 35514882 | 35518317 | 3436 | 156 | 0.314 | 0.053 | hyper | SmallDMR: 143 | lossOfBoundary |
| chr11 | 20690107 | 20693192 | 3086 | 180 | 0.348 | 0.102 | hyper | SmallDMR: 150 | other |
| chr8 | 132051575 | 132055090 | 3516 | 253 | 0.304 | 0.239 | hyper | SmallDMR: 83 | lossOfBoundary |
| chr8 | 72468356 | 72471549 | 3194 | 166 | 0.334 | 0.117 | hyper | SmallDMR: 742 | lossOfBoundary |
| chr7 | 3339234 | 3342464 | 3231 | 247 | 0.33 | 0.065 | hyper | SmallDMR: 21 | boundaryShift |
| chr2 | 235933204 | 235936653 | 3450 | 91 | −0.308 | 0.651 | hypo | SmallDMR: 1770 | novelMethylation |
| chr20 | 24449386 | 24452209 | 2824 | 216 | 0.376 | 0.081 | hyper | SmallDMR: 35 | lossOfBoundary |
| chr10 | 28033400 | 28036407 | 3008 | 213 | 0.351 | 0.097 | hyper | SmallDMR: 193 | other |
| chr8 | 85094124 | 85097366 | 3243 | 150 | 0.325 | 0.13 | hyper | SmallDMR: 510 | boundaryShift |
| chr12 | 24714149 | 24717242 | 3094 | 165 | 0.34 | 0.041 | hyper | SmallDMR: 145 | other |
| chr11 | 27739449 | 27744983 | 5535 | 248 | 0.19 | 0.118 | hyper | SmallDMR: 133 | other |
| chr22 | 26062312 | 26065156 | 2845 | 27 | −0.369 | 0.753 | hypo | SmallDMR: 3690 | other |
| chr1 | 34628535 | 34632537 | 4003 | 244 | 0.262 | 0.064 | hyper | SmallDMR: 162 | boundaryShift |
| chr8 | 65281163 | 65284678 | 3516 | 189 | 0.298 | 0.189 | hyper | SmallDMR: 484 | other |
| chr8 | 24812925 | 24816381 | 3457 | 206 | 0.303 | 0.09 | hyper | SmallDMR: 215 | other |
| chr20 | 50720243 | 50722807 | 2565 | 159 | 0.408 | 0.098 | hyper | SmallDMR: 565 | lossOfBoundary |
| chr18 | 5544506 | 5548672 | 4167 | 25 | −0.251 | 0.711 | hypo | SmallDMR: 10088 | other |
| chr6 | 10881682 | 10884891 | 3210 | 123 | 0.324 | 0.255 | hyper | SmallDMR: 954 | other |
| chr10 | 100991745 | 100996944 | 5200 | 219 | 0.2 | 0.177 | hyper | SmallDMR: 270 | boundaryShift |
| chr11 | 128562106 | 128565519 | 3414 | 217 | 0.303 | 0.083 | hyper | SmallDMR: 211 | other |
| chr3 | 128210180 | 128212550 | 2371 | 175 | 0.435 | 0.115 | hyper | SmallDMR: 658 | other |
| chr13 | 39260101 | 39262646 | 2546 | 144 | 0.405 | 0.096 | hyper | SmallDMR: 130 | boundaryShift |
| chr18 | 25754857 | 25758958 | 4102 | 290 | 0.251 | 0.061 | hyper | SmallDMR: 113 | lossOfBoundary |
| chr12 | 72664965 | 72668243 | 3279 | 220 | 0.313 | 0.143 | hyper | SmallDMR: 169 | lossOfBoundary |
| chr4 | 62065454 | 62069488 | 4035 | 260 | 0.254 | 0.129 | hyper | SmallDMR: 120 | lossOfBoundary |
| chr6 | 118227570 | 118230205 | 2636 | 217 | 0.388 | 0.063 | hyper | SmallDMR: 31 | lossOfBoundary |
| chr8 | 140714169 | 140718258 | 4090 | 294 | 0.25 | 0.103 | hyper | SmallDMR: 65 | other |
| chr7 | 157476522 | 157478768 | 2247 | 197 | 0.455 | 0.126 | hyper | SmallDMR: 262 | other |

TABLE 8

Genomic features of Differentially Methylated Regions (DMRs) in colon cancer.

| | N | # CpG | Genomic size | Median size (bp) | Overlap with islands | Overlap with shores | Overlap with Refseq mRNA TSS |
|---|---|---|---|---|---|---|---|
| Normal genome (reference) | N/A | 28.2M | 3.10 Gb | N/A | 27.7K | 55.4K | 36,983 |
| Hypomethylated blocks | 13,540 | 16.2M | 1.95 Gb | 39,412 | 17.6% | 26.8% | 10,453 |
| Hypermethylated blocks | 2,871 | 485K | 35.8 Mb | 9,213 | 13.4% | 36.4% | 976 |
| Hypomethylated small DMRs | 4,315 | 59.5K | 2.91 Mb | 401 | 2.2% | 51.0% | 1,708 |
| Novel hypomethylated | 448 | 8.35K | 367 Kb | 658 | 2.9% | 19.9% | 30 |
| Shift of methylation boundary | 1,516 | 17.5K | 741 Kb | 261 | 2.1% | 92.8% | 1,313 |
| Hypermethylated small DMRs | 5,810 | 403K | 6.14 Mb | 820 | 67.2% | 17.0% | 3,068 |
| Loss of boundary* | 1,756 | 165K | 2.36 Mb | 1,159 | 80.9% | 3.4% | 1,091 |
| Shift of methylation boundary | 1,774 | 96.3K | 1.40 Mb | 502 | 60.3% | 33.0% | 1,027 |

*As described in the text, loss of boundary DMRs were associated with increase of methylation in the CpG island and a decrease of methylation in the adjacent shore. These were scored as a single event and classify them here since there are more CpGs in the islands than in the shores.

TABLE 9

The overlap of various genomic domains with differentially methylated regions in colon cancer.

| Genomic domain | Size (in GB) | Size (in millions of CpGs) | Overlap with blocks (in GB) | Overlap with blocks (in millions of CpGs) | Odds Ratio |
|---|---|---|---|---|---|
| Repeats | 1.45 | 14.8 | 1.04 GB | 9.33 | 1.4 |
| PMDs | 1.23 | 10.0 | 1.14 GB | 8.45 | 6.5 |
| LOCKs | 0.77 | 5.8 | 697 MB | 5.06 | 6.8 |
| LADs | 1.14 | 8.6 | 989 MB | 7.10 | 4.9 |

The size of genomic domains are shown in column 1 in gigabases and column 2 in number of CpGs. Column 3 shows the overlap in gigabases and Column 4 in number of CpGs. Column 5 shows the observed to expected by chance odds ratio. All the overlaps were statistically significant ($p < 2.2 \times 10\sim^{16}$).

TABLE 10

Enrichment of hypervariably methylated loci identified by the custom Illumina array in blocks identified by bisulfite sequencing.

| | Hypervariable CpGs in all tissue types (custom array) | | Non-variably methylated |
|---|---|---|---|
| | Hypo-methylated | Hyper-methylated | CpGs in colon cancer (Illumina 27k) |
| Number of CpGs | 81 | 52 | 16,049 |
| Inside Hypomethylated Blocks | 63% | 4% | 13% |
| Inside Hypermethylated Blocks | 5% | 37% | 2% |

TABLE 11

Methylation values* observed in CpG islands in cancer compared to normal samples.

| Methylation status in normals | Total | Hypo | No change | Hyper |
|---|---|---|---|---|
| Unmethylated (<=0.2) | 16184 | 0.1% | 83.2% | 16.7% |
| Partial methylated (>=0.2, <=0.8) | 4796 | 17.0% | 46.7% | 36.3% |
| Methylated (>=0.8) | 5527 | 24.0% | 75.9% | 0.1% |

*Average methylation value in each island were then averaged across subject for cancer and normal samples separately

TABLE 12

Gene expression negatively correlates with methylation in small DMRs.

| | Associated Genes | Inversely correlated genes | Percent Inverse correlated |
|---|---|---|---|
| Shift of boundary (hypomethylated) | 2,273 | 1,192 | 52% |
| Novel hypomethylation | 38 | 17 | 45% |
| Other hypomethylated | 442 | 192 | 43% |
| Shift of boundary (hypermethylation) | 1,893 | 532 | 30% |
| Loss of regulation (hypermethylation) | 1,119 | 346 | 31% |
| Other hypermethylated | 1,204 | 335 | 28% |

Each gene represented in a microarray experiment was mapped to the closest small DMR, with a gene and a DMR considered associated if the DMR was within 2 kbp from the transcription start site of the gene; 6,869 genes were mapped and are represented in the table. For each of the small DMR classes, as defined in main text, the number of associated genes that were differentially expressed (FDR < 0.05) and had an inverse relationship was computed.

TABLE 13

Gene ontology enrichment analysis of differentially expressed genes associated with hypomethyiated boundary shifts.

| Gene ontology term | Expected count | Count | Size | Odds ratio | P-value | Q-value |
|---|---|---|---|---|---|---|
| Mitotic cell cycle | 11.6 | 31 | 185 | 3.1 | 3.8 × 10''' | 0.00036 |
| Cell cycle process | 18.7 | 42 | 297 | 2.6 | 5.4 × 10''' | 0.00036 |
| Mitosis | 9.9 | 25 | 157 | 2.9 | 1.5 × 10* | 0.006 |
| Positive regulation of ubiquitin-protein ligase activity during mitotic cell cycle | 3.9 | 14 | 61 | 4.5 | $2.0 \times 10''^{5}$ | 0.0071 |
| Organelle fission | 13.7 | 30 | 216 | 2.5 | $3.6 \times 10''^{b}$ | 0.0097 |

The differentially expressed genes comparing colon cancer samples to normal samples were divided into two groups: those associated hypomethyiated boundary shifts and the rest. The table shows the five categories with statistically significant enrichment (FDRO.01).

TABLE 14

List of genes showing statistically significant over-expression in cancer compared to normal samples and are within 2,000 bp from an outward methylation boundary shift.

| geneName | methDiff | diffExp | qvalue | chr | strand | txStart | txEnd |
|---|---|---|---|---|---|---|---|
| QPCT | −0.287228151 | 2.754401680 | 1.28E−19 | chr2 | 1 | 37571717 | 37600465 |
| ANLN | −0.386314449 | 2.412402373 | 3.29E−13 | chr7 | 1 | 36429415 | 36493400 |
| SLC6A6 | −0.277217014 | 2.372018352 | 2.61E−17 | chr3 | 1 | 14444076 | 14530857 |
| CEP55 | −0.401964569 | 2.249352145 | 7.03E−14 | chr10 | 1 | 95256389 | 95288849 |
| ANLN | −0.386314449 | 2.121207986 | 5.50E−14 | chr7 | 1 | 36429415 | 36493400 |
| TGFBI | −0.387333797 | 2.083655423 | 2.69E−17 | chr5 | 1 | 135364584 | 135399506 |
| ME1 | −0.239140622 | 2.064347685 | 1.07E−11 | chr6 | −1 | 83920108 | 84140790 |
| TRIP13 | −0.391690922 | 1.852594706 | 3.17E−18 | chr5 | 1 | 892758 | 918235 |
| CTPS | −0.283453124 | 1.845547869 | 7.21E−17 | chr1 | 1 | 41445007 | 41478235 |
| ME1 | −0.239140622 | 1.836087668 | 6.29E−13 | chr6 | −1 | 83920108 | 84140790 |
| HELLS | −0.481250286 | 1.786723981 | 7.81E−16 | chr10 | 1 | 96305574 | 96361856 |
| CCNB1 | −0.344279127 | 1.720916748 | 5.09E−10 | chr5 | 1 | 68462837 | 68474072 |
| MET | −0.464402149 | 1.713620728 | 2.19E−25 | chr7 | 1 | 116312446 | 116438440 |
| TRIP6 | −0.311643639 | 1.612698985 | 9.99E−19 | chr7 | 1 | 100464760 | 100471076 |
| | −0.265818173 | 1.584054427 | 3.42E−09 | chr6 | 1 | 31913486 | 31919861 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| IL20RA | −0.326941415 | 1.574006752 | 5.92E−13 | chr6 | −1 | 137321108 | 137366101 |
| TTK | −0.365969645 | 1.554795792 | 5.04E−10 | chr6 | 1 | 80714322 | 80752244 |
| CDK1 | −0.349676581 | 1.554401898 | 2.32E−16 | chr10 | 1 | 62538212 | 62554610 |
| PRC1 | −0.278283026 | 1.553574908 | 3.00E−14 | chr15 | −1 | 91509275 | 91537749 |
| CCNB1 | −0.344279127 | 1.550393107 | 8.02E−14 | chr5 | 1 | 68462837 | 68474072 |
| CDCA2 | −0.264275049 | 1.548451703 | 1.88E−12 | chr8 | 1 | 25316513 | 25365436 |
| ARG2 | −0.353923274 | 1.539462883 | 8.15E−10 | chr14 | 1 | 68086579 | 68118437 |
| PHF19 | −0.410901232 | 1.504592686 | 1.06E−17 | chr9 | −1 | 123617977 | 123639606 |
| SLC6A6 | −0.277217014 | 1.467899072 | 4.24E−13 | chr3 | 1 | 14444076 | 14530857 |
| TK1 | −0.225975437 | 1.465582264 | 1.35E−16 | chr17 | −1 | 76170160 | 76183314 |
| CDK1 | −0.349676581 | 1.462604059 | 1.32E−12 | chr10 | 1 | 62538212 | 62554610 |
| C12orf48 | −0.315593006 | 1.454752076 | 3.05E−11 | chr12 | 1 | 102513956 | 102591298 |
| LRRC6 | −0.254379418 | 1.438052039 | 3.03E−19 | chr8 | −1 | 133584449 | 133687813 |
| CDKN3 | −0.296939585 | 1.437015156 | 1.43E−12 | chr14 | 1 | 54863673 | 54886936 |
| MET | −0.464402149 | 1.432662311 | 1.03E−12 | chr7 | 1 | 116312446 | 116438440 |
| CDKN3 | −0.296939585 | 1.426456138 | 3.41E−13 | chr14 | 1 | 54863673 | 54886936 |
| ITGA2 | −0.273672477 | 1.424782914 | 1.79E−16 | chr5 | 1 | 52285156 | 52390609 |
| GART | −0.265804362 | 1.422971299 | 4.70E−12 | chr21 | −1 | 34876238 | 34915148 |
| KPNA2 | −0.325507566 | 1.420135526 | 7.43E−16 | chr17 | 1 | 66031848 | 66042969 |
| MET | −0.464402149 | 1.409380516 | 1.96E−13 | chr7 | 1 | 116312446 | 116438440 |
| FAM57A | −0.258171163 | 1.405422919 | 7.77E−14 | chr17 | 1 | 635798 | 646074 |
| CDK1 | −0.349676581 | 1.404039029 | 1.58E−11 | chr10 | 1 | 62538212 | 62554610 |
| GPT2 | −0.302235264 | 1.397275797 | 9.65E−14 | chr16 | 1 | 46918290 | 46965201 |
| PDCD2L | −0.244419742 | 1.395394063 | 2.78E−20 | chr19 | 1 | 34895303 | 34917070 |
| C12orf48 | −0.315593006 | 1.384890241 | 6.99E−12 | chr12 | 1 | 102513956 | 102591298 |
| SLC39A10 | −0.242261524 | 1.362347636 | 1.03E−12 | chr2 | 1 | 196521471 | 196602426 |
| HOXB6 | −0.391990817 | 1.360310033 | 7.76E−08 | chr17 | −1 | 46673114 | 46682354 |
| MET | −0.464402149 | 1.353903556 | 7.36E−14 | chr7 | 1 | 116312446 | 116438440 |
| DHFRP1 | −0.33197287 | 1.333474721 | 1.13E−11 | chr5 | −1 | 79922047 | 79950802 |
| | −0.33891476 | 1.309093323 | 1.48E−17 | chr2 | 1 | 173940442 | 174131511 |
| ERO1L | −0.337054537 | 1.300900638 | 9.09E−13 | chr14 | −1 | 53106634 | 53162423 |
| FERMT1 | −0.270407533 | 1.292003455 | 1.24E−19 | chr20 | −1 | 6055492 | 6104191 |
| MOCOS | −0.26317804 | 1.285728037 | 3.95E−07 | chr18 | 1 | 33767482 | 33852120 |
| GART | −0.265804362 | 1.265297033 | 1.52E−16 | chr21 | −1 | 34876238 | 34915148 |
| FERMT1 | −0.270407533 | 1.258010636 | 5.17E−18 | chr20 | −1 | 6055492 | 6104191 |
| C1orf59 | −0.269034512 | 1.256263577 | 3.98E−15 | chr1 | −1 | 109190917 | 109204148 |
| CENPH | −0.258617525 | 1.255179781 | 4.77E−11 | chr5 | 1 | 68485375 | 68506184 |
| RUVBL1 | −0.261371583 | 1.250774746 | 3.25E−18 | chr3 | −1 | 127799803 | 127842667 |
| FBXO5 | −0.274244427 | 1.250044053 | 6.75E−10 | chr6 | −1 | 153291664 | 153304153 |
| SPNS2 | −0.26292891 | 1.24910284 | 2.34E−15 | chr17 | 1 | 4402129 | 4443228 |
| SLC22A3 | −0.419938177 | 1.232083732 | 1.63E−08 | chr6 | 1 | 160769300 | 160873613 |
| SCD | −0.412561336 | 1.23021566 | 9.78E−06 | chr10 | 1 | 102106877 | 102116367 |
| C13orf37 | −0.282975063 | 1.227299642 | 1.53E−13 | chr13 | −1 | 73282495 | 73301825 |
| TK1 | −0.225975437 | 1.215067193 | 9.23E−16 | chr17 | −1 | 76170160 | 76183314 |
| ODC1 | −0.42700535 | 1.211699492 | 2.39E−14 | chr2 | −1 | 10580094 | 10588630 |
| PLK4 | −0.310709849 | 1.195732188 | 1.21E−10 | chr4 | 1 | 128802016 | 128820350 |
| BYSL | −0.306448506 | 1.193699275 | 1.33E−19 | chr6 | 1 | 41888926 | 41900784 |
| ASPM | −0.315933748 | 1.185003139 | 4.09E−08 | chr1 | −1 | 197053258 | 197115824 |
| FERMT1 | −0.270407533 | 1.158992882 | 2.40E−15 | chr20 | −1 | 6055492 | 6104191 |
| GMDS | −0.299511508 | 1.156279571 | 9.93E−16 | chr6 | −1 | 1624041 | 2245915 |
| SHMT2 | −0.240887472 | 1.152051089 | 3.60E−14 | chr12 | 1 | 57623519 | 57628509 |
| C7orf68 | −0.427832848 | 1.152003901 | 2.58E−18 | chr7 | 1 | 128095903 | 128097978 |
| C7orf68 | −0.427832848 | 1.137362258 | 1.25E−19 | chr7 | 1 | 128095903 | 128097978 |
| GMDS | −0.299511508 | 1.123033393 | 9.02E−18 | chr6 | −1 | 1624041 | 2245915 |
| TIMELESS | −0.30942338 | 1.118520353 | 2.14E−14 | chr12 | −1 | 56810158 | 56843200 |
| KPNA2 | −0.325507566 | 1.114430687 | 5.01E−14 | chr17 | 1 | 66031848 | 66042969 |
| RAB23 | −0.340951531 | 1.100310587 | 1.56E−09 | chr6 | −1 | 57054597 | 57086205 |
| AURKA | −0.293961713 | 1.099330524 | 1.24E−11 | chr20 | −1 | 54944446 | 54967261 |
| TACC3 | −0.267804701 | 1.087928887 | 1.23E−12 | chr4 | 1 | 1723266 | 1746898 |
| SQLE | −0.412483745 | 1.08596534 | 7.33E−07 | chr8 | 1 | 126010720 | 126034525 |
| NUP37 | −0.315593006 | 1.085282612 | 2.67E−17 | chr12 | −1 | 102467975 | 102512361 |
| CTHRC1 | −0.324284535 | 1.081056474 | 3.24E−05 | chr8 | 1 | 104383743 | 104395221 |
| RTEL1 | −0.24942297 | 1.069116794 | 9.01E−08 | chr20 | 1 | 62290756 | 62330051 |
| NUFIP1 | −0.272420763 | 1.068531277 | 6.09E−16 | chr13 | −1 | 45513384 | 45563618 |
| PLK1 | −0.269395632 | 1.065948279 | 3.60E−11 | chr16 | 1 | 23690143 | 23701688 |
| C12orf29 | −0.327535911 | 1.064878076 | 6.83E−10 | chr12 | 1 | 88429290 | 88443935 |
| CEP76 | −0.224568396 | 1.054054095 | 1.44E−07 | chr18 | −1 | 12672631 | 12702773 |
| DTYMK | −0.259366156 | 1.052061774 | 6.56E−17 | chr2 | −1 | 242615157 | 242626406 |
| PHF19 | −0.410901232 | 1.042169399 | 4.29E−17 | chr9 | −1 | 123631865 | 123639466 |
| RAD18 | −0.294092376 | 1.040826053 | 2.11E−07 | chr3 | −1 | 8918760 | 9005186 |
| SCD | −0.412561336 | 1.040246085 | 5.54E−06 | chr10 | 1 | 102106881 | 102124591 |
| RAB23 | −0.340951531 | 1.029194137 | 4.06E−11 | chr6 | −1 | 57053607 | 57087078 |
| YAP1 | −0.260585002 | 1.02763996 | 4.63E−09 | chr11 | 1 | 101981210 | 102104154 |
| GSTP1 | −0.335937288 | 1.024251451 | 6.99E−17 | chr11 | 1 | 67351066 | 67354131 |
| NOLC1 | −0.384383152 | 1.020987106 | 5.90E−14 | chr10 | 1 | 103912117 | 103923623 |
| DTYMK | −0.259366156 | 1.012686833 | 2.20E−15 | chr2 | −1 | 242615157 | 242626406 |
| PLEK2 | −0.320540707 | 1.006985665 | 6.83E−14 | chr14 | −1 | 67853702 | 67878828 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| SHMT2 | −0.240887472 | 1.006656875 | 2.45E−17 | chr12 | 1 | 57623519 | 57628509 |
| CEP76 | −0.224568396 | 1.004572951 | 1.07E−10 | chr18 | −1 | 12672631 | 12702773 |
| PLK4 | −0.310709849 | 1.002496079 | 8.78E−08 | chr4 | 1 | 128802016 | 128820350 |
| JAG1 | −0.207653553 | 0.998751445 | 3.94E−10 | chr20 | −1 | 10618332 | 10654608 |
| PKM2 | −0.26154852 | 0.991259837 | 1.30E−11 | chr15 | −1 | 72491373 | 72523328 |
| NKD1 | −0.323367141 | 0.990807307 | 9.53E−10 | chr16 | 1 | 50582241 | 50670647 |
| AURKA | −0.293961713 | 0.990673621 | 5.51E−11 | chr20 | −1 | 54944446 | 54967261 |
| FGGY | −0.275459464 | 0.990581427 | 5.38E−13 | chr1 | 1 | 59762663 | 60228402 |
| SHMT2 | −0.240887472 | 0.989026812 | 6.19E−14 | chr12 | 1 | 57623519 | 57628509 |
| FBXO22OS | −0.249605837 | 0.987940737 | 4.95E−15 | chr15 | 1 | 76196200 | 76227609 |
| SNORD118 | −0.269386914 | 0.983977501 | 4.91E−07 | chr17 | −1 | 8076296 | 8079714 |
| DPCD | −0.218924523 | 0.982360775 | 7.55E−14 | chr10 | 1 | 103348045 | 103369425 |
| AHCY | −0.273213996 | 0.980581533 | 1.87E−18 | chr20 | −1 | 32868074 | 32891154 |
| FZD6 | −0.265219075 | 0.978554009 | 1.15E−11 | chr8 | 1 | 104311100 | 104345087 |
| CDCA2 | −0.264275049 | 0.977693264 | 1.32E−11 | chr8 | 1 | 25316513 | 25365436 |
| WARS2 | −0.214976156 | 0.974056434 | 1.76E−11 | chr1 | −1 | 119573839 | 119683271 |
| MTHFD2 | −0.43988327 | 0.971127387 | 2.68E−13 | chr2 | 1 | 74425689 | 74444692 |
| PGM2L1 | −0.340496727 | 0.965882382 | 8.09E−11 | chr11 | −1 | 74041361 | 74109502 |
| WDHD1 | −0.221635494 | 0.960208966 | 4.74E−10 | chr14 | −1 | 55405668 | 55493795 |
| FHL2 | −0.370777923 | 0.949510686 | 6.20E−11 | chr2 | −1 | 105974169 | 106016124 |
| PGM2L1 | −0.340496727 | 0.940564013 | 1.46E−08 | chr11 | −1 | 74041361 | 74109502 |
| FBXO5 | −0.274244427 | 0.935975694 | 5.50E−10 | chr6 | −1 | 153291664 | 153304153 |
| SQLE | −0.412483745 | 0.934244029 | 3.81E−07 | chr8 | 1 | 126010720 | 126034525 |
| IL20RA | −0.326941415 | 0.931939035 | 1.39E−14 | chr6 | −1 | 137321108 | 137366101 |
| FASN | −0.307722725 | 0.924131378 | 5.66E−11 | chr17 | −1 | 80036215 | 80056106 |
| ABHD2 | −0.335157092 | 0.920873632 | 3.46E−05 | chr15 | 1 | 89631405 | 89745591 |
| KIAA1704 | −0.272420763 | 0.918447128 | 5.26E−10 | chr13 | 1 | 45563687 | 45602405 |
| GART | −0.265804362 | 0.918196342 | 1.56E−15 | chr21 | −1 | 34876238 | 34915148 |
| NOLC1 | −0.384383152 | 0.914043684 | 1.03E−14 | chr10 | 1 | 103912117 | 103923623 |
| FBXO22OS | −0.249605837 | 0.909039543 | 1.93E−10 | chr15 | 1 | 76196200 | 76227609 |
| | −0.33891476 | 0.907054142 | 9.74E−06 | chr2 | 1 | 173940570 | 174091874 |
| VANGL1 | −0.35350898 | 0.906722654 | 1.11E−09 | chr1 | 1 | 116184612 | 116236312 |
| IMMP2L | −0.34514707 | 0.905774603 | 6.28E−17 | chr7 | −1 | 110303110 | 111202347 |
| NKD1 | −0.323367141 | 0.905103602 | 9.77E−08 | chr16 | 1 | 50582241 | 50670647 |
| ZYX | −0.307434113 | 0.902904178 | 9.58E−11 | chr7 | 1 | 143078173 | 143088204 |
| ABHD2 | −0.335157092 | 0.900969804 | 3.31E−07 | chr15 | 1 | 89631405 | 89745591 |
| FBXO22OS | −0.249605837 | 0.900721794 | 1.66E−09 | chr15 | 1 | 76196200 | 76227609 |
| ENAH | −0.297371742 | 0.899092283 | 9.76E−15 | chr1 | −1 | 225680538 | 225840844 |
| INCENP | −0.296869408 | 0.896357006 | 9.14E−06 | chr11 | 1 | 61891445 | 61920635 |
| LACTB2 | −0.399766137 | 0.894630027 | 2.34E−09 | chr8 | −1 | 71549501 | 71581447 |
| ALDH7A1 | −0.296044325 | 0.891523928 | 7.01E−13 | chr5 | −1 | 125877533 | 125931110 |
| ITGA2 | −0.273672477 | 0.889972605 | 3.79E−14 | chr5 | 1 | 52285156 | 52390609 |
| SCD | −0.412561336 | 0.881962999 | 3.65E−05 | chr10 | 1 | 102106881 | 102124591 |
| DHFRP1 | −0.33197287 | 0.881776578 | 8.37E−11 | chr5 | −1 | 79922047 | 79950802 |
| BAX | −0.426714351 | 0.880411505 | 6.30E−07 | chr19 | 1 | 49458134 | 49465055 |
| LACTB2 | −0.399766137 | 0.875181214 | 5.88E−05 | chr8 | −1 | 71549501 | 71581447 |
| MRPS17 | −0.389012137 | 0.873580896 | 2.82E−14 | chr7 | 1 | 56019512 | 56024192 |
| ENO1 | −0.319058202 | 0.872725187 | 1.15E−10 | chr1 | −1 | 8921061 | 8938749 |
| C12orf5 | −0.380595644 | 0.872649011 | 1.95E−07 | chr12 | 1 | 4430359 | 4469188 |
| ERCC8 | −0.28157772 | 0.870429148 | 1.91E−06 | chr5 | −1 | 60169659 | 60240878 |
| PGD | −0.241805413 | 0.864482413 | 4.20E−13 | chr1 | 1 | 10459137 | 10480201 |
| IPO7 | −0.428150813 | 0.862597647 | 1.00E−17 | chr11 | 1 | 9406169 | 9469673 |
| RPP25 | −0.361427208 | 0.858972588 | 2.49E−08 | chr15 | −1 | 75247443 | 75249775 |
| NUP35 | −0.392937687 | 0.858359924 | 2.99E−09 | chr2 | 1 | 183989083 | 184026408 |
| FAM175A | −0.267694635 | 0.85802511 | 8.44E−06 | chr4 | −1 | 84382092 | 84406334 |
| PHLDA2 | −0.34276695 | 0.857310418 | 1.42E−07 | chr11 | −1 | 2949503 | 2950685 |
| MEST | −0.306641166 | 0.856733533 | 1.71E−13 | chr7 | 1 | 130126046 | 130146133 |
| NOP58 | −0.431871435 | 0.855922392 | 2.94E−16 | chr2 | 1 | 203130439 | 203168389 |
| GLRX3 | −0.468137547 | 0.855536417 | 4.57E−14 | chr10 | 1 | 131934663 | 131977888 |
| C1orf135 | −0.251930519 | 0.854987468 | 2.00E−11 | chr1 | −1 | 26160497 | 26185903 |
| C17orf75 | −0.282147578 | 0.853046303 | 1.95E−09 | chr17 | −1 | 30658392 | 30669189 |
| IPO7 | −0.428150813 | 0.85180088 | 3.80E−17 | chr11 | 1 | 9406169 | 9469673 |
| XPO5 | −0.290308924 | 0.85027956 | 1.62E−14 | chr6 | −1 | 43490072 | 43543812 |
| YAP1 | −0.260585002 | 0.8470295 | 3.52E−11 | chr11 | 1 | 101981210 | 102104154 |
| WARS2 | −0.214976156 | 0.845887997 | 5.42E−06 | chr1 | −1 | 119573839 | 119683271 |
| DUS4L | −0.239778252 | 0.845173583 | 1.74E−11 | chr7 | 1 | 107204403 | 107218906 |
| ERO1L | −0.337054537 | 0.844206961 | 2.66E−08 | chr14 | −1 | 53106634 | 53162423 |
| NANP | −0.265582678 | 0.841562243 | 6.12E−13 | chr20 | −1 | 25593571 | 25604811 |
| DNAJC2 | −0.335527424 | 0.840151967 | 5.99E−15 | chr7 | −1 | 102952921 | 102985113 |
| XPO5 | −0.290308924 | 0.838685895 | 2.55E−15 | chr6 | −1 | 43490072 | 43543812 |
| NOLC1 | −0.384383152 | 0.838656605 | 1.11E−12 | chr10 | 1 | 103912117 | 103923623 |
| PPAP2C | −0.241595108 | 0.838211159 | 1.56E−10 | chr19 | −1 | 281048 | 291435 |
| HSPD1 | −0.365274716 | 0.829443889 | 2.30E−13 | chr2 | −1 | 198351305 | 198364771 |
| | −0.33891476 | 0.829083868 | 2.87E−06 | chr2 | 1 | 173940570 | 174091874 |
| EPT1 | −0.286072226 | 0.828758101 | 3.04E−06 | chr2 | 1 | 26568982 | 26618759 |
| C14orf126 | −0.429259277 | 0.824406285 | 5.07E−05 | chr14 | −1 | 31915242 | 31926670 |
| GNPNAT1 | −0.412868705 | 0.822945344 | 1.59E−14 | chr14 | −1 | 53241912 | 53258319 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| PDXK | −0.451405538 | 0.821714738 | 2.26E−13 | chr21 | 1 | 45138978 | 45182188 |
| EPHA1 | −0.279704626 | 0.820944361 | 1.01E−12 | chr7 | −1 | 143088205 | 143105985 |
| | −0.33891476 | 0.819965659 | 1.20E−06 | chr2 | 1 | 173940570 | 174091874 |
| L2HGDH | −0.234782015 | 0.818880596 | 1.55E−10 | chr14 | −1 | 50712120 | 50778947 |
| PTPLAD1 | −0.27257057 | 0.816192599 | 5.85E−09 | chr15 | 1 | 65822825 | 65870693 |
| TOMM34 | −0.299060249 | 0.814773814 | 1.83E−19 | chr20 | −1 | 43570771 | 43589127 |
| CTSH | −0.301656861 | 0.813029733 | 2.03E−06 | chr15 | −1 | 79213400 | 79237433 |
| PUS1 | −0.291126169 | 0.812913155 | 2.32E−11 | chr12 | 1 | 132413813 | 132428404 |
| RSL1D1 | −0.31776943 | 0.809676853 | 1.51E−16 | chr16 | −1 | 11931196 | 11945442 |
| TBC1D7 | −0.327292622 | 0.805149062 | 6.80E−11 | chr6 | −1 | 13305183 | 13328763 |
| TIMM50 | −0.263467531 | 0.800544699 | 1.21E−15 | chr19 | 1 | 39971052 | 39981528 |
| MCFD2 | −0.291486921 | 0.800187491 | 8.42E−10 | chr2 | −1 | 47129013 | 47143007 |
| DNAJC9 | −0.362712454 | 0.79566698 | 1.29E−12 | chr10 | −1 | 75002582 | 75008620 |
| TBRG4 | −0.352890468 | 0.791795428 | 6.00E−19 | chr7 | −1 | 45139699 | 45151317 |
| ALDH7A1 | −0.296044325 | 0.79032756 | 8.34E−11 | chr5 | −1 | 125877533 | 125931110 |
| GCSH | −0.453192502 | 0.787464518 | 9.88E−14 | chr16 | −1 | 81115566 | 81130008 |
| CAMSAP1 | −0.232304633 | 0.785972505 | 1.87E−07 | chr9 | −1 | 138700333 | 138799070 |
| JAG1 | −0.207653553 | 0.785933601 | 4.58E−10 | chr20 | −1 | 10618332 | 10654608 |
| CDK7 | −0.34382059 | 0.783249994 | 5.44E−13 | chr5 | 1 | 68530700 | 68573250 |
| NSUN4 | −0.390831198 | 0.778904391 | 1.25E−13 | chr1 | 1 | 46805849 | 46827863 |
| IPO7 | −0.428150813 | 0.775002569 | 4.64E−15 | chr11 | 1 | 9406169 | 9469673 |
| TROAP | −0.329360048 | 0.770726977 | 3.08E−13 | chr12 | 1 | 49716971 | 49725514 |
| ZMYND19 | −0.276199921 | 0.770129623 | 2.80E−13 | chr9 | −1 | 140476531 | 140484942 |
| C1orf135 | −0.251930519 | 0.768989781 | 7.16E−11 | chr1 | −1 | 26160497 | 26185903 |
| GEMIN5 | −0.309935801 | 0.768826256 | 7.49E−11 | chr5 | −1 | 154266976 | 154317769 |
| MKLN1 | −0.285004864 | 0.762718997 | 2.22E−09 | chr7 | 1 | 131012619 | 131181395 |
| SHB | −0.337673042 | 0.760275993 | 1.17E−08 | chr9 | −1 | 37919131 | 38069208 |
| SKA2 | −0.223170945 | 0.757405762 | 1.35E−05 | chr17 | −1 | 57187308 | 57232800 |
| TNFRSF10A | −0.384420552 | 0.757083317 | 9.22E−06 | chr8 | −1 | 23048064 | 23082639 |
| CKLF | −0.238225994 | 0.756641822 | 1.88E−11 | chr16 | 1 | 66586470 | 66599975 |
| CKS1B | −0.255490761 | 0.756314088 | 3.28E−11 | chr1 | 1 | 154947159 | 154951160 |
| NDUFAF2 | −0.28157772 | 0.756215701 | 1.06E−14 | chr5 | 1 | 60240956 | 60448853 |
| PTPLAD1 | −0.27257057 | 0.754993736 | 1.07E−13 | chr15 | 1 | 65822825 | 65870693 |
| PDXK | −0.451405538 | 0.753333567 | 3.50E−10 | chr21 | 1 | 45138978 | 45182188 |
| RFWD3 | −0.300370479 | 0.751685588 | 1.36E−09 | chr16 | −1 | 74655297 | 74700779 |
| ZC3H8 | −0.269560486 | 0.749208926 | 1.40E−10 | chr2 | −1 | 112973254 | 113012688 |
| NUBPL | −0.389729092 | 0.748925872 | 6.70E−09 | chr14 | 1 | 32030591 | 32330399 |
| ENAH | −0.297371742 | 0.747939499 | 1.99E−09 | chr1 | −1 | 225680538 | 225840844 |
| DDX56 | −0.233165466 | 0.746717992 | 7.36E−15 | chr7 | −1 | 44605016 | 44613601 |
| VANGL1 | −0.35350898 | 0.746078634 | 6.34E−13 | chr1 | 1 | 116184612 | 116236312 |
| UCHL3 | −0.298552217 | 0.744844024 | 5.16E−16 | chr13 | 1 | 76123927 | 76180069 |
| ICA1 | −0.256836172 | 0.74182404 | 2.25E−11 | chr7 | −1 | 8152814 | 8301911 |
| C5orf34 | −0.339621872 | 0.740748574 | 1.74E−10 | chr5 | −1 | 43486803 | 43515247 |
| POLH | −0.290308924 | 0.737584811 | 4.09E−09 | chr6 | 1 | 43543887 | 43583397 |
| JAG1 | −0.207653553 | 0.736825006 | 8.03E−10 | chr20 | −1 | 10618332 | 10654608 |
| IPO7 | −0.428150813 | 0.73656029 | 1.19E−11 | chr11 | 1 | 9406169 | 9469673 |
| ACP1 | −0.243372223 | 0.736343968 | 4.11E−10 | chr2 | 1 | 264872 | 278283 |
| CCT4 | −0.378022827 | 0.733078592 | 1.79E−16 | chr2 | −1 | 62095224 | 62115939 |
| WEE1 | −0.307311914 | 0.73299823 | 2.85E−08 | chr11 | 1 | 9595430 | 9611531 |
| HIBADH | −0.435762995 | 0.732515757 | 2.30E−08 | chr7 | −1 | 27565061 | 27702614 |
| YAP1 | −0.260585002 | 0.72843054 | 2.88E−12 | chr11 | 1 | 101981210 | 102104154 |
| DHFRP1 | −0.33197287 | 0.727823904 | 2.32E−10 | chr5 | −1 | 79922047 | 79950802 |
| FAM161A | −0.256344752 | 0.727276263 | 3.08E−07 | chr2 | −1 | 62051991 | 62081278 |
| EXOC6 | −0.394254414 | 0.727205205 | 2.92E−08 | chr10 | 1 | 94608277 | 94819247 |
| NUFIP1 | −0.272420763 | 0.724642728 | 1.47E−10 | chr13 | −1 | 45513384 | 45563618 |
| PTPLAD1 | −0.27257057 | 0.72301388 | 1.88E−13 | chr15 | 1 | 65822825 | 65870693 |
| ST7OT3 | −0.478497425 | 0.722972073 | 1.81E−10 | chr7 | 1 | 116593396 | 116870157 |
| GART | −0.265804362 | 0.722463568 | 3.05E−06 | chr21 | −1 | 34896316 | 34914420 |
| GTF3C3 | −0.354411257 | 0.720907079 | 9.26E−11 | chr2 | −1 | 197627756 | 197664425 |
| FAM128A | −0.245234229 | 0.720094937 | 3.73E−14 | chr2 | −1 | 132241533 | 132249995 |
| ICA1 | −0.256836172 | 0.719314832 | 1.84E−10 | chr7 | −1 | 8152814 | 8301911 |
| BAX | −0.426714351 | 0.717540312 | 2.04E−06 | chr19 | 1 | 49458134 | 49465055 |
| ENO1 | −0.319058202 | 0.716641772 | 2.86E−14 | chr1 | −1 | 8921061 | 8938749 |
| SUSD1 | −0.322450196 | 0.715526839 | 2.46E−12 | chr9 | −1 | 114803065 | 114937465 |
| SKIL | −0.332370272 | 0.715182799 | 0.000149056 | chr3 | 1 | 170077411 | 170111651 |
| SLC6A6 | −0.277217014 | 0.714295976 | 2.30E−08 | chr3 | 1 | 14444076 | 14530857 |
| UBE3C | −0.265141265 | 0.714147489 | 1.31E−05 | chr7 | 1 | 156931607 | 157062066 |
| MTHFD2 | −0.43988327 | 0.713674028 | 1.51E−08 | chr2 | 1 | 74425689 | 74444692 |
| METTL5 | −0.344642797 | 0.711769057 | 1.99E−15 | chr2 | −1 | 170668267 | 170681424 |
| C7orf44 | −0.31688192 | 0.710412079 | 1.24E−09 | chr7 | −1 | 43678856 | 43769088 |
| NAA38 | −0.28832537 | 0.70683953 | 1.44E−10 | chr7 | 1 | 117824086 | 117832878 |
| PSMDI2 | −0.248429065 | 0.706839498 | 2.82E−11 | chr17 | −1 | 65334032 | 65362743 |
| UBA2 | −0.333463383 | 0.704795848 | 9.21E−17 | chr19 | 1 | 34919268 | 34960795 |
| INTS2 | −0.31571998 | 0.703832765 | 6.97E−08 | chr17 | −1 | 59942735 | 60005377 |
| SCD | −0.412561336 | 0.701871865 | 1.04E−05 | chr10 | 1 | 102106881 | 102124591 |
| ZYX | −0.307434113 | 0.701046775 | 1.48E−09 | chr7 | 1 | 143078173 | 143088204 |
| C12orf45 | −0.340238462 | 0.700170696 | 7.29E−13 | chr12 | 1 | 105380098 | 105388505 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| PHF19 | −0.410901232 | 0.699152416 | 1.46E−15 | chr9 | −1 | 123617977 | 123639606 |
| PTPLAD1 | −0.27257057 | 0.693142858 | 2.79E−16 | chr15 | 1 | 65822825 | 65870693 |
| CCT8 | −0.286031759 | 0.69055968 | 8.33E−15 | chr21 | −1 | 30428645 | 30446118 |
| GTPBP10 | −0.279762111 | 0.689791718 | 9.64E−10 | chr7 | 1 | 89975979 | 90015204 |
| POLR3K | −0.216414146 | 0.686340216 | 8.08E−12 | chr16 | −1 | 96407 | 103628 |
| ZNF200 | −0.352071153 | 0.685460602 | 7.58E−07 | chr16 | −1 | 3272325 | 3285175 |
| DCLRE1A | −0.273346942 | 0.683924106 | 2.36E−11 | chr10 | −1 | 115594488 | 115614142 |
| CSTF3 | −0.245463178 | 0.683219717 | 5.67E−05 | chr11 | −1 | 33106137 | 33183037 |
| CKLF | −0.238225994 | 0.682582084 | 3.39E−09 | chr16 | 1 | 66586470 | 66599975 |
| MAP3K8 | −0.28698722 | 0.682293632 | 6.32E−06 | chr10 | 1 | 30722866 | 30750762 |
| C12orf29 | −0.327535911 | 0.679763512 | 1.21E−07 | chr12 | 1 | 88429290 | 88443935 |
| POLR1D | −0.338281428 | 0.677608966 | 1.64E−14 | chr13 | 1 | 28194903 | 28197589 |
| | −0.33891476 | 0.676454786 | 5.43E−09 | chr2 | 1 | 173940687 | 174132738 |
| C14orf126 | −0.429259277 | 0.676041167 | 2.66E−08 | chr14 | −1 | 31915242 | 31926670 |
| DHFRP1 | −0.33197287 | 0.675947124 | 8.21E−07 | chr5 | −1 | 79922047 | 79950802 |
| CCT5 | −0.247574331 | 0.674240944 | 6.29E−13 | chr5 | 1 | 10250033 | 10266524 |
| POLH | −0.290308924 | 0.671436242 | 8.55E−10 | chr6 | 1 | 43543887 | 43583397 |
| FPGS | −0.280832452 | 0.670652282 | 3.18E−14 | chr9 | 1 | 130565154 | 130576343 |
| GCSH | −0.453192502 | 0.668277808 | 3.59E−11 | chr16 | −1 | 81115566 | 81130008 |
| ATP5S | −0.234782015 | 0.668167795 | 9.47E−10 | chr14 | 1 | 50779047 | 50792668 |
| THEM4 | −0.305755807 | 0.665088298 | 5.75E−08 | chr1 | −1 | 151846060 | 151882284 |
| VANGL1 | −0.35350898 | 0.660771307 | 4.81E−08 | chr1 | 1 | 116184612 | 116236312 |
| GSG2 | −0.315820574 | 0.660724489 | 7.72E−13 | chr17 | 1 | 3627197 | 3629993 |
| PXMP2 | −0.249805307 | 0.6604927 | 2.01E−12 | chr12 | 1 | 133287436 | 133297414 |
| CAMSAP1 | −0.232304633 | 0.65983507 | 2.37E−09 | chr9 | −1 | 138700333 | 138799070 |
| ORMDL2 | −0.26193862 | 0.658369238 | 2.64E−11 | chr12 | 1 | 56211806 | 56214959 |
| C16orf55 | −0.29431772 | 0.658029078 | 4.68E−10 | chr16 | 1 | 89724152 | 89737675 |
| ABHD2 | −0.335157092 | 0.653696306 | 0.003173566 | chr15 | 1 | 89631405 | 89745591 |
| ABHD2 | −0.335157092 | 0.653593114 | 3.49E−05 | chr15 | 1 | 89631405 | 89745591 |
| MRPS28 | −0.221999518 | 0.653297973 | 1.23E−08 | chr8 | −1 | 80831098 | 80942506 |
| KDM1A | −0.338954726 | 0.652790447 | 4.34E−13 | chr1 | 1 | 23345941 | 23410182 |
| PDCD11 | −0.264875391 | 0.651431565 | 2.14E−14 | chr10 | 1 | 105156405 | 105206049 |
| C17orf79 | −0.294507305 | 0.648892607 | 2.08E−16 | chr17 | −1 | 30178883 | 30186256 |
| WEE1 | −0.307311914 | 0.64758364 | 4.79E−09 | chr11 | 1 | 9595430 | 9611531 |
| PDF | −0.259372491 | 0.646134845 | 1.24E−15 | chr16 | −1 | 69360816 | 69373513 |
| LRSAM1 | −0.226251329 | 0.645026571 | 3.85E−09 | chr9 | 1 | 130213784 | 130265778 |
| TNFRSF10A | −0.384420552 | 0.644106779 | 2.33E−10 | chr8 | −1 | 23048064 | 23082639 |
| C16orf88 | −0.272202349 | 0.641570896 | 1.77E−12 | chr16 | −1 | 19717676 | 19726362 |
| PLK4 | −0.310709849 | 0.64050983 | 4.03E−08 | chr4 | 1 | 128802016 | 128820350 |
| DPCD | −0.218924523 | 0.640383481 | 3.65E−14 | chr10 | 1 | 103348045 | 103369425 |
| KIAA0895 | −0.386314449 | 0.639717652 | 5.70E−08 | chr7 | −1 | 36363830 | 36429734 |
| DDX55 | −0.261862563 | 0.636292468 | 2.73E−09 | chr12 | 1 | 124086672 | 124105480 |
| GPHN | −0.351868464 | 0.635572263 | 9.51E−09 | chr14 | 1 | 66974125 | 67648515 |
| WDR36 | −0.308089573 | 0.630736331 | 2.57E−06 | chr5 | 1 | 110427414 | 110469906 |
| CKLF | −0.238225994 | 0.628995779 | 6.08E−10 | chr16 | 1 | 66586470 | 66599975 |
| SRD5A1 | −0.316238694 | 0.62671946 | 4.38E−05 | chr5 | 1 | 6633456 | 6669675 |
| C6orf223 | −0.349827072 | 0.625261279 | 9.74E−10 | chr6 | 1 | 43968337 | 43972877 |
| WDHD1 | −0.221635494 | 0.622503019 | 5.83E−07 | chr14 | −1 | 55405668 | 55493795 |
| SRD5A1 | −0.316238694 | 0.617079084 | 1.94E−06 | chr5 | 1 | 6633456 | 6669675 |
| | −0.379767127 | 0.616780661 | 4.66E−09 | chr2 | 1 | 172864490 | 172947158 |
| CSNK1E | −0.238834552 | 0.615545315 | 8.09E−09 | chr22 | −1 | 38686697 | 38714089 |
| UCHL5 | −0.229547693 | 0.615538747 | 5.89E−05 | chr1 | −1 | 192987535 | 193028539 |
| HSPD1 | −0.365274716 | 0.61459242 | 2.08E−16 | chr2 | −1 | 198351305 | 198364771 |
| SNORD118 | −0.269386914 | 0.614360801 | 1.52E−07 | chr17 | −1 | 8076296 | 8079714 |
| RANGRF | −0.256581556 | 0.613634074 | 4.54E−08 | chr17 | 1 | 8191989 | 8193403 |
| OAS3 | −0.263601714 | 0.613097041 | 0.000497052 | chr12 | 1 | 113376157 | 113411050 |
| EEPD1 | −0.381673022 | 0.612662004 | 1.49E−10 | chr7 | 1 | 36192758 | 36341152 |
| AARSD1 | −0.280574719 | 0.610173181 | 6.33E−13 | chr17 | −1 | 41102543 | 41132020 |
| PRPF19 | −0.313924275 | 0.610127959 | 5.74E−10 | chr11 | −1 | 60658220 | 60674056 |
| ACP1 | −0.243372223 | 0.609269112 | 1.34E−13 | chr2 | 1 | 264869 | 278283 |
| RAB23 | −0.340951531 | 0.607435566 | 0.000229489 | chr6 | −1 | 57053607 | 57087078 |
| GALK2 | −0.238084648 | 0.606353291 | 1.58E−09 | chr15 | 1 | 49447976 | 49622002 |
| BBS2 | −0.340697293 | 0.603768681 | 3.23E−07 | chr16 | −1 | 56518366 | 56554195 |
| SHB | −0.337673042 | 0.603407422 | 1.31E−09 | chr9 | −1 | 37919131 | 38069208 |
| TALDO1 | −0.391999756 | 0.602516825 | 3.62E−12 | chr11 | 1 | 747329 | 765024 |
| SLC27A2 | −0.29609587 | 0.600128428 | 4.53E−07 | chr15 | 1 | 50474394 | 50528592 |
| XPO5 | −0.290308924 | 0.600041308 | 1.76E−15 | chr6 | −1 | 43490072 | 43543812 |
| SNORD118 | −0.269386914 | 0.598972912 | 1.03E−06 | chr17 | −1 | 8076296 | 8079714 |
| SLC27A2 | −0.29609587 | 0.597913672 | 7.12E−06 | chr15 | 1 | 50474394 | 50528592 |
| CENPO | −0.275635182 | 0.596829371 | 6.28E−07 | chr2 | 1 | 25016014 | 25045245 |
| DBR1 | −0.293045877 | 0.595369328 | 0.000125338 | chr3 | −1 | 137879854 | 137893791 |
| TUBGCP4 | −0.329918509 | 0.594748243 | 2.94E−07 | chr15 | 1 | 43663293 | 43698238 |
| PSMC3IP | −0.218053908 | 0.594210465 | 1.78E−07 | chr17 | −1 | 40724329 | 40729747 |
| GTF3C3 | −0.354411257 | 0.594098695 | 4.75E−06 | chr2 | −1 | 197627756 | 197664425 |
| PCBD2 | −0.351750876 | 0.593958149 | 5.27E−08 | chr5 | 1 | 134240596 | 134296967 |
| CSNK1E | −0.238834552 | 0.592596824 | 3.95E−12 | chr22 | −1 | 38694096 | 38713413 |
| DAK | −0.337915954 | 0.592201232 | 2.25E−11 | chr11 | 1 | 61100654 | 61116230 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| SKIL | −0.332370272 | 0.589717331 | 8.30E−08 | chr3 | 1 | 170075514 | 170110536 |
| MMACHC | −0.311345645 | 0.589154662 | 8.98E−08 | chr1 | 1 | 45965725 | 45976739 |
| HSPE1 | −0.365274716 | 0.589092028 | 7.19E−11 | chr2 | 1 | 198364718 | 198368181 |
| HNRNPD | −0.270498972 | 0.588962608 | 2.22E−06 | chr4 | −1 | 83273651 | 83295109 |
| EEPD1 | −0.381673022 | 0.5881191 | 2.96E−09 | chr7 | 1 | 36192758 | 36341152 |
| KARS | −0.361111606 | 0.588087532 | 7.38E−12 | chr16 | −1 | 75661622 | 75681577 |
| NMI | −0.401380326 | 0.587311241 | 1.38E−09 | chr2 | −1 | 152126979 | 152146571 |
| CSTF3 | −0.245463178 | 0.585854628 | 1.22E−08 | chr11 | −1 | 33106137 | 33183037 |
| PLBD1 | −0.318699032 | 0.584355958 | 3.96E−06 | chr12 | −1 | 14656597 | 14720791 |
| TUBA4A | −0.335331285 | 0.583464283 | 4.65E−08 | chr2 | −1 | 220114433 | 220118754 |
| ANAPC7 | −0.358004942 | 0.582975355 | 0.000285228 | chr12 | −1 | 110813276 | 110841535 |
| RABEPK | −0.32443941 | 0.580856648 | 1.46E−11 | chr9 | 1 | 127962882 | 127996334 |
| USP18 | −0.352213294 | 0.576400343 | 0.000134886 | chr22 | 1 | 18632666 | 18660164 |
| CSTF1 | −0.293961713 | 0.576301697 | 1.70E−06 | chr20 | 1 | 54967450 | 54979518 |
| SRPK2 | −0.301338383 | 0.576069908 | 2.27E−05 | chr7 | −1 | 104756823 | 105029341 |
| GPHN | −0.351868464 | 0.575370798 | 3.47E−06 | chr14 | 1 | 66974125 | 67648515 |
| RAB15 | −0.275394533 | 0.574973153 | 1.31E−06 | chr14 | −1 | 65412532 | 65438875 |
| SLC48A1 | −0.243259292 | 0.574186473 | 1.81E−11 | chr12 | 1 | 48166991 | 48176536 |
| PHB | −0.271234016 | 0.570779776 | 2.66E−13 | chr17 | −1 | 47481414 | 47492242 |
| GLRX3 | −0.468137547 | 0.569271144 | 9.83E−14 | chr10 | 1 | 131934663 | 131978640 |
| THEM4 | −0.305755807 | 0.567911313 | 2.03E−08 | chr1 | −1 | 151846060 | 151882284 |
| PSMC2 | −0.335527424 | 0.567378112 | 3.29E−13 | chr7 | 1 | 102985361 | 103009842 |
| RAD18 | −0.294092376 | 0.566055082 | 1.34E−08 | chr3 | −1 | 8918760 | 9005186 |
| ASPSCR1 | −0.429796139 | 0.565948199 | 9.92E−09 | chr17 | 1 | 79935426 | 79975280 |
| FLVCR1 | −0.328081085 | 0.564259882 | 0.000216633 | chr1 | 1 | 213031597 | 213072705 |
| PDCD11 | −0.264875391 | 0.563950729 | 2.64E−13 | chr10 | 1 | 105156405 | 105206049 |
| C13orf34 | −0.282975063 | 0.563850235 | 2.24E−05 | chr13 | 1 | 73302064 | 73330318 |
| SDCCAG3 | −0.252078076 | 0.563677408 | 1.29E−10 | chr9 | −1 | 139296377 | 139305061 |
| CAMSAP1 | −0.232304633 | 0.563552316 | 6.26E−10 | chr9 | −1 | 138700333 | 138799070 |
| HIBADH | −0.435762995 | 0.563421604 | 1.48E−09 | chr7 | −1 | 27565061 | 27702614 |
| SNORD118 | −0.269386914 | 0.562529551 | 5.45E−05 | chr17 | −1 | 8076296 | 8079714 |
| SHB | −0.337673042 | 0.562519134 | 1.74E−08 | chr9 | −1 | 37919131 | 38069208 |
| SPC24 | −0.293998387 | 0.561276565 | 2.40E−09 | chr19 | −1 | 11256170 | 11266458 |
| PSMD1 | −0.289671601 | 0.560442291 | 5.62E−08 | chr2 | 1 | 231921578 | 232037541 |
| KIAA0319 | −0.293263452 | 0.560086475 | 3.06E−07 | chr6 | −1 | 24544335 | 24646383 |
| AARS | −0.450373223 | 0.559649047 | 1.53E−08 | chr16 | −1 | 70286290 | 70323409 |
| THEM4 | −0.305755807 | 0.558859828 | 1.16E−07 | chr1 | −1 | 151846060 | 151882284 |
| KIAA1324 | −0.344894338 | 0.558749164 | 8.48E−05 | chr1 | 1 | 109656729 | 109745853 |
| PERP | −0.420881809 | 0.557602481 | 5.89E−12 | chr6 | −1 | 138411923 | 138428648 |
| PPP2R1B | −0.269985557 | 0.556957945 | 8.20E−05 | chr11 | −1 | 111597632 | 111637169 |
| SAAL1 | −0.305825846 | 0.556790357 | 1.68E−08 | chr11 | −1 | 18101893 | 18127638 |
| BLVRA | −0.385001907 | 0.556720097 | 0.001013 | chr7 | 1 | 43798279 | 43846938 |
| WDR5B | −0.27939038 | 0.556270901 | 5.77E−09 | chr3 | −1 | 122130715 | 122134882 |
| MAP7 | −0.232419099 | 0.556258136 | 1.51E−10 | chr6 | −1 | 136663875 | 136871646 |
| KARS | −0.361111606 | 0.556208481 | 2.59E−14 | chr16 | −1 | 75661622 | 75681577 |
| G2E3 | −0.281280373 | 0.555054321 | 4.91E−05 | chr14 | 1 | 31028364 | 31089269 |
| RAB15 | −0.275394533 | 0.552892366 | 2.21E−06 | chr14 | −1 | 65412532 | 65438875 |
| COPS2 | −0.238084648 | 0.552774759 | 3.12E−10 | chr15 | −1 | 49417473 | 49447854 |
| JHDM1D | −0.36915146 | 0.552690772 | 9.23E−05 | chr7 | −1 | 139784546 | 139876835 |
| TNFRSF10A | −0.384420552 | 0.552397645 | 1.81E−08 | chr8 | −1 | 23048064 | 23082639 |
| PERP | −0.420881809 | 0.552162584 | 3.12E−07 | chr6 | −1 | 138411923 | 138428648 |
| CCDC77 | −0.243970997 | 0.551616519 | 3.47E−06 | chr12 | 1 | 510742 | 551811 |
| DAP3 | −0.3152206 | 0.5514731 | 3.17E−10 | chr1 | 1 | 155658849 | 155708801 |
| ZNF643 | −0.295962761 | 0.550135812 | 7.09E−08 | chr1 | 1 | 40916716 | 40929390 |
| ABHD2 | −0.335157092 | 0.549133592 | 0.00095956 | chr15 | 1 | 89631405 | 89745591 |
| NSUN2 | −0.316238694 | 0.547973307 | 1.07E−08 | chr5 | −1 | 6599352 | 6633404 |
| LRRC2 | −0.24589671 | 0.545930975 | 4.28E−05 | chr3 | −1 | 46556913 | 46608040 |
| TARS | −0.325532408 | 0.545403969 | 4.90E−11 | chr5 | 1 | 33440802 | 33468038 |
| HSPD1 | −0.365274716 | 0.545028989 | 9.50E−09 | chr2 | −1 | 198351305 | 198364771 |
| UBXN10 | −0.339943828 | 0.545015477 | 0.000237589 | chr1 | 1 | 20512578 | 20522541 |
| KLHDC5 | −0.250846871 | 0.54386595 | 5.97E−08 | chr12 | 1 | 27933187 | 27955972 |
| MRPL16 | −0.309271189 | 0.542900113 | 4.97E−11 | chr11 | −1 | 59573612 | 59578345 |
| TGEBR2 | −0.323538725 | 0.542447072 | 6.66E−06 | chr3 | 1 | 30647994 | 30735626 |
| F3 | −0.316302039 | 0.541670859 | 1.79E−05 | chr1 | −1 | 94994781 | 95007356 |
| G2E3 | −0.281280373 | 0.540537962 | 4.57E−05 | chr14 | 1 | 31028364 | 31089269 |
| G2E3 | −0.281280373 | 0.540499443 | 4.34E−05 | chr14 | 1 | 31028364 | 31089269 |
| SLC48A1 | −0.243259292 | 0.539334496 | 8.38E−13 | chr12 | 1 | 48166991 | 48176536 |
| BLVRA | −0.385001907 | 0.538601989 | 0.000539254 | chr7 | 1 | 43798279 | 43846938 |
| C2orf15 | −0.287652418 | 0.538425806 | 2.93E−06 | chr2 | 1 | 99797542 | 99814089 |
| PGM2L1 | −0.340496727 | 0.537717149 | 1.93E−08 | chr11 | −1 | 74041361 | 74109502 |
| MAP7 | −0.232419099 | 0.535524202 | 3.31E−10 | chr6 | −1 | 136663875 | 136871646 |
| WDR36 | −0.308089573 | 0.533711417 | 4.59E−06 | chr5 | 1 | 110427414 | 110469906 |
| UBE3C | −0.265141265 | 0.53369635 | 2.72E−07 | chr7 | 1 | 156931607 | 157062066 |
| G2E3 | −0.281280373 | 0.533312322 | 0.000430128 | chr14 | 1 | 31028364 | 31089269 |
| POLQ | −0.344922003 | 0.532851832 | 1.71E−06 | chr3 | −1 | 121150278 | 121264853 |
| RIF1 | −0.333349128 | 0.532243411 | 0.000275302 | chr2 | 1 | 152266397 | 152331902 |
| SLC2A8 | −0.332165555 | 0.532082027 | 2.22E−09 | chr9 | 1 | 130159421 | 130170177 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| IDE | −0.323456458 | 0.530349431 | 8.90E−05 | chr10 | −1 | 94211441 | 94333833 |
| IDE | −0.323456458 | 0.527778534 | 8.94E−06 | chr10 | −1 | 94211441 | 94333833 |
| FAM175A | −0.267694635 | 0.527678846 | 8.93E−05 | chr4 | −1 | 84382092 | 84406334 |
| ADRM1 | −0.375468714 | 0.525209562 | 5.28E−10 | chr20 | 1 | 60878061 | 60883918 |
| SMPD4 | −0.374036738 | 0.523732921 | 3.13E−10 | chr2 | −1 | 130908981 | 130939166 |
| MSH3 | −0.33197287 | 0.52223272 | 1.97E−06 | chr5 | 1 | 79950467 | 80172279 |
| NENF | −0.26975275 | 0.521863544 | 2.26E−10 | chr1 | 1 | 212606229 | 212619714 |
| ESF1 | −0.253283591 | 0.521398107 | 0.000347678 | chr20 | −1 | 13694969 | 13765532 |
| RNMTL1 | −0.390282429 | 0.520492511 | 4.85E−11 | chr17 | 1 | 685513 | 695749 |
| NAA16 | −0.466228772 | 0.519873768 | 1.55E−06 | chr13 | 1 | 41885341 | 41951166 |
| TROAP | −0.329360048 | 0.519505155 | 3.18E−08 | chr12 | 1 | 49716971 | 49725514 |
| DDX50 | −0.41851803 | 0.518688101 | 1.26E−10 | chr10 | 1 | 70661034 | 70706603 |
| POLH | −0.290308924 | 0.516497497 | 2.30E−06 | chr6 | 1 | 43543887 | 43583397 |
| CEP57 | −0.236391887 | 0.515608821 | 2.49E−05 | chr11 | 1 | 95523642 | 95565854 |
| SQLE | −0.412483745 | 0.515297147 | 9.81E−06 | chr8 | 1 | 126010720 | 126034525 |
| HNRNPA3 | −0.345567093 | 0.514475268 | 2.48E−08 | chr2 | 1 | 178077291 | 178084813 |
| SERBP1 | −0.29363511 | 0.513845306 | 9.16E−11 | chr1 | −1 | 67873493 | 67896098 |
| PATL1 | −0.267856683 | 0.513761723 | 1.32E−07 | chr11 | −1 | 59404194 | 59436511 |
| NARF | −0.327711968 | 0.513555641 | 8.18E−11 | chr17 | 1 | 80416540 | 80446141 |
| UTP23 | −0.374374515 | 0.512941457 | 0.000967853 | chr8 | 1 | 117778742 | 117786923 |
| EIF2A | −0.341781166 | 0.512176892 | 2.46E−13 | chr3 | 1 | 150264481 | 150302029 |
| DNAJC15 | −0.306451735 | 0.512159081 | 5.87E−06 | chr13 | 1 | 43597339 | 43683045 |
| CCIAD2 | −0.368241675 | 0.511834242 | 1.65E−07 | chr4 | −1 | 48887036 | 48908845 |
| GLS2 | −0.369251024 | 0.511815027 | 9.12E−07 | chr12 | −1 | 56864736 | 56882181 |
| EXTL2 | −0.246561032 | 0.5117553 | 1.09E−05 | chr1 | −1 | 101337943 | 101361554 |
| NIP7 | −0.259372491 | 0.509836595 | 0.000103073 | chr16 | 1 | 69373343 | 69377014 |
| ERGIC2 | −0.316674815 | 0.509704344 | 1.46E−07 | chr12 | −1 | 29493601 | 29534143 |
| GNPDA1 | −0.38158971 | 0.509463122 | 1.90E−09 | chr5 | −1 | 141380234 | 141392596 |
| NIP7 | −0.259372491 | 0.509384558 | 1.20E−06 | chr16 | 1 | 69373343 | 69377014 |
| ACLY | −0.31253498 | 0.509338512 | 2.67E−06 | chr17 | −1 | 40023161 | 40075240 |
| C19orf20 | −0.283915594 | 0.5082567 | 2.14E−06 | chr19 | 1 | 507497 | 519423 |
| CARS2 | −0.279867021 | 0.507573136 | 4.90E−10 | chr13 | −1 | 111293787 | 111358485 |
| DEAF1 | −0.256741648 | 0.506175515 | 4.41E−09 | chr11 | −1 | 644225 | 695047 |
| PYCRL | −0.292749271 | 0.506005001 | 8.75E−09 | chr8 | −1 | 144686229 | 144691784 |
| NCBP2 | −0.35437085 | 0.505677709 | 1.12E−07 | chr3 | −1 | 196662278 | 196669468 |
| EXOC6 | −0.394254414 | 0.505488218 | 1.56E−09 | chr10 | 1 | 94608277 | 94819247 |
| MIOS | −0.309348638 | 0.505485258 | 1.18E−07 | chr7 | 1 | 7606503 | 7647127 |
| PMPCA | −0.252078076 | 0.504592963 | 1.43E−11 | chr9 | 1 | 139305112 | 139318213 |
| FAM188B | −0.365084074 | 0.504093174 | 1.07E−09 | chr7 | 1 | 30811033 | 30932002 |
| RPL12 | −0.226251329 | 0.504038829 | 2.68E−15 | chr9 | −1 | 130209953 | 130213684 |
| ABHD2 | −0.335157092 | 0.503105943 | 1.87E−05 | chr15 | 1 | 89631405 | 89745591 |
| ERCC8 | −0.28157772 | 0.502902619 | 7.80E−08 | chr5 | −1 | 60169659 | 60240878 |
| EIF3G | −0.292801028 | 0.50208106 | 6.02E−13 | chr19 | −1 | 10225690 | 10230599 |
| RPL12 | −0.226251329 | 0.501680489 | 1.47E−13 | chr9 | −1 | 130209953 | 130213684 |
| FUT10 | −0.255860029 | 0.500133393 | 7.96E−06 | chr8 | −1 | 33228342 | 33330664 |
| SARNP | −0.26193862 | 0.49998192 | 2.31E−08 | chr12 | −1 | 56146247 | 56211540 |
| RNF24 | −0.283461559 | 0.498475347 | 3.84E−09 | chr20 | −1 | 3912068 | 3996036 |
| NENF | −0.26975275 | 0.497927553 | 3.13E−09 | chr1 | 1 | 212606229 | 212619714 |
| HSD3B7 | −0.20314982 | 0.497791955 | 8.86E−09 | chr16 | 1 | 30996532 | 31000473 |
| FAT1 | −0.290272493 | 0.497178271 | 7.11E−08 | chr4 | −1 | 187508937 | 187645009 |
| PATL1 | −0.267856683 | 0.496677553 | 8.77E−08 | chr11 | −1 | 59404194 | 59436511 |
| PATL1 | −0.267856683 | 0.496018831 | 7.54E−07 | chr11 | −1 | 59404194 | 59436511 |
| MYO6 | −0.43883682 | 0.493770242 | 4.95E−09 | chr6 | 1 | 76458926 | 76626329 |
| RNF24 | −0.283461559 | 0.493276553 | 4.34E−09 | chr20 | −1 | 3912068 | 3996036 |
| EBPL | −0.364898082 | 0.491023884 | 1.63E−10 | chr13 | −1 | 50234862 | 50265611 |
| SAR1A | −0.349589716 | 0.488254276 | 3.95E−05 | chr10 | −1 | 71909960 | 71930279 |
| RPL12 | −0.226251329 | 0.488070209 | 8.37E−15 | chr9 | −1 | 130209953 | 130213684 |
| RWDD2B | −0.329455475 | 0.48547073 | 5.22E−10 | chr21 | −1 | 30376705 | 30391699 |
| HMGCS1 | −0.296054138 | 0.48520563 | 0.026796939 | chr5 | −1 | 43289497 | 43313595 |
| DHX30 | −0.356915978 | 0.484514643 | 5.69E−09 | chr3 | 1 | 47844418 | 47891683 |
| TGFBR2 | −0.323538725 | 0.483851636 | 7.60E−09 | chr3 | 1 | 30647994 | 30735626 |
| PCYT2 | −0.261073405 | 0.48298277 | 1.54E−10 | chr17 | −1 | 79862092 | 79869294 |
| DPY19L4 | −0.354808816 | 0.48269307 | 1.53E−05 | chr8 | 1 | 95732103 | 95806076 |
| METFL13 | −0.251305655 | 0.482391769 | 1.45E−12 | chr1 | 1 | 171750822 | 171766857 |
| ANGEL2 | −0.386058099 | 0.482231251 | 0.000348994 | chr1 | −1 | 213165524 | 213189168 |
| SNRNP70 | −0.352072025 | 0.481756432 | 2.30E−06 | chr19 | 1 | 49588465 | 49611869 |
| HNRNPU | −0.307777645 | 0.481442138 | 8.09E−07 | chr1 | −1 | 245014468 | 245027844 |
| MYEOV | −0.477263493 | 0.4794864 | 3.63E−05 | chr11 | 1 | 69061622 | 69064753 |
| GLS | −0.260544126 | 0.478984396 | 0.004847239 | chr2 | 1 | 191745560 | 191800015 |
| NUFIP1 | −0.272420763 | 0.476234013 | 2.43E−05 | chr13 | −1 | 45513384 | 45563618 |
| QRSL1 | −0.385770406 | 0.47593703 | 7.41E−07 | chr6 | 1 | 107077453 | 107116292 |
| WHSC2 | −0.329016517 | 0.474360834 | 3.15E−08 | chr4 | −1 | 1984441 | 2011837 |
| IFT122 | −0.326575154 | 0.472953894 | 1.15E−08 | chr3 | 1 | 129158968 | 129239194 |
| PSMC6 | −0.25403134 | 0.472037128 | 8.04E−08 | chr14 | 1 | 53173890 | 53195305 |
| STAT1 | −0.350388411 | 0.471996848 | 0.011723869 | chr2 | −1 | 191840263 | 191878894 |
| PSMD1 | −0.289671601 | 0.471330535 | 5.17E−11 | chr2 | 1 | 231921578 | 232037541 |
| SRPK2 | −0.301338383 | 0.471067024 | 0.000251176 | chr7 | −1 | 104756823 | 105029341 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| PSMD4 | −0.258106107 | 0.470437047 | 7.03E−10 | chr1 | 1 | 151227179 | 151239955 |
| FBXO45 | −0.228407257 | 0.470374179 | 3.92E−07 | chr3 | 1 | 196295559 | 196315930 |
| ANAPC7 | −0.358004942 | 0.466614689 | 3.64E−13 | chr12 | −1 | 110811283 | 110841535 |
| PDXK | −0.451405538 | 0.462928243 | 3.75E−11 | chr21 | 1 | 45138978 | 45182188 |
| TWSG1 | −0.325962433 | 0.461428286 | 0.019144724 | chr18 | 1 | 9334765 | 9402418 |
| DHX30 | −0.356915978 | 0.460971725 | 5.79E−09 | chr3 | 1 | 47844418 | 47891683 |
| CGREF1 | −0.258522541 | 0.45945758 | 4.50E−05 | chr2 | −1 | 27323466 | 27341971 |
| LRSAM1 | −0.226251329 | 0.459400767 | 1.45E−08 | chr9 | 1 | 130213784 | 130265778 |
| VPS13C | −0.315743995 | 0.45901679 | 2.17E−10 | chr15 | −1 | 62144588 | 62352672 |
| RBM33 | −0.265224591 | 0.458894378 | 9.05E−06 | chr7 | 1 | 155437145 | 155493877 |
| CEP57 | −0.236391887 | 0.45813928 | 0.000680789 | chr11 | 1 | 95523642 | 95565854 |
| CHAC1 | −0.283992403 | 0.457769412 | 5.45E−06 | chr15 | 1 | 41245347 | 41248717 |
| METTL13 | −0.251305655 | 0.457647306 | 6.66E−08 | chr1 | 1 | 171750822 | 171766857 |
| C1orf56 | −0.421783765 | 0.457335739 | 4.92E−07 | chr1 | 1 | 151020216 | 151023896 |
| FKBP3 | −0.287514591 | 0.457295949 | 1.11E−08 | chr14 | −1 | 45584803 | 45604522 |
| FAMI28B | −0.374036738 | 0.456777094 | 2.41E−12 | chr2 | 1 | 130939501 | 130948300 |
| SNRNP25 | −0.216414146 | 0.456271737 | 3.45E−07 | chr16 | 1 | 103010 | 107669 |
| PBX4 | −0.31001759 | 0.455464005 | 4.84E−06 | chr19 | −1 | 19672524 | 19729725 |
| PITPNB | −0.261582202 | 0.454472217 | 8.06E−12 | chr22 | −1 | 28247657 | 28315256 |
| DDX49 | −0.343473643 | 0.454137569 | 3.16E−10 | chr19 | 1 | 19030494 | 19039436 |
| H2AFJ | −0.277804935 | 0.452317978 | 1.43E−07 | chr12 | 1 | 14927349 | 14927957 |
| WDHD1 | −0.221635494 | 0.450955613 | 2.73E−07 | chr14 | −1 | 55405668 | 55493795 |
| BLVRA | −0.385001907 | 0.450125531 | 0.001227454 | chr7 | 1 | 43798279 | 43846938 |
| COPS2 | −0.238084648 | 0.449761157 | 5.06E−05 | chr15 | −1 | 49417473 | 49447854 |
| GOPC | −0.335694969 | 0.447666995 | 0.00084461 | chr6 | −1 | 117881432 | 117923691 |
| CCT5 | −0.247574331 | 0.446863757 | 4.61E−05 | chr5 | 1 | 10250033 | 10266524 |
| | −0.225423721 | 0.445470046 | 1.41E−06 | chr6 | −1 | 31937587 | 31940069 |
| GCFC1 | −0.29229425 | 0.445395323 | 0.003627747 | chr21 | −1 | 34106210 | 34144169 |
| PSMB6 | −0.358538208 | 0.444510931 | 1.92E−08 | chr17 | 1 | 4699439 | 4701798 |
| LARP4 | −0.441920352 | 0.442904134 | 0.009336652 | chr12 | 1 | 50794650 | 50873779 |
| RSPH1 | −0.242063683 | 0.440651569 | 0.003651772 | chr21 | −1 | 43892596 | 43916464 |
| GLS2 | −0.369251024 | 0.44042743 | 8.53E−08 | chr12 | −1 | 56864736 | 56882181 |
| NFYA | −0.281763826 | 0.43942414 | 0.000194862 | chr6 | 1 | 41040684 | 41067715 |
| CEP57 | −0.236391887 | 0.438163164 | 2.08E−05 | chr11 | 1 | 95523642 | 95565854 |
| SERBP1 | −0.29363511 | 0.437109958 | 3.01E−13 | chr1 | −1 | 67873493 | 67896098 |
| FUBP1 | −0.269302108 | 0.43558565 | 2.65E−07 | chr1 | −1 | 78414090 | 78444770 |
| METTL13 | −0.251305655 | 0.434308428 | 1.86E−11 | chr1 | 1 | 171750822 | 171766857 |
| ERAL1 | −0.285253889 | 0.433867022 | 9.57E−08 | chr17 | 1 | 27182020 | 27188085 |
| GCFC1 | −0.29229425 | 0.433411711 | 0.000978954 | chr21 | −1 | 34106210 | 34144169 |
| RNF24 | −0.283461559 | 0.431234651 | 4.60E−09 | chr20 | −1 | 3912068 | 3996036 |
| ATXN3 | −0.290804143 | 0.431069467 | 0.000479918 | chr14 | −1 | 92529926 | 92572954 |
| WHSC2 | −0.329016517 | 0.430867751 | 1.79E−09 | chr4 | −1 | 1984441 | 2011837 |
| PSMG2 | −0.224568396 | 0.430649254 | 2.36E−10 | chr18 | 1 | 12702425 | 12725739 |
| DBR1 | −0.293045877 | 0.430294324 | 0.000126091 | chr3 | −1 | 137879854 | 137893791 |
| TXLNA | −0.312574182 | 0.429015227 | 2.44E−06 | chr1 | 1 | 32645287 | 32663886 |
| RAGE | −0.309361173 | 0.428032828 | 0.000150291 | chr14 | −1 | 102695179 | 102771531 |
| H2AFJ | −0.277804935 | 0.426395076 | 4.28E−07 | chr12 | 1 | 14927349 | 14927957 |
| CSNK1E | −0.238834552 | 0.426324208 | 9.75E−08 | chr22 | −1 | 38686697 | 38714089 |
| PSMD4 | −0.258106107 | 0.426283039 | 4.96E−13 | chr1 | 1 | 151227179 | 151239955 |
| CCDC21 | −0.299934485 | 0.423797272 | 1.75E−05 | chr1 | 1 | 26560693 | 26605299 |
| MAPKAPK3 | −0.274974325 | 0.423341104 | 1.98E−09 | chr3 | 1 | 50649339 | 50686720 |
| LRFN4 | −0.259494829 | 0.422673626 | 9.81E−08 | chr11 | 1 | 66624589 | 66627946 |
| FKTN | −0.271056262 | 0.422275567 | 1.91E−06 | chr9 | 1 | 108320411 | 108403399 |
| SRD5A1 | −0.316238694 | 0.421586602 | 3.96E−07 | chr5 | 1 | 6633456 | 6669675 |
| TMCO7 | −0.290844829 | 0.419900342 | 4.38E−10 | chr16 | 1 | 68877509 | 69119083 |
| MRPL15 | −0.322838359 | 0.417494082 | 1.40E−09 | chr8 | 1 | 55047781 | 55061074 |
| ANKRD26 | −0.331205651 | 0.414889391 | 6.58E−08 | chr10 | −1 | 27293227 | 27389421 |
| CENPV | −0.284513729 | 0.114773621 | 8.75E−06 | chr17 | −1 | 16245848 | 16256813 |
| MANIB1 | −0.224377818 | 0.414577635 | 1.90E−09 | chr9 | 1 | 139981400 | 140003635 |
| GPR137B | −0.287704623 | 0.41343648 | 0.002490864 | chr1 | 1 | 236305832 | 236372206 |
| TUBA1B | −0.257364469 | 0.413380925 | 3.32E−11 | chr12 | −1 | 49521569 | 49525304 |
| PPP2R1B | −0.269985557 | 0.413330128 | 0.002196055 | chr11 | −1 | 111608605 | 111637169 |
| MYO6 | −0.43883682 | 0.413076045 | 2.59E−05 | chr6 | 1 | 76458926 | 76626329 |
| SEC23B | −0.340659075 | 0.412925431 | 6.01E−07 | chr20 | 1 | 18488199 | 18542059 |
| MED1 | −0.316078763 | 0.412748577 | 1.69E−05 | chr17 | −1 | 37560538 | 37607521 |
| GCLC | −0.285342884 | 0.412461851 | 1.99E−06 | chr6 | −1 | 53362139 | 53409927 |
| G2E3 | −0.281280373 | 0.412202783 | 8.47E−05 | chr14 | 1 | 31028364 | 31089269 |
| ASNA1 | −0.326548953 | 0.411954217 | 2.09E−09 | chr19 | 1 | 12848306 | 12859137 |
| FBXO45 | −0.228407257 | 0.411111387 | 0.001202472 | chr3 | 1 | 196295559 | 196315930 |
| AIDA | −0.275078992 | 0.411005275 | 6.27E−06 | chr1 | −1 | 222841355 | 222885866 |
| NUP50 | −0.566797098 | 0.41089471 | 0.002087528 | chr22 | 1 | 45559722 | 45583892 |
| DAG1 | −0.222775171 | 0.410793593 | 1.99E−08 | chr3 | 1 | 49507565 | 49573044 |
| WDR33 | −0.366636769 | 0.410661679 | 4.42E−06 | chr2 | −1 | 128520107 | 128568745 |
| ATP5S | −0.234782015 | 0.410429584 | 1.63E−08 | chr14 | 1 | 50779047 | 50792668 |
| SERBP1 | −0.29363511 | 0.40990949 | 1.06E−06 | chr1 | −1 | 67873493 | 67896098 |
| LARP4 | −0.441920352 | 0.409370756 | 0.00012349 | chr12 | 1 | 50794650 | 50873779 |
| MITD1 | −0.287652418 | 0.409288185 | 0.000627109 | chr2 | −1 | 99778410 | 99797390 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| SRPK2 | −0.301338383 | 0.40923956 | 5.57E−07 | chr7 | −1 | 104756823 | 105029341 |
| ACP1 | −0.243372223 | 0.407652934 | 4.50E−11 | chr2 | 1 | 264869 | 278283 |
| FAM188B | −0.365084074 | 0.407179109 | 1.56E−07 | chr7 | 1 | 30811033 | 30932002 |
| UBXN10 | −0.339943828 | 0.405868745 | 0.000361623 | chr1 | 1 | 20512578 | 20522541 |
| PLOD3 | −0.257219677 | 0.405471045 | 6.15E−06 | chr7 | −1 | 100849258 | 100860954 |
| XRCC6 | −0.35122645 | 0.404207038 | 5.74E−10 | chr22 | 1 | 42017123 | 42060043 |
| STARD4 | −0.329052253 | 0.403294903 | 0.003367646 | chr5 | −1 | 110831731 | 110848208 |
| ADSS | −0.367643975 | 0.40204654 | 5.57E−05 | chr1 | −1 | 244571796 | 244615436 |
| NFYA | −0.281763826 | 0.400910299 | 7.06E−05 | chr6 | 1 | 41040684 | 41067715 |
| IDE | −0.323456458 | 0.400137839 | 1.26E−05 | chr10 | −1 | 94211441 | 94333833 |
| MAPKAPK3 | −0.274974325 | 0.399559751 | 7.30E−11 | chr3 | 1 | 50649339 | 50686720 |
| TUBA1B | −0.257364469 | 0.39764006 | 1.17E−11 | chr12 | −1 | 49521569 | 49525304 |
| RTEL1 | −0.24942297 | 0.397172815 | 0.000235525 | chr20 | 1 | 62289163 | 62328416 |
| MIOS | −0.309348638 | 0.395711772 | 1.02E−07 | chr7 | 1 | 7606503 | 7647127 |
| TMEM43 | −0.273563381 | 0.395596061 | 1.91E−05 | chr3 | 1 | 14166440 | 14185179 |
| WDR59 | −4.508959879 | 0.393873791 | 2.12E−10 | chr16 | −1 | 74907474 | 75019017 |
| SLC1A4 | −0.308988097 | 0.393835863 | 7.80E−05 | chr2 | 1 | 65216535 | 65250999 |
| ERO1L | −0.337054537 | 0.393126588 | 1.28E−05 | chr14 | −1 | 53106634 | 53162423 |
| CSTF3 | −0.245463178 | 0.392469353 | 0.00612572 | chr11 | −1 | 33162978 | 33183037 |
| PNN | −0.269264438 | 0.391862884 | 0.000821701 | chr14 | 1 | 39644425 | 39652422 |
| CEP57 | −0.236391887 | 0.391701161 | 2.18E−05 | chr11 | 1 | 95523642 | 95565854 |
| DCTN4 | −0.216159533 | 0.391463511 | 0.000121824 | chr5 | −1 | 150088002 | 150138671 |
| LTA4H | −0.275723937 | 0.390887101 | 1.29E−07 | chr12 | −1 | 96394611 | 96429365 |
| PSMD4 | −0.258106107 | 0.390463362 | 3.88E−09 | chr1 | 1 | 151227179 | 151239955 |
| DPY19L3 | −0.375796947 | 0.390436589 | 0.003708824 | chr19 | 1 | 32897031 | 32975236 |
| USE1 | −0.315313456 | 0.390015387 | 1.74E−07 | chr19 | 1 | 17326155 | 17330638 |
| TFCP2 | −0.281247247 | 0.390012591 | 1.28E−06 | chr12 | −1 | 51488624 | 51566664 |
| ANXA2 | −0.415910727 | 0.389991116 | 9.36E−08 | chr15 | −1 | 60639333 | 60690185 |
| NUP50 | −0.566797098 | 0.389803777 | 0.009832382 | chr22 | 1 | 45559722 | 45583892 |
| ICA1 | −0.256836172 | 0.389788733 | 1.15E−05 | chr7 | −1 | 8152814 | 8301911 |
| | −0.247485563 | 0.389268676 | 6.31E−09 | chr6 | −1 | 31919864 | 31926887 |
| ANXA2 | −0.415910727 | 0.387716448 | 1.90E−07 | chr15 | −1 | 60639333 | 60690185 |
| USE1 | −0.315313456 | 0.387397591 | 5.59E−09 | chr19 | 1 | 17326155 | 17330638 |
| TBC1D30 | −0.303436889 | 0.387149474 | 7.66E−05 | chr12 | 1 | 65174589 | 65272083 |
| C17orf81 | −0.247903672 | 0.386971392 | 0.001650026 | chr17 | 1 | 7155372 | 7163250 |
| ANXA2 | −0.415910727 | 0.385293336 | 1.32E−07 | chr15 | −1 | 60639333 | 60690185 |
| PSMB1 | −0.307799737 | 0.385149671 | 5.75E−08 | chr6 | −1 | 170844205 | 170862429 |
| CAPN10 | −0.215228659 | 0.383735779 | 0.031745836 | chr2 | 1 | 241526189 | 241557122 |
| USP45 | −0.2938606 | 0.382977481 | 0.0006119 | chr6 | −1 | 99930137 | 99963365 |
| TUBA1B | −0.257364469 | 0.382884899 | 1.71E−11 | chr12 | −1 | 49521569 | 49525304 |
| C20orf108 | −0.316080368 | 0.382060596 | 2.77E−05 | chr20 | 1 | 54933971 | 54943719 |
| CREB3L2 | −0.258978198 | 0.381502254 | 7.13E−06 | chr7 | −1 | 137559725 | 137686803 |
| TMEM43 | −0.273563381 | 0.379906406 | 1.61E−06 | chr3 | 1 | 14166440 | 14185179 |
| SETD3 | −0.299635792 | 0.378960184 | 1.09E−10 | chr14 | −1 | 99864083 | 99947216 |
| SLC6A6 | −0.277217014 | 0.377888979 | 6.88E−05 | chr3 | 1 | 14444120 | 14489696 |
| DGCR14 | −0.406673531 | 0.377148983 | 0.000197838 | chr22 | −1 | 19117792 | 19132197 |
| SRPK2 | −0.301338383 | 0.3769439 | 0.000935668 | chr7 | −1 | 104756823 | 105029341 |
| PGM2L1 | −0.340496727 | 0.37597791 | 1.58E−06 | chr11 | −1 | 74041361 | 74109502 |
| GBAS | −0.297503974 | 0.375723031 | 2.74E−06 | chr7 | 1 | 56032274 | 56067874 |
| CSTF1 | −0.293961713 | 0.37560835 | 0.000731408 | chr20 | 1 | 54967450 | 54979518 |
| RDH10 | −0.29931104 | 0.374837805 | 0.000556733 | chr8 | 1 | 74207265 | 74237516 |
| C3orf75 | −0.321093023 | 0.374635121 | 5.13E−07 | chr3 | −1 | 47537130 | 47555251 |
| ZNF318 | −0.392401079 | 0.37456982 | 0.000716939 | chr6 | −1 | 43303808 | 43337181 |
| ASPM | −0.315933748 | 0.374561031 | 0.000568467 | chr1 | −1 | 197053258 | 197115824 |
| RB1 | −0.349624422 | 0.372437999 | 0.002659766 | chr13 | 1 | 48877911 | 49056122 |
| TTLL1 | −0.409841903 | 0.372205802 | 1.55E−06 | chr22 | −1 | 43435650 | 43485434 |
| TUBA1B | −0.257364469 | 0.372082411 | 2.02E−10 | chr12 | −1 | 49521569 | 49525304 |
| PARP9 | −0.288010969 | 0.371424167 | 0.009993796 | chr3 | −1 | 122246806 | 122283424 |
| PRPF3 | −0.278351305 | 0.370578407 | 0.001660956 | chr1 | 1 | 150293925 | 150325671 |
| VANGL1 | −0.35350898 | 0.369576977 | 9.03E−05 | chr1 | 1 | 116184574 | 116240845 |
| CLTA | −0.315274216 | 0.369489121 | 2.53E−10 | chr9 | 1 | 36190920 | 36212053 |
| VGLL4 | −0.338819195 | 0.367838887 | 3.24E−07 | chr3 | −1 | 11597544 | 11762220 |
| TUBA1B | −0.257364469 | 0.367796508 | 8.89E−11 | chr12 | −1 | 49521569 | 49525304 |
| PYCR2 | −0.293454524 | 0.366607393 | 7.67E−06 | chr1 | −1 | 226107578 | 226111959 |
| GPX4 | −0.259760253 | 0.36648499 | 3.54E−06 | chr19 | 1 | 1103966 | 1106778 |
| GCFC1 | −0.29229425 | 0.365752243 | 0.000527093 | chr21 | −1 | 34106210 | 34144169 |
| MAD1L1 | −0.361371266 | 0.365192333 | 3.57E−05 | chr7 | −1 | 1855430 | 2272609 |
| TCEB2 | −0.246084148 | 0.365159265 | 7.01E−08 | chr16 | −1 | 2821415 | 2827251 |
| CLTA | −0.315274216 | 0.364342813 | 5.66E−11 | chr9 | 1 | 36190920 | 36212053 |
| SC4MOL | −0.284951579 | 0.364122916 | 0.0058699 | chr4 | 1 | 166248775 | 166264312 |
| SLC19A2 | −0.350423055 | 0.363204219 | 0.006681964 | chr1 | −1 | 169433147 | 169455241 |
| C20orf108 | −0.316080368 | 0.363008296 | 0.000505364 | chr20 | 1 | 54933971 | 54943719 |
| C20orf7 | −0.253283591 | 0.36195865 | 5.21E−05 | chr20 | 1 | 13765596 | 13799067 |
| ZNF318 | −0.392401079 | 0.361916452 | 3.92E−06 | chr6 | −1 | 43303808 | 43337181 |
| ATXN3 | −0.290804143 | 0.361728236 | 0.000977593 | chr14 | −1 | 92529926 | 92572954 |
| GRINL1B | −0.271186633 | 0.361708067 | 0.000890209 | chr15 | 1 | 57884106 | 58006943 |
| NCBP1 | −0.251404024 | 0.360549399 | 0.000170074 | chr9 | 1 | 100395908 | 100436030 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| FAM173B | −0.247574331 | 0.359582157 | 2.06E−05 | chr5 | −1 | 10226845 | 10249998 |
| GTPBP10 | −0.279762111 | 0.359462858 | 1.46E−05 | chr7 | 1 | 89975990 | 90020769 |
| IQCK | −0.272202349 | 0.358117308 | 0.000341889 | chr16 | 1 | 19727778 | 19868907 |
| CLTA | −0.315274216 | 0.357928842 | 1.51E−09 | chr9 | 1 | 36190920 | 36212053 |
| ZMYND10 | −0.292895152 | 0.357885771 | 4.82E−07 | chr3 | −1 | 50378541 | 50384283 |
| PATL1 | −0.267856683 | 0.3573634 | 3.71E−05 | chr11 | −1 | 59404194 | 59436511 |
| CEP57 | −0.236391887 | 0.35571577 | 0.000649532 | chr11 | 1 | 95523642 | 95565854 |
| ZNF200 | −0.352071153 | 0.355081258 | 0.000246102 | chr16 | −1 | 3272325 | 3285175 |
| ZEP1 | −0.383919995 | 0.354620259 | 0.003933037 | chr16 | 1 | 75182480 | 75206114 |
| SLC6A20 | −0.306220658 | 0.353102696 | 0.005740206 | chr3 | −1 | 45796942 | 45838027 |
| MRPL14 | −0.238958426 | 0.352692633 | 5.38E−07 | chr6 | −1 | 44081194 | 44095194 |
| DGCR14 | −0.406673531 | 0.352643911 | 3.36E−08 | chr22 | −1 | 19117792 | 19132197 |
| DDB1 | −0.337915954 | 0.351142185 | 9.35E−08 | chr11 | −1 | 61066920 | 61100666 |
| PSMC3IP | −0.218053908 | 0.350181162 | 1.99E−06 | chr17 | −1 | 40724329 | 40729747 |
| MAP2K1 | −0.322974834 | 0.349526006 | 9.39E−07 | chr15 | 1 | 66679155 | 66783882 |
| KIF20B | −0.294123467 | 0.349467685 | 9.22E−06 | chr10 | 1 | 91461367 | 91534696 |
| FAM161A | −0.256344752 | 0.348176582 | 6.15E−07 | chr2 | −1 | 62051991 | 62081278 |
| OXSM | −0.266638161 | 0.348153141 | 2.18E−06 | chr3 | 1 | 25831571 | 25836025 |
| TRMU | −0.251563131 | 0.348031422 | 2.35E−06 | chr22 | 1 | 46731322 | 46753237 |
| ILKAP | −0.290120143 | 0.347825991 | 1.66E−07 | chr2 | −1 | 239079042 | 239112370 |
| LRRC27 | −0.304569805 | 0.346768968 | 4.48E−05 | chr10 | 1 | 134145658 | 134166899 |
| C20orf7 | −0.253283591 | 0.346589288 | 2.73E−05 | chr20 | 1 | 13765596 | 13799067 |
| RABL3 | −0.291349005 | 0.34599985 | 0.011424525 | chr3 | −1 | 120405528 | 120461384 |
| ACLY | −0.31253498 | 0.345973529 | 6.07E−08 | chr17 | −1 | 40023161 | 40075240 |
| SKA2 | −0.223170945 | 0.345237026 | 8.62E−05 | chr17 | −1 | 57187308 | 57232800 |
| ZBTB5 | −0.378311546 | 0.345004195 | 8.04E−08 | chr9 | −1 | 37438111 | 37465396 |
| ATP9B | −0.272149419 | 0.344252258 | 0.010585229 | chr18 | 1 | 76829397 | 77138278 |
| CCDC90B | −0.370153966 | 0.343294224 | 6.09E−05 | chr11 | −1 | 82972805 | 82997215 |
| EHMT1 | −0.241468906 | 0.343225546 | 0.000900769 | chr9 | 1 | 140513454 | 140730576 |
| TBC1D30 | −0.303436889 | 0.341943875 | 0.009123351 | chr12 | 1 | 65174589 | 65272083 |
| PSMB1 | −0.307799737 | 0.339851023 | 5.59E−09 | chr6 | −1 | 170844205 | 170862429 |
| NICN1 | −0.548623895 | 0.3393548 | 9.19E−05 | chr3 | −1 | 49460379 | 49466674 |
| KLC2 | −0.268390601 | 0.339339688 | 4.90E−05 | chr11 | 1 | 66025190 | 66035300 |
| ACLY | −0.31253498 | 0.339231588 | 5.11E−05 | chr17 | −1 | 40023161 | 40075240 |
| PDSS1 | −0.502228537 | 0.339053762 | 0.000664451 | chr10 | 1 | 26986588 | 27035727 |
| | −0.288397593 | 0.338119049 | 0.001128356 | chr6 | −1 | 32808494 | 32811824 |
| MTCH2 | −0.296519113 | 0.336986118 | 1.32E−06 | chr11 | −1 | 47638858 | 47664206 |
| TMEM14B | −0.315657653 | 0.336287771 | 2.21E−08 | chr6 | 1 | 10747973 | 10757214 |
| MKS1 | −0.307616649 | 0.336036277 | 1.41E−01 | chr17 | −1 | 56282802 | 56296666 |
| SPA17 | −0.242556186 | 0.335215459 | 0.012571454 | chr11 | 1 | 124543740 | 124564685 |
| DPH3 | −0.248616784 | 0.334674571 | 0.005501154 | chr3 | −1 | 16299485 | 16306479 |
| HNRNPU | −0.307777645 | 0.334566531 | 0.004764863 | chr1 | −1 | 245014468 | 245027844 |
| MYO6 | −0.43883682 | 0.333945893 | 0.001249815 | chr6 | 1 | 76458926 | 76626329 |
| IDE | −0.323456458 | 0.331984317 | 1.05E−05 | chr10 | −1 | 94211441 | 94333833 |
| | −0.379767127 | 0.331949275 | 2.11E−05 | chr2 | 1 | 172864490 | 172947158 |
| PNN | −0.269264438 | 0.331519226 | 0.014252964 | chr14 | 1 | 39644425 | 39652422 |
| SOCS4 | −0.221635494 | 0.330469645 | 0.007892043 | chr14 | 1 | 55493948 | 55516206 |
| UCHL5 | −0.229547693 | 0.330271841 | 0.001223918 | chr1 | −1 | 192984889 | 193028626 |
| CCDC97 | −0.216421102 | 0.330088065 | 2.35E−05 | chr19 | 1 | 41816094 | 41830785 |
| CENPB | −0.317753428 | 0.329820214 | 0.000571519 | chr20 | −1 | 3764500 | 3767337 |
| BRF2 | −0.367090072 | 0.329649488 | 5.60E−05 | chr8 | −1 | 37701405 | 37707411 |
| SNORA41 | −0.240137026 | 0.329267135 | 4.95E−09 | chr2 | 1 | 207024309 | 207027652 |
| ESD | −0.332233798 | 0.328445206 | 1.51E−07 | chr13 | −1 | 47345391 | 47371367 |
| BRE | −0.322999708 | 0.32838855 | 2.66E−08 | chr2 | 1 | 28113596 | 28561768 |
| C3orf75 | −0.321093023 | 0.32821367 | 1.92E−08 | chr3 | −1 | 47537130 | 47555251 |
| IWS1 | −0.279959983 | 0.3278804 | 2.55E−05 | chr2 | −1 | 128238382 | 128284044 |
| CHMP4A | −0.25363203 | 0.327877116 | 1.43E−06 | chr14 | −1 | 24678787 | 24683075 |
| DDX49 | −0.343473643 | 0.327839782 | 1.25E−10 | chr19 | 1 | 19030494 | 19039436 |
| U2AF2 | −0.208707084 | 0.327716523 | 0.000256825 | chr19 | 1 | 56165416 | 56186081 |
| FBXO22OS | −0.249605837 | 0.327476528 | 5.52E−05 | chr15 | 1 | 76196200 | 76223313 |
| HNRNPA3 | −0.345567093 | 0.327288323 | 3.38E−05 | chr2 | 1 | 178077291 | 178084813 |
| PIP5K1A | −0.330751684 | 0.326954419 | 0.000959016 | chr1 | 1 | 151171027 | 151222012 |
| ST7OT3 | −0.478497425 | 0.3267267 | 3.69E−05 | chr7 | 1 | 116593381 | 116863961 |
| MAN1B1 | −0.224377818 | 0.326365456 | 1.10E−08 | chr9 | 1 | 139981400 | 140003635 |
| PHB | −0.271234016 | 0.325967794 | 1.83E−07 | chr17 | −1 | 47481414 | 47492242 |
| PTPDC1 | −0.245287948 | 0.325809296 | 0.000578597 | chr9 | 1 | 96793076 | 96872138 |
| TMEM14B | −0.315657653 | 0.325615385 | 4.11E−07 | chr6 | 1 | 10747973 | 10757214 |
| TFCP2 | −0.281247247 | 0.32532495 | 0.000227055 | chr12 | −1 | 51488624 | 51566664 |
| HNRNPU | −0.307777645 | 0.325279473 | 1.31E−07 | chr1 | −1 | 245014468 | 245027844 |
| TMEM18 | −0.366817385 | 0.325126845 | 1.66E−05 | chr2 | −1 | 667335 | 677439 |
| RBM33 | −0.265224591 | 0.325019067 | 0.000924058 | chr7 | 1 | 155437373 | 155574173 |
| C20orf24 | −0.278041821 | 0.324472858 | 2.72E−07 | chr20 | 1 | 35234137 | 35240960 |
| BRAP | −0.374122321 | 0.323919498 | 0.003371223 | chr12 | −1 | 112079951 | 112123790 |
| ARL5B | −0.30954775 | 0.323049278 | 0.0226113 | chr10 | 1 | 18948334 | 18970568 |
| ANKRD26 | −0.331205651 | 0.322554838 | 2.24E−05 | chr10 | −1 | 27293227 | 27389421 |
| OSTC | −0.25588477 | 0.322367509 | 1.79E−07 | chr4 | 1 | 109571740 | 109588976 |
| FLVCR1 | −0.328081085 | 0.321104885 | 0.006568338 | chr1 | 1 | 213031597 | 213072705 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| CHMP4A | −0.25363203 | 0.321039276 | 0.000186079 | chr14 | −1 | 24678787 | 24683075 |
| BRE | −0.322999708 | 0.32064176 | 1.89E−08 | chr2 | 1 | 28113596 | 28561768 |
| C20orf24 | −0.278041821 | 0.32062886 | 1.81E−07 | chr20 | 1 | 35234137 | 35240960 |
| NFYA | −0.281763826 | 0.320626444 | 5.46E−05 | chr6 | 1 | 41040684 | 41067715 |
| COQ7 | −0.338053935 | 0.319963007 | 0.002461308 | chr16 | 1 | 19078921 | 19091417 |
| ICMT | −0.21685651 | 0.319637256 | 2.73E−07 | chr1 | −1 | 6281253 | 6296000 |
| HTRA2 | −0.308238889 | 0.319063639 | 6.91E−05 | chr2 | 1 | 74756504 | 74760472 |
| RDH10 | −0.29931104 | 0.318836875 | 0.000625094 | chr8 | 1 | 74207265 | 74237516 |
| INCENP | −0.296869408 | 0.318793464 | 0.000325907 | chr11 | 1 | 61891445 | 61920635 |
| PPME1 | −0.304566241 | 0.318525884 | 2.34E−09 | chr11 | 1 | 73882368 | 73965747 |
| BAG4 | −0.36579053 | 0.31781079 | 0.001960183 | chr8 | 1 | 38034312 | 38070809 |
| RTN4IP1 | −0.385770406 | 0.31780948 | 0.005821078 | chr6 | −1 | 107019846 | 107077362 |
| MED1 | −0.316078763 | 0.317748819 | 0.002752309 | chr17 | −1 | 37562854 | 37607521 |
| EIF2AK4 | −0.289889834 | 0.31661428 | 0.001076009 | chr15 | 1 | 40226347 | 40327797 |
| LRRC61 | −0.31760788 | 0.316051765 | 1.63E−05 | chr7 | 1 | 150020352 | 150035192 |
| ESD | −0.332233798 | 0.316040888 | 3.64E−07 | chr13 | −1 | 47345391 | 47371367 |
| C11orf83 | −0.321989833 | 0.315797494 | 2.32E−05 | chr11 | 1 | 62439126 | 62439848 |
| SARNP | −0.26193862 | 0.315488437 | 7.03E−06 | chr12 | −1 | 56146247 | 56211540 |
| | −0.225423721 | 0.314954787 | 3.35E−05 | chr6 | 1 | 31939608 | 31949228 |
| CENPV | −0.284513729 | 0.313833197 | 0.000632947 | chr17 | −1 | 16245848 | 16256813 |
| ESCO1 | −0.274017091 | 0.313444684 | 8.62E−05 | chr18 | −1 | 19109264 | 19180845 |
| KPNA4 | −0.291750548 | 0.313284758 | 0.003588897 | chr3 | −1 | 160212783 | 160283376 |
| | −0.33891476 | 0.310807033 | 5.82E−05 | chr2 | 1 | 173940570 | 174091874 |
| ROCK2 | −0.376931699 | 0.31046092 | 4.30E−05 | chr2 | −1 | 11319887 | 11484711 |
| HTRA2 | −0.308238889 | 0.310089328 | 4.67E−07 | chr2 | 1 | 74756504 | 74760472 |
| AKAP11 | −0.303168028 | 0.30961878 | 7.45E−05 | chr13 | 1 | 42846289 | 42897396 |
| CCDC21 | −0.299934485 | 0.309023043 | 0.000108549 | chr1 | 1 | 26560693 | 26605299 |
| | −0.225423721 | 0.309006256 | 1.24E−05 | chr6 | −1 | 31937587 | 31940069 |
| DHX57 | −0.284647233 | 0.308522622 | 2.11E−05 | chr2 | −1 | 39024871 | 39103049 |
| DNTTIP1 | −0.303772028 | 0.307559527 | 0.003022301 | chr20 | 1 | 44420576 | 44440066 |
| ETAA1 | −0.328099626 | 0.307153729 | 0.00069992 | chr2 | 1 | 67624451 | 67637677 |
| CNIH4 | −0.286188384 | 0.306598143 | 0.00423316 | chr1 | 1 | 224544552 | 224567154 |
| PRPSAP1 | −0.254262624 | 0.306011283 | 1.17E−07 | chr17 | −1 | 74307014 | 74350230 |
| HEXA | −0.324343034 | 0.305820942 | 0.000102138 | chr15 | −1 | 72635775 | 72668817 |
| PDSS2 | −0.245888559 | 0.305143305 | 0.004311838 | chr6 | −1 | 107585390 | 107780768 |
| GPR19 | −0.328224193 | 0.304496347 | 3.32E−05 | chr12 | −1 | 12813995 | 12849121 |
| C3orf67 | −0.324588491 | 0.304257849 | 1.46E−06 | chr3 | −1 | 58727733 | 59035810 |
| BRE | −0.322999708 | 0.304018373 | 3.68E−08 | chr2 | 1 | 28113596 | 28561768 |
| ASXL2 | −0.463695644 | 0.303172395 | 0.001675772 | chr2 | −1 | 25960557 | 26101385 |
| NHLRC2 | −0.273346942 | 0.302062874 | 0.002122423 | chr10 | 1 | 115614420 | 115676953 |
| POLD3 | −0.426504699 | 0.30196859 | 0.001454831 | chr11 | 1 | 74303629 | 74353765 |
| TRAPPC6A | −0.339851214 | 0.301253824 | 2.17E−05 | chr19 | −1 | 45666187 | 45681485 |
| C1orf56 | −0.421783765 | 0.300324813 | 0.034014371 | chr1 | 1 | 151020216 | 151023896 |
| RPIA | −0.309904287 | 0.300228981 | 0.00040091 | chr2 | 1 | 88991162 | 89050427 |
| PPP2R1B | −0.269985557 | 0.300119404 | 0.000686702 | chr11 | −1 | 111608605 | 111637169 |
| GPHN | −0.351868464 | 0.300088303 | 0.000580681 | chr14 | 1 | 66974125 | 67648515 |
| PTPDC1 | −0.245287948 | 0.29966189 | 0.00020657 | chr9 | 1 | 96793076 | 96872138 |
| MRPL49 | −0.406804065 | 0.299548507 | 3.78E−07 | chr11 | 1 | 64889728 | 64894841 |
| MKKS | −0.249140135 | 0.299381998 | 2.97E−05 | chr20 | −1 | 10385832 | 10414870 |
| XYLB | −0.325646114 | 0.298456177 | 0.000370036 | chr3 | 1 | 38388270 | 38456467 |
| MSRB2 | −0.408148607 | 0.298049078 | 8.88E−06 | chr10 | 1 | 23384435 | 23410942 |
| PNN | −0.269264438 | 0.297937794 | 0.005612002 | chr14 | 1 | 39644425 | 39652422 |
| CTSB | −0.309186459 | 0.297799527 | 0.000725681 | chr8 | −1 | 11700033 | 11725738 |
| CD81 | −0.274970263 | 0.296499219 | 0.00019669 | chr11 | 1 | 2398520 | 2418627 |
| SEL1L3 | −0.279664792 | 0.296454426 | 2.04E−06 | chr4 | −1 | 25749055 | 25865217 |
| KPNA4 | −0.291750548 | 0.295531594 | 8.14E−06 | chr3 | −1 | 160212783 | 160283376 |
| SLC1A4 | −0.308988097 | 0.295132955 | 0.00017921 | chr2 | 1 | 65216535 | 65250999 |
| RASL11A | −0.237118658 | 0.295132892 | 0.001944027 | chr13 | 1 | 27844464 | 27847827 |
| ROPN1L | −0.320073344 | 0.294441374 | 0.001973813 | chr5 | 1 | 10441636 | 10465136 |
| PYCR2 | −0.293454524 | 0.293532102 | 2.40E−05 | chr1 | −1 | 226107578 | 226111959 |
| SMAD2 | −0.355652369 | 0.293105469 | 0.009713946 | chr18 | −1 | 45357922 | 45456930 |
| HNRNPD | −0.270498972 | 0.292946285 | 0.000267841 | chr4 | −1 | 83273651 | 83295109 |
| GCC1 | −0.281291202 | 0.292606877 | 1.24E−07 | chr7 | −1 | 127220672 | 127225661 |
| SERBP1 | −0.29363511 | 0.29218459 | 0.002589163 | chr1 | −1 | 67873493 | 67896098 |
| ENSA | −0.251337512 | 0.291670526 | 0.001771143 | chr1 | −1 | 150593727 | 150602072 |
| UTP23 | −0.374374515 | 0.291620044 | 0.001465454 | chr8 | 1 | 117778742 | 117786923 |
| ORC4L | −0.238091428 | 0.291286758 | 0.010195528 | chr2 | −1 | 148691981 | 148778292 |
| WDR59 | −0.508959879 | 0.290785158 | 7.06E−06 | chr16 | −1 | 74907474 | 75019017 |
| C20or124 | −0.278041821 | 0.290700552 | 7.95E−07 | chr20 | 1 | 35234137 | 35240960 |
| ATP6V1H | −0.354448605 | 0.290649641 | 0.000252654 | chr8 | −1 | 54628116 | 54755547 |
| STK38 | −0.265962322 | 0.290560158 | 0.000340764 | chr6 | −1 | 36461669 | 36515247 |
| SEC23B | −0.340659075 | 0.290445553 | 0.008117135 | chr20 | 1 | 18488199 | 18542059 |
| SOD1 | −0.301587643 | 0.290408479 | 1.34E−05 | chr21 | 1 | 33031935 | 33041244 |
| TWSG1 | −0.325962433 | 0.289821866 | 0.011350703 | chr18 | 1 | 9334765 | 9402418 |
| SDHC | −0.268373166 | 0.289741367 | 0.000174639 | chr1 | 1 | 161284047 | 161332984 |
| C19orf55 | −0.265538386 | 0.288967257 | 0.00432928 | chr19 | 1 | 36249044 | 36260077 |
| PTOV1 | −0.390769905 | 0.288238005 | 0.001740157 | chr19 | 1 | 50354138 | 50363990 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| NAA16 | −0.466228772 | 0.28723025 | 0.02734293 | chr13 | 1 | 41885341 | 41951166 |
| C5orf22 | −0.323327912 | 0.287133007 | 0.046141333 | chr5 | 1 | 31532373 | 31555165 |
| FAM76A | −0.336636978 | 0.286145642 | 0.000106186 | chr1 | 1 | 28052490 | 28089633 |
| ZXDC | −0.388243791 | 0.285635909 | 0.001098803 | chr3 | −1 | 126179926 | 126194708 |
| SLC1A4 | −0.308988097 | 0.28563389 | 0.003322963 | chr2 | 1 | 65216535 | 65250999 |
| LUC7L | −0.322125243 | 0.2854486 | 0.037389133 | chr16 | −1 | 238968 | 279462 |
| NCBP2 | −0.35437085 | 0.284960143 | 0.000256337 | chr3 | −1 | 196662278 | 196669468 |
| TNFAIP8 | −0.23871888 | 0.284650699 | 0.028805426 | chr5 | 1 | 118690009 | 118730293 |
| TMEM216 | −0.237893736 | 0.284623004 | 3.69E−06 | chr11 | 1 | 61159865 | 61166323 |
| PPP5C | −0.301902566 | 0.28441208 | 8.58E−05 | chr19 | 1 | 46850294 | 46894109 |
| LARP4 | −0.441920352 | 0.284398319 | 0.001096515 | chr12 | 1 | 50794650 | 50873779 |
| HNRNPD | −0.270498972 | 0.28430902 | 0.017009884 | chr4 | −1 | 83273651 | 83295109 |
| FDXACB1 | −0.321542807 | 0.284275784 | 0.018503415 | chr11 | −1 | 111652919 | 111742004 |
| C1orf9 | −0.27026984 | 0.283762125 | 0.000215883 | chr1 | 1 | 172501489 | 172580971 |
| PPME1 | −0.304566241 | 0.283613761 | 2.75E−08 | chr11 | 1 | 73882368 | 73965747 |
| RSF1 | −0.244529243 | 0.283236748 | 0.013331292 | chr11 | −1 | 77371041 | 77531880 |
| RFESD | −0.334412968 | 0.281765902 | 3.54E−05 | chr5 | 1 | 94982458 | 94991894 |
| ERP29 | −0.300938141 | 0.28169008 | 2.99E−05 | chr12 | 1 | 112451152 | 112461024 |
| L2HGDH | −0.234782015 | 0.281457486 | 3.40E−06 | chr14 | −1 | 50712120 | 50778947 |
| MED20 | −0.306448506 | 0.281320908 | 1.23E−06 | chr6 | −1 | 41873092 | 41888837 |
| SRPK2 | −0.301338383 | 0.281293084 | 0.000134988 | chr7 | −1 | 104756823 | 105029341 |
| COMMD5 | −0.441770249 | 0.280633576 | 1.03E−05 | chr8 | −1 | 146075552 | 146078932 |
| MKS1 | −0.307616649 | 0.280311679 | 2.81E−05 | chr17 | −1 | 56282803 | 56296666 |
| NFX1 | −0.284450733 | 0.280039705 | 0.010754654 | chr9 | 1 | 33290509 | 33371155 |
| C2orf60 | −0.324785351 | 0.279217588 | 4.81E−06 | chr2 | −1 | 200794698 | 200820459 |
| MAP7 | −0.232419099 | 0.278644953 | 0.000157567 | chr6 | −1 | 136663875 | 136871646 |
| CMC1 | −0.284020829 | 0.278289086 | 0.001866284 | chr3 | 1 | 28283086 | 28366633 |
| FAM24B | −0.318682025 | 0.276598614 | 0.000532451 | chr10 | −1 | 124608594 | 124639114 |
| IFT88 | −0.265596692 | 0.27589642 | 0.000476071 | chr13 | 1 | 21141208 | 21265501 |
| CREB3L4 | −0.210442017 | 0.275616911 | 0.004132305 | chr1 | 1 | 153940379 | 153946839 |
| HMGN4 | −0.207414827 | 0.27558188 | 3.59E−06 | chr6 | 1 | 26538639 | 26546482 |
| KIAA1279 | −0.257616414 | 0.274798022 | 0.000804998 | chr10 | 1 | 70748487 | 70776738 |
| ANAPC2 | −0.294481831 | 0.274772021 | 0.002846399 | chr9 | −1 | 140069236 | 140082989 |
| UTP23 | −0.374374515 | 0.274727629 | 0.017033035 | chr8 | 1 | 117778742 | 117786923 |
| PIGB | −0.44469494 | 0.274696365 | 0.000992609 | chr15 | 1 | 55611133 | 55647845 |
| COQ7 | −0.338053935 | 0.272966046 | 0.002075319 | chr16 | 1 | 19078921 | 19091417 |
| PHAX | −0.313178185 | 0.272698658 | 0.000989986 | chr5 | 1 | 125935960 | 125962944 |
| SLC31A1 | −0.234494526 | 0.27247291 | 0.012793448 | chr9 | 1 | 115983842 | 116026772 |
| MORN2 | −0.284647233 | 0.272345217 | 0.01474394 | chr2 | 1 | 39103103 | 39109850 |
| ISOC2 | −0.343599679 | 0.271799885 | 0.003251463 | chr19 | −1 | 55964345 | 55973049 |
| PIGB | −0.44469494 | 0.271571495 | 0.004821511 | chr15 | 1 | 55611133 | 55647845 |
| TIGD1 | −0.369573272 | 0.270320642 | 0.012986093 | chr2 | −1 | 233412779 | 233415226 |
| ZBED3 | −0.240099625 | 0.270062413 | 0.007176586 | chr5 | −1 | 76367897 | 76383148 |
| FBXO45 | −0.228407257 | 0.269760372 | 0.001837268 | chr3 | 1 | 196295559 | 196315930 |
| KIAA1704 | −0.272420763 | 0.269304031 | 0.019292559 | chr13 | 1 | 45563755 | 45607742 |
| DLST | −0.263197371 | 0.268984711 | 0.006138887 | chr14 | 1 | 75348619 | 75370443 |
| HMOX2 | −0.261263874 | 0.268156798 | 6.75E−05 | chr16 | 1 | 4526380 | 4560348 |
| ENSA | −0.251337512 | 0.268093768 | 0.004668268 | chr1 | −1 | 150596096 | 150602053 |
| IQCE | −0.339575937 | 0.267671879 | 0.006479191 | chr7 | 1 | 2598632 | 2654368 |
| NFX1 | −0.284450733 | 0.267474977 | 0.006666736 | chr9 | 1 | 33290509 | 33371155 |
| PHF5A | −0.322027613 | 0.267451505 | 0.007672976 | chr22 | −1 | 41855721 | 41864729 |
| NDUFA7 | −0.252441473 | 0.266811861 | 5.24E−06 | chr19 | −1 | 8376234 | 8386280 |
| PPIL4 | −0.401690896 | 0.266681526 | 0.028739864 | chr6 | −1 | 149825869 | 149867174 |
| C2orf60 | −0.324785351 | 0.266144313 | 0.000639377 | chr2 | −1 | 200794698 | 200820459 |
| STK38 | −0.265962322 | 0.265843616 | 0.001730184 | chr6 | −1 | 36461669 | 36515247 |
| ASPM | −0.315933748 | 0.265101026 | 0.000444641 | chr1 | −1 | 197053258 | 197115824 |
| DUSP6 | −0.421794981 | 0.263858008 | 0.018789761 | chr12 | −1 | 89741839 | 89746296 |
| HEBP2 | −0.294543757 | 0.262839637 | 1.50E−06 | chr6 | 1 | 138725356 | 138734310 |
| HBXIP | −0.22650417 | 0.262706119 | 8.29E−06 | chr1 | −1 | 110943871 | 110950560 |
| GOPC | −0.335694969 | 0.262611678 | 0.015028112 | chr6 | −1 | 117881432 | 117923691 |
| SMAD2 | −0.355652369 | 0.262541292 | 0.000729011 | chr18 | −1 | 45357922 | 45456930 |
| DCTN4 | −0.216159533 | 0.262405287 | 4.65E−06 | chr5 | −1 | 150088002 | 150138671 |
| GOPC | −0.335694969 | 0.262083104 | 0.000305851 | chr6 | −1 | 117881432 | 117923691 |
| HEBP1 | −0.268525561 | 0.260875236 | 0.038292344 | chr12 | −1 | 13127803 | 13153221 |
| PSMC2 | −0.335527424 | 0.26064094 | 0.045816386 | chr7 | 1 | 102985361 | 103009842 |
| TEX264 | −0.282459047 | 0.260376359 | 7.72E−06 | chr3 | 1 | 51705248 | 51738339 |
| NEK3 | −0.308457391 | 0.259810753 | 0.02572221 | chr13 | −1 | 52706783 | 52733724 |
| JOSD2 | −0.29879725 | 0.259261204 | 0.0032112 | chr19 | −1 | 51009259 | 51014477 |
| PTGES2 | −0.27452633 | 0.258797215 | 1.42E−05 | chr9 | −1 | 130882972 | 130890741 |
| EPT1 | −0.286072226 | 0.258783558 | 0.001441785 | chr2 | 1 | 26568982 | 26618759 |
| GCLC | −0.285342884 | 0.258395056 | 0.000665358 | chr6 | −1 | 53362139 | 53409927 |
| COG5 | −0.239778252 | 0.258363981 | 0.016099573 | chr7 | −1 | 106842189 | 107204485 |
| PHAX | −0.313178185 | 0.258144523 | 0.044160417 | chr5 | 1 | 125935960 | 125962944 |
| RPL17 | −0.270500948 | 0.257962512 | 0.028497526 | chr18 | −1 | 47015796 | 47017814 |
| RDH10 | −0.29931104 | 0.257485677 | 0.002367952 | chr8 | 1 | 74207265 | 74237516 |
| C20orf108 | −0.316080368 | 0.256922933 | 0.0002806 | chr20 | 1 | 54933971 | 54943719 |
| RPL36AL | −0.310966562 | 0.256748947 | 4.44E−06 | chr14 | −1 | 50085407 | 50087361 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| WDR53 | −0.228407257 | 0.256102911 | 0.001020651 | chr3 | −1 | 196281056 | 196295510 |
| HNRNPD | −0.270498972 | 0.255818394 | 0.001910296 | chr4 | −1 | 83273651 | 83295109 |
| ZKSCAN1 | −0.295926961 | 0.255679743 | 0.019872896 | chr7 | 1 | 99613204 | 99636631 |
| MDN1 | −0.323383819 | 0.255635275 | 0.010116651 | chr6 | −1 | 90352218 | 90529442 |
| COMMD5 | −0.441770249 | 0.25550232 | 0.000106261 | chr8 | −1 | 146075552 | 146078932 |
| IQCH | −0.291086472 | 0.255491036 | 4.88E−05 | chr15 | 1 | 67547169 | 67794142 |
| KIAA1704 | −0.272420763 | 0.255239159 | 0.048538694 | chr13 | 1 | 45563755 | 45607742 |
| RPS6KL1 | −0.259682274 | 0.254390248 | 0.000688209 | chr14 | −1 | 75372347 | 75389145 |
| ELL2 | −0.363180893 | 0.253430294 | 0.022297225 | chr5 | −1 | 95220802 | 95297775 |
| C4orf23 | −0.315455915 | 0.253413485 | 1.93E−05 | chr4 | 1 | 8442532 | 8478253 |
| DAG1 | −0.222775171 | 0.253408278 | 0.000211878 | chr3 | 1 | 49507565 | 49573044 |
| DUSP6 | −0.421794981 | 0.253379004 | 0.018685938 | chr12 | −1 | 89741839 | 89746296 |
| VGLL4 | −0.338819195 | 0.25277911 | 0.006514183 | chr3 | −1 | 11597544 | 11762220 |
| TNFAIP8 | −0.23871888 | 0.252662179 | 0.022627018 | chr5 | 1 | 118690009 | 118730293 |
| BAG4 | −0.36579053 | 0.251969411 | 0.001961102 | chr8 | 1 | 38034312 | 38070809 |
| EIF4E2 | −0.369573272 | 0.251616958 | 6.19E−05 | chr2 | 1 | 233414762 | 233433920 |
| NACAP1 | −0.342446473 | 0.251485765 | 1.36E−09 | chr12 | −1 | 57094565 | 57119083 |
| SERBP1 | −0.29363511 | 0.25141299 | 1.35E−06 | chr1 | −1 | 67873493 | 67896098 |
| HMGN4 | −0.207414827 | 0.25121774 | 6.81E−05 | chr6 | 1 | 26538639 | 26546482 |
| LAP3 | −0.333762016 | 0.251215537 | 0.005772231 | chr4 | 1 | 17578815 | 17609591 |
| ESF1 | −0.253283591 | 0.250955687 | 0.008353744 | chr20 | −1 | 13694969 | 13765532 |
| TM7SF3 | −0.281259298 | 0.249855668 | 0.002154465 | chr12 | −1 | 27124519 | 27167339 |
| PHAX | −0.313178185 | 0.24773213 | 0.046681146 | chr5 | 1 | 125935960 | 125962944 |
| AASDH | −0.24460245 | 0.245784979 | 0.007349758 | chr4 | −1 | 57204456 | 57253666 |
| HNRNPH3 | −0.364665187 | 0.245711493 | 0.006079061 | chr10 | 1 | 70091832 | 70102944 |
| C17orf81 | −0.247903672 | 0.245481137 | 0.001667237 | chr17 | 1 | 7155372 | 7163250 |
| COMMD5 | −0.441770249 | 0.24460423 | 0.002447571 | chr8 | −1 | 146075552 | 146078932 |
| IQCH | −0.291086472 | 0.244452903 | 1.05E−05 | chr15 | 1 | 67547169 | 67794142 |
| HN1 | −0.352915116 | 0.243996671 | 0.000979556 | chr17 | −1 | 73131343 | 73150778 |
| MED1 | −0.316078763 | 0.243837247 | 0.008788836 | chr17 | −1 | 37562854 | 37607521 |
| WDR60 | −0.389032296 | 0.243712351 | 0.000300271 | chr7 | 1 | 158649269 | 158738880 |
| DCP1A | −0.37393939 | 0.243107657 | 0.015402264 | chr3 | −1 | 53317448 | 53381637 |
| QRSL1 | −0.385770406 | 0.242655501 | 0.033329157 | chr6 | 1 | 107077453 | 107116292 |
| ERCC3 | −0.392019389 | 0.242649264 | 0.004948282 | chr2 | −1 | 128014866 | 128051752 |
| CREB1 | −0.442958754 | 0.242362293 | 0.026815326 | chr2 | 1 | 208394616 | 208468155 |
| IWS1 | −0.279959983 | 0.242288644 | 0.000355171 | chr2 | −1 | 128238382 | 128284044 |
| STX10 | −0.24548072 | 0.242138115 | 6.00E−07 | chr19 | −1 | 13254903 | 13261052 |
| KPNA4 | −0.291750548 | 0.241978566 | 0.000978887 | chr3 | −1 | 160212783 | 160283376 |
| HBXIP | −0.22650417 | 0.241859734 | 0.0001587 | chr1 | −1 | 110943871 | 110950560 |
| UNC93B1 | −0.262448866 | 0.241830815 | 0.004974303 | chr11 | −1 | 67758575 | 67771593 |
| SIK2 | −0.255639754 | 0.241680119 | 0.001022483 | chr11 | 1 | 111473192 | 111601577 |
| IQCH | −0.291086472 | 0.240445624 | 4.87E−05 | chr15 | 1 | 67547169 | 67794142 |
| POLL | −0.218924523 | 0.240262076 | 0.00067314 | chr10 | −1 | 103338639 | 103347966 |
| SPATA13 | −0.406111741 | 0.23969374 | 0.012176701 | chr13 | 1 | 24734887 | 24881210 |
| PSMD12 | −0.248429065 | 0.239365644 | 0.002533351 | chr17 | −1 | 65334032 | 65362743 |
| TMEM18 | −0.366817385 | 0.238269476 | 0.010915957 | chr2 | −1 | 667335 | 677439 |
| FAM76B | −0.236391887 | 0.238245555 | 0.022350557 | chr11 | −1 | 95502106 | 95522954 |
| HNRNPA3 | −0.345567093 | 0.237898969 | 0.004638488 | chr2 | 1 | 178077477 | 178086111 |
| NDUFS8 | −0.248581907 | 0.237816023 | 0.008569348 | chr11 | 1 | 67798094 | 67804114 |
| UBA52 | −0.303994501 | 0.237743741 | 2.01E−08 | chr19 | 1 | 18682614 | 18688269 |
| TM7SF3 | −0.281259298 | 0.237387852 | 0.004970843 | chr12 | −1 | 27124519 | 27167339 |
| RTN4IP1 | −0.385770406 | 0.236305218 | 0.028704102 | chr6 | −1 | 107019846 | 107077362 |
| SPATA13 | −0.406111741 | 0.235469392 | 0.002410546 | chr13 | 1 | 24734861 | 24798936 |
| RIF1 | −0.333349128 | 0.235074379 | 0.02790839 | chr2 | 1 | 152266455 | 152333863 |
| ZNF428 | −0.270702519 | 0.233993112 | 0.000942811 | chr19 | −1 | 44111377 | 44124006 |
| EIF4E2 | −0.369573272 | 0.233736252 | 0.000298064 | chr2 | 1 | 233414762 | 233433920 |
| SEL1L3 | −0.279664792 | 0.23345406 | 0.000110772 | chr4 | −1 | 25749055 | 25865217 |
| MIB2 | −0.251711462 | 0.233070065 | 0.014264956 | chr1 | 1 | 1550884 | 1565985 |
| PDXK | −0.451405538 | 0.232657066 | 8.42E−05 | chr21 | 1 | 45138978 | 45182188 |
| NACAP1 | −0.342446473 | 0.231993323 | 4.49E−09 | chr12 | −1 | 57094565 | 57119083 |
| NDUFS8 | −0.248581907 | 0.231799343 | 0.000342283 | chr11 | 1 | 67798094 | 67804114 |
| CBLL1 | −0.319197999 | 0.230551304 | 0.031055773 | chr7 | 1 | 107384142 | 107400029 |
| LRRC2 | −0.24589671 | 0.229714562 | 0.00157909 | chr3 | −1 | 46556913 | 46608040 |
| IQCE | −0.339575937 | 0.229341828 | 0.018805575 | chr7 | 1 | 2598632 | 2654368 |
| MOCOS | −0.26317804 | 0.229136307 | 0.00167835 | chr18 | 1 | 33767482 | 33852120 |
| RTEL1 | −0.24942297 | 0.228977279 | 0.000153908 | chr20 | 1 | 62289163 | 62327606 |
| | −0.247485563 | 0.228857324 | 4.31E−06 | chr6 | 1 | 31926857 | 31937532 |
| POLR2L | −0.32790758 | 0.228740978 | 0.00633064 | chr11 | −1 | 839721 | 842545 |
| SDHC | −0.268373166 | 0.228249718 | 0.001145497 | chr1 | 1 | 161284047 | 161332984 |
| TEX264 | −0.282459047 | 0.227925078 | 6.47E−05 | chr3 | 1 | 51705248 | 51738339 |
| ENO3 | −0.239178 | 0.22767744 | 0.001851468 | chr17 | 1 | 4854390 | 4860426 |
| SETD3 | −0.299635792 | 0.227594182 | 0.000663135 | chr14 | −1 | 99876141 | 99947125 |
| TEX264 | −0.282459047 | 0.227145496 | 9.38E−05 | chr3 | 1 | 51705248 | 51738339 |
| ATP5S | −0.234782015 | 0.226774004 | 0.014577283 | chr14 | 1 | 50779047 | 50789743 |
| ROCK2 | −0.376931699 | 0.225720089 | 0.002372911 | chr2 | −1 | 11319887 | 11484711 |
| FOXN2 | −0.296549353 | 0.225405722 | 0.004958872 | chr2 | 1 | 48541849 | 48606433 |
| WDR59 | −0.508959879 | 0.225202159 | 0.001611494 | chr16 | −1 | 74907474 | 75019017 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| FAM161A | −0.256344752 | 0.225159978 | 0.000203183 | chr2 | −1 | 62051991 | 62081278 |
| | −0.286391544 | 0.224339418 | 0.022441647 | chr1 | 1 | 233463514 | 233520894 |
| ZNF589 | −0.308092571 | 0.224088382 | 0.01320704 | chr3 | 1 | 48282590 | 48312477 |
| CAPN10 | −0.215228659 | 0.223593268 | 0.00293259 | chr2 | 1 | 241526133 | 241538526 |
| CTSB | −0.309186459 | 0.223326074 | 0.001251129 | chr8 | −1 | 11700033 | 11725738 |
| DNTTIP1 | −0.303772028 | 0.223253012 | 0.005562276 | chr20 | 1 | 44420576 | 44440066 |
| RWDD4A | −0.367487665 | 0.221987754 | 0.000431143 | chr4 | −1 | 184560788 | 184580378 |
| ENSA | −0.251337512 | 0.220849497 | 0.017954766 | chr1 | −1 | 150599530 | 150602053 |
| ADK | −0.241940696 | 0.220179424 | 0.011099027 | chr10 | 1 | 75936444 | 76469061 |
| SLC1A4 | −0.308988097 | 0.21984612 | 0.003014375 | chr2 | 1 | 65216535 | 65250999 |
| CD2BP2 | −0.246901578 | 0.218720419 | 8.93E−06 | chr16 | −1 | 30362087 | 30366682 |
| CNIH4 | −0.286188384 | 0.218572814 | 0.007465584 | chr1 | 1 | 224544552 | 224567154 |
| RTEL1 | −0.24942297 | 0.218236696 | 0.012312633 | chr20 | 1 | 62289163 | 62327606 |
| | −0.330163571 | 0.217938644 | 3.80E−06 | chr6 | −1 | 31694815 | 31698394 |
| ZNF697 | −0.285615275 | 0.217890916 | 0.026932223 | chr1 | −1 | 120162000 | 120190390 |
| MBD4 | −0.326575154 | 0.217830565 | 0.040163792 | chr3 | −1 | 129149787 | 129158872 |
| C1orf58 | −0.275078992 | 0.217719245 | 0.028287267 | chr1 | 1 | 222885895 | 222908538 |
| MOSPD3 | −0.301219721 | 0.216523212 | 0.000442534 | chr7 | 1 | 100209725 | 100212949 |
| AASDH | −0.24460245 | 0.21611587 | 0.021452164 | chr4 | −1 | 57204456 | 57253666 |
| C2orf47 | −0.324785351 | 0.21589926 | 0.000312216 | chr2 | 1 | 200820326 | 200828848 |
| MMADHC | −0.265383202 | 0.215158501 | 3.39E−07 | chr2 | −1 | 150426148 | 150444330 |
| WDR33 | −0.366636769 | 0.214378714 | 0.001006555 | chr2 | −1 | 128458596 | 128568721 |
| LSM11 | −0.239070625 | 0.213103159 | 0.015851834 | chr5 | 1 | 157170755 | 157187717 |
| FN3KRP | −0.258605213 | 0.213007101 | 0.034290656 | chr17 | 1 | 80674582 | 80685892 |
| NCBP1 | −0.251404024 | 0.21266354 | 0.011140508 | chr9 | 1 | 100395908 | 100436030 |
| UQCC | −0.318513573 | 0.212363978 | 0.003763106 | chr20 | −1 | 33890369 | 33999944 |
| RBM33 | −0.265224591 | 0.212273402 | 0.003736565 | chr7 | 1 | 155437373 | 155574173 |
| C16orf88 | −0.272202349 | 0.211548111 | 4.71E−05 | chr16 | −1 | 19717676 | 19726362 |
| SERBP1 | −0.29363511 | 0.211459771 | 0.017562036 | chr1 | −1 | 67873493 | 67896098 |
| HIST1H3I | −0.253736937 | 0.211366113 | 0.0039775 | chr6 | −1 | 27839683 | 27840093 |
| NAGLU | −0.361867945 | 0.210599622 | 0.004873705 | chr17 | 1 | 40687951 | 40696464 |
| ZNF668 | −0.282985758 | 0.210132911 | 0.00037216 | chr16 | −1 | 31072171 | 31085577 |
| BAG4 | −0.36579053 | 0.20886034 | 0.010375397 | chr8 | 1 | 38034312 | 38070809 |
| C2orf79 | −0.275635182 | 0.208635961 | 0.000349842 | chr2 | −1 | 25012855 | 25016251 |
| ARL5B | −0.30954775 | 0.208538989 | 0.008971183 | chr10 | 1 | 18948334 | 18970568 |
| ARG2 | −0.353923274 | 0.208130192 | 0.009724127 | chr14 | 1 | 68086579 | 68118437 |
| BRD9 | −0.391690922 | 0.207933989 | 2.05E−06 | chr5 | −1 | 864238 | 892661 |
| PRPF4B | −0.258675393 | 0.207736724 | 0.048433746 | chr6 | 1 | 4021560 | 4062141 |
| TMEM79 | −0.28814387 | 0.207702924 | 0.000589245 | chr1 | 1 | 156252739 | 156262234 |
| ZBED3 | −0.240099625 | 0.207588603 | 0.002109014 | chr5 | −1 | 76367897 | 76383148 |
| MTIF3 | −0.308984575 | 0.207096259 | 0.000235207 | chr13 | −1 | 28009780 | 28024701 |
| HNRNPA3 | −0.345567093 | 0.207065767 | 0.035969594 | chr2 | 1 | 178077477 | 178086111 |
| PRPF4B | −0.258675393 | 0.206775918 | 0.0007869 | chr6 | 1 | 4021560 | 4062141 |
| RBM33 | −0.265224591 | 0.206292959 | 0.004885864 | chr7 | 1 | 155437145 | 155493877 |
| BEAR | −0.345325231 | 0.205916784 | 0.005229164 | chr16 | 1 | 14726672 | 14763093 |
| RPS15 | −0.366521564 | 0.204812055 | 7.34E−08 | chr19 | 1 | 1438363 | 1440492 |
| RNASEN | −0.323327912 | 0.204735252 | 0.001757762 | chr5 | −1 | 31401169 | 31532168 |
| TMED9 | −0.362181166 | 0.204379838 | 0.002121877 | chr5 | 1 | 177019159 | 177023125 |
| DRAP1 | −0.304144949 | 0.203963513 | 0.007475415 | chr11 | 1 | 65686728 | 65689031 |
| HMGN4 | −0.207414827 | 0.203301495 | 0.000785941 | chr6 | 1 | 26538639 | 26546482 |
| SDHC | −0.268373166 | 0.20271015 | 7.45E−05 | chr1 | 1 | 161284047 | 161332984 |
| MED20 | −0.306448506 | 0.201491874 | 0.003856186 | chr6 | −1 | 41873092 | 41888837 |
| ARL6IP1 | −0.255299482 | 0.201133664 | 0.005341398 | chr16 | −1 | 18802991 | 18812917 |
| FXC1 | −0.400110753 | 0.200816677 | 0.040990593 | chr11 | 1 | 6502690 | 6505909 |
| ENSA | −0.251337512 | 0.200682675 | 0.00273695 | chr1 | −1 | 150596096 | 150602053 |
| ASF1A | −0.293415186 | 0.200449032 | 0.024567634 | chr6 | 1 | 119215384 | 119230332 |
| TSSC4 | −0.25495048 | 0.198841744 | 0.000696997 | chr11 | 1 | 2421718 | 2425106 |
| CISH | −0.274974325 | 0.198661891 | 0.000494064 | chr3 | −1 | 50643927 | 50649203 |
| C6orf130 | −0.281763826 | 0.198582257 | 0.002808047 | chr6 | −1 | 41032517 | 41040330 |
| ENAH | −0.297371742 | 0.198191826 | 0.00638419 | chr1 | −1 | 225680538 | 225840844 |
| COG5 | −0.239778252 | 0.196879153 | 0.026218096 | chr7 | −1 | 106842189 | 107204485 |
| CISH | −0.274974325 | 0.195952875 | 0.000347984 | chr3 | −1 | 50643927 | 50649203 |
| SFT2D3 | −0.331824877 | 0.1956986 | 0.001228807 | chr2 | 1 | 128458597 | 128461385 |
| DEPDC6 | −0.319715962 | 0.195268925 | 0.045207173 | chr8 | 1 | 120885900 | 121063157 |
| CDC20B | −0.383282634 | 0.193396674 | 0.001607889 | chr5 | −1 | 54408823 | 54469003 |
| LUC7L | −0.322125243 | 0.193382226 | 0.008404655 | chr16 | −1 | 238968 | 279462 |
| ECHDC1 | −0.355326207 | 0.193281817 | 0.035310513 | chr6 | −1 | 127609857 | 127664745 |
| LARP4 | −0.441920352 | 0.192714139 | 0.009855961 | chr12 | 1 | 50794650 | 50873779 |
| SLC38A7 | −0.287708322 | 0.192191172 | 0.016466806 | chr16 | −1 | 58699013 | 58718674 |
| ZNF709 | −0.333291789 | 0.192095306 | 0.047148109 | chr19 | −1 | 12571998 | 12595643 |
| EHMT1 | −0.241468906 | 0.191928566 | 0.006694348 | chr9 | 1 | 140513454 | 140730576 |
| C3orf19 | −0.365475119 | 0.191633864 | 0.037208297 | chr3 | 1 | 14693271 | 14714166 |
| FBXO34 | −0.310537562 | 0.190408434 | 0.004968945 | chr14 | 1 | 55738021 | 55820329 |
| SOCS4 | −0.221635494 | 0.190363551 | 0.030552367 | chr14 | 1 | 55493948 | 55516206 |
| MBD4 | −0.326575154 | 0.190101405 | 0.030399016 | chr3 | −1 | 129149787 | 129158872 |
| ZNF828 | −0.247162136 | 0.189606014 | 0.004731333 | chr13 | 1 | 115079988 | 115092796 |
| FAM76B | −0.236391887 | 0.188895264 | 0.031508416 | chr11 | −1 | 95502106 | 95522954 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| TMED2 | −0.238864154 | 0.188736288 | 0.031601869 | chr12 | 1 | 124069076 | 124082681 |
| RAB11FIP5 | −0.23740607 | 0.188692829 | 0.002314502 | chr2 | −1 | 73300510 | 73340146 |
| RTN3 | −0.273559188 | 0.187729043 | 0.000640369 | chr11 | 1 | 63448922 | 63527337 |
| RAB22A | −0.257197954 | 0.187606344 | 0.009278068 | chr20 | 1 | 56884752 | 56942563 |
| RPL17 | −0.270500948 | 0.187496627 | 0.000316926 | chr18 | −1 | 47014858 | 47018906 |
| LUC7L | −0.322125243 | 0.187482062 | 0.008875607 | chr16 | −1 | 238968 | 279462 |
| E4F1 | −0.314780615 | 0.187463536 | 0.007604251 | chr16 | 1 | 2273567 | 2285743 |
| NFYA | −0.281763826 | 0.187323516 | 0.006454767 | chr6 | 1 | 41040684 | 41067715 |
| RPL27 | −0.290548908 | 0.18694156 | 6.81E−06 | chr17 | 1 | 41150446 | 41154956 |
| ECHDC1 | −0.355326207 | 0.185879935 | 0.023581092 | chr6 | −1 | 127609857 | 127664745 |
| POLR2H | −0.289927146 | 0.184724665 | 0.002708717 | chr3 | 1 | 184079506 | 184086382 |
| DTX3L | −0.312452653 | 0.184492192 | 0.026590419 | chr3 | 1 | 122283085 | 122294050 |
| ZNF839 | −0.338895641 | 0.184191726 | 0.002762849 | chr14 | 1 | 102786096 | 102809044 |
| RAD18 | −0.294092376 | 0.183299766 | 0.001102363 | chr3 | −1 | 8918760 | 9005186 |
| ZNF251 | −0.340718978 | 0.183016527 | 0.009696152 | chr8 | −1 | 145946295 | 145980970 |
| MKLN1 | −0.285004864 | 0.182861126 | 0.027872814 | chr7 | 1 | 131012619 | 131181395 |
| NEK3 | −0.308457391 | 0.182527193 | 0.029590799 | chr13 | −1 | 52706783 | 52733724 |
| ECHDC1 | −0.355326207 | 0.182233872 | 0.030122483 | chr6 | −1 | 127609857 | 127664745 |
| RTEL1 | −0.24942297 | 0.18181089 | 0.009750693 | chr20 | 1 | 62289163 | 62327606 |
| GOPC | −0.335694969 | 0.18135179 | 0.008913284 | chr6 | 1 | 117881432 | 117923691 |
| SNX25 | −0.230619058 | 0.181321736 | 0.00508148 | chr4 | 1 | 186125391 | 186285125 |
| RPL17 | −0.270500948 | 0.181205032 | 0.000336704 | chr18 | −1 | 47014858 | 47018906 |
| ACOT13 | −0.354368463 | 0.18057648 | 0.023336259 | chr6 | 1 | 24667299 | 24701942 |
| NFX1 | −0.284450733 | 0.180005388 | 0.005070766 | chr9 | 1 | 33290510 | 33365271 |
| UBXN10 | −0.339943828 | 0.178892308 | 0.016472937 | chr1 | 1 | 20512578 | 20522541 |
| TMED2 | −0.238864154 | 0.178614843 | 0.045271549 | chr12 | 1 | 124069076 | 124082681 |
| PELI1 | −0.263776086 | 0.17833332 | 0.004144771 | chr2 | −1 | 64319786 | 64371588 |
| TMED9 | −0.362181166 | 0.178197266 | 0.016340136 | chr5 | 1 | 177019159 | 177023125 |
| AARSD1 | −0.280574719 | 0.177812046 | 0.000880047 | chr17 | −1 | 41120107 | 41132545 |
| SNTB2 | −0.300511266 | 0.177235272 | 0.018065978 | chr16 | 1 | 69221032 | 69342955 |
| TIRAP | −0.323262221 | 0.176640436 | 0.002976945 | chr11 | 1 | 126152982 | 126164828 |
| AAGAB | −0.291086472 | 0.175898347 | 0.049778227 | chr15 | −1 | 67493371 | 67547074 |
| ZNHIT1 | −0.257219677 | 0.175337489 | 0.008461241 | chr7 | 1 | 100860949 | 100867471 |
| RPL17 | −0.270500948 | 0.175220399 | 0.000132726 | chr18 | −1 | 47014858 | 47018906 |
| C2CD3 | −0.304566241 | 0.174564094 | 0.004587842 | chr11 | −1 | 73724430 | 73882064 |
| DCP1A | −0.37393939 | 0.174172186 | 0.008924473 | chr3 | −1 | 53317448 | 53381637 |
| SLC35F5 | −0.242253514 | 0.172677635 | 0.008053508 | chr2 | −1 | 114470369 | 114514400 |
| ZNF589 | −0.308092571 | 0.17235098 | 0.008160301 | chr3 | 1 | 48282590 | 48312477 |
| C4orf41 | −0.367487665 | 0.172272241 | 0.046163245 | chr4 | 1 | 184580420 | 184634745 |
| DUS4L | −0.239778252 | 0.171733422 | 0.015329732 | chr7 | 1 | 107204403 | 107218906 |
| ATP9B | −0.272149419 | 0.171598972 | 0.007401813 | chr18 | 1 | 76829397 | 77138278 |
| KLHDC10 | −0.422630708 | 0.171455233 | 0.025949102 | chr7 | 1 | 129710350 | 129773596 |
| SDHC | −0.268373166 | 0.170267544 | 0.029404858 | chr1 | 1 | 161284047 | 161332984 |
| DNAJC9 | −0.362712454 | 0.169673626 | 0.03135362 | chr10 | −1 | 75002582 | 75008620 |
| WFDC3 | −0.303772028 | 0.169358703 | 0.034842302 | chr20 | −1 | 44402847 | 44420547 |
| TUBG2 | −0.331145925 | 0.168978567 | 0.007156872 | chr17 | 1 | 40811266 | 40819021 |
| HNRNPH3 | −0.364665187 | 0.168636613 | 0.019803317 | chr10 | 1 | 70091832 | 70102944 |
| NEU3 | −0.238234754 | 0.168607098 | 0.00769773 | chr11 | 1 | 74699179 | 74718741 |
| NDUFB2 | −0.284421962 | 0.168594199 | 0.006711868 | chr7 | 1 | 140396471 | 140422590 |
| SUB1 | −0.360871485 | 0.167909752 | 0.012598882 | chr5 | 1 | 32585605 | 32604185 |
| ORC4L | −0.238091428 | 0.167153184 | 0.007382173 | chr2 | −1 | 148691981 | 148778292 |
| CTTN | −0.306355934 | 0.167097047 | 0.016552457 | chr11 | 1 | 70244650 | 70282681 |
| GTF2E1 | −0.291349005 | 0.166147044 | 0.007656982 | chr3 | 1 | 120461579 | 120501916 |
| RANBP10 | −0.315427602 | 0.165856155 | 0.009310847 | chr16 | −1 | 67757005 | 67840555 |
| NDUFB6 | −0.269773941 | 0.165153749 | 8.48E−05 | chr9 | −1 | 32552997 | 32573160 |
| U2AF2 | −0.208707084 | 0.164821088 | 0.005026224 | chr19 | 1 | 56165416 | 56186081 |
| PITPNA | −0.317543209 | 0.164787865 | 0.024251008 | chr17 | −1 | 1421287 | 1466110 |
| GLE1 | −0.21471907 | 0.164688923 | 0.005880602 | chr9 | 1 | 131267010 | 131302156 |
| HOOK2 | −0.247534635 | 0.164562585 | 0.012002635 | chr19 | −1 | 12873817 | 12886434 |
| PDS5B | −0.323312404 | 0.163100947 | 0.046015774 | chr13 | 1 | 33160564 | 33352157 |
| HIST1H3F | −0.327602788 | 0.163048806 | 0.006703769 | chr6 | −1 | 26250423 | 26250833 |
| MFAP1 | −0.224961111 | 0.16272895 | 0.013987432 | chr15 | −1 | 44096690 | 44117000 |
| FBXL18 | −0.279247645 | 0.162168754 | 0.00104894 | chr7 | −1 | 5528880 | 5553382 |
| FAU | −0.406804065 | 0.161929641 | 0.000297229 | chr11 | −1 | 64888103 | 64889660 |
| CDC20B | −0.383282634 | 0.161646367 | 0.004442713 | chr5 | −1 | 54408823 | 54469003 |
| ANAPC16 | −0.236656505 | 0.161380554 | 0.001393966 | chr10 | 1 | 73975806 | 73993587 |
| TRAF2 | −0.390824094 | 0.160954856 | 0.004567106 | chr9 | 1 | 139780970 | 139821059 |
| MDN1 | −0.323383819 | 0.160289758 | 0.010822148 | chr6 | −1 | 90353231 | 90529442 |
| MDN1 | −0.323383819 | 0.159439627 | 0.025894028 | chr6 | −1 | 90353231 | 90529442 |
| KLHL36 | −0.287914731 | 0.158563684 | 0.017189251 | chr16 | 1 | 84682107 | 84701292 |
| EEPD1 | −0.381673022 | 0.158255959 | 0.00114505 | chr7 | 1 | 36192758 | 36341152 |
| RANBP10 | −0.315427602 | 0.158083428 | 0.00357063 | chr16 | −1 | 67757005 | 67840555 |
| STUB1 | −0.207566771 | 0.15766592 | 0.00420275 | chr16 | 1 | 730276 | 732753 |
| SGTA | −0.377305347 | 0.156641041 | 0.000905684 | chr19 | −1 | 2755395 | 2783315 |
| PARN | −0.288966717 | 0.156584121 | 0.012747738 | chr16 | −1 | 14529559 | 14724124 |
| AIDA | −0.275078992 | 0.156446601 | 0.003998314 | chr1 | −1 | 222841355 | 222885866 |
| C1orf151 | −0.295885095 | 0.156140688 | 3.48E−05 | chr1 | 1 | 19923484 | 19956314 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| CAMSAP1 | −0.232304633 | 0.154584448 | 0.003500052 | chr9 | −1 | 138700333 | 138799070 |
| GLE1 | −0.21471907 | 0.154575495 | 0.048115631 | chr9 | 1 | 131266979 | 131304567 |
| FUBP1 | −0.269302108 | 0.154423734 | 0.015358702 | chr1 | −1 | 78413199 | 78444777 |
| STUB1 | −0.207566771 | 0.153912233 | 0.002187832 | chr16 | 1 | 730276 | 732753 |
| FUT10 | −0.255860029 | 0.153688953 | 0.005536724 | chr8 | −1 | 33228342 | 33330664 |
| ICMT | −0.21685651 | 0.152232106 | 0.015216296 | chr1 | −1 | 6281253 | 6296000 |
| LRBA | −0.315333638 | 0.151893065 | 0.010448278 | chr4 | −1 | 151185811 | 151936649 |
| EHMT1 | −0.241468906 | 0.150791458 | 0.013619894 | chr9 | 1 | 140513454 | 140730576 |
| FTL | −0.40992921 | 0.150732024 | 0.002344711 | chr19 | 1 | 49468566 | 49470135 |
| GCA | −0.298984935 | 0.150493917 | 0.026770541 | chr2 | 1 | 163200598 | 163217930 |
| VHL | −0.322679425 | 0.150010619 | 0.048079287 | chr3 | 1 | 10182692 | 10193904 |
| C20orf11 | −0.245288407 | 0.14936575 | 0.00821144 | chr20 | 1 | 61569471 | 61576996 |
| GLE1 | −0.21471907 | 0.147240709 | 0.033090498 | chr9 | 1 | 131266979 | 131304567 |
| ZMYND10 | −0.292895152 | 0.146712105 | 0.026612085 | chr3 | −1 | 50378541 | 50384283 |
| UTP23 | −0.374374515 | 0.146611717 | 0.013067857 | chr8 | 1 | 117778742 | 117786923 |
| ZNF800 | −0.328840317 | 0.146273616 | 0.040079467 | chr7 | −1 | 127010097 | 127032745 |
| ANAPC16 | −0.236656505 | 0.146205702 | 0.000286552 | chr10 | 1 | 73975806 | 73993587 |
| CCDC101 | −0.379871865 | 0.14603909 | 0.007688959 | chr16 | 1 | 28565247 | 28603111 |
| LSM1 | −0.36579053 | 0.145809293 | 0.002659766 | chr8 | −1 | 38020861 | 38034026 |
| ZXDC | −0.388243791 | 0.145399232 | 0.016752984 | chr3 | −1 | 126156444 | 126194762 |
| CISH | −0.274974325 | 0.145147773 | 0.017359591 | chr3 | −1 | 50643927 | 50649203 |
| MAP2K7 | −0.239304567 | 0.144528938 | 0.025928281 | chr19 | 1 | 7968776 | 7979363 |
| RPS13 | −0.37147841 | 0.144381377 | 1.10E−05 | chr11 | −1 | 17095939 | 17099220 |
| MSH3 | −0.33197287 | 0.143517844 | 0.015896109 | chr5 | 1 | 79950467 | 80172279 |
| NFX1 | −0.284450733 | 0.143446264 | 0.014695532 | chr9 | 1 | 33290509 | 33371155 |
| TM7SF3 | −0.281259298 | 0.143055372 | 0.043963475 | chr12 | −1 | 27124519 | 27167339 |
| SSNA1 | −0.294481831 | 0.142992315 | 0.003593741 | chr9 | 1 | 140083099 | 140084822 |
| JAG1 | −0.207653553 | 0.141910631 | 0.038493212 | chr20 | −1 | 10618332 | 10654608 |
| RFESD | −0.334412968 | 0.138496486 | 0.042433641 | chr5 | 1 | 94982458 | 94991894 |
| RPRD2 | −0.324095455 | 0.138444802 | 0.032478704 | chr1 | 1 | 150337126 | 150449042 |
| GSTK1 | −0.308788461 | 0.138131347 | 0.014538232 | chr7 | 1 | 142960522 | 142966088 |
| SNORD118 | −0.269386914 | 0.137651173 | 0.04365142 | chr17 | −1 | 8076296 | 8079714 |
| TGM2 | −0.299628157 | 0.136635576 | 0.046681146 | chr20 | −1 | 36756863 | 36793774 |
| PDDC1 | −0.34266226 | 0.135701804 | 0.01059529 | chr11 | −1 | 767225 | 777484 |
| E2F1 | −0.257226115 | 0.134080862 | 0.014042676 | chr20 | −1 | 32263489 | 32274210 |
| FKBP15 | −0.234494526 | 0.133751679 | 0.001575025 | chr9 | −1 | 115923286 | 115983598 |
| ZNF839 | −0.338895641 | 0.13254872 | 0.027084505 | chr14 | 1 | 102786096 | 102809044 |
| ACOX3 | −0.315455915 | 0.130554453 | 0.031006081 | chr4 | −1 | 8368439 | 8442450 |
| LYPLA2 | −0.248433242 | 0.129501428 | 0.012651101 | chr1 | 1 | 24117460 | 24122029 |
| ZC3H4 | −0.517757699 | 0.129458801 | 0.020656821 | chr19 | −1 | 47567449 | 47617009 |
| TRIM41 | −0.225225314 | 0.129032229 | 0.048659242 | chr5 | 1 | 180650290 | 180662808 |
| NDUFB2 | −0.284421962 | 0.128404241 | 0.014881978 | chr7 | 1 | 140396471 | 140422590 |
| CYB561D2 | −0.306400325 | 0.12830587 | 0.019098432 | chr3 | 1 | 50388126 | 50391500 |
| HNRNPH3 | −0.364665187 | 0.127667928 | 0.042931425 | chr10 | 1 | 70091832 | 70102944 |
| MBLAC1 | −0.260766689 | 0.126590252 | 0.030855091 | chr7 | 1 | 99724317 | 99726118 |
| C11orf68 | −0.304144949 | 0.125480629 | 0.018923113 | chr11 | −1 | 65684281 | 65686531 |
| STUB1 | −0.207566771 | 0.12452866 | 0.013277159 | chr16 | 1 | 730276 | 732753 |
| GTF2B | −0.312543543 | 0.124424797 | 0.03431258 | chr1 | −1 | 89318615 | 89357301 |
| | −0.225423721 | 0.12416237 | 0.006205245 | chr6 | 1 | 31939608 | 31949228 |
| UBR3 | −0.344642797 | 0.124057629 | 0.001866437 | chr2 | 1 | 170684018 | 170940637 |
| IQCK | −0.272202349 | 0.123469882 | 0.04078684 | chr16 | 1 | 19727778 | 19868907 |
| RANBP10 | −0.315427602 | 0.123149588 | 0.020181357 | chr16 | −1 | 67757005 | 67840555 |
| CAPN1 | −0.371381368 | 0.12269716 | 0.049861321 | chr11 | 1 | 64949343 | 64979476 |
| EFR3A | −0.329905044 | 0.12192648 | 0.045753502 | chr8 | 1 | 132916335 | 133025889 |
| TATDN2 | −0.281563426 | 0.120041142 | 0.010070144 | chr3 | 1 | 10289707 | 10322900 |
| ADIPOR1 | −0.222354088 | 0.119248118 | 0.008669656 | chr1 | −1 | 202909951 | 202927517 |
| SLC48A1 | −0.243259292 | 0.118141827 | 0.049293803 | chr12 | 1 | 48166991 | 48176536 |
| C2CD3 | −0.304566241 | 0.117898755 | 0.02071424 | chr11 | −1 | 73724430 | 73882064 |
| POLR2L | −0.32790758 | 0.117102078 | 0.027745289 | chr11 | −1 | 839721 | 842545 |
| SLC38A7 | −0.287708322 | 0.115656321 | 0.035591081 | chr16 | −1 | 58699013 | 58718674 |
| ZNF697 | −0.285615275 | 0.114911371 | 0.027013127 | chr1 | −1 | 120162000 | 120190390 |
| USP4 | −0.220679768 | 0.114459518 | 0.023789104 | chr3 | −1 | 49315264 | 49377466 |
| | −0.340034255 | 0.112566416 | 0.007423627 | chr1 | −1 | 247150269 | 247171210 |
| NDUFB2 | −0.284421962 | 0.112507547 | 0.034290656 | chr7 | 1 | 140396471 | 140422590 |
| RRAGA | −0.378924933 | 0.111128217 | 0.01910305 | chr9 | 1 | 19049372 | 19051019 |
| FAM161A | −0.256344752 | 0.11046809 | 0.002229884 | chr2 | −1 | 62051991 | 62081278 |
| ANGEL2 | −0.386058099 | 0.110047064 | 0.012069939 | chr1 | −1 | 213180327 | 213189168 |
| RAD18 | −0.294092376 | 0.109844952 | 0.025671988 | chr3 | −1 | 8918760 | 9005186 |
| FBXO31 | −0.338742144 | 0.10983136 | 0.036850372 | chr16 | −1 | 87362944 | 87417394 |
| TATDN2 | −0.281563426 | 0.109762843 | 0.033195763 | chr3 | 1 | 10289707 | 10322900 |
| DNAJC9 | −0.362712454 | 0.109400292 | 0.039051442 | chr10 | −1 | 75002582 | 75008620 |
| RNF181 | −0.293406944 | 0.109205066 | 0.015530169 | chr2 | 1 | 85822857 | 85824704 |
| PXMP2 | −0.249805307 | 0.108969797 | 0.02925455 | chr12 | 1 | 133287436 | 133295746 |
| COPE | −0.343473643 | 0.10818861 | 0.043136212 | chr19 | −1 | 19010323 | 19030199 |
| RPL41 | −0.279151527 | 0.107417407 | 5.80E−05 | chr12 | 1 | 56510572 | 56511308 |
| WHSC2 | −0.329016517 | 0.105970321 | 0.015863743 | chr4 | −1 | 1984441 | 2011837 |
| TMED2 | −0.238864154 | 0.105035201 | 0.015444836 | chr12 | 1 | 124069076 | 124082681 |

TABLE 14-continued

List of genes showing statistically significant over-expression in cancer compared to normal samples and are within 2,000 bp from an outward methylation boundary shift.

| | | | | | | | |
|---|---|---|---|---|---|---|---|
| RPS28 | −0.252441473 | 0.104337089 | 0.006397904 | chr19 | 1 | 8386384 | 8387278 |
| TRPC4AP | −0.420345973 | 0.103761538 | 0.021125114 | chr20 | −1 | 33590207 | 33680674 |
| C1orf56 | −0.421783765 | 0.103495874 | 0.036623214 | chr1 | 1 | 151020216 | 151023896 |
| CCDC101 | −0.379871865 | 0.100050955 | 0.030767786 | chr16 | 1 | 28565247 | 28603111 |
| FKBP15 | −0.234494526 | 0.099742471 | 0.013493827 | chr9 | −1 | 115923286 | 115983598 |
| C19orf55 | −0.265538386 | 0.099394395 | 0.016475512 | chr19 | 1 | 36249117 | 36259447 |
| SLC39A1 | −0.249518474 | 0.099224424 | 0.047311692 | chr1 | −1 | 153931575 | 153936048 |
| C3orf1 | −0.256014544 | 0.098068182 | 0.028620778 | chr3 | 1 | 119217379 | 119243937 |
| ZNF410 | −0.212557239 | 0.097841091 | 0.0229483 | chr14 | 1 | 74353574 | 74398980 |
| RANGRF | −0.256581556 | 0.097053625 | 0.0429601 | chr17 | 1 | 8191989 | 8192904 |
| RPTOR | −0.322737642 | 0.096188417 | 0.038807285 | chr17 | 1 | 78518625 | 78940173 |
| HARBI1 | −0.228571217 | 0.09522732 | 0.023940738 | chr11 | −1 | 46624411 | 46638777 |
| FAM192A | −0.291697248 | 0.095171857 | 0.028782031 | chr16 | −1 | 57186387 | 57219976 |
| RABEPK | −0.32443941 | 0.090453228 | 0.022127909 | chr9 | 1 | 127962824 | 127984666 |
| MORF4 | −0.367250341 | 0.089105317 | 0.042713428 | chr15 | 1 | 79165211 | 79190475 |
| ARMC2 | −0.325357455 | 0.080694621 | 0.035527188 | chr6 | 1 | 109169625 | 109295186 |
| UBAP1 | −0.27003315 | 0.075360164 | 0.039322863 | chr9 | 1 | 34179011 | 34252521 |
| KIAA1430 | −0.230619058 | 0.073236235 | 0.036554003 | chr4 | −1 | 186090180 | 186125182 |
| SNORD73A | −0.245144596 | 0.070121069 | 0.008430314 | chr4 | 1 | 152020725 | 152025804 |
| EIF4G2 | −0.261394891 | 0.070102425 | 0.032635321 | chr11 | −1 | 10818593 | 10830017 |
| SNORD73A | −0.245144596 | 0.063919673 | 0.04188973 | chr4 | 1 | 152020725 | 152025804 |
| SNORD73A | −0.245144596 | 0.063555007 | 0.015705811 | chr4 | 1 | 152020725 | 152025804 |

| geneName | affyid | DMRstart | DMRend | Distance To TSS |
|---|---|---|---|---|
| QPCT | 205174_s_at | 37571717 | 37571717 | −261 |
| ANLN | 222608_s_at | 36429415 | 36429415 | −759 |
| SLC6A6 | 228754_at | 14444076 | 14444076 | −590 |
| CEP55 | 218542_at | 95256389 | 95256389 | 509 |
| ANLN | 1552619_a_at | 36429415 | 36429415 | −759 |
| TGFBI | 201506_at | 135364584 | 135364584 | 548 |
| ME1 | 204058_at | 84140790 | 84140790 | −757 |
| TRIP13 | 204033_at | 892758 | 892758 | −743 |
| CTPS | 202613_at | 41445007 | 41445007 | 1600 |
| ME1 | 204059_s_at | 84140790 | 84140790 | −757 |
| HELLS | 223556_at | 96305574 | 96305574 | −1367 |
| CCNB1 | 228729_at | 68462837 | 68462837 | 1104 |
| MET | 203510_at | 116312446 | 116312446 | −950 |
| TRIP6 | 209129_at | 100464760 | 100464760 | −1046 |
| | 202357_s_at | 31913486 | 31913486 | 693 |
| IL20RA | 219115_s_at | 137366101 | 137366101 | −235 |
| TTK | 204822_at | 80714322 | 80714322 | −1083 |
| CDK1 | 203213_at | 62538212 | 62538212 | 1643 |
| PRC1 | 218009_s_at | 91537749 | 91537749 | −939 |
| CCNB1 | 214710_s_at | 68462837 | 68462837 | 1104 |
| CDCA2 | 226661_at | 25316513 | 25316513 | 1442 |
| ARG2 | 203946_s_at | 68086579 | 68086579 | −1290 |
| PHF19 | 227212_s_at | 123639606 | 123639606 | 1550 |
| SLC6A6 | 205920_at | 14444076 | 14444076 | −590 |
| TK1 | 1554408_a_at | 76183314 | 76183314 | −443 |
| CDK1 | 210559_s_at | 62538212 | 62538212 | 1643 |
| C12orf48 | 227928_at | 102513956 | 102513956 | −822 |
| LRRC6 | 206483_at | 133687813 | 133687813 | 953 |
| CDKN3 | 1555758_a_at | 54863673 | 54863673 | 1205 |
| MET | 213816_s_at | 116312446 | 116312446 | −950 |
| CDKN3 | 209714_s_at | 54863673 | 54863673 | 1205 |
| ITGA2 | 227314_at | 52285156 | 52285156 | −1396 |
| GART | 217445_s_at | 34915148 | 34915148 | 1539 |
| KPNA2 | 211762_s_at | 66031848 | 66031848 | −926 |
| MET | 213807_x_at | 116312446 | 116312446 | −950 |
| FAM57A | 218898_at | 635798 | 635798 | 1089 |
| CDK1 | 203214_x_at | 62538212 | 62538212 | 1643 |
| GPT2 | 224839_s_at | 46918290 | 46918290 | 868 |
| PDCD2L | 224467_s_at | 34895303 | 34895303 | −511 |
| C12orf48 | 220060_s_at | 102513956 | 102513956 | −822 |
| SLC39A10 | 225295_at | 196521471 | 196521471 | −365 |
| HOXB6 | 205366_s_at | 46682354 | 46682354 | −426 |
| MET | 211599_x_at | 116312446 | 116312446 | −950 |
| DHFRP1 | 202533_s_at | 79950802 | 79950802 | −784 |
| | 222757_s_at | 173940442 | 173940442 | 1785 |
| ERO1L | 222646_s_at | 53162423 | 53162423 | 1515 |
| FERMT1 | 218796_at | 6104191 | 6104191 | −318 |
| MOCOS | 219959_at | 33767482 | 33767482 | 708 |
| GART | 212378_at | 34915148 | 34915148 | 1539 |
| FERMT1 | 60474_at | 6104191 | 6104191 | −318 |
| C1orf59 | 225841_at | 109204148 | 109204148 | −200 |
| CENPH | 231772_x_at | 68485375 | 68485375 | −859 |

TABLE 14-continued

List of genes showing statistically significant over-expression in cancer compared to normal samples and are within 2,000 bp from an outward methylation boundary shift.

| | | | | |
|---|---|---|---|---|
| RUVBL1 | 201614_s_at | 127842667 | 127842667 | −439 |
| FBXO5 | 218875_s_at | 153304153 | 153304153 | 1194 |
| SPNS2 | 225671_at | 4402129 | 4402129 | 1848 |
| SLC22A3 | 205421_at | 160769300 | 160769300 | 1247 |
| SCD | 211708_s_at | 102106877 | 102106877 | 981 |
| C13orf37 | 225578_at | 73301825 | 73301825 | −1370 |
| TK1 | 202338_at | 76183314 | 76183314 | −443 |
| ODC1 | 200790_at | 10588630 | 10588630 | 1291 |
| PLK4 | 204887_s_at | 128802016 | 128802016 | −580 |
| BYSL | 203612_at | 41888926 | 41888926 | −1093 |
| ASPM | 219918_s_at | 197115824 | 197115824 | 1628 |
| FERMT1 | 229545_at | 6104191 | 6104191 | −318 |
| GMDS | 204875_s_at | 2245915 | 2245915 | 1328 |
| SHMT2 | 214437_s_at | 57623519 | 57623519 | 1011 |
| C7orf68 | 1554452_a_at | 128095903 | 128095903 | 1102 |
| C7orf68 | 218507_at | 128095903 | 128095903 | 1102 |
| GMDS | 214106_s_at | 2245915 | 2245915 | 1328 |
| TIMELESS | 203046_s_at | 56843200 | 56843200 | −562 |
| KPNA2 | 201088_at | 66031848 | 66031848 | −926 |
| RAB23 | 220955_x_at | 57086205 | 57086205 | 579 |
| AURKA | 208079_s_at | 54967261 | 54967261 | 1023 |
| TACC3 | 218308_at | 1723266 | 1723266 | 1005 |
| SQLE | 213562_s_at | 126010720 | 126010720 | 1102 |
| NUP37 | 218622_at | 102512361 | 102512361 | −525 |
| CTHRC1 | 225681_at | 104383743 | 104383743 | −1092 |
| RTEL1 | 206467_x_at | 62290756 | 62290756 | 0 |
| NUFIP1 | 205135_s_at | 45563618 | 45563618 | 827 |
| PLK1 | 202240_at | 23690143 | 23690143 | 1313 |
| C12orf29 | 228378_at | 88429290 | 88429290 | −396 |
| CEP76 | 52285_f_at | 12702773 | 12702773 | 968 |
| DTYMK | 1553984_s_at | 242626406 | 242626406 | −1460 |
| PHF19 | 227211_at | 123639466 | 123639466 | 1410 |
| RAD18 | 224200_s_at | 9005186 | 9005186 | −1043 |
| SCD | 200832_s_at | 102106881 | 102106881 | 977 |
| RAB23 | 223463_at | 57087078 | 57087078 | 1452 |
| YAP1 | 213342_at | 101981210 | 101981210 | −875 |
| GSTP1 | 200824_at | 67351066 | 67351066 | −740 |
| NOLC1 | 205895_s_at | 103912117 | 103912117 | −513 |
| DTYMK | 203270_at | 242626406 | 242626406 | −1460 |
| PLEK2 | 218644_at | 67878828 | 67878828 | −490 |
| SHMT2 | 214096_s_at | 57623519 | 57623519 | 1011 |
| CEP76 | 219311_at | 12702773 | 12702773 | 968 |
| PLK4 | 204886_at | 128802016 | 128802016 | −580 |
| JAG1 | 209098_s_at | 10654608 | 10654608 | −1306 |
| PKM2 | 201251_at | 72523328 | 72523328 | −1684 |
| NKD1 | 229481_at | 50582241 | 50582241 | 965 |
| AURKA | 204092_s_at | 54967261 | 54967261 | 1023 |
| FGGY | 219718_at | 59762663 | 59762663 | −1010 |
| SHMT2 | 214095_at | 57623519 | 57623519 | 1011 |
| FBXO22OS | 225736_at | 76196200 | 76196200 | 1253 |
| SNORD118 | 224496_s_at | 8079714 | 8079714 | −807 |
| DPCD | 1553976_a_at | 103348045 | 103348045 | 822 |
| AHCY | 200903_s_at | 32891154 | 32891154 | 912 |
| FZD6 | 203987_at | 104311100 | 104311100 | 885 |
| CDCA2 | 236957_at | 25316513 | 25316513 | 1442 |
| WARS2 | 218766_s_at | 119683271 | 119683271 | −673 |
| MTHFD2 | 201761_at | 74425689 | 74425689 | −358 |
| PGM2L1 | 229553_at | 74109502 | 74109502 | −956 |
| WDHD1 | 204728_s_at | 55493795 | 55493795 | 859 |
| FHL2 | 202949_s_at | 106016124 | 106016124 | 1979 |
| PGM2L1 | 229256_at | 74109502 | 74109502 | −956 |
| FBXO5 | 234863_x_at | 153304153 | 153304153 | 1194 |
| SQLE | 209218_at | 126010720 | 126010720 | 1102 |
| IL20RA | 222829_s_at | 137366101 | 137366101 | −235 |
| FASN | 212218_s_at | 80056106 | 80056106 | −1406 |
| ABHD2 | 228490_at | 89631405 | 89631405 | 1331 |
| KIAA1704 | 220171_x_at | 45563687 | 45563687 | −896 |
| GART | 212379_at | 34915148 | 34915148 | 1539 |
| NOLC1 | 211949_s_at | 103912117 | 103912117 | −513 |
| FBXO22OS | 225737_s_at | 76196200 | 76196200 | 1253 |
| | 223519_at | 173940570 | 173940570 | 1657 |
| VANGL1 | 219330_at | 116184612 | 116184612 | −470 |
| IMMP2L | 227153_at | 111202347 | 111202347 | −661 |
| NKD1 | 1553115_at | 50582241 | 50582241 | 965 |
| ZYX | 200808_s_at | 143078173 | 143078173 | −1292 |
| ABHD2 | 205566_at | 89631405 | 89631405 | 1331 |
| FBXO22OS | 225734_at | 76196200 | 76196200 | 1253 |

TABLE 14-continued

List of genes showing statistically significant over-expression in cancer compared to normal samples and are within 2,000 bp from an outward methylation boundary shift.

| | | | | |
|---|---|---|---|---|
| ENAH | 222433_at | 225840844 | 225840844 | −1432 |
| INCENP | 242787_at | 61891445 | 61891445 | 1307 |
| LACTB2 | 222714_s_at | 71581447 | 71581447 | 1093 |
| ALDH7A1 | 208950_s_at | 125931110 | 125931110 | 1325 |
| ITGA2 | 205032_at | 52285156 | 52285156 | −1396 |
| SCD | 211162_x_at | 102106881 | 102106881 | 977 |
| DHFRP1 | 48808_at | 79950802 | 79950802 | −784 |
| BAX | 211833_s_at | 49458134 | 49458134 | −627 |
| LACTB2 | 218701_at | 71581447 | 71581447 | 1093 |
| MRPS17 | 218982_s_at | 56019512 | 56019512 | −841 |
| ENO1 | 217294_s_at | 8938749 | 8938749 | 1328 |
| C12orf5 | 219099_at | 4430359 | 4430359 | 1093 |
| ERCC8 | 1554883_a_at | 60240878 | 60240878 | 840 |
| PGD | 201118_at | 10459137 | 10459137 | 1096 |
| IPO7 | 200994_at | 9406169 | 9406169 | −285 |
| RPP25 | 219143_s_at | 75249775 | 75249775 | 1379 |
| NUP35 | 225470_at | 183989083 | 183989083 | −741 |
| FAM175A | 233543_s_at | 84406334 | 84406334 | 984 |
| PHLDA2 | 209803_s_at | 2950685 | 2950685 | 1320 |
| MEST | 202016_at | 130126046 | 130126046 | −282 |
| NOP58 | 223096_at | 203130439 | 203130439 | −1051 |
| GLRX3 | 209080_x_at | 131934663 | 131934663 | −508 |
| C1orf135 | 220011_at | 26185903 | 26185903 | 767 |
| C17orf75 | 203830_at | 30669189 | 30669189 | −640 |
| IPO7 | 200992_at | 9406169 | 9406169 | −285 |
| XPO5 | 223057_s_at | 43543812 | 43543812 | −964 |
| YAP1 | 224894_at | 101981210 | 101981210 | −875 |
| WARS2 | 222734_at | 119683271 | 119683271 | −673 |
| DUS4L | 205761_s_at | 107204403 | 107204403 | 850 |
| ERO1L | 218498_s_at | 53162423 | 53162423 | 1515 |
| NANP | 228073_at | 25604811 | 25604811 | 1323 |
| DNAJC2 | 213097_s_at | 102985113 | 102985113 | −438 |
| XPO5 | 223055_s_at | 43543812 | 43543812 | −964 |
| NOLC1 | 211951_at | 103912117 | 103912117 | −513 |
| PPAP2C | 209529_at | 291435 | 291435 | 1840 |
| HSPD1 | 200806_s_at | 198364771 | 198364771 | −1677 |
| | 225662_at | 173940570 | 173940570 | 1657 |
| EPT1 | 1555274_a_at | 26568982 | 26568982 | −1458 |
| C14orf126 | 1553801_a_at | 31926670 | 31926670 | 960 |
| GNPNAT1 | 225853_at | 53258319 | 53258319 | 1066 |
| PDXK | 202671_s_at | 45138978 | 45138978 | 1446 |
| EPHA1 | 205977_s_at | 143105985 | 143105985 | 673 |
| | 225665_at | 173940570 | 173940570 | 1657 |
| L2HGDH | 224460_s_at | 50778947 | 50778947 | 1023 |
| PTPLAD1 | 217777_s_at | 65822825 | 65822825 | −469 |
| TOMM34 | 201870_at | 43589127 | 43589127 | 1241 |
| CTSH | 202295_s_at | 79237433 | 79237433 | −720 |
| PUS1 | 218670_at | 132413813 | 132413813 | −920 |
| RSL1D1 | 212018_s_at | 11945442 | 11945442 | −726 |
| TBC1D7 | 223461_at | 13328763 | 13328763 | −746 |
| TIMM50 | 224913_s_at | 39971052 | 39971052 | −231 |
| MCFD2 | 212246_at | 47143007 | 47143007 | 1226 |
| DNAJC9 | 213088_s_at | 75008620 | 75008620 | 202 |
| TBRG4 | 220789_s_at | 45151317 | 45151317 | 1314 |
| ALDH7A1 | 208951_at | 125931110 | 125931110 | 1325 |
| GCSH | 213129_s_at | 81130008 | 81130008 | −565 |
| CAMSAP1 | 212711_at | 138799070 | 138799070 | 1398 |
| JAG1 | 216268_s_at | 10654608 | 10654608 | −1306 |
| CDK7 | 211297_s_at | 68530700 | 68530700 | 924 |
| NSUN4 | 226351_at | 46805849 | 46805849 | −515 |
| IPO7 | 200993_at | 9406169 | 9406169 | −285 |
| TROAP | 1568596_a_at | 49716971 | 49716971 | −700 |
| ZMYND19 | 227477_at | 140484942 | 140484942 | 1064 |
| C1orf135 | 222946_s_at | 26185903 | 26185903 | 767 |
| GEMIN5 | 225712_at | 154317769 | 154317769 | −395 |
| MKLN1 | 204423_at | 131012619 | 131012619 | −1092 |
| SHB | 1557458_s_at | 38069208 | 38069208 | −1133 |
| SKA2 | 225686_at | 57232800 | 57232800 | 1693 |
| TNFRSF10A | 231775_at | 23082639 | 23082639 | −806 |
| CKLF | 221058_s_at | 66586470 | 66586470 | 1622 |
| CKS1B | 201897_s_at | 154947159 | 154947159 | 1810 |
| NDUFAF2 | 228355_s_at | 60240956 | 60240956 | −918 |
| PTPLAD1 | 222404_x_at | 65822825 | 65822825 | −469 |
| PDXK | 218018_at | 45138978 | 45138978 | 1446 |
| RFWD3 | 218564_at | 74700779 | 74700779 | −1051 |
| ZC3H8 | 223506_at | 113012688 | 113012688 | 950 |
| NUBPL | 220176_at | 32030591 | 32030591 | −541 |

TABLE 14-continued

List of genes showing statistically significant over-expression in cancer compared to normal samples and are within 2,000 bp from an outward methylation boundary shift.

| | | | | |
|---|---|---|---|---|
| ENAH | 217820_s_at | 225840844 | 225840844 | −1432 |
| DDX56 | 217754_at | 44613601 | 44613601 | 960 |
| VANGL1 | 229997_at | 116184612 | 116184612 | −470 |
| UCHL3 | 204616_at | 76123927 | 76123927 | −675 |
| ICA1 | 210547_x_at | 8301911 | 8301911 | −817 |
| C5orf34 | 229886_at | 43515247 | 43515247 | 1218 |
| POLH | 1557701_s_at | 43543887 | 43543887 | 889 |
| JAG1 | 209099_x_at | 10654608 | 10654608 | −1306 |
| IPO7 | 200995_at | 9406169 | 9406169 | −285 |
| ACP1 | 201629_s_at | 264872 | 264872 | 1366 |
| CCT4 | 200877_at | 62115939 | 62115939 | −465 |
| WEE1 | 212533_at | 9595430 | 9595430 | −1298 |
| HIBADH | 231955_s_at | 27702614 | 27702614 | −653 |
| YAP1 | 224895_at | 101981210 | 101981210 | −875 |
| DHFRP1 | 202534_x_at | 79950802 | 79950802 | −784 |
| FAM161A | 242584_at | 62081278 | 62081278 | 938 |
| EXOC6 | 233924_s_at | 94608277 | 94608277 | −1158 |
| NUFIP1 | 205134_s_at | 45563618 | 45563618 | 827 |
| PTPLAD1 | 234000_s_at | 65822825 | 65822825 | −469 |
| ST7OT3 | 207871_s_at | 116593396 | 116593396 | −658 |
| GART | 210005_at | 34914420 | 34914420 | 811 |
| GTF3C3 | 218343_s_at | 197664425 | 197664425 | −726 |
| FAM128A | 213166_x_at | 132249995 | 132249995 | −1687 |
| ICA1 | 207949_s_at | 8301911 | 8301911 | −817 |
| BAX | 208478_s_at | 49458134 | 49458134 | −627 |
| ENO1 | 201231_s_at | 8938749 | 8938749 | 1328 |
| SUSD1 | 226264_at | 114937465 | 114937465 | −827 |
| SKIL | 217591_at | 170077411 | 170077411 | −435 |
| SLC6A6 | 205921_s_at | 14444076 | 14444076 | −590 |
| UBE3C | 1554794_a_at | 156931607 | 156931607 | 1361 |
| MTHFD2 | 234976_x_at | 74425689 | 74425689 | −358 |
| METTL5 | 221570_s_at | 170681424 | 170681424 | −814 |
| C7orf44 | 209445_x_at | 43769088 | 43769088 | −1021 |
| NAA38 | 219119_at | 117824086 | 117824086 | −992 |
| PSMDI2 | 202352_s_at | 65362743 | 65362743 | 1176 |
| UBA2 | 201177_s_at | 34919268 | 34919268 | −531 |
| INTS2 | 224308_s_at | 60005377 | 60005377 | −492 |
| SCD | 200831_s_at | 102106881 | 102106881 | 977 |
| ZYX | 215706_x_at | 143078173 | 143078173 | −1292 |
| C12orf45 | 226349_at | 105380098 | 105380098 | −475 |
| PHF19 | 225533_at | 123639606 | 123639606 | 1550 |
| PTPLAD1 | 222405_at | 65822825 | 65822825 | −469 |
| CCT8 | 200873_s_at | 30446118 | 30446118 | 1632 |
| GTPBP10 | 234311_s_at | 89975979 | 89975979 | −1015 |
| POLR3K | 218866_s_at | 103628 | 103628 | 1047 |
| ZNF200 | 207338_s_at | 3285175 | 3285175 | −806 |
| DCLRE1A | 209804_at | 115614142 | 115614142 | 761 |
| CSTF3 | 229666_s_at | 33183037 | 33183037 | 1661 |
| CKLF | 219161_s_at | 66586470 | 66586470 | 1622 |
| MAP3K8 | 205027_s_at | 30722866 | 30722866 | −1094 |
| C12orf29 | 213701_at | 88429290 | 88429290 | −396 |
| POLR1D | 218258_at | 28194903 | 28194903 | −1553 |
| | 218833_at | 173940687 | 173940687 | 1540 |
| C14orf126 | 227158_at | 31926670 | 31926670 | 960 |
| DHFRP1 | 202532_s_at | 79950802 | 79950802 | −784 |
| CCT5 | 208696_at | 10250033 | 10250033 | 1696 |
| POLH | 222879_s_at | 43543887 | 43543887 | 889 |
| FPGS | 202945_at | 130565154 | 130565154 | 1051 |
| GCSH | 213133_s_at | 81130008 | 81130008 | −565 |
| ATP5S | 213995_at | 50779047 | 50779047 | −1123 |
| THEM4 | 229253_at | 151882284 | 151882284 | −463 |
| VANGL1 | 229492_at | 116184612 | 116184612 | −470 |
| GSG2 | 223759_s_at | 3627197 | 3627197 | 996 |
| PXMP2 | 1555943_at | 133287436 | 133287436 | 888 |
| CAMSAP1 | 212712_at | 138799070 | 138799070 | 1398 |
| ORMDL2 | 218556_at | 56211806 | 56211806 | 844 |
| C16orf55 | 230811_at | 89724152 | 89724152 | 1235 |
| ABHD2 | 87100_at | 89631405 | 89631405 | 1331 |
| ABHD2 | 63825_at | 89631405 | 89631405 | 1331 |
| MRPS28 | 219819_s_at | 80942506 | 80942506 | −841 |
| KDM1A | 212348_s_at | 23345941 | 23345941 | −696 |
| PDCD11 | 212422_at | 105156405 | 105156405 | −1019 |
| C17orf79 | 225096_at | 30186256 | 30186256 | −488 |
| WEE1 | 215711_s_at | 9595430 | 9595430 | −1298 |
| PDF | 219575_s_at | 69373513 | 69373513 | −1151 |
| LRSAM1 | 235449_at | 130213784 | 130213784 | 1092 |
| TNFRSF10A | 1552648_a_at | 23082639 | 23082639 | −806 |

TABLE 14-continued

List of genes showing statistically significant over-expression in cancer compared to normal samples and are within 2,000 bp from an outward methylation boundary shift.

| | | | | |
|---|---|---|---|---|
| C16orf88 | 213237_at | 19726362 | 19726362 | −780 |
| PLK4 | 211088_s_at | 128802016 | 128802016 | −580 |
| DPCD | 226009_at | 103348045 | 103348045 | 822 |
| KIAA0895 | 213424_at | 36429734 | 36429734 | 1078 |
| DDX55 | 231843_at | 124086672 | 124086672 | −883 |
| GPHN | 220773_s_at | 66974125 | 66974125 | −640 |
| WDR36 | 238677_at | 110427414 | 110427414 | −60 |
| CKLF | 223451_s_at | 66586470 | 66586470 | 1622 |
| SRD5A1 | 210959_s_at | 6633456 | 6633456 | −1370 |
| C6orf223 | 230944_at | 43968337 | 43968337 | 0 |
| WDHD1 | 216228_s_at | 55493795 | 55493795 | 859 |
| SRD5A1 | 204675_at | 6633456 | 6633456 | −1370 |
| | 227805_at | 172864490 | 172864490 | −217 |
| CSNK1E | 225756_at | 38714089 | 38714089 | −539 |
| UCHL5 | 220083_x_at | 193028539 | 193028539 | 1268 |
| HSPD1 | 200807_s_at | 198364771 | 198364771 | −1677 |
| SNORD118 | 239824_s_at | 8079714 | 8079714 | −807 |
| RANGRF | 218526_s_at | 8191989 | 8191989 | −832 |
| OAS3 | 218400_at | 113376157 | 113376157 | 1319 |
| EEPD1 | 225631_at | 36192758 | 36192758 | −746 |
| AARSD1 | 222064_s_at | 41132020 | 41132020 | 347 |
| PRPF19 | 203103_s_at | 60674056 | 60674056 | −990 |
| ACP1 | 215227_x_at | 264869 | 264869 | 1369 |
| RAB23 | 229504_at | 57087078 | 57087078 | 1452 |
| GALK2 | 205219_s_at | 49447976 | 49447976 | −1441 |
| BBS2 | 223227_at | 56554195 | 56554195 | 1252 |
| SHB | 204657_a_at | 38069208 | 38069208 | −1133 |
| TALDO1 | 201463_s_at | 747329 | 747329 | 1421 |
| SLC27A2 | 205769_at | 50474394 | 50474394 | 1333 |
| XPO5 | 223056_s_at | 43543812 | 43543812 | −964 |
| SNORD118 | 238590_x_at | 8079714 | 8079714 | −807 |
| SLC27A2 | 205708_s_at | 50474394 | 50474394 | 1333 |
| CENPO | 226118_at | 25016014 | 25016014 | −846 |
| DBR1 | 234295_at | 137893791 | 137893791 | 1138 |
| TUBGCP4 | 211337_s_at | 43663293 | 43663293 | 948 |
| PSMC3IP | 213951_s_at | 40729747 | 40729747 | 828 |
| GTF3C3 | 222604_at | 197664425 | 197664425 | −726 |
| PCBD2 | 1554894_a_at | 134240596 | 134240596 | 1333 |
| CSNK1E | 222015_at | 38713413 | 38713413 | −1215 |
| DAK | 218688_at | 61100654 | 61100654 | 812 |
| SKIL | 206675_s_at | 170075514 | 170075514 | 1147 |
| MMACHC | 211774_s_at | 45965725 | 45965725 | 1200 |
| HSPE1 | 205133_s_at | 198364718 | 198364718 | 1730 |
| HNRNPD | 209330_s_at | 83295109 | 83295109 | −1616 |
| EEPD1 | 225630_at | 36192758 | 36192758 | −746 |
| KARS | 200840_at | 75681577 | 75681577 | 862 |
| NMI | 203964_at | 152146571 | 152146571 | 1086 |
| CSTF3 | 203947_at | 33183037 | 33183037 | 1661 |
| PLBD1 | 218454_at | 14720791 | 14720791 | −595 |
| TUBA4A | 212242_at | 220118754 | 220118754 | 1937 |
| ANAPC7 | 225521_at | 110841535 | 110841535 | −710 |
| RABEPK | 203150_at | 127962882 | 127962882 | −975 |
| USP18 | 219211_at | 18632666 | 18632666 | 784 |
| CSTF1 | 202190_at | 54967450 | 54967450 | −1212 |
| SRPK2 | 1558254_s_at | 105029341 | 105029341 | −807 |
| GPHN | 223319_at | 66974125 | 66974125 | −640 |
| RAB15 | 59697_at | 65438875 | 65438875 | −810 |
| SLC48A1 | 218417_s_at | 48166991 | 48166991 | −497 |
| PHB | 200658_s_at | 47492242 | 47492242 | −1192 |
| GLRX3 | 214205_x_at | 131934663 | 131934663 | −508 |
| THEM4 | 243492_at | 151882284 | 151882284 | −463 |
| PSMC2 | 201068_s_at | 102985361 | 102985361 | 190 |
| RAD18 | 223417_at | 9005186 | 9005186 | −1043 |
| ASPSCR1 | 218908_at | 79935426 | 79935426 | 1014 |
| FLVCR1 | 222906_at | 213031597 | 213031597 | 917 |
| PDCD11 | 212424_at | 105156405 | 105156405 | −1019 |
| C13orf34 | 219544_at | 73302064 | 73302064 | 1131 |
| SDCCAG3 | 218427_at | 139305061 | 139305061 | −1069 |
| CAMSAP1 | 212710_at | 138799070 | 138799070 | 1398 |
| HIBADH | 224812_at | 27702614 | 27702614 | −653 |
| SNORD118 | 224495_at | 8079714 | 8079714 | −807 |
| SHB | 204656_at | 38069208 | 38069208 | −1133 |
| SPC24 | 235572_at | 11266458 | 11266458 | 656 |
| PSMD1 | 201198_s_at | 231921578 | 231921578 | 1189 |
| KIAA0319 | 206017_at | 24646383 | 24646383 | −692 |
| AARS | 201000_at | 70323409 | 70323409 | 1250 |
| THEM4 | 1553118_at | 151882284 | 151882284 | −463 |

TABLE 14-continued

List of genes showing statistically significant over-expression in cancer compared to normal samples and are within 2,000 bp from an outward methylation boundary shift.

| | | | | |
|---|---|---|---|---|
| KIAA1324 | 243349_at | 109656729 | 109656729 | −1672 |
| PERP | 222392_x_at | 138428648 | 138428648 | 1690 |
| PPP2R1B | 202884_s_at | 111637169 | 111637169 | −996 |
| SAAL1 | 225614_at | 18127638 | 18127638 | −488 |
| BLVRA | 203771_s_at | 43798279 | 43798279 | 917 |
| WDR5B | 219538_at | 122134882 | 122134882 | −1127 |
| MAP7 | 202889_x_at | 136871646 | 136871646 | −774 |
| KARS | 200079_s_at | 75681577 | 75681577 | 862 |
| G2E3 | 223255_at | 31028364 | 31028364 | −885 |
| RAB15 | 221810_at | 65438875 | 65438875 | −810 |
| COPS2 | 202467_s_at | 49447854 | 49447854 | 1319 |
| JHDM1D | 225142_at | 139876835 | 139876835 | −1311 |
| TNFRSF10A | 241371_at | 23082639 | 23082639 | −806 |
| PERP | 217744_s_at | 138428648 | 138428648 | 1690 |
| CCDC77 | 224521_s_at | 510742 | 510742 | −561 |
| DAP3 | 208822_s_at | 155658849 | 155658849 | 933 |
| ZNF643 | 207219_at | 40916716 | 40916716 | −1567 |
| ABHD2 | 221815_at | 89631405 | 89631405 | 1331 |
| NSUN2 | 223076_s_at | 6633404 | 6633404 | 1318 |
| LRRC2 | 219949_at | 46608040 | 46608040 | −234 |
| TARS | 201263_at | 33440802 | 33440802 | 1714 |
| HSPD1 | 243372_at | 198364771 | 198364771 | −1677 |
| UBXN10 | 238657_a1 | 20512578 | 20512578 | −390 |
| KLHDC5 | 225963_at | 27933187 | 27933187 | −852 |
| MRPL16 | 217980_s_at | 59578345 | 59578345 | 1074 |
| TGEBR2 | 207334_s_at | 30647994 | 30647994 | 1908 |
| F3 | 204363_at | 95007356 | 95007356 | 793 |
| G2E3 | 223257_at | 31028364 | 31028364 | −885 |
| G2E3 | 223258_s_at | 31028364 | 31028364 | −885 |
| SLC48A1 | 48106_at | 48166991 | 48166991 | −497 |
| BLVRA | 203773_x_at | 43798279 | 43798279 | 917 |
| C2orf15 | 243887_at | 99797542 | 99797542 | 1120 |
| PGM2L1 | 238417_at | 74109502 | 74109502 | −956 |
| MAP7 | 215471_s_at | 136871646 | 136871646 | −774 |
| WDR36 | 226180_at | 110427414 | 110427414 | −60 |
| UBE3C | 201817_4 | 156931607 | 156931607 | 1361 |
| G2E3 | 223254_s_at | 31028364 | 31028364 | −885 |
| POLQ | 219510_at | 121264853 | 121264853 | −1103 |
| RIF1 | 214700_x_at | 152266397 | 152266397 | −340 |
| SLC2A8 | 218985_at | 130159421 | 130159421 | −1131 |
| IDE | 217496_s_at | 94333833 | 94333833 | 1275 |
| IDE | 203328_x_at | 94333833 | 94333833 | 1275 |
| FAM175A | 226521_s_at | 84406334 | 84406334 | 984 |
| ADRM1 | 201281_at | 60878061 | 60878061 | 1209 |
| SMPD4 | 207856_s_at | 130939166 | 130939166 | 948 |
| MSH3 | 210947_s_at | 79950467 | 79950467 | 1119 |
| NENF | 214075_at | 212606229 | 212606229 | −956 |
| ESF1 | 222765_x_at | 13765532 | 13765532 | −1474 |
| RNMTL1 | 218993_at | 685513 | 685513 | −924 |
| NAA16 | 1555450_a_at | 41885341 | 41885341 | −391 |
| TROAP | 204649_at | 49716971 | 49716971 | −700 |
| DDX50 | 221699_s_at | 70661034 | 70661034 | −651 |
| POLH | 233852_at | 43543887 | 43543887 | 889 |
| CEP57 | 203491_s_at | 95523642 | 95523642 | 1256 |
| SQLE | 213577_at | 126010720 | 126010720 | 1102 |
| HNRNPA3 | 211931_s_at | 178077291 | 178077291 | −994 |
| SERBP1 | 209669_a_at | 67896098 | 67896098 | −1338 |
| PATL1 | 235234_at | 59436511 | 59436511 | −1162 |
| NARF | 219862_s_at | 80416540 | 80416540 | −923 |
| UTP23 | 238562_at | 117778742 | 117778742 | −638 |
| EIF2A | 223015_at | 150264481 | 150264481 | 1080 |
| DNAJC15 | 218435_at | 43597339 | 43597339 | −76 |
| CCIAD2 | 225314_at | 48908845 | 48908845 | 945 |
| GLS2 | 205531_s_at | 56882181 | 56882181 | 1060 |
| EXTL2 | 209537_at | 101361554 | 101361554 | −1140 |
| NIP7 | 223397_s_at | 69373343 | 69373343 | 1321 |
| ERGIC2 | 226422_at | 29534143 | 29534143 | −582 |
| GNPDA1 | 202382_s_at | 141392596 | 141392596 | −675 |
| NIP7 | 219031_s_at | 69373343 | 69373343 | 1321 |
| ACLY | 210337_s_at | 40075240 | 40075240 | −972 |
| C19orf20 | 227903_x_at | 507497 | 507497 | 1231 |
| CARS2 | 218153_at | 111358485 | 111358485 | 853 |
| DEAF1 | 209407_s_at | 695047 | 695047 | −1744 |
| PYCRL | 218944_at | 144691784 | 144691784 | −889 |
| NCBP2 | 201521_s_at | 196669468 | 196669468 | −1003 |
| EXOC6 | 226259_at | 94608277 | 94608277 | −1158 |
| MIOS | 206800_s_at | 7606503 | 7606503 | −604 |

TABLE 14-continued

List of genes showing statistically significant over-expression in cancer compared to normal samples and are within 2,000 bp from an outward methylation boundary shift.

| | | | | |
|---|---|---|---|---|
| PMPCA | 212088_at | 139305112 | 139305112 | 1018 |
| FAM188B | 1557141_at | 30811033 | 30811033 | −594 |
| RPL12 | 200088_x_at | 130213684 | 130213684 | −1192 |
| ABHD2 | 225337_at | 89631405 | 89631405 | 1331 |
| ERCC8 | 205162_at | 60240878 | 60240878 | 840 |
| EIF3G | 208887_at | 10230599 | 10230599 | −629 |
| RPL12 | 214271_x_at | 130213684 | 130213684 | −1192 |
| FUT10 | 235472_at | 33330664 | 33330664 | 1935 |
| SARNP | 224914_s_at | 56211540 | 56211540 | −1110 |
| RNF24 | 204669_s_at | 3996036 | 3996036 | −735 |
| NENF | 218407_x_at | 212606229 | 212606229 | −956 |
| HSD3B7 | 222817_at | 30996532 | 30996532 | 453 |
| FAT1 | 201579_at | 187645009 | 187645009 | 1722 |
| PATL1 | 235235_s_at | 59436511 | 59436511 | −1162 |
| PATL1 | 225468_at | 59436511 | 59436511 | −1162 |
| MYO6 | 210480_s_at | 76458926 | 76458926 | 1177 |
| RNF24 | 204668_at | 3996036 | 3996036 | −735 |
| EBPL | 223306_at | 50265611 | 50265611 | −380 |
| SAR1A | 201543_s_at | 71930279 | 71930279 | −694 |
| RPL12 | 200809_x_at | 130213684 | 130213684 | −1192 |
| RWDD2B | 218377_s_at | 30391699 | 30391699 | −448 |
| HMGCS1 | 205822_s_at | 43313595 | 43313595 | 1163 |
| DHX30 | 204355_at | 47844418 | 47844418 | −1025 |
| TGFBR2 | 208944_at | 30647994 | 30647994 | 1908 |
| PCYT2 | 209577_at | 79869294 | 79869294 | 1154 |
| DPY19L4 | 213391_at | 95732103 | 95732103 | −944 |
| METFL13 | 206468_s_at | 171750822 | 171750822 | 1069 |
| ANGEL2 | 221826_at | 213189168 | 213189168 | −548 |
| SNRNP70 | 201221_s_at | 49588465 | 49588465 | −695 |
| HNRNPU | 200593_s_at | 245027844 | 245027844 | −606 |
| MYEOV | 227342_s_at | 69061622 | 69061622 | 0 |
| GLS | 223079_s_at | 191745560 | 191745560 | −1119 |
| NUFIP1 | 205136_s_at | 45563618 | 45563618 | 827 |
| QRSL1 | 218949_s_at | 107077453 | 107077453 | −1333 |
| WHSC2 | 203112_s_at | 2011837 | 2011837 | −276 |
| IFT122 | 220744_s_at | 129158968 | 129158968 | −1267 |
| PSMC6 | 201699_at | 53173890 | 53173890 | 1313 |
| STAT1 | 209969_s_at | 191878894 | 191878894 | 1156 |
| PSMD1 | 201199_s_at | 231921578 | 231921578 | 1189 |
| SRPK2 | 230091_at | 105029341 | 105029341 | −807 |
| PSMD4 | 210460_s_at | 151227179 | 151227179 | 1258 |
| FBXO45 | 225099_at | 196295559 | 196295559 | −966 |
| ANAPC7 | 225554_s_at | 110841535 | 110841535 | −710 |
| PDXK | 222492_at | 45138978 | 45138978 | 1446 |
| TWSG1 | 219201_s_at | 9334765 | 9334765 | −994 |
| DHX30 | 212674_s_at | 47844418 | 47844418 | −1025 |
| CGREF1 | 205937_at | 27341971 | 27341971 | −400 |
| LRSAM1 | 227675_at | 130213784 | 130213784 | 1092 |
| VPS13C | 218396_at | 62352672 | 62352672 | −1090 |
| RBM33 | 1554095_at | 155437145 | 155437145 | 1819 |
| CEP57 | 203493_s_at | 95523642 | 95523642 | 1256 |
| CHAC1 | 219270_at | 41245347 | 41245347 | −494 |
| METTL13 | 212407_at | 171750822 | 171750822 | 1069 |
| C1orf56 | 223459_s_at | 151020216 | 151020216 | −485 |
| FKBP3 | 218003_s_at | 45604522 | 45604522 | 1652 |
| FAMI28B | 212995_x_at | 130939501 | 130939501 | −1283 |
| SNRNP25 | 218493_at | 103010 | 103010 | −429 |
| PBX4 | 230536_at | 19729725 | 19729725 | −518 |
| PITPNB | 202522_at | 28315256 | 28315256 | 1207 |
| DDX49 | 210811_s_at | 19030494 | 19030494 | −1155 |
| H2AFJ | 225245_x_at | 14927349 | 14927349 | 1706 |
| WDHD1 | 204727_at | 55493795 | 55493795 | 859 |
| BLVRA | 211729_x_at | 43798279 | 43798279 | 917 |
| COPS2 | 209838_at | 49447854 | 49447854 | 1319 |
| GOPC | 227214_at | 117923691 | 117923691 | −918 |
| CCT5 | 229068_at | 10250033 | 10250033 | 1696 |
| | 215982_s_at | 31940069 | 31940069 | 875 |
| GCFC1 | 218515_at | 34144169 | 34144169 | −1504 |
| PSMB6 | 208827_at | 4699439 | 4699439 | −502 |
| LARP4 | 214155_s_at | 50794650 | 50794650 | −669 |
| RSPH1 | 230093_at | 43916464 | 43916464 | 1001 |
| GLS2 | 1564706_s_at | 56882181 | 56882181 | 1060 |
| NFYA | 204109_s_at | 41040684 | 41040684 | −1704 |
| CEP57 | 203492_x_at | 95523642 | 95523642 | 1256 |
| SERBP1 | 210466_s_at | 67896098 | 67896098 | −1338 |
| FUBP1 | 203091_at | 78444770 | 78444770 | 1853 |
| METTL13 | 212405_s_at | 171750822 | 171750822 | 1069 |

TABLE 14-continued

List of genes showing statistically significant over-expression in cancer compared to normal samples and are within 2,000 bp from an outward methylation boundary shift.

| | | | | |
|---|---|---|---|---|
| ERAL1 | 212087_s_at | 27182020 | 27182020 | −768 |
| GCFC1 | 221158_at | 34144169 | 34144169 | −1504 |
| RNF24 | 210706_s_at | 3996036 | 3996036 | −735 |
| ATXN3 | 205415_s_at | 92572954 | 92572954 | −440 |
| WHSC2 | 34225_at | 2011837 | 2011837 | −276 |
| PSMG2 | 218467_at | 12702425 | 12702425 | −620 |
| DBR1 | 219149_x_at | 137893791 | 137893791 | 1138 |
| TXLNA | 212300_at | 32645287 | 32645287 | −508 |
| RAGE | 205130_at | 102771531 | 102771531 | −664 |
| H2AFJ | 224301_x_at | 14927349 | 14927349 | 1706 |
| CSNK1E | 202332_at | 38714089 | 38714089 | −539 |
| PSMD4 | 200882_s_at | 151227179 | 151227179 | 1258 |
| CCDC21 | 227818_at | 26560693 | 26560693 | 1259 |
| MAPKAPK3 | 202787_s_at | 50649339 | 50649339 | −1345 |
| LRFN4 | 219491_at | 66624589 | 66624589 | 575 |
| FKTN | 205283_at | 108320411 | 108320411 | −1015 |
| SRD5A1 | 211056_s_at | 6633456 | 6633456 | −1370 |
| TMCO7 | 226467_at | 68877509 | 68877509 | −688 |
| MRPL15 | 218027_at | 55047781 | 55047781 | −526 |
| ANKRD26 | 205706_s_at | 27389421 | 27389421 | −727 |
| CENPV | 226611_s_at | 16256813 | 16256813 | 1476 |
| MANIB1 | 65884_at | 139981400 | 139981400 | 1075 |
| GPR137B | 204137_at | 236305832 | 236305832 | −1848 |
| TUBA1B | 212639_x_at | 49525304 | 49525304 | −1445 |
| PPP2R1B | 202886_s_at | 111637169 | 111637169 | −996 |
| MYO6 | 203216_s_at | 76458926 | 76458926 | 1177 |
| SEC23B | 201583_s_at | 18488199 | 18488199 | −604 |
| MED1 | 225456_at | 37607521 | 37607521 | 914 |
| GCLC | 202923_s_at | 53409927 | 53409927 | −401 |
| G2E3 | 223256_at | 31028364 | 31028364 | −885 |
| ASNA1 | 202024_at | 12848306 | 12848306 | −1266 |
| FBXO45 | 225100_at | 196295559 | 196295559 | −966 |
| AIDA | 220199_s_at | 222885866 | 222885866 | −1619 |
| NUP50 | 218295_s_at | 45559722 | 45559722 | −956 |
| DAG1 | 205417_s_at | 49507565 | 49507565 | −974 |
| WDR33 | 222763_s_at | 128568745 | 128568745 | 1440 |
| ATP5S | 206992_s_at | 50779047 | 50779047 | −1123 |
| SERBP1 | 217725_x_at | 67896098 | 67896098 | −1338 |
| LARP4 | 1555384_a_at | 50794650 | 50794650 | −669 |
| MITD1 | 226329_s_at | 99797390 | 99797390 | −1272 |
| SRPK2 | 214931_s_at | 105029341 | 105029341 | −807 |
| ACP1 | 201630_s_at | 264869 | 264869 | 1369 |
| FAM188B | 235559_at | 30811033 | 30811033 | −594 |
| UBXN10 | 232109_at | 20512578 | 20512578 | −390 |
| PLOD3 | 202185_at | 100860954 | 100860954 | 1056 |
| XRCC6 | 200792_at | 42017123 | 42017123 | −1320 |
| STARD4 | 226390_at | 110848208 | 110848208 | −1062 |
| ADSS | 221761_at | 244615436 | 244615436 | 485 |
| NFYA | 204107_at | 41040684 | 41040684 | −1704 |
| IDE | 241300_at | 94333833 | 94333833 | 1275 |
| MAPKAPK3 | 202788_at | 50649339 | 50649339 | −1345 |
| TUBA1B | 213646_x_at | 49525304 | 49525304 | −1445 |
| RTEL1 | 216325_x_at | 62289163 | 62289163 | 1455 |
| MIOS | 211724_x_at | 7606503 | 7606503 | −604 |
| TMEM43 | 222418_s_at | 14166440 | 14166440 | −1225 |
| WDR59 | 221981_s_at | 75019017 | 75019017 | −403 |
| SLC1A4 | 209610_s_at | 65216535 | 65216535 | 1620 |
| ERO1L | 225750_at | 53162423 | 53162423 | 1515 |
| CSTF3 | 229665_at | 33183037 | 33183037 | 1661 |
| PNN | 212037_at | 39644425 | 39644425 | −835 |
| CEP57 | 209862_s_at | 95523642 | 95523642 | 1256 |
| DCTN4 | 218013_x_at | 150138671 | 150138671 | −363 |
| LTA4H | 208771_s_at | 96429365 | 96429365 | 1334 |
| PSMD4 | 211609_x_at | 151227179 | 151227179 | 1258 |
| DPY19L3 | 225633_at | 32897031 | 32897031 | 423 |
| USE1 | 219348_at | 17326155 | 17326155 | 651 |
| TFCP2 | 209338_at | 51566664 | 51566664 | −1168 |
| ANXA2 | 213503_x_at | 60690185 | 60690185 | 1563 |
| NUP50 | 222583_s_at | 45559722 | 45559722 | −956 |
| ICA1 | 204002_s_at | 8301911 | 8301911 | −817 |
| | 209219_at | 31926887 | 31926887 | 815 |
| ANXA2 | 210427_x_at | 60690185 | 60690185 | 1563 |
| USE1 | 221706_s_at | 17326155 | 17326155 | 651 |
| TBC1D30 | 213912_at | 65174589 | 65174589 | −551 |
| C17orf81 | 219260_s_at | 7155372 | 7155372 | 1242 |
| ANXA2 | 201590_x_at | 60690185 | 60690185 | 1563 |
| PSMB1 | 200876_s_at | 170862429 | 170862429 | 1342 |

TABLE 14-continued

List of genes showing statistically significant over-expression in cancer compared to normal samples and are within 2,000 bp from an outward methylation boundary shift.

| | | | | |
|---|---|---|---|---|
| CAPN10 | 221040_at | 241526189 | 241526189 | 1153 |
| USP45 | 224441_s_at | 99963365 | 99963365 | 1246 |
| TUBA1B | 211072_x_at | 49525304 | 49525304 | −1445 |
| C20orf108 | 224693_at | 54933971 | 54933971 | −549 |
| CREB3L2 | 228759_at | 137686803 | 137686803 | −850 |
| TMEM43 | 217795_s_at | 14166440 | 14166440 | −1225 |
| SETD3 | 212465_at | 99947216 | 99947216 | 1843 |
| SLC6A6 | 211030_s_at | 14444120 | 14444120 | −634 |
| DGCR14 | 204383_at | 19132197 | 19132197 | −472 |
| SRPK2 | 203182_s_at | 105029341 | 105029341 | −807 |
| PGM2L1 | 235149_at | 74109502 | 74109502 | −956 |
| GBAS | 201816_s_at | 56032274 | 56032274 | −542 |
| CSTF1 | 32723_at | 54967450 | 54967450 | −1212 |
| RDH10 | 226021_at | 74207265 | 74207265 | 1334 |
| C3orf75 | 229863_s_at | 47555251 | 47555251 | −615 |
| ZNF318 | 203521_s_at | 43337181 | 43337181 | −1063 |
| ASPM | 239002_at | 197115824 | 197115824 | 1628 |
| RB1 | 211540_s_at | 48877911 | 48877911 | −917 |
| TTLL1 | 205652_s_at | 43485434 | 43485434 | −513 |
| TUBA1B | 201090_x_at | 49525304 | 49525304 | −1445 |
| PARP9 | 223220_s_at | 122283424 | 122283424 | −885 |
| PRPF3 | 202251_at | 150293925 | 150293925 | −548 |
| VANGL1 | 229134_at | 116184574 | 116184574 | −432 |
| CLTA | 204050_s_at | 36190920 | 36190920 | 1468 |
| VGLL4 | 212399_s_at | 11762220 | 11762220 | −782 |
| TUBA1B | 211058_x_at | 49525304 | 49525304 | −1445 |
| PYCR2 | 231715_s_at | 226111959 | 226111959 | −761 |
| GPX4 | 201106_at | 1103966 | 1103966 | 1576 |
| GCFC1 | 1555125_at | 34144169 | 34144169 | −1504 |
| MAD1L1 | 204857_at | 2272609 | 2272609 | −606 |
| TCEB2 | 200085_s_at | 2827251 | 2827251 | 1043 |
| CLTA | 200960_x_at | 36190920 | 36190920 | 1468 |
| SC4MOL | 209146_at | 166248775 | 166248775 | −1105 |
| SLC19A2 | 209681_at | 169455241 | 169455241 | −1326 |
| C20orf108 | 224690_at | 54933971 | 54933971 | −549 |
| C20orf7 | 227160_s_at | 13765596 | 13765596 | 1410 |
| ZNF318 | 203520_s_at | 43337181 | 43337181 | −1063 |
| ATXN3 | 205416_s_at | 92572954 | 92572954 | −440 |
| GRINL1B | 212241_at | 57884106 | 57884106 | −584 |
| NCBP1 | 209520_s_at | 100395908 | 100395908 | 1543 |
| FAM173B | 225670_at | 10249998 | 10249998 | −1731 |
| GTPBP10 | 239773_at | 89975990 | 89975990 | −1026 |
| IQCK | 213392_at | 19727778 | 19727778 | 0 |
| CLTA | 216295_s_at | 36190920 | 36190920 | 1468 |
| ZMYND10 | 203246_s_at | 50384283 | 50384283 | 619 |
| PATL1 | 225466_at | 59436511 | 59436511 | −1162 |
| CEP57 | 203494_s_at | 95523642 | 95523642 | 1256 |
| ZNF200 | 214706_at | 3285175 | 3285175 | −806 |
| ZEP1 | 226807_at | 75182480 | 75182480 | 836 |
| SLC6A20 | 219614_s_at | 45838027 | 45838027 | 751 |
| MRPL14 | 225201_s_at | 44095194 | 44095194 | 1437 |
| DGCR14 | 32032_at | 19132197 | 19132197 | −472 |
| DDB1 | 208619_at | 61100666 | 61100666 | −800 |
| PSMC3IP | 205956_x_at | 40729747 | 40729747 | 828 |
| MAP2K1 | 202670_at | 66679155 | 66679155 | −660 |
| KIF20B | 205235_s_at | 91461367 | 91461367 | 1116 |
| FAM161A | 1557385_at | 62081278 | 62081278 | 938 |
| OXSM | 219133_at | 25831571 | 25831571 | −904 |
| TRMU | 213634_s_at | 46731322 | 46731322 | −301 |
| ILKAP | 221548_s_at | 239112370 | 239112370 | 1481 |
| LRRC27 | 1558483_at | 134145658 | 134145658 | 739 |
| C20orf7 | 222894_x_at | 13765596 | 13765596 | 1410 |
| RABL3 | 226089_at | 120461384 | 120461384 | −1339 |
| ACLY | 201127_s_at | 40075240 | 40075240 | −972 |
| SKA2 | 225684_at | 57232800 | 57232800 | 1693 |
| ZBTB5 | 203026_at | 37465396 | 37465396 | −1923 |
| ATP9B | 214934_at | 76829397 | 76829397 | 1305 |
| CCDC90B | 218288_s_at | 82997215 | 82997215 | −621 |
| EHMT1 | 225461_at | 140513454 | 140513454 | −1226 |
| TBC1D30 | 213913_s_at | 65174589 | 65174589 | −551 |
| PSMB1 | 214288_s_at | 170862429 | 170862429 | 1342 |
| NICN1 | 223442_at | 49466674 | 49466674 | 792 |
| KLC2 | 218906_x_at | 66025190 | 66025190 | −1370 |
| ACLY | 201128_s_at | 40075240 | 40075240 | −972 |
| PDSS1 | 220865_s_at | 26986588 | 26986588 | −791 |
| | 209040_s_at | 32811824 | 32811824 | 991 |
| MTCH2 | 217772_s_at | 47664206 | 47664206 | −740 |

TABLE 14-continued

List of genes showing statistically significant over-expression in cancer compared to normal samples and are within 2,000 bp from an outward methylation boundary shift.

| | | | | |
|---|---|---|---|---|
| TMEM14B | 223133_at | 10747973 | 10747973 | −631 |
| MKS1 | 1555820_a_at | 56296666 | 56296666 | −682 |
| SPA17 | 205406_s_at | 124543740 | 124543740 | −847 |
| DPH3 | 225195_at | 16306479 | 16306479 | −1321 |
| HNRNPU | 216855_s_at | 245027844 | 245027844 | −606 |
| MYO6 | 203215_s_at | 76458926 | 76458926 | 1177 |
| IDE | 203327_at | 94333833 | 94333833 | 1275 |
| | 1569029_at | 172864490 | 172864490 | −217 |
| PNN | 1567214_a_at | 39644425 | 39644425 | −835 |
| SOCS4 | 1552792_at | 55493948 | 55493948 | −1012 |
| UCHL5 | 219960_s_at | 193028626 | 193028626 | 1355 |
| CCDC97 | 235495_at | 41816094 | 41816094 | 1117 |
| CENPB | 212437_at | 3767337 | 3767337 | 972 |
| BRF2 | 218954_s_at | 37707411 | 37707411 | −560 |
| SNORA41 | 200705_s_at | 207024309 | 207024309 | −1328 |
| ESD | 209009_at | 47371367 | 47371367 | −620 |
| BRE | 211566_x_at | 28113596 | 28113596 | 851 |
| C3orf75 | 223277_at | 47555251 | 47555251 | −615 |
| IWS1 | 224768_at | 128284044 | 128284044 | −1211 |
| CHMP4A | 218571_s_at | 24683075 | 24683075 | −971 |
| DDX49 | 31807_at | 19030494 | 19030494 | −1155 |
| U2AF2 | 218381_s_at | 56165416 | 56165416 | −663 |
| FBXO22OS | 219638_at | 76196200 | 76196200 | 1253 |
| HNRNPA3 | 211933_s_at | 178077291 | 178077291 | −994 |
| PIP5K1A | 211205_x_at | 151171027 | 151171027 | 1250 |
| ST7OT3 | 207524_at | 116593381 | 116593381 | −643 |
| MAN1B1 | 218636_s_at | 139981400 | 139981400 | 1075 |
| PHB | 200659_s_at | 47492242 | 47492242 | −1192 |
| PTPDC1 | 238841_at | 96793076 | 96793076 | 774 |
| TMEM14B | 221452_s_at | 10747973 | 10747973 | −631 |
| TFCP2 | 207627_s_at | 51566664 | 51566664 | −1168 |
| HNRNPU | 200594_x_at | 245027844 | 245027844 | −606 |
| TMEM18 | 225489_at | 677439 | 677439 | 1216 |
| RBM33 | 226732_at | 155437373 | 155437373 | 1591 |
| C20orf24 | 224376_s_at | 35234137 | 35234137 | −609 |
| BRAP | 209922_at | 112123790 | 112123790 | 1022 |
| ARL5B | 242727_at | 18948334 | 18948334 | 1567 |
| ANKRD26 | 205705_at | 27389421 | 27389421 | −727 |
| OSTC | 223001_at | 109571740 | 109571740 | −1076 |
| FLVCR1 | 228191_at | 213031597 | 213031597 | 917 |
| CHMP4A | 218572_at | 24683075 | 24683075 | −971 |
| BRE | 212645_x_at | 28113596 | 28113596 | 851 |
| C20orf24 | 223880_x_at | 35234137 | 35234137 | −609 |
| NFYA | 204108_at | 41040684 | 41040684 | −1704 |
| COQ7 | 210820_x_at | 19078921 | 19078921 | −377 |
| ICMT | 201609_x_at | 6296000 | 6296000 | 1150 |
| HTRA2 | 203089_s_at | 74756504 | 74756504 | −605 |
| RDH10 | 1552378_s_at | 74207265 | 74207265 | 1334 |
| INCENP | 219769_at | 61891445 | 61891445 | 1307 |
| PPME1 | 217841_s_at | 73882368 | 73882368 | 1052 |
| BAG4 | 219624_at | 38034312 | 38034312 | −1369 |
| RTN4IP1 | 224509_s_at | 107077362 | 107077362 | 1242 |
| MED1 | 203497_at | 37607521 | 37607521 | 914 |
| EIF2AK4 | 225164_s_at | 40226347 | 40226347 | −637 |
| LRRC61 | 218907_s_at | 150020352 | 150020352 | 1201 |
| ESD | 215096_s_at | 47371367 | 47371367 | −620 |
| C11orf83 | 229099_at | 62439126 | 62439126 | 1139 |
| SARNP | 229069_at | 56211540 | 56211540 | −1110 |
| | 204090_at | 31939608 | 31939608 | −414 |
| CENPV | 226610_at | 16256813 | 16256813 | 1476 |
| ESCO1 | 226866_at | 19180845 | 19180845 | 1727 |
| KPNA4 | 209653_at | 160283376 | 160283376 | −1247 |
| | 238613_at | 173940570 | 173940570 | 1657 |
| ROCK2 | 211504_x_at | 11484711 | 11484711 | −1319 |
| HTRA2 | 211152_s_at | 74756504 | 74756504 | −605 |
| AKAP11 | 203156_at | 42846289 | 42846289 | −982 |
| CCDC21 | 219611_s_at | 26560693 | 26560693 | 1259 |
| | 38157_at | 31940069 | 31940069 | 875 |
| DHX57 | 213420_at | 39103049 | 39103049 | −686 |
| DNTTIP1 | 234942_s_at | 44420576 | 44420576 | −685 |
| ETAA1 | 219216_at | 67624451 | 67624451 | 1299 |
| CNIH4 | 218728_s_at | 224544552 | 224544552 | 1458 |
| PRPSAP1 | 202529_at | 74350230 | 74350230 | −741 |
| HEXA | 201765_s_at | 72668817 | 72668817 | −332 |
| PDSS2 | 1555886_at | 107780768 | 107780768 | 1050 |
| GPR19 | 207183_at | 12849121 | 12849121 | 212 |
| C3orf67 | 239697_x_at | 59035810 | 59035810 | 658 |

TABLE 14-continued

List of genes showing statistically significant over-expression in cancer compared to normal samples and are within 2,000 bp from an outward methylation boundary shift.

| | | | | |
|---|---|---|---|---|
| BRE | 205550_s_at | 28113596 | 28113596 | 851 |
| ASXL2 | 226251_at | 26101385 | 26101385 | −653 |
| NHLRC2 | 235356_at | 115614420 | 115614420 | −1039 |
| POLD3 | 212836_at | 74303629 | 74303629 | −496 |
| TRAPPC6A | 204985_s_at | 45681485 | 45681485 | −1862 |
| C1orf56 | 221222_s_at | 151020216 | 151020216 | −485 |
| RPIA | 212973_at | 88991162 | 88991162 | −847 |
| PPP2R1B | 202883_s_at | 111637169 | 111637169 | −996 |
| GPHN | 234941_s_at | 66974125 | 66974125 | −640 |
| PTPDC1 | 229517_at | 96793076 | 96793076 | 774 |
| MRPL49 | 201717_at | 64889728 | 64889728 | 749 |
| MKKS | 222530_s_at | 10414870 | 10414870 | 951 |
| XYLB | 208318_s_at | 38388270 | 38388270 | 956 |
| MSRB2 | 218773_s_at | 23384435 | 23384435 | 1144 |
| PNN | 212036_s_at | 39644425 | 39644425 | −835 |
| CTSB | 200838_at | 11725738 | 11725738 | 1705 |
| CD81 | 200675_at | 2398520 | 2398520 | −459 |
| SEL1L3 | 212314_at | 25865217 | 25865217 | −478 |
| KPNA4 | 225268_at | 160283376 | 160283376 | −1247 |
| SLC1A4 | 209611_s_at | 65216535 | 65216535 | 1620 |
| RASL11A | 238353_at | 27844464 | 27844464 | 1455 |
| ROPN1L | 223609_at | 10441636 | 10441636 | −952 |
| PYCR2 | 224855_at | 226111959 | 226111959 | −761 |
| SMAD2 | 203077_s_at | 45456930 | 45456930 | −1373 |
| HNRNPD | 221481_x_at | 83295109 | 83295109 | −1616 |
| GCC1 | 218912_at | 127225661 | 127225661 | 966 |
| SERBP1 | 227369_at | 67896098 | 67896098 | −1338 |
| ENSA | 228851_s_at | 150602072 | 150602072 | −818 |
| UTP23 | 227836_at | 117778742 | 117778742 | −638 |
| ORC4L | 203352_at | 148778292 | 148778292 | 1406 |
| WDR59 | 218505_at | 75019017 | 75019017 | −403 |
| C20or124 | 217835_x_at | 35234137 | 35234137 | −609 |
| ATP6V1H | 221504_s_at | 54755547 | 54755547 | 1181 |
| STK38 | 202951_at | 36515247 | 36515247 | −500 |
| SEC23B | 210293_s_at | 18488199 | 18488199 | −604 |
| SOD1 | 200642_at | 33031935 | 33031935 | 1480 |
| TWSG1 | 225406_at | 9334765 | 9334765 | −994 |
| SDHC | 202004_x_at | 161284047 | 161284047 | −554 |
| C19orf55 | 1553162_x_at | 36249044 | 36249044 | 873 |
| PTOV1 | 212032_s_at | 50354138 | 50354138 | −456 |
| NAA16 | 219378_at | 41885341 | 41885341 | −391 |
| C5orf22 | 1552660_a_at | 31532373 | 31532373 | −1115 |
| FAM76A | 216897_s_at | 28052490 | 28052490 | −657 |
| ZXDC | 230106_at | 126194708 | 126194708 | −963 |
| SLC1A4 | 212810_s_at | 65216535 | 65216535 | 1620 |
| LUC7L | 1557067_s_at | 279462 | 279462 | −443 |
| NCBP2 | 201517_at | 196669468 | 196669468 | −1003 |
| TNFAIP8 | 210260_s_at | 118690009 | 118690009 | 935 |
| TMEM216 | 223305_at | 61159865 | 61159865 | −340 |
| PPP5C | 201979_s_at | 46850294 | 46850294 | −908 |
| LARP4 | 238960_s_at | 50794650 | 50794650 | −669 |
| HNRNPD | 221480_at | 83295109 | 83295109 | −1616 |
| FDXACB1 | 228817_at | 111742004 | 111742004 | −753 |
| C1orf9 | 203429_s_at | 172501489 | 172501489 | −1054 |
| PPME1 | 49077_at | 73882368 | 73882368 | 1052 |
| RSF1 | 229885_at | 77531880 | 77531880 | −1232 |
| RFESD | 239142_at | 94982458 | 94982458 | 1311 |
| ERP29 | 201216_at | 112451152 | 112451152 | −1174 |
| L2HGDH | 220089_at | 50778947 | 50778947 | 1023 |
| MED20 | 212872_s_at | 41888837 | 41888837 | 1004 |
| SRPK2 | 203181_x_at | 105029341 | 105029341 | −807 |
| COMMD5 | 223198_x_at | 146078932 | 146078932 | −299 |
| MKS1 | 218630_at | 56296666 | 56296666 | −682 |
| NFX1 | 1553348_a_at | 33290509 | 33290509 | 1386 |
| C2orf60 | 235181_at | 200820459 | 200820459 | 1282 |
| MAP7 | 202890_at | 136871646 | 136871646 | −774 |
| CMC1 | 228283_at | 28283086 | 28283086 | −828 |
| FAM24B | 231146_at | 124639114 | 124639114 | 784 |
| IFT88 | 204703_at | 21141208 | 21141208 | 1019 |
| CREB3L4 | 226455_at | 153940379 | 153940379 | −1532 |
| HMGN4 | 202579_x_at | 26538639 | 26538639 | 983 |
| KIAA1279 | 212453_at | 70748487 | 70748487 | −577 |
| ANAPC2 | 218555_at | 140082989 | 140082989 | −1299 |
| UTP23 | 238561_s_at | 117778742 | 117778742 | −638 |
| PIGB | 242760_x_at | 55611133 | 55611133 | −503 |
| COQ7 | 209746_s_at | 19078921 | 19078921 | −377 |
| PHAX | 231812_x_at | 125935960 | 125935960 | 0 |

TABLE 14-continued

List of genes showing statistically significant over-expression in cancer compared to normal samples and are within 2,000 bp from an outward methylation boundary shift.

| | | | | |
|---|---|---|---|---|
| SLC31A1 | 203971_at | 115983842 | 115983842 | 1129 |
| MORN2 | 226790_at | 39103103 | 39103103 | 632 |
| ISOC2 | 218893_at | 55973049 | 55973049 | −815 |
| PIGB | 205452_at | 55611133 | 55611133 | −503 |
| TIGD1 | 1553099_at | 233415226 | 233415226 | 503 |
| ZBED3 | 235109_at | 76383148 | 76383148 | −909 |
| FBXO45 | 242294_at | 196295559 | 196295559 | −966 |
| KIAA1704 | 229891_x_at | 45563755 | 45563755 | −964 |
| DLST | 215210_s_at | 75348619 | 75348619 | 1043 |
| HMOX2 | 218120_s_at | 4526380 | 4526380 | 1160 |
| ENSA | 221487_s_at | 150602053 | 150602053 | −837 |
| IQCE | 204202_at | 2598632 | 2598632 | 1165 |
| NFX1 | 202585_s_at | 33290509 | 33290509 | 1386 |
| PHF5A | 225309_at | 41864729 | 41864729 | 763 |
| NDUFA7 | 202785_at | 8386280 | 8386280 | 1031 |
| PPIL4 | 226472_at | 149867174 | 149867174 | −733 |
| C2orf60 | 235686_at | 200820459 | 200820459 | 1282 |
| STK38 | 1553117_a_at | 36515247 | 36515247 | −500 |
| ASPM | 232238_at | 197115824 | 197115824 | 1628 |
| DUSP6 | 208893_s_at | 89746296 | 89746296 | 1825 |
| HEBP2 | 203430_at | 138725356 | 138725356 | −1075 |
| HBXIP | 202299_s_at | 110950560 | 110950560 | −608 |
| GOPC | 225023_at | 117923691 | 117923691 | −918 |
| SMAD2 | 203076_s_at | 45456930 | 45456930 | −1373 |
| DCTN4 | 222488_s_at | 150138671 | 150138671 | −363 |
| GOPC | 225022_at | 117923691 | 117923691 | −918 |
| HEBP1 | 218450_at | 13153221 | 13153221 | 645 |
| PSMC2 | 238020_at | 102985361 | 102985361 | 190 |
| TEX264 | 218548_x_at | 51705248 | 51705248 | −897 |
| NEK3 | 211089_s_at | 52733724 | 52733724 | −347 |
| JOSD2 | 227096_at | 51014477 | 51014477 | −853 |
| PTGES2 | 218083_at | 130890741 | 130890741 | −550 |
| EPT1 | 224888_at | 26568982 | 26568982 | −1458 |
| GCLC | 202922_at | 53409927 | 53409927 | −401 |
| COG5 | 203630_s_at | 107204485 | 107204485 | −768 |
| PHAX | 235767_x_at | 125935960 | 125935960 | 0 |
| RPL17 | 214291_at | 47017814 | 47017814 | 309 |
| RDH10 | 227467_at | 74207265 | 74207265 | 1334 |
| C20orf108 | 208080_at | 54933971 | 54933971 | −549 |
| RPL36AL | 207585_s_at | 50087361 | 50087361 | 1082 |
| WDR53 | 227814_at | 196295510 | 196295510 | 917 |
| HNRNPD | 200073_s_at | 83295109 | 83295109 | −1616 |
| ZKSCAN1 | 214900_at | 99613204 | 99613204 | 1299 |
| MDN1 | 212693_at | 90529442 | 90529442 | −1030 |
| COMMD5 | 223819_x_at | 146078932 | 146078932 | −299 |
| IQCH | 224165_s_at | 67547169 | 67547169 | −1682 |
| KIAA1704 | 223606_x_at | 45563755 | 45563755 | −964 |
| RPS6KL1 | 223534_s_at | 75389145 | 75389145 | −225 |
| ELL2 | 214446_at | 95297775 | 95297775 | −530 |
| C4orf23 | 235097_at | 8442532 | 8442532 | 1115 |
| DAG1 | 212128_s_at | 49507565 | 49507565 | −974 |
| DUSP6 | 208891_at | 89746296 | 89746296 | 1825 |
| VGLL4 | 214004_s_at | 11762220 | 11762220 | −782 |
| TNFAIP8 | 208296_x_at | 118690009 | 118690009 | 935 |
| BAG4 | 228189_at | 38034312 | 38034312 | −1369 |
| EIF4E2 | 213571_s_at | 233414762 | 233414762 | −39 |
| NACAP1 | 200735_x_at | 57119083 | 57119083 | −707 |
| SERBP1 | 217724_at | 67896098 | 67896098 | −1338 |
| HMGN4 | 209786_at | 26538639 | 26538639 | 983 |
| LAP3 | 217933_s_at | 17578815 | 17578815 | −870 |
| ESF1 | 218859_s_at | 13765532 | 13765532 | −1474 |
| TM7SF3 | 222477_s_at | 27167339 | 27167339 | −778 |
| PHAX | 234405_s_at | 125935960 | 125935960 | 0 |
| AASDH | 228041_at | 57253666 | 57253666 | 1168 |
| HNRNPH3 | 210110_x_at | 70091832 | 70091832 | −937 |
| C17orf81 | 223286_at | 7155372 | 7155372 | 1242 |
| COMMD5 | 224387_at | 146078932 | 146078932 | −299 |
| IQCH | 239812_s_at | 67547169 | 67547169 | −1682 |
| HN1 | 217755_at | 73150778 | 73150778 | 1633 |
| MED1 | 203496_s_at | 37607521 | 37607521 | 914 |
| WDR60 | 219251_s_at | 158649269 | 158649269 | −698 |
| DCP1A | 225443_at | 53381637 | 53381637 | −702 |
| QRSL1 | 241933_at | 107077453 | 107077453 | −1333 |
| ERCC3 | 202176_at | 128051752 | 128051752 | −581 |
| CREB1 | 237289_at | 208394616 | 208394616 | −1412 |
| IWS1 | 224775_at | 128284044 | 128284044 | −1211 |
| STX10 | 212625_at | 13261052 | 13261052 | 1180 |

TABLE 14-continued

List of genes showing statistically significant over-expression in cancer compared to normal samples and are within 2,000 bp from an outward methylation boundary shift.

| | | | | |
|---|---|---|---|---|
| KPNA4 | 225267_at | 160283376 | 160283376 | −1247 |
| HBXIP | 202300_at | 110950560 | 110950560 | −608 |
| UNC93B1 | 225869_s_at | 67771593 | 67771593 | −625 |
| SIK2 | 223430_at | 111473192 | 111473192 | −902 |
| IQCH | 220361_at | 67547169 | 67547169 | −1682 |
| POLL | 221049_s_at | 103347966 | 103347966 | −901 |
| SPATA13 | 225564_at | 24734887 | 24734887 | −548 |
| PSMD12 | 202353_s_at | 65362743 | 65362743 | 1176 |
| TMEM18 | 225487_at | 677439 | 677439 | 1216 |
| FAM76B | 1553750_a_at | 95522954 | 95522954 | −1944 |
| HNRNPA3 | 211932_at | 178077477 | 178077477 | −1180 |
| NDUFS8 | 203189_s_at | 67798094 | 67798094 | −806 |
| UBA52 | 221700_s_at | 18682614 | 18682614 | −756 |
| TM7SF3 | 226478_at | 27167339 | 27167339 | −778 |
| RTN4IP1 | 1555679_a_at | 107077362 | 107077362 | 1242 |
| SPATA13 | 1557470_at | 24734861 | 24734861 | −522 |
| RIF1 | 226503_at | 152266455 | 152266455 | −398 |
| ZNF428 | 215429_s_at | 44124006 | 44124006 | −718 |
| EIF4E2 | 209393_s_at | 233414762 | 233414762 | −39 |
| SEL1L3 | 212311_at | 25865217 | 25865217 | −478 |
| MIB2 | 228261_at | 1550884 | 1550884 | 1336 |
| PDXK | 218019_s_at | 45138978 | 45138978 | 1446 |
| NACAP1 | 208635_x_at | 57119083 | 57119083 | −707 |
| NDUFS8 | 203190_at | 67798094 | 67798094 | −806 |
| CBLL1 | 220018_at | 107384142 | 107384142 | −811 |
| LRRC2 | 231781_s_at | 46608040 | 46608040 | −234 |
| IQCE | 217124_at | 2598632 | 2598632 | 1165 |
| MOCOS | 238576_at | 33767482 | 33767482 | 708 |
| RTEL1 | 211526_s_at | 62289163 | 62289163 | 1455 |
| | 203727_at | 31926857 | 31926857 | −785 |
| POLR2L | 211730_s_at | 842545 | 842545 | 1089 |
| SDHC | 210131_x_at | 161284047 | 161284047 | −554 |
| TEX264 | 223964_x_at | 51705248 | 51705248 | −897 |
| ENO3 | 204483_at | 4854390 | 4854390 | 51 |
| SETD3 | 229940_at | 99947125 | 99947125 | 1752 |
| TEX264 | 233350_s_at | 51705248 | 51705248 | −897 |
| ATP5S | 206993_at | 50779047 | 50779047 | −1123 |
| ROCK2 | 202762_at | 11484711 | 11484711 | −1319 |
| FOXN2 | 206708_at | 48541849 | 48541849 | −1059 |
| WDR59 | 219586_at | 75019017 | 75019017 | −403 |
| FAM161A | 1564467_at | 62081278 | 62081278 | 938 |
| | 228565_at | 233463514 | 233463514 | 1448 |
| ZNF589 | 210062_s_at | 48282590 | 48282590 | −279 |
| CAPN10 | 219333_s_at | 241526133 | 241526133 | 1209 |
| CTSB | 200839_s_at | 11725738 | 11725738 | 1705 |
| DNTTIP1 | 224825_at | 44420576 | 44420576 | −685 |
| RWDD4A | 225574_at | 184580378 | 184580378 | 898 |
| ENSA | 228852_at | 150602053 | 150602053 | −837 |
| ADK | 204120_s_at | 75936444 | 75936444 | 925 |
| SLC1A4 | 212811_x_at | 65216535 | 65216535 | 1620 |
| CD2BP2 | 202257_s_at | 30366682 | 30366682 | 1079 |
| CNIH4 | 223993_s_at | 224544552 | 224544552 | 1458 |
| RTEL1 | 206092_x_at | 62289163 | 62289163 | 1455 |
| | 208659_at | 31698394 | 31698394 | −257 |
| ZNF697 | 227080_at | 120190390 | 120190390 | −1202 |
| MBD4 | 214047_s_at | 129158872 | 129158872 | 1171 |
| C1orf58 | 239078_at | 222885895 | 222885895 | 1590 |
| MOSPD3 | 219070_s_at | 100209725 | 100209725 | −746 |
| AASDH | 235435_at | 57253666 | 57253666 | 1168 |
| C2orf47 | 219176_at | 200820326 | 200820326 | −1149 |
| MMADHC | 217883_at | 150444330 | 150444330 | −504 |
| WDR33 | 223146_at | 128568721 | 128568721 | 1416 |
| LSM11 | 241599_at | 157170755 | 157170755 | −662 |
| FN3KRP | 218210_at | 80674582 | 80674582 | −760 |
| NCBP1 | 209519_at | 100395908 | 100395908 | 1543 |
| UQCC | 222470_s_at | 33999944 | 33999944 | −537 |
| RBM33 | 238801_at | 155437373 | 155437373 | 1591 |
| C16orf88 | 213235_at | 19726362 | 19726362 | −780 |
| SERBP1 | 228129_at | 67896098 | 67896098 | −1338 |
| HIST1H3I | 214509_at | 27840093 | 27840093 | 743 |
| NAGLU | 204360_s_at | 40687951 | 40687951 | −298 |
| ZNF668 | 219047_s_at | 31085577 | 31085577 | 1801 |
| BAG4 | 222909_s_at | 38034312 | 38034312 | −1369 |
| C2orf79 | 226243_at | 25016251 | 25016251 | 1083 |
| ARL5B | 226345_at | 18948334 | 18948334 | 1567 |
| ARG2 | 203945_at | 68086579 | 68086579 | −1290 |
| BRD9 | 220155_s _at | 892661 | 892661 | 646 |

TABLE 14-continued

List of genes showing statistically significant over-expression in cancer compared to normal samples and are within 2,000 bp from an outward methylation boundary shift.

| | | | | |
|---|---|---|---|---|
| PRPF4B | 211090_s_at | 4021560 | 4021560 | −1778 |
| TMEM79 | 223544_at | 156252739 | 156252739 | 1110 |
| ZBED3 | 228402_at | 76383148 | 76383148 | −909 |
| MTIF3 | 223356_s_at | 28024701 | 28024701 | −1269 |
| HNRNPA3 | 206809_s_at | 178077477 | 178077477 | −1180 |
| PRPF4B | 202126_at | 4021560 | 4021560 | −1778 |
| RBM33 | 1554096_a_at | 155437145 | 155437145 | 1819 |
| BEAR | 218056_at | 14726672 | 14726672 | −663 |
| RPS15 | 200819_s_at | 1438363 | 1438363 | 1364 |
| RNASEN | 218269_at | 31532168 | 31532168 | 910 |
| TMED9 | 205812_s_at | 177019159 | 177019159 | −863 |
| DRAP1 | 203258_at | 65686728 | 65686728 | 1284 |
| HMGN4 | 209787_s_at | 26538639 | 26538639 | 983 |
| SDHC | 215088_s_at | 161284047 | 161284047 | −554 |
| MED20 | 206961_s_at | 41888837 | 41888837 | 1004 |
| ARL6IP1 | 211935_at | 18812917 | 18812917 | 1596 |
| FXC1 | 217981_s_at | 6502690 | 6502690 | 976 |
| ENSA | 221486_at | 150602053 | 150602053 | −837 |
| ASF1A | 203428_s_at | 119215384 | 119215384 | 1786 |
| TSSC4 | 218612_s_at | 2421718 | 2421718 | 1313 |
| CISH | 223377_x_at | 50649203 | 50649203 | 1209 |
| C6orf130 | 213322_at | 41040330 | 41040330 | 1350 |
| ENAH | 222434_at | 225840844 | 225840844 | −1432 |
| COG5 | 203629_s_at | 107204485 | 107204485 | −768 |
| CISH | 221223_x_at | 50649203 | 50649203 | 1209 |
| SFT2D3 | 226639_at | 128458597 | 128458597 | −163 |
| DEPDC6 | 218858_at | 120885900 | 120885900 | −484 |
| CDC20B | 1564674_a_at | 54469003 | 54469003 | 1625 |
| LUC7L | 220143_x_at | 279462 | 279462 | −443 |
| ECHDC1 | 233124_s_at | 127664745 | 127664745 | −937 |
| LARP4 | 212714_at | 50794650 | 50794650 | −669 |
| SLC38A7 | 228951_at | 58718674 | 58718674 | −468 |
| ZNF709 | 242028_at | 12595643 | 12595643 | −596 |
| EHMT1 | 219339_s_at | 140513454 | 140513454 | −1226 |
| C3orf19 | 1558094_s_at | 14693271 | 14693271 | 859 |
| FBXO34 | 218539_at | 55738021 | 55738021 | 1504 |
| SOCS4 | 226178_at | 55493948 | 55493948 | −1012 |
| MBD4 | 209580_s_at | 129158872 | 129158872 | 1171 |
| ZNF828 | 226194_at | 115079988 | 115079988 | −943 |
| FAM76B | 232048_at | 95522954 | 95522954 | −1944 |
| TMED2 | 204427_s_at | 124069076 | 124069076 | 1130 |
| RAB11FIP5 | 210879_s_at | 73340146 | 73340146 | 1664 |
| RTN3 | 224564_s_at | 63448922 | 63448922 | −566 |
| RAB22A | 218360_at | 56884752 | 56884752 | 1334 |
| RPL17 | 212270_x_at | 47018906 | 47018906 | 1401 |
| LUC7L | 223546_x_at | 279462 | 279462 | 443 |
| E4F1 | 218524_at | 2273567 | 2273567 | 1123 |
| NFYA | 215720_s_at | 41040684 | 41040684 | −1704 |
| RPL27 | 200025_s_at | 41150446 | 41150446 | −1117 |
| ECHDC1 | 223088_x_at | 127664745 | 127664745 | −937 |
| POLR2H | 209302_at | 184079506 | 184079506 | −1153 |
| DTX3L | 225415_at | 122283085 | 122283085 | −885 |
| ZNF839 | 219086_at | 102786096 | 102786096 | −1405 |
| RAD18 | 238748_at | 9005186 | 9005186 | −1043 |
| ZNF251 | 226754_at | 145980970 | 145980970 | 1083 |
| MKLN1 | 242984_at | 131012619 | 131012619 | −1092 |
| NEK3 | 213116_at | 52733724 | 52733724 | −347 |
| ECHDC1 | 219974_x_at | 127664745 | 127664745 | −937 |
| RTEL1 | 213829_x_at | 62289163 | 62289163 | 1455 |
| GOPC | 227215_at | 117923691 | 117923691 | −918 |
| SNX25 | 1555388_s_at | 186125391 | 186125391 | −1336 |
| RPL17 | 212537_x_at | 47018906 | 47018906 | 1401 |
| ACOT13 | 204565_at | 24667299 | 24667299 | 1079 |
| NFX1 | 227651_at | 33290510 | 33290510 | 1385 |
| UBXN10 | 230092_at | 20512578 | 20512578 | −390 |
| TMED2 | 204426_at | 124069076 | 124069076 | 1130 |
| PELI1 | 218319_at | 64371588 | 64371588 | −395 |
| TMED9 | 208757_at | 177019159 | 177019159 | −863 |
| AARSD1 | 238740_at | 41132545 | 41132545 | 872 |
| SNTB2 | 238925_at | 69221032 | 69221032 | 1776 |
| TIRAP | 1552804_a_at | 126152982 | 126152982 | 884 |
| AAGAB | 202852_s_at | 67547074 | 67547074 | 1587 |
| ZNHIT1 | 201541_s_at | 100860949 | 100860949 | −1051 |
| RPL17 | 200038_s_at | 47018906 | 47018906 | 1401 |
| C2CD3 | 213199_at | 73882064 | 73882064 | −1356 |
| DCP1A | 218508_at | 53381637 | 53381637 | −702 |
| SLC35F5 | 225872_at | 114514400 | 114514400 | −952 |

TABLE 14-continued

List of genes showing statistically significant over-expression in cancer compared to normal samples and are within 2,000 bp from an outward methylation boundary shift.

| | | | | |
|---|---|---|---|---|
| ZNF589 | 210061_at | 48282590 | 48282590 | −279 |
| C4orf41 | 233558_s_at | 184580420 | 184580420 | −940 |
| DUS4L | 205762_s_at | 107204403 | 107204403 | 850 |
| ATP9B | 214010_s_at | 76829397 | 76829397 | 1305 |
| KLHDC10 | 209256_s_at | 129710350 | 129710350 | −761 |
| SDHC | 216591_s_at | 161284047 | 161284047 | −554 |
| DNAJC9 | 222499_at | 75008620 | 75008620 | 202 |
| WFDC3 | 232602_at | 44420547 | 44420547 | 656 |
| TUBG2 | 203894_at | 40811266 | 40811266 | −705 |
| HNRNPH3 | 210588_x_at | 70091832 | 70091832 | −937 |
| NEU3 | 216083_s_at | 74699179 | 74699179 | 1847 |
| NDUFB2 | 218201_at | 140396471 | 140396471 | 1164 |
| SUB1 | 224587_at | 32585605 | 32585605 | −384 |
| ORC4L | 203351_s_at | 148778292 | 148778292 | 1406 |
| CTTN | 214074_s_at | 70244650 | 70244650 | −1139 |
| GTF2E1 | 205930_at | 120461579 | 120461579 | 1144 |
| RANBP10 | 53987_at | 67840555 | 67840555 | 1138 |
| NDUFB6 | 203613_s_at | 32573160 | 32573160 | −531 |
| U2AF2 | 218382_s_at | 56165416 | 56165416 | −663 |
| PITPNA | 201192_s_at | 1466110 | 1466110 | −660 |
| GLE1 | 206921_at | 131267010 | 131267010 | −1114 |
| HOOK2 | 218780_at | 12886434 | 12886434 | −591 |
| PDS5B | 207956_x_at | 33160564 | 33160564 | −993 |
| HIST1H3F | 208506_at | 26250833 | 26250833 | 1259 |
| MFAP1 | 203406_at | 44117000 | 44117000 | 1126 |
| FBXL18 | 220896_at | 5553382 | 5553382 | −959 |
| FAU | 200019_s_at | 64889660 | 64889660 | −817 |
| CDC20B | 1553655_at | 54469003 | 54469003 | 1625 |
| ANAPC16 | 224665_at | 73975806 | 73975806 | 939 |
| TRAF2 | 204413_at | 139780970 | 139780970 | −1023 |
| MDN1 | 227797_x_at | 90529442 | 90529442 | −1030 |
| MDN1 | 221311_x_at | 90529442 | 90529442 | −1030 |
| KLHL36 | 219453_at | 84682107 | 84682107 | −776 |
| EEPD1 | 1569640_s_at | 36192758 | 36192758 | −746 |
| RANBP10 | 221809_at | 67840555 | 67840555 | 1138 |
| STUB1 | 227625_s_at | 730276 | 730276 | 1185 |
| SGTA | 201396_s_at | 2783315 | 2783315 | −1418 |
| PARN | 203905_at | 14724124 | 14724124 | −436 |
| AIDA | 226801_s_at | 222885866 | 222885866 | −1619 |
| C1orf151 | 224867_at | 19923484 | 19923484 | 1271 |
| CAMSAP1 | 220410_s_at | 138799070 | 138799070 | 1398 |
| GLE1 | 206920_s_at | 131266979 | 131266979 | −1083 |
| FUBP1 | 214094_at | 78444777 | 78444777 | 1860 |
| STUB1 | 233049_x_at | 730276 | 730276 | 1185 |
| FUT10 | 239020_at | 33330664 | 33330664 | 1935 |
| ICMT | 201611_s_at | 6296000 | 6296000 | 1150 |
| LRBA | 212692_s_at | 151936649 | 151936649 | −1770 |
| EHMT1 | 222873_s_at | 140513454 | 140513454 | −1226 |
| FTL | 213187_x_at | 49468566 | 49468566 | 1083 |
| GCA | 203765_at | 163200598 | 163200598 | −467 |
| VHL | 1559227_s_at | 10182692 | 10182692 | 0 |
| C20orf11 | 218448_at | 61569471 | 61569471 | 1046 |
| GLE1 | 225371_at | 131266979 | 131266979 | −1083 |
| ZMYND10 | 216663_s_at | 50384283 | 50384283 | 619 |
| UTP23 | 227402_s_at | 117778742 | 117778742 | −638 |
| ZNF800 | 227101_at | 127032745 | 127032745 | 1842 |
| ANAPC16 | 224664_at | 73975806 | 73975806 | 939 |
| CCDC101 | 221822_at | 28565247 | 28565247 | −355 |
| LSM1 | 203534_at | 38034026 | 38034026 | 1083 |
| ZXDC | 218639_s_at | 126194762 | 126194762 | −909 |
| CISH | 223961_s_at | 50649203 | 50649203 | 1209 |
| MAP2K7 | 209952_s_at | 7968776 | 7968776 | −1199 |
| RPS13 | 200018_at | 17099220 | 17099220 | −1085 |
| MSH3 | 205887_x_at | 79950467 | 79950467 | 1119 |
| NFX1 | 202584_at | 33290509 | 33290509 | 1386 |
| TM7SF3 | 217974_at | 27167339 | 27167339 | −778 |
| SSNA1 | 210378_s_at | 140083099 | 140083099 | 1189 |
| JAG1 | 209097_s_at | 10654608 | 10654608 | −1306 |
| RFESD | 236305_at | 94982458 | 94982458 | 1311 |
| RPRD2 | 235415_at | 150337126 | 150337126 | −1601 |
| GSTK1 | 217751_at | 142960522 | 142960522 | 1050 |
| SNORD118 | 235490_at | 8079714 | 8079714 | −807 |
| TGM2 | 211003_x_at | 36793774 | 36793774 | 439 |
| PDDC1 | 227968_at | 777484 | 777484 | −940 |
| E2F1 | 2028_s_at | 32274210 | 32274210 | −665 |
| FKBP15 | 212663_at | 115983598 | 115983598 | −1373 |
| ZNF839 | 221709_s_at | 102786096 | 102786096 | −1405 |

TABLE 14-continued

List of genes showing statistically significant over-expression in cancer compared to normal samples and are within 2,000 bp from an outward methylation boundary shift.

| | | | | |
|---|---|---|---|---|
| ACOX3 | 204242_s_at | 8442450 | 8442450 | −1197 |
| LYPLA2 | 215568_x_at | 24117460 | 24117460 | −518 |
| ZC3H4 | 213390_at | 47617009 | 47617009 | −648 |
| TRIM41 | 226445_s_at | 180650290 | 180650290 | −1526 |
| NDUFB2 | 218200_s_at | 140396471 | 140396471 | 1164 |
| CYB561D2 | 209665_at | 50388126 | 50388126 | 752 |
| HNRNPH3 | 207127_s_at | 70091832 | 70091832 | −937 |
| MBLAC1 | 1554170_a_at | 99724317 | 99724317 | −876 |
| C11orf68 | 221534_at | 65686531 | 65686531 | −1481 |
| STUB1 | 217934_x_at | 730276 | 730276 | 1185 |
| GTF2B | 208066_s_at | 89357301 | 89357301 | −787 |
| | 36019_at | 31939608 | 31939608 | −414 |
| UBR3 | 241244_at | 170684018 | 170684018 | −1624 |
| IQCK | 215130_s_at | 19727778 | 19727778 | 0 |
| RANBP10 | 1558773_s_at | 67840555 | 67840555 | 1138 |
| CAPN1 | 200752_s_at | 64949343 | 64949343 | 965 |
| EFR3A | 212149_at | 132916335 | 132916335 | −556 |
| TATDN2 | 203648_at | 10289707 | 10289707 | −121 |
| ADIPOR1 | 217748_at | 202927517 | 202927517 | 1164 |
| SLC48A1 | 218416_s_at | 48166991 | 48166991 | −497 |
| C2CD3 | 231708_at | 73882064 | 73882064 | −1356 |
| POLR2L | 202586_at | 842545 | 842545 | 1089 |
| SLC38A7 | 218727_at | 58718674 | 58718674 | −468 |
| ZNF697 | 1553702_at | 120190390 | 120190390 | −1202 |
| USP4 | 211800_s_at | 49377466 | 49377466 | −780 |
| | 208273_at | 247171210 | 247171210 | 827 |
| NDUFB2 | 240391_at | 140396471 | 140396471 | 1164 |
| RRAGA | 201628_s_at | 19049372 | 19049372 | −739 |
| FAM161A | 239090_at | 62081278 | 62081278 | 938 |
| ANGEL2 | 217630_at | 213189168 | 213189168 | −548 |
| RAD18 | 238670_at | 9005186 | 9005186 | −1043 |
| FBXO31 | 224162_s_at | 87417394 | 87417394 | 1495 |
| TATDN2 | 1565580_s_at | 10289707 | 10289707 | −121 |
| DNAJC9 | 229701_at | 75008620 | 75008620 | 202 |
| RNF181 | 223064_at | 85822857 | 85822857 | −897 |
| PXMP2 | 1553837_at | 133287436 | 133287436 | 888 |
| COPE | 201264_at | 19030199 | 19030199 | 860 |
| RPL41 | 201492_s_at | 56510572 | 56510572 | −1285 |
| WHSC2 | 244260_at | 2011837 | 2011837 | −276 |
| TMED2 | 200087_s_at | 124069076 | 124069076 | 1130 |
| RPS28 | 208904_s_at | 8386384 | 8386384 | −1135 |
| TRPC4AP | 212059_s_at | 33680674 | 33680674 | −482 |
| C1orf56 | 230468_s_at | 151020216 | 151020216 | −485 |
| CCDC101 | 48117_at | 28565247 | 28565247 | −355 |
| FKBP15 | 31826_at | 115983598 | 115983598 | −1373 |
| C19orf55 | 242640_at | 36249117 | 36249117 | 800 |
| SLC39A1 | 217778_at | 153936048 | 153936048 | −1038 |
| C3orf1 | 223004_s_at | 119217379 | 119217379 | −789 |
| ZNF410 | 202010_s_at | 74353574 | 74353574 | 1619 |
| RANGRF | 223554_s_at | 8191989 | 8191989 | −832 |
| RPTOR | 225715_at | 78518625 | 78518625 | −763 |
| HARBI1 | 241498_at | 46638777 | 46638777 | 689 |
| FAM192A | 222460_a_at | 57219976 | 57219976 | 1155 |
| RABEPK | 1558021_at | 127962824 | 127962824 | −917 |
| MORF4 | 221381_s_at | 79165211 | 79165211 | −973 |
| ARMC2 | 223866_at | 109169625 | 109169625 | −528 |
| UBAP1 | 46270_at | 34179011 | 34179011 | 1216 |
| KIAA1430 | 1554550_at | 186125182 | 186125182 | 1127 |
| SNORD73A | 201257_x_at | 152020725 | 152020725 | 1741 |
| EIF4G2 | 200004_at | 10830017 | 10830017 | −1755 |
| SNORD73A | 200099_s_at | 152020725 | 152020725 | 1741 |
| SNORD73A | 212391_x_at | 152020725 | 152020725 | 1741 |

TABLE 15

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| DSC3 | 3043 | 0 | 1724347 | 0 | 9.29E−08 | 12 | 0 | chr18 | −1 | 28570052 | 28622781 | 206032_at | 28625824 | 28638204 |
| CXCL5 | 177140 | 433359 | 53823 | 166 | 9.29E−08 | 21 | 0 | chr4 | −1 | 74861359 | 74864496 | 214974_x_at | 74642141 | 74687356 |
| PAH | 0 | 0 | 37070 | 127 | 9.29E−08 | 8 | 0 | chr12 | −1 | 103232104 | 103311381 | 205719_s_at | 103311276 | 103339573 |
| CXCL5 | 177140 | 433359 | 53823 | 166 | 1.39E−07 | 21 | 0 | chr4 | −1 | 74861359 | 74864496 | 215101_s_at | 74642141 | 74687356 |
| INHBA | 0 | 660770 | 183342 | 2473 | 3.17E−07 | 67 | 0 | chr7 | −1 | 41724712 | 41742706 | 227140_at | 40180732 | 41744986 |
| MMP10 | 0 | 1366568 | 311747 | 310916 | 4.18E−07 | 67 | 0 | chr11 | −1 | 102641245 | 102651359 | 205680_at | 102461598 | 102927599 |
| LPL | 7052 | 0 | 0 | 560 | 8.05E−07 | 50 | 0 | chr8 | 1 | 19796284 | 19824769 | 203548_s_at | 19803336 | 20054515 |
| SLCO1B3 | 0 | 4904 | 439417 | 257633 | 1.01E−06 | 71 | 0 | chr12 | 1 | 20963638 | 21069658 | 206354_at | 20541064 | 21590451 |
| SRPX2 | 67966 | 0 | 1480794 | 7420 | 1.07E−06 | 67 | 0 | chrX | 1 | 99899215 | 99926296 | 205499_at | 99676689 | 99831249 |
| STC1 | 0 | 138264 | 126756 | 127558 | 1.09E−06 | 29 | 0 | chr8 | −1 | 23699428 | 23712320 | 204597_x_at | 23587917 | 24765322 |
| CA2 | 4312 | 0 | 1278765 | 0 | 1.09E−06 | 100 | 100 | chr8 | 1 | 86376131 | 86393721 | 209301_at | 86360205 | 86371819 |
| CXCL11 | 0 | 203627 | 29629 | 45097 | 1.73E−06 | 75 | 0 | chr4 | −1 | 76954835 | 76957350 | 211122_s_at | 76956471 | 76975325 |
| STC1 | 0 | 138264 | 126756 | 127558 | 1.78E−06 | 12 | 0 | chr8 | −1 | 23699428 | 23712320 | 204595_s_at | 23587917 | 24765322 |
| IL13RA2 | 0 | 0 | 214202 | 170371 | 1.89E−06 | 46 | 0 | chrX | −1 | 114238538 | 114253536 | 206172_at | 113834443 | 114461778 |
| CLDN1 | 61858 | 407043 | 1166 | 0 | 3.46E−06 | 46 | 0 | chr3 | −1 | 190023490 | 190040264 | 218182_s_at | 189951990 | 189978406 |
| SLC35D3 | 29910 | 34906 | 930 | 0 | 3.78E−06 | 33 | 0 | chr6 | 1 | 137243402 | 137246777 | 231341_at | 137273312 | 137298915 |
| EPHX4 | 197 | 441874 | 0 | 0 | 3.78E−06 | 42 | 0 | chr1 | 1 | 92495539 | 92529093 | 239579_at | 92358039 | 92495342 |
| ACSL6 | 464 | 0 | 13 | 0 | 4.06E−06 | 33 | 0 | chr5 | −1 | 131285666 | 131347355 | 229725_at | 131347819 | 131524774 |
| CCL26 | 0 | 420490 | 148093 | 32496 | 4.37E−06 | 17 | 0 | chr7 | −1 | 75398851 | 75401575 | 223710_at | 75369111 | 75503808 |
| CST1 | 0 | 0 | 327852 | 112934 | 4.39E−06 | 42 | 0 | chr20 | −1 | 23728190 | 23731574 | 206224_at | 23641665 | 24442368 |
| MAGEA6 | 0 | 0 | 60268 | 0 | 5.60E−06 | 4 | 0 | chrX | 1 | 151867214 | 151870825 | 209942_x_at | 151863274 | 151869775 |
| GIF | 73110 | 0 | 35703 | 34594 | 5.91E−06 | 75 | 0 | chr11 | −1 | 59596748 | 59612974 | 207033_at | 59686084 | 59872871 |
| ZIC2 | 23214 | 0 | 3338 | 0 | 8.36E−06 | 4 | 0 | chr13 | 1 | 100634026 | 100639018 | 223642_at | 100657240 | 100718965 |
| TCN1 | 52043 | 0 | 56770 | 31539 | 8.36E−06 | 100 | 0 | chr11 | −1 | 59620284 | 59634041 | 205513_at | 59686084 | 59872871 |
| C8orf84 | 385 | 0 | 203092 | 0 | 8.97E−06 | 67 | 0 | chr8 | −1 | 73978132 | 74005507 | 235209_at | 74005892 | 74199003 |
| MMP7 | 0 | 1116667 | 61846 | 77695 | 8.97E−06 | 100 | 0 | chr11 | −1 | 102391268 | 102401458 | 204259_at | 102352665 | 102432092 |
| REG4 | 27196 | 95725 | 162475 | 41607 | 8.97E−06 | 50 | 0 | chr1 | −1 | 120343793 | 120354203 | 238984_at | 120309254 | 120327007 |
| C8orf84 | 385 | 0 | 203092 | 0 | 1.12E−05 | 79 | 0 | chr8 | −1 | 73978132 | 74005507 | 235210_s_at | 74005892 | 74199003 |
| KRT6A | 0 | 0 | 107645 | 107801 | 1.12E−05 | 8 | 0 | chr12 | −1 | 52880958 | 52886972 | 209125_at | 52702607 | 53107910 |
| CHI3L1 | 0 | 27501 | 45438 | 58380 | 1.12E−05 | 79 | 0 | chr1 | −1 | 203148059 | 203155877 | 209395_at | 203097543 | 203236398 |
| SIM2 | 13424 | 0 | 955 | 0 | 1.34E−05 | 8 | 0 | chr21 | 1 | 38071434 | 38122218 | 241726_at | 37854364 | 38058010 |
| CLDN2 | 0 | 0 | 352095 | 78873 | 1.34E−05 | 96 | 0 | chrX | 1 | 106163634 | 106174091 | 223509_at | 106114542 | 106178629 |
| LRP8 | 6542 | 23727 | 236781 | 189 | 1.34E−05 | 38 | 0 | chr1 | −1 | 53711217 | 53793686 | 205282_at | 53800228 | 54201098 |
| KRT6B | 0 | 0 | 94307 | 84810 | 1.37E−05 | 50 | 0 | chr12 | −1 | 52840437 | 52845910 | 213680_at | 52702607 | 53107910 |
| TAC1 | 11501 | 0 | 0 | 0 | 1.37E−05 | 21 | 0 | chr7 | 1 | 97361220 | 97369784 | 206552_s_at | 96804192 | 97349719 |
| ULBP2 | 27393 | 0 | 6084 | 0 | 1.38E−05 | 12 | 0 | chr6 | 1 | 150263136 | 150270371 | 238542_at | 150290529 | 150301470 |
| ZG16 | 0 | 1422910 | 6544 | 6772 | 1.42E−05 | 96 | 100 | chr16 | 1 | 29789590 | 29792969 | 214142_at | 29776286 | 29790986 |
| COL11A1 | 0 | 0 | 0 | 494441 | 1.42E−05 | 4 | 0 | chr1 | −1 | 103342023 | 103574047 | 37892_at | 101706840 | 103791505 |
| KRT23 | 0 | 117197 | 18451 | 73570 | 1.50E−05 | 33 | 0 | chr17 | −1 | 39078948 | 39093672 | 218963_s_at | 39079223 | 39102520 |
| CADPS | 0 | 0 | 102346 | 103213 | 1.54E−05 | 79 | 0 | chr3 | −1 | 62384023 | 62467530 | 1568603_at | 62439298 | 62528066 |
| WISP3 | 0 | 851967 | 33840 | 33132 | 1.55E−05 | 17 | 0 | chr6 | 1 | 112375275 | 112390889 | 210861_s_at | 112194877 | 112392175 |
| GPR109B | 0 | 1056158 | 45936 | 49105 | 1.68E−05 | 8 | 0 | chr12 | −1 | 123185840 | 123187890 | 205220_at | 123128681 | 123233349 |
| PCCA | 22372 | 89337 | 11076 | 0 | 1.69E−05 | 100 | 100 | chr13 | 1 | 100741337 | 101182686 | 203860_at | 100657240 | 100718965 |
| MMP3 | 0 | 1429529 | 374708 | 247955 | 1.73E−05 | 96 | 0 | chr11 | −1 | 102706532 | 102714320 | 205828_at | 102461598 | 102927599 |
| CEL | 13070 | 47185 | 19830 | 9222 | 1.86E−05 | 4 | 0 | chr9 | 1 | 135937365 | 135947248 | 205910_s_at | 135950435 | 135964747 |
| IL1A | 0 | 111363 | 351669 | 19592 | 2.12E−05 | 17 | 0 | chr2 | −1 | 113531492 | 113542167 | 210118_s_at | 113535635 | 113544577 |
| CHI3L1 | 0 | 27501 | 45438 | 58380 | 2.50E−05 | 71 | 0 | chr1 | −1 | 203148059 | 203155877 | 209396_s_at | 203097543 | 203236398 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| TMPRSS3 | 0 | 0 | 0 | 89883 | 2.64E−05 | 8 | 0 | chr21 | −1 | 43801985 | 43816200 | 223949_at | 43805856 | 43823604 |
| ACSL6 | 464 | 0 | 13 | 0 | 2.64E−05 | 46 | 0 | chr5 | −1 | 131285666 | 131347355 | 211207_s_at | 131347819 | 131524774 |
| SERPINE1 | 1942 | 32911 | 30688 | 27163 | 2.85E−05 | 12 | 0 | chr7 | 1 | 100770370 | 100782547 | 202628_s_at | 100701852 | 100768428 |
| SLC28A3 | 0 | 0 | 328881 | 199897 | 2.92E−05 | 79 | 0 | chr9 | −1 | 86890372 | 86955598 | 232277_at | 86933053 | 87278151 |
| TNIP3 | 0 | 25056 | 215296 | 91791 | 3.13E−05 | 4 | 0 | chr4 | −1 | 122052563 | 122085495 | 220655_at | 121997815 | 122289891 |
| MAGEA6 | 0 | 0 | 60268 | 0 | 3.27E−05 | 4 | 0 | chrX | 1 | 151867214 | 151870825 | 214612_x_at | 151863274 | 151869775 |
| TACSTD2 | 4441 | 0 | 421 | 0 | 3.43E−05 | 96 | 0 | chr1 | −1 | 59041099 | 59043166 | 202286_s_at | 59013255 | 59038725 |
| DEFB4A | 9169 | 9560 | 730487 | 60370 | 3.63E−05 | 4 | 0 | chr8 | 1 | 7752151 | 7754233 | 207356_at | 7731334 | 7742982 |
| PHLDA1 | 48055 | 741822 | 731051 | 0 | 3.63E−05 | 75 | 0 | chr12 | −1 | 76419227 | 76425556 | 217999_s_at | 76344741 | 76377501 |
| PRDM13 | 16559 | 0 | 0 | 81 | 3.73E−05 | 4 | 0 | chr6 | 1 | 100054606 | 100062635 | 221168_at | 100071165 | 100441380 |
| PDPN | 97 | 0 | 0 | 117 | 3.90E−05 | 8 | 0 | chr1 | 1 | 13909960 | 13944452 | 221898_at | 13844945 | 13909863 |
| KRT80 | 45942 | 117950 | 40964 | 39420 | 3.94E−05 | 54 | 0 | chr12 | −1 | 52562780 | 52585784 | 231849_at | 52481071 | 52539842 |
| PTPN13 | 6744 | 174491 | 296250 | 0 | 3.94E−05 | 54 | 0 | chr4 | 1 | 87515468 | 87736310 | 204201_s_at | 87484267 | 87508724 |
| ACSL6 | 464 | 0 | 13 | 0 | 3.96E−05 | 12 | 0 | chr5 | −1 | 131285666 | 131347355 | 213683_at | 131347819 | 131524774 |
| MSX2 | 8523 | 0 | 77 | 0 | 4.04E−05 | 83 | 0 | chr5 | 1 | 174151536 | 174157902 | 210319_x_at | 174137456 | 174143013 |
| HS6ST2 | 9861 | 0 | 1214351 | 0 | 4.37E−05 | 33 | 0 | chrX | −1 | 131760038 | 132091358 | 230030_at | 132101219 | 132274423 |
| MSX2 | 8523 | 0 | 77 | 0 | 4.37E−05 | 88 | 0 | chr5 | 1 | 174151536 | 174157902 | 205555_s_at | 174137456 | 174143013 |
| DSC3 | 3043 | 0 | 1724347 | 0 | 4.80E−05 | 12 | 0 | chr18 | −1 | 28570052 | 28622781 | 206033_s_at | 28625824 | 28638204 |
| ARNTL2 | 47335 | 1197254 | 1004 | 0 | 5.00E−05 | 79 | 0 | chr12 | 1 | 27485988 | 27573466 | 220658_s_at | 27397668 | 27438653 |
| CLDN1 | 61858 | 407043 | 1166 | 0 | 5.14E−05 | 92 | 0 | chr3 | −1 | 190023490 | 190040264 | 222549_at | 189951990 | 189978406 |
| CA1 | 22155 | 0 | 1164764 | 88636 | 5.42E−05 | 67 | 100 | chr8 | −1 | 86240458 | 86262130 | 205950_s_at | 86284285 | 86332544 |
| BMP7 | 5454 | 0 | 0 | 0 | 5.47E−05 | 17 | 0 | chr20 | −1 | 55743804 | 55841684 | 209591_s_at | 55847138 | 55925397 |
| SERPINE1 | 1942 | 32911 | 30688 | 27163 | 5.80E−05 | 8 | 0 | chr7 | 1 | 100770370 | 100782547 | 202627_s_at | 100701852 | 100768428 |
| REG1B | 0 | 0 | 93943 | 94526 | 5.80E−05 | 46 | 8 | chr2 | −1 | 79312157 | 79315119 | 205886_at | 79220617 | 79739679 |
| CEACAM7 | 11681 | 0 | 120452 | 156380 | 6.15E−05 | 100 | 100 | chr19 | −1 | 42177235 | 42192296 | 206199_at | 42168674 | 42180615 |
| WDR72 | 0 | 0 | 2906 | 3070 | 6.20E−05 | 25 | 0 | chr15 | −1 | 53805938 | 54055075 | 236741_at | 54052067 | 55473630 |
| HOXA10 | 25501 | 0 | 518 | 129 | 6.26E−05 | 100 | 100 | chr7 | −1 | 27210852 | 27219880 | 213150_at | 27245381 | 27250842 |
| SERPIND1 | 1422 | 138166 | 102460 | 69373 | 6.50E−05 | 4 | 0 | chr22 | 1 | 21128167 | 21142008 | 205576_at | 21129589 | 21137392 |
| LRRC34 | 15 | 73145 | 8885 | 16 | 6.67E−05 | 12 | 0 | chr3 | −1 | 169511216 | 169530452 | 236918_s_at | 169530467 | 169549519 |
| CA9 | 40997 | 203852 | 147 | 1796 | 7.21E−05 | 29 | 0 | chr9 | 1 | 35673853 | 35681156 | 205199_at | 35621412 | 35632856 |
| RAI2 | 6717 | 0 | 1134625 | 0 | 7.51E−05 | 38 | 54 | chrX | −1 | 17818171 | 17879356 | 219440_at | 17772790 | 17872639 |
| PCDHB9 | 56150 | 0 | 22029 | 1472 | 7.60E−05 | 33 | 0 | chr5 | 1 | 140571952 | 140575213 | 223854_at | 140493790 | 140515802 |
| VSIG1 | 0 | 0 | 108613 | 46177 | 8.05E−05 | 8 | 0 | chrX | 1 | 107288244 | 107322327 | 243764_at | 107183860 | 107324359 |
| PTGS2 | 276 | 433823 | 1362224 | 0 | 8.13E−05 | 17 | 0 | chr1 | −1 | 186640923 | 186649555 | 1554997_s_at | 186400111 | 186649279 |
| TCEA3 | 35942 | 236181 | 57047 | 0 | 8.65E−05 | 100 | 100 | chr1 | −1 | 23707554 | 23751233 | 226388_at | 23787175 | 23806389 |
| C8orf84 | 385 | 0 | 203092 | 0 | 9.17E−05 | 33 | 0 | chr8 | −1 | 73976780 | 74005507 | 230661_at | 74005892 | 74199003 |
| SLC7A11 | 13988 | 1242952 | 1036798 | 318232 | 9.84E−05 | 92 | 17 | chr4 | −1 | 139085251 | 139163503 | 209921_at | 139177491 | 139929775 |
| FAP | 0 | 91710 | 99867 | 100531 | 0.000103138 | 4 | 0 | chr2 | −1 | 163027200 | 163100045 | 209955_s_at | 163054893 | 163117608 |
| CDH3 | 10717 | 0 | 109640 | 0 | 0.000109956 | 88 | 0 | chr16 | 1 | 68678739 | 68732971 | 203256_at | 68600291 | 68668022 |
| FABP1 | 0 | 0 | 73419 | 42057 | 0.000110684 | 100 | 100 | chr2 | −1 | 88422510 | 88427635 | 205892_s_at | 88427215 | 88441743 |
| PADI2 | 13112 | 18516 | 29773 | 0 | 0.000111884 | 96 | 100 | chr1 | −1 | 17393256 | 17445930 | 209791_at | 17459042 | 17465128 |
| DUSP4 | 13858 | 0 | 178908 | 0 | 0.000117074 | 33 | 0 | chr8 | −1 | 29190581 | 29208185 | 226034_at | 29139381 | 29194327 |
| C2CD4A | 2804 | 13533 | 2160 | 652 | 0.000117391 | 96 | 0 | chr15 | 1 | 62359176 | 62363109 | 241031_at | 62361980 | 62380410 |
| S100A12 | 0 | 0 | 113621 | 160300 | 0.000117807 | 0 | 0 | chr1 | −1 | 153346184 | 153348125 | 205863_at | 153243308 | 153489968 |
| DSG3 | 54535 | 0 | 1319370 | 49795 | 0.00011886 | 8 | 0 | chr18 | 1 | 29027758 | 29058665 | 235075_at | 29082293 | 29096608 |
| ART3 | 0 | 228624 | 4632 | 20100 | 0.000121332 | 71 | 0 | chr4 | 1 | 76932353 | 77033955 | 210147_at | 76919327 | 76934310 |
| ADAM12 | 5580 | 42987 | 0 | 0 | 0.000122955 | 4 | 0 | chr10 | −1 | 127700950 | 128077024 | 226777_at | 128082604 | 128586018 |
| CEL | 13070 | 47185 | 19830 | 9222 | 0.000126064 | 4 | 0 | chr9 | 1 | 135937365 | 135947248 | 1553970_s_at | 135950435 | 135964747 |
| SLC4A4 | 5471 | 428134 | 2044 | 0 | 0.000130954 | 96 | 100 | chr4 | 1 | 72053003 | 72435434 | 203908_at | 72058474 | 73433711 |

TABLE 15-continued

| Genes with higher gene expression variability in cancer compared to normal. | | | | | | | | | | | | | | |
|---|---|---|---|---|---|---|---|---|---|---|---|---|---|---|
| gene | dist2block | dist2PMD | dist2DMR | dist2CGI | p-value | Cancer % On | Normal % On | chr | strand | txStart | txEnd | affyid | blockStart | blockEnd |
| PTGES | 0 | 494854 | 20546 | 14772 | 0.00013104 | 0 | 0 | chr9 | −1 | 132500610 | 132515326 | 210367_s_at | 132512031 | 132561852 |
| SLAIN1 | 232 | 0 | 217279 | 0 | 0.00014771 | 8 | 0 | chr13 | 1 | 78272023 | 78338259 | 225619_at | 77904087 | 78271791 |
| TNFRSF11B | 275 | 186437 | 254731 | 7 | 0.00014771 | 25 | 0 | chr8 | −1 | 119935797 | 119964383 | 204932_at | 119964658 | 120167597 |
| MYO1A | 25283 | 60167 | 88409 | 28374 | 0.000157753 | 100 | 100 | chr12 | −1 | 57422301 | 57443901 | 211916_s_at | 57405720 | 57418618 |
| C15orf48 | 32564 | 30098 | 241689 | 0 | 0.000170778 | 100 | 100 | chr15 | 1 | 45722807 | 45725647 | 223484_at | 45684488 | 45690243 |
| NME5 | 0 | 96998 | 0 | 39557 | 0.00017316 | 29 | 0 | chr5 | −1 | 137450866 | 137475104 | 206197_at | 137375472 | 137501136 |
| HS6ST2 | 9861 | 0 | 1214351 | 0 | 0.000174438 | 4 | 0 | chrX | −1 | 131760038 | 132091358 | 1552766_at | 132101219 | 132274423 |
| RNF183 | 78021 | 151296 | 3884 | 23246 | 0.000178243 | 58 | 0 | chr9 | −1 | 116059480 | 116061476 | 235153_at | 116139497 | 116148523 |
| ELF5 | 0 | 10079 | 91338 | 72488 | 0.000179381 | 4 | 0 | chr11 | −1 | 34500342 | 34533346 | 220625_s_at | 34494011 | 34594197 |
| ONECUT2 | 14893 | 0 | 3622 | 208 | 0.000185671 | 4 | 0 | chr18 | 1 | 55102917 | 55158530 | 239911_at | 55021604 | 55088024 |
| ALKBH3 | 45238 | 81068 | 720 | 0 | 0.000190181 | 29 | 4 | chr11 | 1 | 43902357 | 43941823 | 226127_at | 43947595 | 43956807 |
| SLC7A11 | 13988 | 1242952 | 1036798 | 318232 | 0.000192417 | 25 | 0 | chr4 | −1 | 139085251 | 139163503 | 207528_s_at | 139177491 | 139929775 |
| KIAA1549 | 4077 | 166603 | 19826 | 295 | 0.000212477 | 0 | 0 | chr7 | −1 | 138516126 | 138666064 | 223575_at | 138670141 | 138700109 |
| FAM40B | 56013 | 281509 | 56881 | 0 | 0.000213786 | 8 | 0 | chr7 | 1 | 129074274 | 129128240 | 231880_at | 128993853 | 129018261 |
| SLC26A2 | 32757 | 179508 | 228976 | 0 | 0.000227716 | 100 | 100 | chr5 | 1 | 149340300 | 149366968 | 205097_at | 149286630 | 149307543 |
| IL24 | 0 | 17411 | 154100 | 11905 | 0.000229307 | 0 | 0 | chr1 | 1 | 207070789 | 207077210 | 206569_at | 206911264 | 207078912 |
| KLK6 | 0 | 0 | 47520 | 32986 | 0.000242481 | 38 | 0 | chr19 | −1 | 51461888 | 51472929 | 204733_at | 51416341 | 51518249 |
| CYP4X1 | 7364 | 0 | 202593 | 0 | 0.00024585 | 92 | 0 | chr1 | 1 | 47489240 | 47516423 | 227702_at | 47190239 | 47481876 |
| CCDC113 | 6027 | 1363 | 212841 | 0 | 0.000247123 | 75 | 0 | chr16 | 1 | 58283863 | 58317740 | 222890_at | 58234237 | 58277836 |
| TRIB3 | 4872 | 119260 | 19871 | 229 | 0.000248853 | 17 | 0 | chr20 | 1 | 361261 | 378203 | 1555788_a_at | 345685 | 356389 |
| CXCL6 | 14858 | 271077 | 107500 | 207 | 0.000261126 | 25 | 0 | chr4 | 1 | 74702214 | 74704477 | 206336_at | 74642141 | 74687356 |
| KRT17 | 0 | 4354 | 109288 | 23912 | 0.000261126 | 8 | 0 | chr17 | −1 | 39775689 | 39780829 | 205157_s_at | 39711383 | 39800097 |
| CKMT2 | 27560 | 654859 | 19763 | 68217 | 0.000283189 | 4 | 0 | chr5 | 1 | 80529104 | 80562216 | 205295_at | 80495827 | 80501544 |
| STC2 | 3650 | 59111 | 12552 | 0 | 0.000283189 | 4 | 0 | chr5 | −1 | 172741716 | 172756506 | 203438_at | 172760156 | 173021332 |
| NMU | 6001 | 0 | 157023 | 0 | 0.000289919 | 100 | 29 | chr4 | −1 | 56461398 | 56502465 | 206023_at | 56508466 | 56603043 |
| CPS1 | 0 | 0 | 784146 | 79725 | 0.00029186 | 21 | 0 | chr2 | 1 | 211421262 | 211543831 | 217564_s_at | 211343341 | 213393136 |
| PSAT1 | 4606 | 81878 | 309115 | 0 | 0.000301096 | 83 | 0 | chr9 | 1 | 80912059 | 80945009 | 220892_s_at | 80894673 | 80907453 |
| MAGEA11 | 0 | 27700 | 759730 | 56214 | 0.000301842 | 4 | 0 | chrX | 1 | 148769894 | 148797942 | 210503_at | 148749972 | 148848717 |
| GAL | 5837 | 718558 | 415 | 0 | 0.000302226 | 33 | 0 | chr11 | 1 | 68451983 | 68458643 | 214240_at | 68381628 | 68446146 |
| RTEL1 | 23159 | 171199 | 0 | 293 | 0.000302707 | 33 | 0 | chr20 | 1 | 62290756 | 62330051 | 206467_x_at | 62313915 | 62327968 |
| IL1B | 16253 | 59050 | 319384 | 71905 | 0.000303787 | 38 | 0 | chr2 | −1 | 113587328 | 113594480 | 39402_at | 113610733 | 113629323 |
| SNTB1 | 9028 | 883489 | 685812 | 0 | 0.000316413 | 42 | 0 | chr8 | −1 | 121547985 | 121824309 | 214708_at | 121833337 | 122288541 |
| PHGDH | 0 | 0 | 62782 | 335 | 0.000327764 | 33 | 0 | chr1 | 1 | 120254510 | 120286838 | 201397_at | 120200649 | 120254790 |
| ITLN1 | 0 | 0 | 96438 | 83006 | 0.000359862 | 100 | 100 | chr1 | −1 | 160846329 | 160854960 | 223597_at | 160549158 | 160942166 |
| DUSP27 | 0 | 0 | 25138 | 27294 | 0.000359862 | 62 | 0 | chr1 | 1 | 167063282 | 167098366 | 232252_at | 167045377 | 167065026 |
| ALPK3 | 46220 | 339086 | 548054 | 282 | 0.000361358 | 21 | 0 | chr15 | 1 | 85359911 | 85416713 | 228342_s_at | 85406131 | 85454098 |
| CES2 | 18044 | 214137 | 40796 | 0 | 0.000361478 | 100 | 100 | chr16 | 1 | 66968363 | 66978999 | 209667_at | 66940239 | 66950319 |
| VAV2 | 7763 | 337252 | 3505 | 0 | 0.000364999 | 0 | 71 | chr9 | −1 | 136627016 | 136857432 | 226063_at | 136865195 | 136884947 |
| ADAMDEC1 | 0 | 0 | 528257 | 529037 | 0.000366542 | 100 | 100 | chr8 | 1 | 24241872 | 24263526 | 206134_at | 23587917 | 24765322 |
| ODAM | 0 | 0 | 992834 | 491642 | 0.000373326 | 79 | 0 | chr4 | 1 | 71062213 | 71070293 | 220133_at | 70727714 | 71551169 |
| TTC26 | 134 | 319063 | 96385 | 0 | 0.000376398 | 0 | 0 | chr7 | 1 | 138818524 | 138876732 | 235949_at | 138818658 | 138824296 |
| SLC6A6 | 578 | 110921 | 590 | 0 | 0.000386778 | 12 | 0 | chr3 | 1 | 14444076 | 14530857 | 205921_s_at | 14444654 | 14452211 |
| TMEM17 | 6750 | 56979 | 198513 | 0 | 0.000395806 | 8 | 0 | chr2 | −1 | 62727356 | 62733476 | 1557137_at | 62740226 | 62870904 |
| DSC3 | 3043 | 0 | 1724347 | 0 | 0.000415129 | 12 | 0 | chr18 | −1 | 28570052 | 28622781 | 244107_at | 28625824 | 28638204 |
| PKIB | 321 | 0 | 209064 | 0 | 0.000427117 | 100 | 100 | chr6 | 1 | 122931377 | 123047037 | 223551_at | 122804831 | 122931056 |
| CXCR2 | 0 | 0 | 198359 | 90927 | 0.00043038 | 12 | 0 | chr2 | 1 | 218990727 | 219001976 | 207008_at | 218875402 | 219075651 |
| SERPINA3 | 0 | 0 | 14178 | 155979 | 0.000448005 | 50 | 0 | chr14 | 1 | 95078634 | 95090397 | 202376_at | 95071921 | 95226467 |
| FAM176A | 13377 | 141546 | 0 | 0 | 0.000455315 | 0 | 0 | chr2 | −1 | 75719444 | 75788039 | 227828_s_at | 75801416 | 75869723 |
| COL11A1 | 0 | 0 | 0 | 494441 | 0.000455576 | 4 | 0 | chr1 | −1 | 103342023 | 103574047 | 204320_at | 101706840 | 103791505 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| AP1S3 | 88506 | 450562 | 108395 | 0 | 0.000455576 | 92 | 12 | chr2 | −1 | 224616403 | 224702319 | 1555731_a_at | 224584621 | 224613813 |
| GRHL1 | 4565 | 1540723 | 61525 | 0 | 0.000466402 | 46 | 0 | chr2 | 1 | 10091827 | 10142405 | 222830_at | 10077338 | 10087262 |
| SLC26A2 | 32757 | 179508 | 228976 | 0 | 0.000470422 | 100 | 100 | chr5 | 1 | 149340300 | 149366968 | 224959_at | 149286630 | 149307543 |
| KCNJ15 | 0 | 99468 | 339397 | 339395 | 0.000492912 | 4 | 0 | chr21 | 1 | 39628663 | 39673743 | 210119_at | 39300209 | 39888752 |
| DDIT4L | 9870 | 19353 | 0 | 127 | 0.000495686 | 0 | 0 | chr4 | −1 | 101107027 | 101111625 | 228057_at | 100876732 | 101101755 |
| | 4417 | 2070 | 148395 | 17655 | 0.0004971 | 4 | 0 | chr6 | −1 | 30899130 | 30899952 | 244056_at | 30904369 | 30923128 |
| HS6ST2 | 9861 | 0 | 1214351 | 0 | 0.000506632 | 50 | 4 | chrX | −1 | 131760038 | 132091358 | 1552767_a_at | 132101219 | 132274423 |
| SERPINB4 | 0 | 0 | 292763 | 221174 | 0.000507296 | 8 | 0 | chr18 | −1 | 61304493 | 61311532 | 209720_s_at | 61174562 | 61603221 |
| PROK2 | 7372 | 0 | 0 | 0 | 0.00050836 | 0 | 0 | chr3 | −1 | 71820807 | 71834357 | 232629_at | 71841729 | 72200853 |
| SLCO3A1 | 4664 | 7928 | 61741 | 0 | 0.000514943 | 4 | 0 | chr15 | 1 | 92396925 | 92709133 | 219229_at | 92090952 | 92392261 |
| DKK1 | 3687 | 335939 | 1893734 | 0 | 0.000525644 | 12 | 0 | chr10 | 1 | 54074056 | 54077417 | 204602_at | 54077743 | 54709456 |
| SERPINB7 | 0 | 23623 | 161651 | 160757 | 0.000527835 | 4 | 0 | chr18 | 1 | 61442644 | 61472604 | 206421_s_at | 61174562 | 61603221 |
| ASB9 | 0 | 0 | 519278 | 65100 | 0.000547606 | 50 | 0 | chrX | −1 | 15262109 | 15288270 | 205673_s_at | 15279573 | 15314091 |
| CHST4 | 0 | 0 | 84153 | 63775 | 0.00055017 | 12 | 0 | chr16 | 1 | 71560036 | 71572488 | 220446_s_at | 71508877 | 71649407 |
| TESC | 6115 | 0 | 43582 | 0 | 0.000554983 | 33 | 0 | chr12 | −1 | 117476729 | 117537274 | 218872_at | 117515108 | 117531159 |
| IL8 | 35918 | 175086 | 203491 | 96198 | 0.000563037 | 88 | 0 | chr4 | 1 | 74606223 | 74609433 | 211506_s_at | 74642141 | 74687356 |
| TRIB3 | 4872 | 119260 | 19871 | 229 | 0.00056632 | 58 | 0 | chr20 | 1 | 361261 | 378203 | 218145_at | 345685 | 356389 |
| SLC16A4 | 21634 | 24830 | 17520 | 16245 | 0.000571565 | 50 | 0 | chr1 | −1 | 110905482 | 110933648 | 205234_at | 110955282 | 111098047 |
| PAX9 | 13797 | 0 | 31 | 5 | 0.000589145 | 0 | 0 | chr14 | 1 | 37126782 | 37147007 | 231145_at | 37059570 | 37112985 |
| GABRP | 0 | 0 | 279091 | 38924 | 0.000596619 | 46 | 0 | chr5 | 1 | 170210723 | 170241051 | 205044_at | 170176247 | 170287040 |
| HES6 | 3526 | 296497 | 8396 | 0 | 0.000600568 | 96 | 46 | chr2 | −1 | 239146908 | 239148765 | 226446_at | 239114888 | 239145239 |
| FCGR3B | 11381 | 12381 | 9312 | 18618 | 0.00061377 | 29 | 0 | chr1 | −1 | 161592986 | 161600996 | 204007_at | 161612377 | 161624111 |
| IL6 | 0 | 302027 | 174951 | 60081 | 0.000615947 | 4 | 0 | chr7 | 1 | 22765503 | 22771621 | 205207_at | 22589544 | 22845416 |
| GAD1 | 7116 | 0 | 1433 | 0 | 0.000615947 | 4 | 0 | chr2 | 1 | 171673072 | 171717661 | 205278_at | 171642386 | 171665956 |
| FAM92A1 | 1711 | 491948 | 138 | 0 | 0.000623382 | 75 | 0 | chr8 | 1 | 94712773 | 94740669 | 235391_at | 93986519 | 94711062 |
| NRCAM | 0 | 115683 | 152289 | 153023 | 0.000634468 | 17 | 0 | chr7 | −1 | 107788094 | 107797082 | 204105_s_at | 107660496 | 108089223 |
| DHRS2 | 3771 | 0 | 52475 | 52617 | 0.000637004 | 4 | 0 | chr14 | 1 | 24099378 | 24113734 | 214079_at | 24103149 | 24412077 |
| KLK12 | 0 | 0 | 17019 | 2672 | 0.00065012 | 50 | 0 | chr19 | −1 | 51532348 | 51538148 | 220782_x_at | 51523889 | 51568096 |
| S100A2 | 65 | 64964 | 1056 | 29500 | 0.000669388 | 88 | 0 | chr1 | −1 | 153533584 | 153538341 | 204268_at | 153538406 | 153589115 |
| KLK10 | 458 | 0 | 2302 | 627 | 0.000689459 | 83 | 0 | chr19 | −1 | 51516001 | 51523431 | 209792_s_at | 51523889 | 51568096 |
| SOX1 | 13118 | 0 | 0 | 0 | 0.000691062 | 4 | 0 | chr13 | 1 | 112721913 | 112726020 | 237472_at | 112735031 | 112751564 |
| BNIP3 | 9283 | 14576 | 0 | 0 | 0.000719793 | 54 | 62 | chr10 | −1 | 133781578 | 133795435 | 201849_at | 133804718 | 133843600 |
| HEPACAM2 | 0 | 0 | 347647 | 182820 | 0.000736786 | 100 | 100 | chr7 | −1 | 92817899 | 92855837 | 242601_at | 92468948 | 92863507 |
| DUSP4 | 13858 | 0 | 178908 | 0 | 0.000740191 | 46 | 0 | chr8 | −1 | 29190581 | 29208185 | 204014_at | 29139381 | 29194327 |
| C12orf48 | 6330 | 151915 | 822 | 0 | 0.000740191 | 83 | 0 | chr12 | 1 | 102513956 | 102591298 | 220060_s_at | 102520286 | 102528156 |
| FZD3 | 9953 | 0 | 130703 | 0 | 0.00074544 | 4 | 0 | chr8 | 1 | 28351773 | 28431788 | 227499_at | 28335606 | 28341820 |
| PLCE1 | 40899 | 160558 | 34595 | 36367 | 0.000769807 | 100 | 100 | chr10 | 1 | 95790569 | 96088146 | 205112_at | 95693652 | 95749670 |
| ANXA9 | 63673 | 728884 | 64891 | 6542 | 0.000778227 | 4 | 0 | chr1 | 1 | 150954493 | 150968110 | 211712_s_at | 150852840 | 150890820 |
| KCNMA1 | 5882 | 451642 | 229 | 0 | 0.000780843 | 100 | 100 | chr10 | −1 | 78644639 | 79398353 | 221584_s_at | 77832723 | 79392471 |
| CLCA1 | 0 | 0 | 311181 | 71967 | 0.000793251 | 100 | 100 | chr1 | 1 | 86934051 | 86965942 | 210107_at | 86862111 | 86977585 |
| SLC26A3 | 15586 | 0 | 56970 | 58630 | 0.000795509 | 100 | 100 | chr7 | −1 | 107405917 | 107443652 | 206143_at | 107459238 | 107531437 |
| AP1S3 | 88506 | 450562 | 108395 | 0 | 0.000828049 | 96 | 0 | chr2 | −1 | 224616403 | 224702319 | 1555733_s_at | 224584621 | 224613813 |
| SCARA5 | 0 | 0 | 99938 | 70430 | 0.000859851 | 75 | 100 | chr8 | −1 | 27727399 | 27850198 | 229839_at | 27695516 | 27942212 |
| MALL | 0 | 71431 | 2237 | 555 | 0.000869551 | 100 | 100 | chr2 | −1 | 110841447 | 110874143 | 209373_at | 110873609 | 110962342 |
| TNS4 | 0 | 58626 | 537 | 57542 | 0.000879134 | 67 | 0 | chr17 | −1 | 38632080 | 38657849 | 230398_at | 38645632 | 38669338 |
| PROM2 | 0 | 3927 | 0 | 66652 | 0.000901221 | 100 | 100 | chr2 | 1 | 95940201 | 95957054 | 1552797_s_at | 95939815 | 96011110 |
| DUSP4 | 13858 | 0 | 178908 | 0 | 0.000904271 | 54 | 0 | chr8 | −1 | 29190581 | 29208185 | 204015_s_at | 29139381 | 29194327 |
| SLC6A14 | 0 | 0 | 1098999 | 482392 | 0.000936009 | 79 | 17 | chrX | 1 | 115567790 | 115592625 | 219795_at | 115555306 | 115682087 |
| IL1B | 16253 | 59050 | 319384 | 71905 | 0.000962689 | 42 | 0 | chr2 | −1 | 113587328 | 113594480 | 205067_at | 113610733 | 113629323 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| FAIM2 | 11804 | 46014 | 0 | 0 | 0.000964227 | 58 | 0 | chr12 | −1 | 50260680 | 50297720 | 203619_s_at | 50280106 | 50285916 |
| SNTB1 | 9028 | 883489 | 685812 | 0 | 0.000983371 | 38 | 0 | chr8 | −1 | 121547985 | 121824309 | 208608_s_at | 121833337 | 122288541 |
| IL11 | 1283 | 183625 | 2042 | 891 | 0.000995344 | 0 | 0 | chr19 | −1 | 55875757 | 55881814 | 206924_at | 55866329 | 55880531 |
| IL17A | 0 | 0 | 476841 | 97965 | 0.001006616 | 0 | 0 | chr6 | 1 | 52051185 | 52055436 | 216876_s_at | 50824075 | 52126759 |
| C13orf18 | 164 | 10379 | 1112 | 0 | 0.001013305 | 96 | 100 | chr13 | −1 | 46917099 | 46961621 | 219471_at | 46961785 | 46974863 |
| CES2 | 18044 | 214137 | 40796 | 0 | 0.001013305 | 71 | 100 | chr16 | 1 | 66968363 | 66978999 | 213509_x_at | 66940239 | 66950319 |
| TMPRSS3 | 0 | 0 | 301 | 90638 | 0.001022735 | 21 | 0 | chr21 | −1 | 43791999 | 43816955 | 220177_s_at | 43805856 | 43823604 |
| ESM1 | 0 | 17247 | 101321 | 101319 | 0.001039369 | 0 | 0 | chr5 | −1 | 54273692 | 54281491 | 208394_x_at | 54182326 | 54468722 |
| FREM2 | 8369 | 0 | 0 | 0 | 0.001043428 | 38 | 0 | chr13 | 1 | 39261266 | 39460074 | 230964_at | 39269635 | 39581012 |
| KIAA1199 | 70807 | 341262 | 810 | 0 | 0.001052308 | 79 | 0 | chr15 | 1 | 81071684 | 81244117 | 1554685_a_at | 80992262 | 81000877 |
| IGFL2 | 2793 | 0 | 124992 | 69055 | 0.001072308 | 17 | 0 | chr19 | 1 | 46651500 | 46664559 | 231148_at | 46581016 | 46648707 |
| SLC26A2 | 32757 | 179508 | 228976 | 0 | 0.001084707 | 88 | 100 | chr5 | 1 | 149340300 | 149366968 | 224963_at | 149286630 | 149307543 |
| C8orf84 | 385 | 0 | 203092 | 0 | 0.00109793 | 0 | 0 | chr8 | −1 | 73978132 | 74005507 | 214725_at | 74005892 | 74199003 |
| TSPAN1 | 6480 | 236655 | 22728 | 7826 | 0.001100033 | 100 | 100 | chr1 | 1 | 46640759 | 46651630 | 209114_at | 46647239 | 46652840 |
| STC1 | 0 | 138264 | 126756 | 127558 | 0.001118866 | 8 | 0 | chr8 | −1 | 23699428 | 23712320 | 204596_s_at | 23587917 | 24765322 |
| GPR37 | 5278 | 177084 | 588 | 0 | 0.001135355 | 8 | 0 | chr7 | −1 | 124386051 | 124405681 | 209631_s_at | 124410959 | 124470571 |
| | 5912 | 0 | 940 | 22 | 0.001162416 | 88 | 100 | chr16 | 1 | 23765948 | 23770272 | 206149_at | 23727829 | 23760036 |
| TMEM182 | 104499 | 29798 | 113058 | 0 | 0.001185773 | 33 | 0 | chr2 | 1 | 103353367 | 103433875 | 238867_at | 103457866 | 105456231 |
| FRMD5 | 470 | 475280 | 93258 | 0 | 0.00118591 | 25 | 0 | chr15 | −1 | 44162962 | 44487429 | 230831_at | 44487899 | 44575216 |
| TTC9 | 8629 | 0 | 386549 | 0 | 0.001191826 | 8 | 0 | chr14 | 1 | 71108504 | 71142077 | 213172_at | 71072550 | 71099875 |
| DSG3 | 54535 | 0 | 1319370 | 49795 | 0.00119268 | 8 | 0 | chr18 | 1 | 29027758 | 29058665 | 205595_at | 29082293 | 29096608 |
| SEMA6A | 5595 | 0 | 1644 | 0 | 0.001199877 | 92 | 100 | chr5 | −1 | 115779312 | 115910630 | 223449_at | 115916225 | 118236347 |
| AZGP1 | 0 | 21715 | 0 | 21427 | 0.001206646 | 92 | 25 | chr7 | −1 | 99564353 | 99573780 | 209309_at | 99559725 | 99587874 |
| SERPINA7 | 0 | 0 | 214154 | 214274 | 0.001218309 | 4 | 0 | chrX | −1 | 105277197 | 105281385 | 206386_at | 105078443 | 105854952 |
| GRIN2D | 68402 | 339943 | 2509 | 932 | 0.001224705 | 62 | 0 | chr19 | 1 | 48898132 | 48948187 | 229883_at | 48966534 | 48971598 |
| KIAA0802 | 0 | 107368 | 108401 | 9811 | 0.00122728 | 17 | 0 | chr18 | 1 | 8717369 | 8832776 | 213358_at | 8716599 | 8784601 |
| UNC93A | 0 | 0 | 374649 | 59720 | 0.001232525 | 0 | 0 | chr6 | 1 | 167704803 | 167729507 | 214382_at | 167702535 | 167760131 |
| TNFRSF10C | 11022 | 216376 | 0 | 0 | 0.001277837 | 8 | 0 | chr8 | 1 | 22960432 | 22974950 | 206222_at | 22942117 | 22949410 |
| AMIGO2 | 10567 | 350000 | 247537 | 0 | 0.001281293 | 75 | 96 | chr12 | −1 | 47469490 | 47473734 | 222108_at | 47233188 | 47463167 |
| HOXA10 | 40252 | 0 | 9331 | 0 | 0.001281293 | 100 | 100 | chr7 | −1 | 27202057 | 27205129 | 214651_s_at | 27245381 | 27250842 |
| PCDHA6 | 9260 | 0 | 41430 | 76 | 0.001281293 | 12 | 0 | chr5 | 1 | 140207650 | 140391929 | 210674_s_at | 140189536 | 140198390 |
| CYP1B1 | 7396 | 296826 | 0 | 0 | 0.001302935 | 8 | 0 | chr2 | −1 | 38294652 | 38303323 | 202435_s_at | 38253683 | 38295927 |
| PLEKHB1 | 0 | 314870 | 46796 | 14578 | 0.001304027 | 88 | 33 | chr11 | 1 | 73357223 | 73373862 | 209504_s_at | 73309661 | 73366647 |
| LRP8 | 6542 | 23727 | 236781 | 189 | 0.001312395 | 21 | 0 | chr1 | −1 | 53711217 | 53793686 | 208433_s_at | 53800228 | 54201098 |
| SEMG1 | 0 | 0 | 108281 | 86312 | 0.001314082 | 4 | 0 | chr20 | 1 | 43835638 | 43838413 | 206442_at | 43734130 | 43921921 |
| SPRR1A | 0 | 0 | 275572 | 224368 | 0.001314082 | 8 | 0 | chr1 | 1 | 152957707 | 152957976 | 213796_at | 152590080 | 153227464 |
| DDC | 51941 | 0 | 2920 | 92797 | 0.001326413 | 100 | 100 | chr7 | −1 | 50526134 | 50628751 | 205311_at | 50680692 | 50851568 |
| BRCA2 | 96 | 447610 | 224177 | 0 | 0.001339698 | 25 | 0 | chr13 | 1 | 32889611 | 32973347 | 208368_s_at | 32605926 | 32889515 |
| LRRC34 | 15 | 73145 | 8885 | 16 | 0.001339698 | 4 | 0 | chr3 | −1 | 169511216 | 169530452 | 236917_at | 169530467 | 169549519 |
| PTP4A3 | 6191 | 28812 | 95970 | 3655 | 0.001354276 | 8 | 0 | chr8 | 1 | 142432007 | 142441620 | 209695_at | 142438198 | 142528142 |
| KRT20 | 0 | 65004 | 0 | 21377 | 0.001374569 | 100 | 100 | chr17 | −1 | 39030852 | 39041479 | 213953_at | 39041424 | 39053830 |
| IMPA2 | 5934 | 118574 | 56859 | 0 | 0.001377702 | 100 | 100 | chr18 | 1 | 11981427 | 12030876 | 203126_at | 11953602 | 11975493 |
| FCGBP | 59730 | 0 | 10001 | 9921 | 0.001386452 | 100 | 100 | chr19 | −1 | 40353964 | 40440533 | 203240_at | 40339674 | 40380803 |
| MMP19 | 0 | 123001 | 23793 | 12422 | 0.001426821 | 4 | 0 | chr12 | −1 | 56229244 | 56236735 | 204575_s_at | 56228700 | 56291334 |
| FANCI | 6706 | 91817 | 116018 | 0 | 0.001438878 | 92 | 17 | chr15 | 1 | 89787180 | 89860492 | 213008_at | 89745309 | 89780474 |
| ALDH1A2 | 4835 | 0 | 0 | 0 | 0.001451445 | 8 | 0 | chr15 | −1 | 58245622 | 58358616 | 207016_s_at | 58363451 | 58617872 |
| GOLM1 | 15636 | 65708 | 576489 | 0 | 0.001481535 | 100 | 100 | chr9 | −1 | 88641061 | 88714473 | 217771_at | 88730109 | 88871030 |
| LIMCH1 | 871 | 0 | 102792 | 0 | 0.00148522 | 83 | 8 | chr4 | 1 | 41362802 | 41701029 | 212325_at | 41363673 | 41742043 |
| C10orf81 | 11080 | 0 | 82276 | 83362 | 0.00148522 | 8 | 0 | chr10 | 1 | 115531012 | 115542192 | 219857_at | 115508037 | 115519932 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| GUCA2A | 0 | 12975 | 127841 | 18697 | 0.001489389 | 50 | 100 | chr1 | −1 | 42628362 | 42630389 | 207003_at | 42502000 | 42631368 |
| MATN2 | 12519 | 380486 | 557256 | 1 | 0.001516526 | 100 | 100 | chr8 | 1 | 98881311 | 99047940 | 202350_s_at | 98893830 | 99036276 |
| C2orf15 | 29140 | 14379 | 40714 | 0 | 0.001531965 | 0 | 0 | chr2 | 1 | 99757948 | 99767950 | 1552740_at | 99562157 | 99728808 |
| SLC39A5 | 28709 | 510113 | 6484 | 5472 | 0.001534757 | 75 | 100 | chr12 | 1 | 56623847 | 56631630 | 1552281_at | 56652556 | 56659940 |
| COL8A1 | 0 | 570008 | 0 | 179295 | 0.001535013 | 17 | 0 | chr3 | 1 | 99357319 | 99518070 | 226237_at | 98620955 | 99531832 |
| SATB2 | 37318 | 0 | 11387 | 0 | 0.001539121 | 100 | 100 | chr2 | −1 | 200134223 | 200322819 | 213435_at | 200360137 | 200523461 |
| CES2 | 18044 | 214137 | 40796 | 0 | 0.001557981 | 83 | 100 | chr16 | 1 | 66968363 | 66978999 | 209668_x_at | 66940239 | 66950319 |
| NKAIN2 | 8658 | 0 | 0 | 0 | 0.001591582 | 17 | 0 | chr6 | 1 | 124125286 | 125146803 | 242002_at | 123321699 | 124116628 |
| CWH43 | 563 | 0 | 80364 | 0 | 0.001665747 | 88 | 100 | chr4 | 1 | 48988264 | 49064096 | 220723_s_at | 48988827 | 49138512 |
| NRXN3 | 0 | 0 | 684659 | 627586 | 0.001684009 | 8 | 0 | chr14 | 1 | 79117568 | 80328307 | 205795_at | 78447748 | 79745133 |
| CDC45 | 51839 | 113019 | 43833 | 0 | 0.001694424 | 96 | 0 | chr22 | 1 | 19466982 | 19508135 | 204126_s_at | 19518821 | 19699558 |
| C11orf82 | 76157 | 93378 | 105251 | 12886 | 0.001696204 | 75 | 0 | chr11 | 1 | 82625731 | 82645697 | 228281_at | 82453054 | 82549574 |
| KLK8 | 0 | 0 | 15491 | 957 | 0.001744371 | 8 | 0 | chr19 | −1 | 51499264 | 51504958 | 206125_s_at | 51416341 | 51518249 |
| PARVB | 7238 | 106423 | 24533 | 2421 | 0.001764143 | 0 | 0 | chr22 | 1 | 44395091 | 44564803 | 37966_at | 44402329 | 44414770 |
| EPB41L3 | 7072 | 0 | 1 | 0 | 0.001821533 | 58 | 100 | chr18 | −1 | 5392383 | 5544241 | 206710_s_at | 5301384 | 5537169 |
| SLC6A6 | 578 | 110921 | 590 | 0 | 0.001821533 | 25 | 0 | chr3 | 1 | 14444076 | 14530857 | 205920_at | 14444654 | 14452211 |
| TRPM2 | 5692 | 15527 | 0 | 10520 | 0.001827718 | 21 | 0 | chr21 | 1 | 45770046 | 45862964 | 205708_s_at | 45775738 | 45829179 |
| PFN2 | 7485 | 818415 | 1077 | 0 | 0.001842406 | 100 | 100 | chr3 | −1 | 149682691 | 149688896 | 204992_s_at | 149696381 | 149956030 |
| METTL7A | 15852 | 905200 | 249298 | 81609 | 0.001866301 | 100 | 100 | chr12 | 1 | 51318534 | 51326300 | 207761_s_at | 51222303 | 51302682 |
| SLC35E4 | 350 | 111638 | 93435 | 0 | 0.001877575 | 50 | 0 | chr22 | 1 | 31031639 | 31043880 | 1568623_a_at | 31020352 | 31031289 |
| LMCD1 | 13641 | 68392 | 265740 | 0 | 0.001883614 | 29 | 0 | chr3 | 1 | 8543393 | 8609805 | 218574_s_at | 8557034 | 8619335 |
| ITM2A | 0 | 0 | 967161 | 967865 | 0.001894732 | 92 | 100 | chrX | −1 | 78615881 | 78622856 | 202746_at | 77395364 | 78853597 |
| IL33 | 58636 | 0 | 170466 | 170672 | 0.001913861 | 88 | 8 | chr9 | 1 | 6241682 | 6257983 | 209821_at | 6019920 | 6183046 |
| LDLRAD3 | 3286 | 567797 | 18139 | 15 | 0.001913861 | 8 | 0 | chr11 | 1 | 35965628 | 36253686 | 234985_at | 35838203 | 35962342 |
| OTUB2 | 110 | 102476 | 627 | 0 | 0.00191985 | 29 | 0 | chr14 | 1 | 94492724 | 94515276 | 219369_s_at | 94439878 | 94492614 |
| COL1A1 | 65 | 0 | 83795 | 0 | 0.00194236 | 12 | 0 | chr17 | −1 | 48260650 | 48278993 | 202311_s_at | 48279058 | 48350325 |
| ORC1L | 17988 | 947282 | 147164 | 0 | 0.001943513 | 46 | 0 | chr1 | −1 | 52838501 | 52870131 | 205085_at | 52888119 | 52983719 |
| DPEP1 | 19757 | 435809 | 62 | 17221 | 0.001950809 | 83 | 0 | chr16 | 1 | 89696691 | 89704864 | 205983_at | 89665675 | 89676934 |
| SLC7A11 | 13988 | 1242952 | 1036798 | 318232 | 0.001962998 | 83 | 8 | chr4 | −1 | 139085251 | 139163503 | 217678_at | 139177491 | 139929775 |
| SEMA6D | 39235 | 92023 | 458933 | 0 | 0.001994059 | 88 | 100 | chr15 | 1 | 48010686 | 48066417 | 226492_at | 47932866 | 47971451 |
| HOMER1 | 6148 | 204205 | 97600 | 0 | 0.00199715 | 25 | 0 | chr5 | −1 | 78668459 | 78810040 | 213793_s_at | 78816188 | 78902854 |
| FST | 6188 | 821995 | 492479 | 0 | 0.002000986 | 0 | 0 | chr5 | 1 | 52776239 | 52782964 | 226847_at | 52782427 | 52847175 |
| WDHD1 | 92088 | 846453 | 859 | 0 | 0.002013991 | 33 | 0 | chr14 | −1 | 55405668 | 55493795 | 204728_s_at | 55585883 | 55595666 |
| CYB5R2 | 4230 | 0 | 161206 | 0 | 0.002028451 | 62 | 0 | chr11 | −1 | 7686326 | 7694821 | 220230_s_at | 7699051 | 8008893 |
| DAPL1 | 0 | 0 | 175754 | 173026 | 0.002039682 | 21 | 0 | chr2 | 1 | 159651829 | 159672505 | 229290_at | 159537049 | 159766248 |
| GABRB2 | 1772 | 0 | 300190 | 1044 | 0.002054068 | 38 | 12 | chr5 | −1 | 160715436 | 160973649 | 242344_at | 160975421 | 162777424 |
| CNTN3 | 0 | 137020 | 92114 | 93216 | 0.002108873 | 83 | 100 | chr3 | −1 | 74311719 | 74570291 | 229831_at | 73680359 | 74663468 |
| MRPS21 | 14016 | 512912 | 0 | 188 | 0.002172338 | 92 | 100 | chr1 | 1 | 150266289 | 150281414 | 222997_s_at | 150280305 | 150293469 |
| PROX1 | 25455 | 0 | 198574 | 444 | 0.002188037 | 79 | 8 | chr1 | 1 | 214161860 | 214214596 | 229376_at | 214119835 | 214136405 |
| CENPI | 28109 | 2081 | 1024583 | 2149 | 0.00219666 | 33 | 0 | chrX | 1 | 100355426 | 100418670 | 214804_at | 100322117 | 100327317 |
| TSPAN7 | 4606 | 0 | 270817 | 0 | 0.002203838 | 100 | 100 | chrX | 1 | 38420623 | 38548167 | 202242_at | 38224466 | 38416017 |
| C2orf70 | 398 | 0 | 57679 | 0 | 0.002205452 | 12 | 0 | chr2 | 1 | 26785450 | 26802400 | 231126_at | 26726754 | 26785052 |
| FZD3 | 9953 | 0 | 130703 | 0 | 0.002234066 | 12 | 0 | chr8 | 1 | 28351773 | 28431788 | 219683_at | 28335606 | 28341820 |
| MCM10 | 48555 | 103559 | 109128 | 0 | 0.002297013 | 38 | 0 | chr10 | 1 | 13203554 | 13253104 | 222962_s_at | 13142558 | 13154999 |
| RBM11 | 75 | 0 | 188490 | 0 | 0.002297137 | 0 | 0 | chr21 | 1 | 15588499 | 15600693 | 232549_at | 15436705 | 15588424 |
| TRIM29 | 5142 | 0 | 98850 | 152 | 0.002321878 | 54 | 0 | chr11 | −1 | 119981983 | 120008863 | 211002_s_at | 120014005 | 120039592 |
| NOTUM | 16275 | 1453763 | 17271 | 0 | 0.00235196 | 21 | 0 | chr17 | −1 | 79910388 | 79919169 | 228649_at | 79897558 | 79902894 |
| TFAP2A | 16995 | 0 | 1617 | 151 | 0.002379161 | 25 | 0 | chr6 | −1 | 10396916 | 10415470 | 204653_at | 10432465 | 10690667 |
| C1orf21 | 13835 | 962814 | 181815 | 0 | 0.002389438 | 100 | 100 | chr1 | 1 | 184356192 | 184598154 | 223125_s_at | 184051705 | 184342357 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| CEACAM7 | 11681 | 0 | 120452 | 156380 | 0.002391996 | 100 | 100 | chr19 | −1 | 42177235 | 42192296 | 206198_s_at | 42168674 | 42180615 |
| UNC5CL | 698 | 0 | 0 | 10686 | 0.00239258 | 58 | 0 | chr6 | −1 | 40994772 | 41006928 | 231008_at | 41007626 | 41015478 |
| PKIA | 0 | 10890 | 0 | 98 | 0.002409055 | 8 | 0 | chr8 | 1 | 79428336 | 79515485 | 204612_at | 77921809 | 79428387 |
| GALNT12 | 40725 | 79801 | 25166 | 0 | 0.002417303 | 100 | 100 | chr9 | 1 | 101569981 | 101612363 | 218885_s_at | 101610706 | 101698371 |
| PTP4A3 | 6191 | 28812 | 95970 | 3655 | 0.002489148 | 58 | 0 | chr8 | 1 | 142432007 | 142441620 | 206574_s_at | 142438198 | 142528142 |
| | 2926 | 252659 | 10711 | 3406 | 0.002527591 | 79 | 0 | chr6 | 1 | 31674681 | 31685695 | 207457_s_at | 31677607 | 31688229 |
| REEP1 | 2617 | 0 | 141400 | 0 | 0.002541043 | 8 | 0 | chr2 | −1 | 86441116 | 86564777 | 204365_s_at | 86567394 | 86601683 |
| FPR1 | 0 | 0 | 32167 | 31941 | 0.002554978 | 4 | 0 | chr19 | −1 | 52249027 | 52255150 | 205119_s_at | 52231520 | 52381753 |
| SLC28A3 | 0 | 0 | 328881 | 199897 | 0.002657296 | 4 | 0 | chr9 | −1 | 86890372 | 86955598 | 220475_at | 86933053 | 87278151 |
| PVRL3 | 7338 | 266721 | 1013140 | 0 | 0.002657296 | 96 | 100 | chr3 | 1 | 110790590 | 110854801 | 213325_at | 110621522 | 110783252 |
| SLC4A11 | 10931 | 416811 | 0 | 0 | 0.002667872 | 4 | 0 | chr20 | −1 | 3208063 | 3218812 | 223748_at | 3229743 | 3381098 |
| C10orf81 | 11080 | 0 | 82276 | 83362 | 0.002669553 | 12 | 0 | chr10 | 1 | 115531012 | 115542192 | 1554190_s_at | 115508037 | 115519932 |
| REG3A | 0 | 0 | 165703 | 166286 | 0.002707981 | 54 | 17 | chr2 | −1 | 79384132 | 79386879 | 205815_at | 79220617 | 79739679 |
| ADAMTS2 | 5556 | 65010 | 0 | 0 | 0.002708834 | 4 | 0 | chr5 | −1 | 178537852 | 178772385 | 226311_at | 178777941 | 178949264 |
| SLC38A5 | 13368 | 13508 | 396184 | 5665 | 0.002713218 | 83 | 0 | chrX | −1 | 48316920 | 48328565 | 234973_at | 48286581 | 48315197 |
| BAG2 | 18242 | 274918 | 48321 | 0 | 0.002737327 | 38 | 12 | chr6 | 1 | 57037124 | 57049735 | 209406_at | 57055366 | 57077011 |
| PQLC3 | 0 | 337052 | 686 | 62 | 0.002754994 | 100 | 100 | chr2 | 1 | 11295498 | 11319000 | 225579_at | 11055610 | 11295549 |
| CDKN2B | 4209 | 0 | 3285 | 0 | 0.002768858 | 62 | 100 | chr9 | −1 | 22002902 | 22009280 | 236313_at | 22013489 | 22435022 |
| ADH4 | 0 | 275530 | 803300 | 55318 | 0.002805008 | 33 | 4 | chr4 | −1 | 100044818 | 100065448 | 231678_s_at | 100019863 | 100066623 |
| LGR5 | 68682 | 0 | 316400 | 0 | 0.002805793 | 96 | 0 | chr12 | 1 | 71833813 | 71978622 | 210393_at | 71715727 | 71765131 |
| PDE10A | 6449 | 335577 | 0 | 0 | 0.002827076 | 0 | 0 | chr6 | −1 | 165740776 | 166075588 | 205501_at | 163846971 | 166069139 |
| TEAD2 | 3186 | 22475 | 21505 | 23 | 0.002839581 | 62 | 0 | chr19 | −1 | 49843857 | 49865714 | 226408_at | 49868900 | 49924222 |
| NPTX2 | 7167 | 0 | 0 | 0 | 0.002857438 | 17 | 8 | chr7 | 1 | 98246609 | 98259180 | 213479_at | 98253776 | 98462956 |
| RBPMS | 5020 | 428515 | 302946 | 0 | 0.002878689 | 46 | 0 | chr8 | 1 | 30241944 | 30429734 | 207836_s_at | 30056395 | 30236924 |
| KIAA0895 | 114 | 83742 | 1078 | 0 | 0.002880769 | 4 | 0 | chr7 | −1 | 36363830 | 36429734 | 213424_at | 36429848 | 36443570 |
| REN | 0 | 152072 | 31966 | 14340 | 0.00288615 | 29 | 0 | chr1 | −1 | 204123947 | 204135450 | 206367_at | 204133982 | 204159320 |
| HOXA10 | 40252 | 0 | 9331 | 0 | 0.002898676 | 100 | 100 | chr7 | −1 | 27202057 | 27205129 | 209905_at | 27245381 | 27250842 |
| PROX1 | 24881 | 0 | 199148 | 0 | 0.002908057 | 83 | 8 | chr1 | 1 | 214161286 | 214209282 | 207401_at | 214119835 | 214136405 |
| FXYD3 | 5468 | 10995 | 109288 | 8247 | 0.002928236 | 100 | 100 | chr19 | 1 | 35607166 | 35615227 | 202489_s_at | 35532020 | 35601698 |
| HPGD | 29020 | 0 | 897 | 211 | 0.002991419 | 100 | 100 | chr4 | −1 | 175411328 | 175444049 | 203914_x_at | 175473069 | 175750280 |
| DUOXA2 | 7716 | 0 | 14639 | 0 | 0.002999027 | 83 | 8 | chr15 | 1 | 45406519 | 45410619 | 230615_at | 45360487 | 45398803 |
| PLAU | 17455 | 550920 | 266454 | 0 | 0.003050955 | 42 | 12 | chr10 | 1 | 75670915 | 75677255 | 205479_s_at | 75635405 | 75653460 |
| SEC16B | 23333 | 178344 | 464015 | 15109 | 0.003071079 | 21 | 0 | chr1 | −1 | 177898955 | 177991722 | 1552880_at | 178015055 | 178026664 |
| COL12A1 | 6612 | 0 | 518 | 0 | 0.003085838 | 29 | 0 | chr6 | −1 | 75794042 | 75915767 | 231879_at | 75795161 | 75909155 |
| EPB41L3 | 7072 | 0 | 1 | 0 | 0.003096029 | 29 | 100 | chr18 | −1 | 5392383 | 5544241 | 212681_at | 5301384 | 5537169 |
| GRAMD2 | 8017 | 202811 | 34876 | 16 | 0.003103196 | 0 | 0 | chr15 | −1 | 72452148 | 72490136 | 229616_s_at | 72476997 | 72482119 |
| TBX3 | 24750 | 0 | 2373 | 0 | 0.003144084 | 96 | 0 | chr12 | −1 | 115108059 | 115121969 | 229576_s_at | 115146719 | 115165673 |
| FADS1 | 18815 | 221038 | 10149 | 0 | 0.003163942 | 4 | 0 | chr11 | −1 | 61567099 | 61584463 | 208962_s_at | 61603278 | 61658533 |
| EPHB1 | 9320 | 0 | 0 | 0 | 0.00316428 | 0 | 0 | chr3 | 1 | 134514104 | 134979309 | 230425_at | 134523424 | 135675199 |
| PCDH7 | 7610 | 0 | 0 | 0 | 0.003194669 | 0 | 0 | chr4 | 1 | 30722037 | 30733590 | 205534_at | 27027813 | 30714427 |
| WDHD1 | 92088 | 846453 | 859 | 0 | 0.003201735 | 8 | 0 | chr14 | −1 | 55405668 | 55493795 | 204727_at | 55585883 | 55595666 |
| HGF | 0 | 1062718 | 672168 | 158638 | 0.003204291 | 4 | 0 | chr7 | −1 | 81372007 | 81399347 | 210997_at | 81084866 | 82065278 |
| PCK1 | 20626 | 0 | 0 | 35885 | 0.003208323 | 92 | 100 | chr20 | 1 | 56136136 | 56141513 | 208383_s_at | 56156762 | 56182232 |
| HIBADH | 261 | 179138 | 653 | 0 | 0.003210374 | 100 | 100 | chr7 | −1 | 27565061 | 27702614 | 224812_at | 27702875 | 27718744 |
| KITLG | 39939 | 1538368 | 4325 | 0 | 0.003210374 | 100 | 100 | chr12 | −1 | 88886566 | 88974238 | 226534_at | 89014177 | 89032174 |
| GPR110 | 17758 | 0 | 33938 | 266357 | 0.003210374 | 17 | 0 | chr6 | −1 | 46965440 | 47010099 | 238689_at | 46821624 | 46992341 |
| KANK1 | 207 | 0 | 33014 | 0 | 0.003216108 | 100 | 100 | chr9 | 1 | 470291 | 746105 | 213005_s_at | 215466 | 470084 |
| DIAPH3 | 5832 | 24008 | 309923 | 0 | 0.003217707 | 25 | 0 | chr13 | −1 | 60239717 | 60737992 | 232596_at | 60743824 | 60965589 |
| SKAP2 | 2048 | 229114 | 230564 | 0 | 0.003230505 | 92 | 100 | chr7 | −1 | 26706681 | 26904362 | 204362_at | 26906410 | 27124857 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| PLAU | 17455 | 550920 | 266454 | 0 | 0.003254959 | 54 | 8 | chr10 | 1 | 75670915 | 75677255 | 211668_s_at | 75635405 | 75653460 |
| ERCC6L | 39022 | 54379 | 326940 | 0 | 0.003263889 | 58 | 0 | chrX | −1 | 71424510 | 71458897 | 219650_at | 71497919 | 71515951 |
| C10orf99 | 16995 | 0 | 2088807 | 20706 | 0.003263889 | 100 | 100 | chr10 | 1 | 85933494 | 85945050 | 227735_s_at | 85905537 | 85916499 |
| SCAND3 | 8892 | 0 | 0 | 0 | 0.003293145 | 4 | 4 | chr6 | −1 | 28539405 | 28555112 | 244758_at | 28517288 | 28546220 |
| ALDH1L1 | 8694 | 0 | 0 | 0 | 0.003352198 | 71 | 8 | chr3 | −1 | 125822414 | 125898762 | 205208_at | 125907456 | 125925541 |
| KRT17 | 0 | 4354 | 109288 | 23912 | 0.003353993 | 12 | 0 | chr17 | −1 | 39775689 | 39780829 | 212236_x_at | 39711383 | 39800097 |
| NRXN3 | 424 | 55406 | 1312745 | 0 | 0.003363152 | 29 | 4 | chr14 | 1 | 79745654 | 80330758 | 229649_at | 79746078 | 81177275 |
| SSBP2 | 5703 | 167173 | 101368 | 0 | 0.003368706 | 12 | 96 | chr5 | −1 | 80708840 | 81047072 | 203787_at | 80695952 | 81041369 |
| CXCL14 | 10624 | 0 | 0 | 0 | 0.003412183 | 100 | 100 | chr5 | −1 | 134906376 | 134914754 | 222484_s_at | 134885256 | 134904130 |
| OSR2 | 22376 | 950424 | 0 | 97 | 0.003412303 | 17 | 0 | chr8 | 1 | 99960401 | 99964332 | 213568_at | 99872825 | 99938025 |
| SLC22A3 | 16044 | 0 | 1247 | 0 | 0.003446418 | 54 | 0 | chr6 | 1 | 160769300 | 160873613 | 205421_at | 160746813 | 160753256 |
| BNIP3 | 9283 | 14576 | 0 | 0 | 0.003472643 | 38 | 0 | chr10 | −1 | 133781578 | 133795435 | 201848_s_at | 133804718 | 133843600 |
| RPL39L | 8168 | 170035 | 0 | 0 | 0.003495557 | 29 | 0 | chr3 | −1 | 186838736 | 186857272 | 210115_at | 186801434 | 186849104 |
| DPYSL2 | 4669 | 31326 | 64311 | 0 | 0.003543874 | 100 | 100 | chr8 | 1 | 26435410 | 26515694 | 200762_at | 26379928 | 26430741 |
| SYT13 | 15714 | 0 | 835 | 0 | 0.003551455 | 100 | 100 | chr11 | −1 | 45261853 | 45307884 | 226086_at | 45323598 | 45677905 |
| MPP1 | 13827 | 0 | 1120290 | 0 | 0.003552925 | 75 | 100 | chrX | −1 | 154006959 | 154033796 | 202974_at | 154047623 | 154060810 |
| TAF8 | 33772 | 366228 | 127288 | 0 | 0.003585984 | 0 | 0 | chr6 | 1 | 42018251 | 42025527 | 229412_at | 42052023 | 42066504 |
| HPGD | 29020 | 0 | 897 | 211 | 0.003598904 | 100 | 100 | chr4 | −1 | 175411328 | 175444049 | 211548_s_at | 175473069 | 175750280 |
| CKAP2L | 13381 | 131276 | 331756 | 0 | 0.00365173 | 71 | 0 | chr2 | −1 | 113494184 | 113522254 | 229610_at | 113535635 | 113544577 |
| TSPAN5 | 5138 | 448802 | 1288968 | 0 | 0.003652172 | 46 | 0 | chr4 | −1 | 99391518 | 99579780 | 209890_at | 99567766 | 99574642 |
| LRRC2 | 53418 | 93043 | 234 | 233 | 0.00366087 | 17 | 0 | chr3 | −1 | 46556913 | 46608040 | 219949_at | 46521837 | 46554622 |
| HSPA4L | 1457 | 312425 | 52403 | 0 | 0.003687998 | 62 | 0 | chr4 | 1 | 128702976 | 128754197 | 205543_at | 128632751 | 128701519 |
| SIM2 | 13424 | 0 | 955 | 0 | 0.003704607 | 8 | 0 | chr21 | 1 | 38071434 | 38122218 | 206558_at | 37854364 | 38058010 |
| KLHL13 | 7956 | 0 | 2781970 | 6 | 0.003739396 | 17 | 46 | chrX | −1 | 117031776 | 117250761 | 227875_at | 117106826 | 117242805 |
| DNAJC12 | 2849 | 77859 | 492612 | 11624 | 0.003743751 | 8 | 0 | chr10 | −1 | 69570966 | 69597854 | 223722_at | 69574994 | 69595005 |
| GGCT | 611 | 149016 | 27028 | 0 | 0.003748202 | 100 | 100 | chr7 | −1 | 30536237 | 30544460 | 215380_s_at | 30545071 | 30559850 |
| HSPA2 | 53719 | 287625 | 3196 | 4252 | 0.003845752 | 100 | 100 | chr14 | 1 | 65002623 | 65009955 | 211538_s_at | 65056342 | 65079340 |
| KRT7 | 44630 | 76780 | 0 | 0 | 0.003873112 | 33 | 0 | chr12 | 1 | 52626954 | 52642709 | 209016_s_at | 52671584 | 52701887 |
| AQP3 | 1990 | 242392 | 62813 | 0 | 0.003898169 | 100 | 100 | chr9 | −1 | 33441152 | 33447609 | 39248_at | 33379626 | 33445619 |
| CHST3 | 6059 | 164128 | 751 | 0 | 0.003934905 | 0 | 0 | chr10 | 1 | 73724123 | 73773322 | 209834_at | 73649045 | 73718064 |
| IL22 | 0 | 33550 | 1078651 | 78564 | 0.003952088 | 0 | 0 | chr12 | −1 | 68642025 | 68647284 | 222974_at | 68214442 | 68689811 |
| ALDH1A1 | 0 | 0 | 474142 | 587226 | 0.003964488 | 100 | 100 | chr9 | −1 | 75515578 | 75567971 | 212224_at | 75457522 | 75752046 |
| NPW | 48936 | 89521 | 27719 | 198 | 0.004034202 | 46 | 0 | chr16 | 1 | 2069521 | 2070755 | 243110_x_at | 2015477 | 2020585 |
| C3orf70 | 15242 | 346505 | 805 | 0 | 0.00403475 | 100 | 100 | chr3 | −1 | 184795838 | 184870802 | 242447_at | 184886044 | 184907969 |
| IRAK1 | 84219 | 38624 | 371925 | 0 | 0.004051199 | 100 | 100 | chrX | −1 | 153275951 | 153285431 | 201587_s_at | 153369650 | 153421858 |
| TRIM7 | 17180 | 0 | 16352 | 0 | 0.004060682 | 54 | 0 | chr5 | −1 | 180630118 | 180632293 | 223694_at | 180608872 | 180615113 |
| HIGD1A | 12070 | 39063 | 30766 | 0 | 0.004061557 | 96 | 100 | chr3 | −1 | 42824404 | 42845934 | 242317_at | 42858004 | 42922198 |
| AZGP1 | 0 | 21715 | 0 | 21427 | 0.004128575 | 71 | 4 | chr7 | −1 | 99564353 | 99573780 | 217014_s_at | 99559725 | 99587874 |
| SPP1 | 0 | 35842 | 31363 | 31662 | 0.004147984 | 42 | 29 | chr4 | 1 | 88896819 | 88904562 | 209875_s_at | 88397786 | 88924190 |
| POLH | 2218 | 271864 | 889 | 0 | 0.004148482 | 42 | 0 | chr6 | 1 | 43543887 | 43583397 | 1557701_s_at | 43546105 | 43556976 |
| KLHL32 | 125 | 0 | 907481 | 0 | 0.004173878 | 0 | 0 | chr6 | 1 | 97372605 | 97588630 | 1553765_a_at | 97372730 | 97587856 |
| SMOC2 | 4622 | 0 | 63315 | 0 | 0.004174854 | 62 | 100 | chr6 | 1 | 168841831 | 169068674 | 223235_s_at | 168783231 | 168837209 |
| AXIN2 | 8092 | 78226 | 15167 | 0 | 0.00427155 | 100 | 0 | chr17 | −1 | 63524685 | 63557765 | 224176_s_at | 63519783 | 63549673 |
| BEX4 | 7464 | 0 | 339 | 0 | 0.004274184 | 71 | 100 | chrX | 1 | 102470020 | 102472174 | 215440_s_at | 102196004 | 102462556 |
| HOXA7 | 49085 | 2820 | 9620 | 0 | 0.004282668 | 75 | 96 | chr7 | −1 | 27193346 | 27196296 | 235753_at | 27245381 | 27250842 |
| LPAR1 | 3875 | 1350143 | 1948 | 0 | 0.004336624 | 79 | 100 | chr9 | −1 | 113635543 | 113800323 | 204036_at | 113804198 | 114122387 |
| CBR3 | 6229 | 29079 | 23074 | 0 | 0.004357415 | 54 | 0 | chr21 | 1 | 37507210 | 37518864 | 205379_at | 37495606 | 37500981 |
| SAA2 | 0 | 0 | 141879 | 39275 | 0.004362905 | 12 | 0 | chr11 | −1 | 18266787 | 18270182 | 214456_x_at | 18127733 | 18275128 |
| MNS1 | 12444 | 25374 | 98230 | 0 | 0.004380081 | 54 | 0 | chr15 | −1 | 56720929 | 56757335 | 219703_at | 56769779 | 56928295 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| HOXA5 | 58606 | 0 | 0 | 0 | 0.004380081 | 71 | 100 | chr7 | −1 | 27180671 | 27183463 | 213844_at | 26906410 | 27124857 |
| NR5A2 | 5318 | 0 | 6748 | 7745 | 0.004423695 | 83 | 100 | chr1 | 1 | 199996730 | 200146552 | 210174_at | 199963808 | 199991412 |
| BDNF | 9780 | 0 | 0 | 0 | 0.004428973 | 0 | 0 | chr11 | −1 | 27676440 | 27743605 | 206382_s_at | 27753385 | 28035841 |
| FXYD3 | 5468 | 10995 | 109288 | 8247 | 0.004428973 | 100 | 100 | chr19 | 1 | 35607166 | 35615227 | 202488_s_at | 35532020 | 35601698 |
| TRIM7 | 17059 | 0 | 16473 | 0 | 0.004439342 | 17 | 0 | chr5 | −1 | 180620924 | 180632172 | 239694_at | 180608872 | 180615113 |
| DRP2 | 0 | 0 | 905251 | 28020 | 0.004443074 | 4 | 0 | chrX | 1 | 100474758 | 100519486 | 1556627_at | 100405981 | 100558831 |
| ARHGAP11A | 46368 | 214982 | 145634 | 0 | 0.00444838 | 17 | 0 | chr15 | 1 | 32907691 | 32932150 | 204492_at | 32855210 | 32861323 |
| SERPINA1 | 2908 | 3274 | 206743 | 215325 | 0.004450684 | 58 | 0 | chr14 | −1 | 94843084 | 94856974 | 230318_at | 94641762 | 94854066 |
| PHLDA1 | 48055 | 741822 | 731051 | 0 | 0.004496546 | 100 | 0 | chr12 | −1 | 76419227 | 76425556 | 217997_at | 76344741 | 76377501 |
| MND1 | 72580 | 305250 | 95023 | 0 | 0.004496662 | 92 | 8 | chr4 | 1 | 154265801 | 154336270 | 223700_at | 154338381 | 154379219 |
| CYP27B1 | 78118 | 0 | 2427 | 975 | 0.004508014 | 0 | 0 | chr12 | −1 | 58156118 | 58160976 | 205676_at | 58030134 | 58082858 |
| C10orf99 | 16995 | 0 | 2088807 | 20706 | 0.004545862 | 100 | 100 | chr10 | 1 | 85933494 | 85945050 | 227736_at | 85905537 | 85916499 |
| CNTNAP3 | 104064 | 0 | 665225 | 0 | 0.004552087 | 0 | 0 | chr9 | −1 | 39072764 | 39288135 | 223796_at | 39052051 | 39184071 |
| SERPINB3 | 0 | 0 | 275098 | 238839 | 0.004559531 | 8 | 0 | chr18 | −1 | 61322431 | 61329197 | 209719_x_at | 61174562 | 61603221 |
| PCP4 | 0 | 0 | 254344 | 276995 | 0.00457272 | 33 | 0 | chr21 | 1 | 41239243 | 41301322 | 205549_at | 41035457 | 42212925 |
| SESN1 | 60269 | 192557 | 1006 | 0 | 0.00457387 | 100 | 100 | chr6 | −1 | 109307645 | 109330751 | 218346_s_at | 109256128 | 109270482 |
| GALNT1 | 65177 | 71479 | 295199 | 72259 | 0.004579726 | 100 | 100 | chr18 | 1 | 33234524 | 33291798 | 201722_s_at | 33299701 | 33526942 |
| PCDHB15 | 14067 | 0 | 75058 | 1464 | 0.004601108 | 0 | 0 | chr5 | 1 | 140624981 | 140627742 | 231789_at | 140639048 | 140655207 |
| PHLDA1 | 48055 | 741822 | 731051 | 0 | 0.00463039 | 46 | 0 | chr12 | −1 | 76419227 | 76425556 | 218000_s_at | 76344741 | 76377501 |
| VPS4B | 3152 | 29328 | 514602 | 0 | 0.004643759 | 100 | 100 | chr18 | −1 | 61056423 | 61089693 | 218171_at | 61092845 | 61122314 |
| PDGFRB | 1459 | 0 | 33853 | 10605 | 0.004718827 | 0 | 0 | chr5 | −1 | 149493400 | 149535423 | 202273_at | 149511810 | 149533964 |
| DEFA1 | 0 | 0 | 269575 | 111748 | 0.004733051 | 4 | 0 | chr8 | −1 | 6835172 | 6837602 | 205033_s_at | 6701491 | 6988157 |
| TNFRSF10C | 11022 | 216376 | 0 | 0 | 0.00475574 | 25 | 0 | chr8 | 1 | 22960432 | 22974950 | 211163_s_at | 22942117 | 22949410 |
| LCN15 | 8214 | 371215 | 10045 | 3810 | 0.00475574 | 75 | 4 | chr9 | −1 | 139654086 | 139658965 | 1569532_a_at | 139667179 | 139674915 |
| DNAH14 | 308 | 14006 | 311502 | 0 | 0.00475574 | 54 | 0 | chr1 | 1 | 225117384 | 225212306 | 242283_at | 224812470 | 225117076 |
| C7orf30 | 69 | 464657 | 49983 | 0 | 0.004772303 | 100 | 100 | chr7 | 1 | 23338819 | 23351348 | 226385_s_at | 23287523 | 23338750 |
| RLN2 | 0 | 0 | 1107179 | 492 | 0.004782597 | 0 | 0 | chr9 | −1 | 5299868 | 5304969 | 214519_s_at | 5135871 | 5359217 |
| GMPR | 3068 | 126785 | 41358 | 0 | 0.004785154 | 8 | 0 | chr6 | 1 | 16238807 | 16295417 | 204187_at | 16241875 | 16300322 |
| KCNJ8 | 59018 | 39013 | 165933 | 116980 | 0.004810307 | 0 | 0 | chr12 | −1 | 21917889 | 21927747 | 205304_s_at | 21986765 | 22093905 |
| CMBL | 103137 | 211137 | 33849 | 224 | 0.004811555 | 100 | 100 | chr5 | −1 | 10279389 | 10308138 | 227522_at | 10178498 | 10205001 |
| IL17RD | 7797 | 145558 | 793989 | 24 | 0.004811555 | 42 | 0 | chr3 | −1 | 57124010 | 57199403 | 227997_at | 57207200 | 57253382 |
| TXNL1 | 29870 | 403083 | 713517 | 0 | 0.004815834 | 100 | 100 | chr18 | −1 | 54264439 | 54305920 | 201588_at | 53453587 | 54276050 |
| WDR4 | 46030 | 52709 | 194889 | 0 | 0.004822918 | 42 | 0 | chr21 | −1 | 44263204 | 44299641 | 226882_x_at | 44232396 | 44253611 |
| RPGRIP1L | 104649 | 115271 | 269831 | 0 | 0.004877379 | 21 | 0 | chr16 | −1 | 53633824 | 53737771 | 213959_s_at | 53540989 | 53633122 |
| MAGEA2B | 10 | 3745 | 76144 | 15620 | 0.004877379 | 0 | 0 | chrX | 1 | 151883090 | 151887096 | 1553830_s_at | 151883100 | 151948085 |
| SLC2A1 | 8398 | 47087 | 49663 | 0 | 0.004914882 | 62 | 71 | chr1 | −1 | 43391519 | 43424501 | 201250_s_at | 43401524 | 43416103 |
| OTUB2 | 110 | 102476 | 627 | 0 | 0.004914882 | 33 | 0 | chr14 | 1 | 94492724 | 94515276 | 222878_s_at | 94439878 | 94492614 |
| MAOA | 94610 | 0 | 3422165 | 0 | 0.004926885 | 100 | 100 | chrX | 1 | 43515467 | 43606068 | 204388_s_at | 43202978 | 43420857 |
| NR3C1 | 5153 | 816543 | 515 | 0 | 0.00493573 | 29 | 100 | chr5 | −1 | 142657496 | 142783265 | 216321_s_at | 142609282 | 142778112 |
| IGFBP5 | 5281 | 1391508 | 229 | 763 | 0.004969324 | 17 | 0 | chr2 | −1 | 217536828 | 217560248 | 211958_at | 217565529 | 218843435 |
| MNAT1 | 18597 | 171232 | 1829 | 10707 | 0.004983683 | 0 | 0 | chr14 | 1 | 61201480 | 61436671 | 203565_s_at | 61128150 | 61182883 |
| WDR12 | 10314 | 974807 | 39754 | 0 | 0.004993019 | 100 | 100 | chr2 | −1 | 203745323 | 203776949 | 218512_at | 203787263 | 203833499 |
| SLC16A7 | 0 | 179392 | 1749500 | 92618 | 0.005016111 | 42 | 92 | chr12 | 1 | 60083126 | 60175407 | 207057_at | 59990530 | 62574045 |
| C13orf18 | 164 | 10379 | 1112 | 0 | 0.005023906 | 100 | 100 | chr13 | −1 | 46917099 | 46961621 | 44790_s_at | 46961785 | 46974863 |
| ANGPT2 | 42076 | 168337 | 0 | 3286 | 0.00505811 | 4 | 0 | chr8 | −1 | 6357172 | 6420930 | 211148_s_at | 6463006 | 6468475 |
| MAGEA2B | 10 | 3745 | 76144 | 15620 | 0.005068014 | 4 | 0 | chrX | 1 | 151883090 | 151887096 | 214603_at | 151883100 | 151948085 |
| SMOC2 | 4622 | 0 | 63315 | 0 | 0.005076311 | 12 | 0 | chr6 | 1 | 168841831 | 169065106 | 243946_at | 168783231 | 168837209 |
| MUCL1 | 0 | 0 | 304264 | 265707 | 0.005086226 | 0 | 0 | chr12 | 1 | 55248299 | 55252170 | 1553602_at | 54982626 | 56039891 |
| ALDH1A3 | 8795 | 0 | 766 | 0 | 0.005086226 | 58 | 67 | chr15 | 1 | 101419581 | 101456831 | 203180_at | 101396316 | 101410786 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| STK31 | 0 | 53690 | 32 | 29108 | 0.005090232 | 4 | 0 | chr7 | 1 | 23749786 | 23872132 | 223883_s_at | 23735576 | 23771279 |
| VSNL1 | 64090 | 0 | 3072 | 0 | 0.005118909 | 88 | 12 | chr2 | 1 | 17720393 | 17837345 | 203798_s_at | 16689858 | 17656303 |
| LEMD1 | 0 | 0 | 33330 | 33648 | 0.005143478 | 4 | 0 | chr1 | −1 | 205350506 | 205391182 | 229927_at | 205321228 | 205399229 |
| ARMC10 | 43100 | 167437 | 74969 | 0 | 0.005165251 | 100 | 100 | chr7 | 1 | 102715328 | 102740205 | 1554480_a_at | 102667148 | 102672228 |
| C16orf46 | 20137 | 71682 | 19755 | 0 | 0.005189253 | 4 | 0 | chr16 | −1 | 81087102 | 81110818 | 230281_at | 81130955 | 81268589 |
| KCNH8 | 5094 | 0 | 2261718 | 0 | 0.005198671 | 8 | 0 | chr3 | 1 | 19189946 | 19577138 | 1552742_at | 18493624 | 19184852 |
| GALNT12 | 40725 | 79801 | 25166 | 0 | 0.005226977 | 100 | 100 | chr9 | 1 | 101569981 | 101612363 | 222773_s_at | 101610706 | 101698371 |
| SSX2IP | 7856 | 291185 | 201941 | 0 | 0.005226977 | 17 | 0 | chr1 | −1 | 85109390 | 85156228 | 210871_x_at | 85164084 | 85353693 |
| FAM131B | 44849 | 109966 | 16747 | 0 | 0.005288211 | 8 | 0 | chr7 | −1 | 143050493 | 143059845 | 205368_at | 143104694 | 143110401 |
| DIO2 | 0 | 47592 | 739972 | 349508 | 0.005293947 | 4 | 0 | chr14 | −1 | 80664089 | 80677840 | 203700_s_at | 79746078 | 81177275 |
| F2RL2 | 0 | 75014 | 196847 | 91862 | 0.005303581 | 50 | 0 | chr5 | −1 | 75911328 | 75919259 | 230147_at | 75704188 | 76002246 |
| WISP1 | 0 | 452493 | 31774 | 105017 | 0.00531349 | 0 | 0 | chr8 | 1 | 134203312 | 134241569 | 235821_at | 134138989 | 134219769 |
| NEFL | 8077 | 0 | 0 | 324 | 0.005319168 | 12 | 0 | chr8 | −1 | 24808468 | 24814624 | 221805_at | 24822701 | 24846167 |
| MUM1L1 | 0 | 0 | 345067 | 345187 | 0.005348525 | 0 | 0 | chrX | 1 | 105412298 | 105452949 | 229160_at | 105078443 | 105854952 |
| ASCL2 | 3141 | 0 | 3602 | 0 | 0.00534907 | 100 | 83 | chr11 | −1 | 2289725 | 2292182 | 229215_at | 2282737 | 2289041 |
| ABHD6 | 13918 | 0 | 59807 | 0 | 0.005386873 | 75 | 100 | chr3 | 1 | 58223233 | 58280459 | 221552_at | 58168892 | 58209315 |
| KHDRBS3 | 2801 | 0 | 792549 | 0 | 0.005428065 | 92 | 96 | chr8 | 1 | 136469700 | 136659838 | 209781_s_at | 135846364 | 136466899 |
| NEB | 0 | 0 | 324944 | 93475 | 0.005534664 | 4 | 0 | chr2 | −1 | 152341850 | 152591001 | 205054_at | 152462337 | 152632425 |
| PHF19 | 42431 | 530714 | 1410 | 0 | 0.005543562 | 71 | 0 | chr9 | −1 | 123631865 | 123639466 | 227211_at | 123588593 | 123597035 |
| PM20D2 | 2177 | 37513 | 27542 | 0 | 0.005545656 | 100 | 100 | chr6 | 1 | 89855769 | 89875284 | 225421_at | 89844813 | 89853592 |
| CFD | 819 | 470664 | 11788 | 853 | 0.005571608 | 100 | 100 | chr19 | 1 | 859665 | 863606 | 205382_s_at | 848149 | 858846 |
| LFNG | 4598 | 443999 | 1994 | 0 | 0.00560566 | 100 | 100 | chr7 | 1 | 2559476 | 2568063 | 228762_at | 2564074 | 2572016 |
| PSPH | 74712 | 53210 | 27835 | 0 | 0.005610634 | 38 | 0 | chr7 | −1 | 56078760 | 56119297 | 205194_at | 56194009 | 56238727 |
| TCF12 | 2967 | 348114 | 30231 | 0 | 0.0056393 | 100 | 100 | chr15 | 1 | 57210823 | 57582051 | 208986_at | 57185279 | 57207856 |
| NAT6 | 66135 | 68166 | 16171 | 0 | 0.005674819 | 88 | 4 | chr3 | −1 | 50333883 | 50336831 | 210619_s_at | 50402966 | 50540137 |
| JUB | 2044 | 251690 | 2398 | 0 | 0.005679632 | 8 | 0 | chr14 | −1 | 23440383 | 23451851 | 225807_at | 23440519 | 23449807 |
| ESCO2 | 41076 | 62011 | 160178 | 0 | 0.005685292 | 62 | 4 | chr8 | 1 | 27632071 | 27662742 | 235588_at | 27549414 | 27590995 |
| B3GNT6 | 0 | 763082 | 4259 | 5258 | 0.005685292 | 79 | 88 | chr11 | 1 | 76745435 | 76753003 | 1552833_at | 76733720 | 76753433 |
| | 67105 | 35285 | 457334 | 0 | 0.005688368 | 12 | 0 | chr16 | 1 | 20817785 | 20860990 | 215215_s_at | 20884890 | 20897335 |
| TMEM71 | 0 | 22095 | 86054 | 14528 | 0.005762863 | 75 | 17 | chr8 | −1 | 133722194 | 133772914 | 238429_at | 133739160 | 133781519 |
| SMPDL3A | 892 | 57987 | 206357 | 0 | 0.00577302 | 100 | 100 | chr6 | 1 | 123110315 | 123130865 | 213624_at | 122931724 | 123109423 |
| ANGPT2 | 42076 | 168337 | 0 | 3286 | 0.005783769 | 8 | 0 | chr8 | −1 | 6357172 | 6420930 | 205572_at | 6463006 | 6468475 |
| RGMB | 12354 | 217102 | 78532 | 0 | 0.005789055 | 83 | 79 | chr5 | 1 | 98104999 | 98132198 | 227339_at | 97979164 | 98092645 |
| HAUS6 | 27324 | 133116 | 1424 | 6 | 0.005801603 | 0 | 0 | chr9 | −1 | 19053141 | 19103117 | 218602_s_at | 19130441 | 19142908 |
| MB | 0 | 373502 | 32847 | 65506 | 0.005815531 | 96 | 100 | chr22 | −1 | 36002811 | 36013503 | 204179_at | 35937556 | 36034465 |
| SFXN3 | 12433 | 29020 | 17300 | 0 | 0.005844456 | 25 | 0 | chr10 | 1 | 102790991 | 102800998 | 220974_x_at | 102773407 | 102778558 |
| ARNT2 | 5356 | 23746 | 0 | 0 | 0.005859934 | 12 | 0 | chr15 | 1 | 80696692 | 80890269 | 202986_at | 80549855 | 80691336 |
| ITPK1 | 3461 | 182015 | 13120 | 0 | 0.005935433 | 100 | 100 | chr14 | −1 | 93407054 | 93582263 | 210740_s_at | 93585724 | 93597102 |
| PRIM2 | 3769 | 132439 | 93977 | 92291 | 0.005940743 | 17 | 0 | chr6 | 1 | 57179603 | 57191161 | 1554885_a_at | 57138323 | 57175834 |
| MEP1A | 0 | 0 | 142666 | 57810 | 0.005945543 | 100 | 100 | chr6 | 1 | 46761127 | 46807515 | 206000_at | 46708815 | 46761211 |
| C12orf66 | 10369 | 67663 | 167822 | 0 | 0.005972623 | 0 | 0 | chr12 | −1 | 64581359 | 64616071 | 1554068_s_at | 64626440 | 64778018 |
| RRM2B | 36911 | 40521 | 154213 | 135 | 0.005989519 | 83 | 100 | chr8 | −1 | 103216732 | 103251346 | 223342_at | 103136798 | 103214435 |
| AQP3 | 1990 | 242392 | 62813 | 0 | 0.005993406 | 12 | 0 | chr9 | −1 | 33441152 | 33447609 | 39249_at | 33379626 | 33445619 |
| RBPMS | 5020 | 428515 | 302946 | 0 | 0.006039127 | 96 | 100 | chr8 | 1 | 30241944 | 30405027 | 209487_at | 30056395 | 30236924 |
| POLR3G | 28075 | 53539 | 804435 | 0 | 0.006093044 | 33 | 0 | chr5 | 1 | 89770706 | 89810370 | 206653_at | 89711697 | 89742631 |
| CEACAM7 | 11681 | 0 | 120452 | 156380 | 0.006112623 | 100 | 100 | chr19 | −1 | 42177235 | 42192296 | 211848_s_at | 42168674 | 42180615 |
| MCM4 | 27413 | 243954 | 552986 | 0 | 0.006122886 | 83 | 0 | chr8 | 1 | 48873494 | 48890068 | 212141_at | 48900907 | 48917534 |
| FRZB | 4855 | 399866 | 256110 | 0 | 0.006122886 | 92 | 100 | chr2 | −1 | 183698002 | 183731890 | 203697_at | 183645523 | 183727035 |
| CHFR | 9151 | 454256 | 0 | 0 | 0.006177685 | 17 | 33 | chr12 | −1 | 133416938 | 133464184 | 223931_s_at | 133408647 | 133455033 |

TABLE 15-continued

| Genes with higher gene expression variability in cancer compared to normal. | | | | | | | | | | | | | | |
|---|---|---|---|---|---|---|---|---|---|---|---|---|---|---|
| gene | dist2block | dist2PMD | dist2DMR | dist2CGI | p-value | Cancer % On | Normal % On | chr | strand | txStart | txEnd | affyid | blockStart | blockEnd |
| PLCE1 | 40899 | 160558 | 34595 | 36367 | 0.006221938 | 100 | 100 | chr10 | 1 | 95790569 | 96088146 | 205111_s_at | 95693652 | 95749670 |
| CTTNBP2 | 17317 | 9204 | 912 | 0 | 0.006221992 | 88 | 25 | chr7 | −1 | 117350705 | 117513561 | 232136_s_at | 117460302 | 117496244 |
| DCN | 0 | 193541 | 221247 | 224232 | 0.006222875 | 100 | 100 | chr12 | −1 | 91539036 | 91572329 | 201893_x_at | 90355184 | 91783891 |
| PTPRN2 | 26628 | 0 | 17535 | 0 | 0.006300279 | 83 | 79 | chr7 | −1 | 157331750 | 158380480 | 203030_s_at | 158307672 | 158353852 |
| ZNF511 | 32126 | 168032 | 10778 | 13 | 0.006311751 | 92 | 0 | chr10 | 1 | 135121979 | 135126662 | 225307_at | 135075469 | 135089853 |
| FIGNL1 | 15639 | 24459 | 227 | 0 | 0.006315512 | 79 | 0 | chr7 | −1 | 50511831 | 50518048 | 1552921_a_at | 50411178 | 50502409 |
| FAM46C | 7420 | 330078 | 3265 | 0 | 0.006339909 | 100 | 100 | chr1 | 1 | 118148556 | 118170994 | 226811_at | 118118373 | 118141136 |
| RUNX1 | 72946 | 202856 | 217967 | 0 | 0.006361713 | 100 | 100 | chr21 | −1 | 36160098 | 36260987 | 209360_s_at | 36333933 | 36366356 |
| TNFRSF11B | 275 | 186437 | 254731 | 7 | 0.006361899 | 100 | 67 | chr8 | −1 | 119935797 | 119964383 | 204933_s_at | 119964658 | 120167597 |
| FANCI | 6706 | 91817 | 116018 | 0 | 0.006370144 | 96 | 38 | chr15 | 1 | 89787180 | 89860492 | 213007_at | 89745309 | 89780474 |
| FAM55D | 169059 | 0 | 153769 | 155897 | 0.006375204 | 100 | 100 | chr11 | −1 | 114441314 | 114466484 | 220645_at | 114635543 | 115368482 |
| ALDH4A1 | 1773 | 51861 | 1615 | 0 | 0.006382891 | 0 | 0 | chr1 | −1 | 19197926 | 19229275 | 211552_s_at | 19220360 | 19227502 |
| PTGS2 | 276 | 433823 | 1362224 | 0 | 0.006383418 | 50 | 12 | chr1 | −1 | 186640923 | 186649555 | 204748_at | 186400111 | 186649279 |
| SLITRK6 | 0 | 38377 | 1915741 | 1919725 | 0.00642599 | 100 | 100 | chr13 | −1 | 86366925 | 86373623 | 232176_at | 84465407 | 86760270 |
| TNFRSF17 | 6954 | 613536 | 61867 | 11294 | 0.006435719 | 88 | 100 | chr16 | 1 | 12058964 | 12061925 | 206641_at | 12029195 | 12052010 |
| EXO1 | 4705 | 38104 | 423412 | 0 | 0.006435719 | 88 | 0 | chr1 | 1 | 242011482 | 242053241 | 204603_at | 241811234 | 242006777 |
| OXGR1 | 3922 | 0 | 695 | 0 | 0.006477776 | 75 | 0 | chr13 | −1 | 97637973 | 97646604 | 1553319_at | 97594765 | 97642682 |
| LRRC8E | 1865 | 99389 | 14093 | 0 | 0.006484922 | 8 | 0 | chr19 | 1 | 7953390 | 7966906 | 239433_at | 7946329 | 7951525 |
| AHNAK2 | 10172 | 35738 | 45285 | 0 | 0.006490786 | 12 | 8 | chr14 | −1 | 105403591 | 105444694 | 212992_at | 105404695 | 105434522 |
| ORM1 | 0 | 174844 | 64246 | 74804 | 0.006492246 | 4 | 0 | chr9 | 1 | 117085336 | 117088755 | 205041_s_at | 116925630 | 117094770 |
| FMO3 | 0 | 26641 | 425601 | 394500 | 0.00652394 | 0 | 0 | chr1 | 1 | 171060018 | 171086959 | 40665_at | 170873486 | 171302735 |
| ADAMTS9 | 10154 | 121285 | 2226 | 0 | 0.006534678 | 12 | 0 | chr3 | −1 | 64501490 | 64673676 | 1554697_at | 64683830 | 65328910 |
| PMAIP1 | 9473 | 181841 | 202782 | 0 | 0.006554339 | 83 | 50 | chr18 | 1 | 57567180 | 57571538 | 204286_s_at | 57576653 | 58987404 |
| RARRES1 | 54613 | 106822 | 161139 | 0 | 0.006565659 | 100 | 100 | chr3 | −1 | 158414681 | 158450485 | 221872_at | 158505098 | 158516616 |
| APLF | 5396 | 38196 | 1717 | 0 | 0.006567242 | 0 | 0 | chr2 | 1 | 68694693 | 68807294 | 241379_at | 68700089 | 68870315 |
| TLR4 | 46892 | 0 | 288376 | 40618 | 0.00658545 | 67 | 0 | chr9 | 1 | 120466610 | 120478053 | 232068_s_at | 120183010 | 120419718 |
| PTPRN2 | 26628 | 0 | 17535 | 0 | 0.006586901 | 8 | 0 | chr7 | −1 | 157331750 | 158380480 | 211534_x_at | 158307672 | 158353852 |
| UGT2A3 | 203785 | 0 | 1237673 | 601587 | 0.00659923 | 71 | 100 | chr4 | −1 | 69794181 | 69817509 | 219948_x_at | 69587469 | 69613724 |
| GGT6 | 3019 | 50624 | 20116 | 4891 | 0.006618473 | 100 | 100 | chr17 | −1 | 4460224 | 4463876 | 236225_at | 4466895 | 4476679 |
| CLCN4 | 46290 | 14977 | 1424365 | 1297 | 0.006620275 | 0 | 0 | chrX | 1 | 10125024 | 10205700 | 205148_s_at | 10171314 | 10410830 |
| TFPI | 0 | 226612 | 663709 | 664298 | 0.006670769 | 71 | 100 | chr2 | −1 | 188328957 | 188378368 | 213258_at | 187714106 | 189156378 |
| ABHD2 | 0 | 222408 | 1331 | 142 | 0.006675411 | 100 | 100 | chr15 | 1 | 89631405 | 89745591 | 225337_at | 89625750 | 89631521 |
| EDNRA | 4870 | 421533 | 0 | 115 | 0.006697313 | 0 | 0 | chr4 | 1 | 148402084 | 148466106 | 216235_s_at | 148406954 | 148533951 |
| INHBA | 0 | 660770 | 183342 | 2473 | 0.006702605 | 8 | 0 | chr7 | −1 | 41724712 | 41742706 | 210511_s_at | 40180732 | 41744986 |
| WHSC1 | 100147 | 115631 | 105661 | 20585 | 0.006750952 | 33 | 0 | chr4 | 1 | 1894572 | 1983934 | 209054_s_at | 1769186 | 1794425 |
| CSPP1 | 26760 | 350844 | 640 | 0 | 0.006825026 | 0 | 0 | chr8 | 1 | 67976603 | 68108494 | 1554873_at | 67941025 | 67949843 |
| RPL7L1 | 16688 | 354650 | 10177 | 10797 | 0.006851352 | 100 | 100 | chr6 | 1 | 42847373 | 42857634 | 225515_s_at | 42864061 | 42879234 |
| GCSH | 947 | 52492 | 565 | 0 | 0.00685861 | 100 | 100 | chr16 | −1 | 81115566 | 81130008 | 213129_s_at | 81130955 | 81268589 |
| FRZB | 4855 | 399866 | 256110 | 0 | 0.006909155 | 79 | 100 | chr2 | −1 | 183698002 | 183731890 | 203698_s_at | 183645523 | 183727035 |
| WDHD1 | 92088 | 846453 | 859 | 0 | 0.006921728 | 17 | 0 | chr14 | −1 | 55405668 | 55493795 | 216228_s_at | 55585883 | 55595666 |
| KLK12 | 0 | 0 | 17019 | 2672 | 0.006924307 | 29 | 0 | chr19 | −1 | 51532348 | 51538148 | 234316_x_at | 51523889 | 51568096 |
| RGS20 | 0 | 166920 | 10002 | 8258 | 0.006968335 | 4 | 0 | chr8 | 1 | 54764368 | 54871861 | 210138_at | 54758387 | 54783035 |
| SMARCA1 | 10854 | 0 | 1534744 | 70 | 0.006980988 | 8 | 0 | chrX | −1 | 128580482 | 128657477 | 215294_s_at | 125623341 | 128646623 |
| BEX2 | 3672 | 0 | 95279 | 0 | 0.006993088 | 50 | 96 | chrX | −1 | 102564274 | 102565974 | 224367_at | 102485299 | 102562302 |
| CHEK1 | 59968 | 69755 | 129286 | 198 | 0.006993088 | 92 | 58 | chr11 | 1 | 125495036 | 125525640 | 205394_at | 125555004 | 125751240 |
| SESN3 | 11213 | 0 | 78834 | 0 | 0.006993884 | 46 | 0 | chr11 | −1 | 94906133 | 94964246 | 235683_at | 94887006 | 94953033 |
| ASNS | 6214 | 20622 | 87822 | 0 | 0.006993884 | 100 | 100 | chr7 | −1 | 97481440 | 97501443 | 205047_s_at | 97507657 | 97556859 |
| APCDD1 | 4839 | 234624 | 271377 | 0 | 0.00701885 | 100 | 96 | chr18 | 1 | 10454625 | 10488698 | 225016_at | 10139155 | 10449786 |
| PCSK1 | 0 | 0 | 0 | 0 | 0.00701885 | 79 | 42 | chr5 | −1 | 95726119 | 95768984 | 205825_at | 95680613 | 95991182 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| ALPK3 | 46220 | 339086 | 548054 | 282 | 0.007043138 | 17 | 0 | chr15 | 1 | 85359911 | 85416713 | 214846_s_at | 85406131 | 85454098 |
| RAP1GAP | 4403 | 0 | 144855 | 0 | 0.007043647 | 100 | 100 | chr1 | −1 | 21922714 | 21995799 | 203911_at | 21986130 | 21991396 |
| TFDP1 | 1421 | 597056 | 1616 | 18434 | 0.007056944 | 100 | 100 | chr13 | 1 | 114239056 | 114295504 | 212330_at | 114186307 | 114237635 |
| BBS5 | 0 | 33933 | 115599 | 194 | 0.007118082 | 0 | 0 | chr2 | 1 | 170335688 | 170363165 | 230697_at | 170228679 | 170335841 |
| UCHL5 | 70932 | 2904839 | 1268 | 0 | 0.007122593 | 62 | 8 | chr1 | −1 | 192987535 | 193028539 | 220083_x_at | 192778234 | 192957607 |
| NUDC | 94796 | 500803 | 57244 | 0 | 0.007139932 | 100 | 100 | chr1 | 1 | 27248217 | 27273353 | 210574_s_at | 27343013 | 27420641 |
| ZNF670 | 216 | 151321 | 71674 | 0 | 0.007142127 | 0 | 0 | chr1 | −1 | 247200086 | 247242057 | 223898_at | 247242273 | 247262239 |
| WFS1 | 3411 | 2476 | 1841 | 0 | 0.007150778 | 12 | 0 | chr4 | 1 | 6271576 | 6304610 | 1555270_a_at | 6225827 | 6268165 |
| NFIA | 40838 | 50567 | 1255 | 774 | 0.00715277 | 100 | 100 | chr1 | 1 | 61547980 | 61928465 | 226806_s_at | 61332157 | 61507142 |
| TNNC2 | 2447 | 65790 | 42493 | 0 | 0.007199876 | 0 | 0 | chr20 | −1 | 44451853 | 44462384 | 205388_at | 44453207 | 44459937 |
| CWH43 | 563 | 0 | 80364 | 0 | 0.007205399 | 96 | 100 | chr4 | 1 | 48988264 | 49064096 | 220724_at | 48988827 | 49138512 |
| KIAA1199 | 70807 | 341262 | 810 | 0 | 0.007214607 | 100 | 0 | chr15 | 1 | 81071684 | 81244117 | 212942_s_at | 80992262 | 81000877 |
| LRP11 | 9320 | 53146 | 58236 | 0 | 0.007229319 | 100 | 100 | chr6 | −1 | 150139934 | 150185162 | 225060_at | 150163935 | 150175842 |
| UBE2T | 152230 | 117730 | 126950 | 0 | 0.007229319 | 100 | 100 | chr1 | −1 | 202300785 | 202311108 | 223229_at | 202122325 | 202158878 |
| SHCBP1 | 3840 | 73038 | 263620 | 163 | 0.00723122 | 88 | 4 | chr16 | −1 | 46614466 | 46655538 | 219493_at | 46659378 | 46690504 |
| MMP1 | 0 | 1384100 | 329279 | 293384 | 0.007323802 | 100 | 38 | chr11 | −1 | 102660651 | 102668891 | 204475_at | 102461598 | 102927599 |
| SDCCAG8 | 6806 | 205980 | 12151 | 582 | 0.00733569 | 0 | 0 | chr1 | 1 | 243419358 | 243663394 | 227785_at | 243426164 | 243432981 |
| CENPI | 28109 | 2081 | 1024583 | 2149 | 0.007348151 | 8 | 0 | chrX | 1 | 100355426 | 100418670 | 207590_s_at | 100322117 | 100327317 |
| PTGDR | 12721 | 0 | 1113 | 0 | 0.007362564 | 38 | 75 | chr14 | 1 | 52734431 | 52743442 | 234165_at | 52747152 | 52773244 |
| E2F7 | 1762 | 116510 | 259553 | 0 | 0.007372299 | 71 | 0 | chr12 | −1 | 77415026 | 77459360 | 228033_at | 77461122 | 77718302 |
| CHCHD7 | 6521 | 23090 | 53987 | 0 | 0.007411413 | 8 | 4 | chr8 | 1 | 57124357 | 57131174 | 218642_s_at | 57075584 | 57117836 |
| FSTL5 | 0 | 0 | 1921 | 1002275 | 0.007411413 | 0 | 0 | chr4 | −1 | 162305049 | 163085187 | 232010_at | 161308668 | 164025969 |
| SNRPA1 | 22184 | 16991 | 29468 | 0 | 0.007481179 | 100 | 100 | chr15 | −1 | 101821715 | 101835487 | 216977_x_at | 101800931 | 101813303 |
| ANXA10 | 0 | 40240 | 857281 | 225884 | 0.007571785 | 8 | 0 | chr4 | 1 | 169013666 | 169108841 | 210143_at | 168164267 | 169123358 |
| CATSPERB | 169343 | 0 | 156080 | 103789 | 0.00757793 | 17 | 0 | chr14 | −1 | 92047118 | 92198413 | 220293_at | 92012720 | 92029070 |
| SCRN1 | 65215 | 95938 | 105001 | 0 | 0.007586555 | 38 | 96 | chr7 | −1 | 29959719 | 30029414 | 201462_at | 29846782 | 29964199 |
| NOS2 | 1202 | 0 | 195863 | 6580 | 0.007649679 | 46 | 21 | chr17 | −1 | 26083792 | 26127525 | 210037_s_at | 26128727 | 26142314 |
| SPTLC1 | 140 | 692515 | 164591 | 0 | 0.007699666 | 25 | 0 | chr9 | −1 | 94841343 | 94877665 | 1554053_at | 94877805 | 94903458 |
| | 82812 | 157890 | 0 | 162117 | 0.007737899 | 4 | 0 | chr1 | 1 | 183155488 | 183209534 | 207517_at | 183238300 | 183365030 |
| TTC26 | 134 | 319063 | 96385 | 0 | 0.007775656 | 0 | 0 | chr7 | 1 | 138818524 | 138876732 | 219758_at | 138818658 | 138824296 |
| HPGD | 29020 | 0 | 897 | 211 | 0.007836885 | 100 | 100 | chr4 | −1 | 175411328 | 175444049 | 203913_s_at | 175473069 | 175750280 |
| CXCL14 | 10624 | 0 | 0 | 0 | 0.00785922 | 100 | 100 | chr5 | −1 | 134906376 | 134914754 | 218002_s_at | 134885256 | 134904130 |
| FOSL1 | 28251 | 394572 | 12506 | 0 | 0.007861179 | 4 | 0 | chr11 | −1 | 65660060 | 65667997 | 204420_at | 65696248 | 65712296 |
| MTUS2 | 0 | 0 | 306572 | 203849 | 0.00787038 | 0 | 0 | chr13 | 1 | 29598748 | 30077892 | 214961_at | 29394960 | 30082468 |
| SYT1 | 1827 | 331903 | 0 | 59372 | 0.007901212 | 4 | 0 | chr12 | 1 | 79257773 | 79844059 | 203998_s_at | 77719476 | 79255946 |
| SPRR1B | 0 | 0 | 229601 | 270339 | 0.007908228 | 0 | 0 | chr1 | 1 | 153003678 | 153005376 | 205064_at | 152590080 | 153227464 |
| CELSR3 | 29283 | 285351 | 294 | 0 | 0.007913195 | 8 | 0 | chr3 | −1 | 48673902 | 48700348 | 40020_at | 48665793 | 48671065 |
| PLAC8 | 18960 | 35022 | 369255 | 4645 | 0.007920803 | 100 | 100 | chr4 | −1 | 84011201 | 84035955 | 219014_at | 84054915 | 84091835 |
| TTYH3 | 463 | 331890 | 8525 | 0 | 0.007931402 | 4 | 0 | chr7 | 1 | 2671585 | 2704436 | 224674_at | 2652027 | 2671122 |
| PAIP1 | 150472 | 132937 | 43152 | 0 | 0.007964417 | 100 | 100 | chr5 | −1 | 43526369 | 43557181 | 209063_x_at | 43707653 | 44801662 |
| WASF1 | 5015 | 72104 | 177474 | 237 | 0.008018388 | 0 | 0 | chr6 | −1 | 110421022 | 110501204 | 204165_at | 110305944 | 110496189 |
| FIGNL1 | 15639 | 24459 | 227 | 0 | 0.008059769 | 96 | 58 | chr7 | −1 | 50511831 | 50518048 | 222843_at | 50411178 | 50502409 |
| CAB39L | 40439 | 673735 | 94785 | 42387 | 0.008123848 | 21 | 0 | chr13 | −1 | 49882786 | 49975735 | 225914_s_at | 49910626 | 49935296 |
| TBX3 | 24750 | 0 | 2373 | 0 | 0.00818073 | 92 | 0 | chr12 | −1 | 115108059 | 115121969 | 225544_at | 115146719 | 115165673 |
| HOXA3 | 34357 | 0 | 4121 | 2874 | 0.008207064 | 75 | 100 | chr7 | −1 | 27145803 | 27159214 | 235521_at | 26906410 | 27124857 |
| PLAUR | 22004 | 113659 | 28944 | 1249 | 0.008221225 | 62 | 79 | chr19 | −1 | 44152732 | 44174502 | 211924_s_at | 44144524 | 44152498 |
| THEM4 | 233 | 68907 | 463 | 0 | 0.008372633 | 4 | 0 | chr1 | −1 | 151846060 | 151882284 | 243492_at | 151882517 | 151889814 |
| DHRS11 | 22529 | 27559 | 49515 | 0 | 0.008390721 | 100 | 100 | chr17 | 1 | 34948329 | 34957235 | 218756_s_at | 34970858 | 34995823 |
| GPR160 | 12606 | 88220 | 67957 | 68 | 0.008451173 | 100 | 100 | chr3 | 1 | 169755527 | 169801918 | 223423_at | 169715685 | 169742921 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| SLC11A2 | 119326 | 801726 | 145824 | 1660 | 0.008462409 | 100 | 100 | chr12 | −1 | 51379775 | 51422008 | 203123_s_at | 51222303 | 51302682 |
| MCM4 | 27413 | 243954 | 552986 | 0 | 0.008507646 | 96 | 88 | chr8 | 1 | 48873494 | 48890068 | 222036_s_at | 48900907 | 48917534 |
| FCGRT | 91398 | 67431 | 22007 | 912 | 0.008507809 | 100 | 100 | chr19 | 1 | 50015620 | 50029588 | 218831_s_at | 49868900 | 49924222 |
| FAM89A | 1723 | 17386 | 7712 | 0 | 0.00851459 | 0 | 0 | chr1 | −1 | 231154704 | 231175992 | 226448_at | 231166967 | 231174269 |
| VMO1 | 24107 | 136479 | 0 | 167 | 0.008538416 | 4 | 0 | chr17 | −1 | 4688581 | 4689731 | 235751_s_at | 4649629 | 4665624 |
| CHFR | 9151 | 454256 | 0 | 0 | 0.008542648 | 79 | 100 | chr12 | −1 | 133416938 | 133464184 | 218803_at | 133408647 | 133455033 |
| CENPN | 34230 | 107603 | 90470 | 32 | 0.008622413 | 8 | 0 | chr16 | 1 | 81040103 | 81065090 | 222118_at | 81074333 | 81080865 |
| PAQR5 | 69804 | 178339 | 155373 | 0 | 0.008637134 | 96 | 100 | chr15 | 1 | 69591286 | 69699986 | 242871_at | 69513721 | 69521482 |
| ATP5L | 41972 | 47313 | 75356 | 158 | 0.008637134 | 100 | 100 | chr11 | 1 | 118272104 | 118280559 | 208745_at | 118154350 | 118230132 |
| ZCCHC17 | 38485 | 137572 | 115437 | 0 | 0.008662099 | 0 | 0 | chr1 | 1 | 31769842 | 31837783 | 223107_s_at | 31714207 | 31731357 |
| ITGA5 | 277 | 30684 | 0 | 0 | 0.008703242 | 0 | 0 | chr12 | −1 | 54789049 | 54813050 | 201389_at | 54813327 | 54945812 |
| CCNB1IP1 | 33109 | 61008 | 68385 | 80401 | 0.008707548 | 100 | 100 | chr14 | −1 | 20779529 | 20801169 | 217988_at | 20193580 | 20768060 |
| BMP7 | 5454 | 0 | 0 | 0 | 0.008717821 | 4 | 0 | chr20 | −1 | 55743804 | 55841684 | 209590_at | 55847138 | 55925397 |
| AMT | 11020 | 124811 | 5525 | 6293 | 0.008718676 | 100 | 100 | chr3 | −1 | 49454212 | 49460186 | 204294_at | 49471206 | 49481487 |
| RASSF6 | 33 | 55128 | 323449 | 6 | 0.00874794 | 100 | 100 | chr4 | −1 | 74437267 | 74486265 | 229147_at | 74486298 | 74535501 |
| SPIRE1 | 21223 | 438132 | 9561 | 0 | 0.00875898 | 4 | 0 | chr18 | −1 | 12446512 | 12658133 | 1559517_a_at | 12441323 | 12636910 |
| COL17A1 | 0 | 5749 | 32184 | 35690 | 0.008769642 | 100 | 100 | chr10 | −1 | 105791044 | 105845760 | 204636_at | 105844743 | 105868832 |
| ATP8B1 | 79054 | 200036 | 289920 | 70018 | 0.00879718 | 100 | 100 | chr18 | −1 | 55313658 | 55399039 | 226302_at | 55478093 | 55674977 |
| CDKN1A | 27016 | 274412 | 64539 | 0 | 0.00879718 | 100 | 100 | chr6 | 1 | 36646435 | 36655116 | 202284_s_at | 36673451 | 36686525 |
| PRIM2 | 6588 | 129620 | 96796 | 95110 | 0.008843523 | 83 | 29 | chr6 | 1 | 57182422 | 57398317 | 215708_s_at | 57138323 | 57175834 |
| WDR72 | 0 | 0 | 2906 | 3070 | 0.008858464 | 92 | 21 | chr15 | −1 | 53805938 | 54055075 | 227174_at | 54052067 | 55473630 |
| PLCB1 | 14935 | 160823 | 0 | 61 | 0.008858464 | 71 | 33 | chr20 | 1 | 8112824 | 8865547 | 213222_at | 8127759 | 8559260 |
| FDPS | 141476 | 135266 | 3386 | 0 | 0.008878079 | 100 | 100 | chr1 | 1 | 155278643 | 155290456 | 201275_at | 155113201 | 155137167 |
| BCL2 | 51274 | 128340 | 616934 | 0 | 0.008898763 | 79 | 100 | chr18 | −1 | 60790579 | 60987361 | 203685_at | 61038635 | 61057090 |
| TMEM182 | 104499 | 29798 | 113058 | 0 | 0.008903431 | 12 | 0 | chr2 | 1 | 103353367 | 103433875 | 1553301_a_at | 103457866 | 105456231 |
| NGFRAP1 | 3709 | 0 | 160573 | 54 | 0.00890749 | 100 | 100 | chrX | 1 | 102631268 | 102633005 | 217963_s_at | 102634977 | 102811380 |
| KIAA1524 | 36645 | 122701 | 285591 | 3618 | 0.008969512 | 58 | 0 | chr3 | −1 | 108268833 | 108304610 | 231855_at | 108209044 | 108267965 |
| CDKN1C | 23286 | 173545 | 3082 | 0 | 0.009058443 | 0 | 0 | chr11 | −1 | 2904443 | 2906970 | 219534_x_at | 2872158 | 2883684 |
| TGIF2 | 10295 | 145304 | 31489 | 0 | 0.009072496 | 0 | 0 | chr20 | 1 | 35201891 | 35222353 | 218724_s_at | 35172560 | 35191596 |
| NEIL3 | 1918 | 732017 | 516274 | 0 | 0.009072496 | 42 | 0 | chr4 | 1 | 178230990 | 178284097 | 219502_at | 177721702 | 178229072 |
| C4BPA | 0 | 0 | 51888 | 50764 | 0.009104341 | 29 | 4 | chr1 | 1 | 207277607 | 207318317 | 205654_at | 207260913 | 207425013 |
| PIGX | 11244 | 236375 | 75360 | 0 | 0.00910822 | 71 | 4 | chr3 | 1 | 196439229 | 196462878 | 1552291_at | 196371361 | 196427985 |
| CBFA2T3 | 0 | 0 | 14059 | 9079 | 0.00912857 | 8 | 0 | chr16 | −1 | 88941266 | 89043373 | 208056_s_at | 89008629 | 89156863 |
| PLA2G16 | 82511 | 78484 | 16350 | 0 | 0.009172671 | 79 | 33 | chr11 | −1 | 63341946 | 63381909 | 209581_at | 63274913 | 63299398 |
| EPB41L3 | 7072 | 0 | 1 | 0 | 0.009186762 | 50 | 100 | chr18 | −1 | 5392383 | 5544241 | 211776_s_at | 5301384 | 5537169 |
| EIF2B3 | 255406 | 55132 | 173037 | 0 | 0.009186762 | 29 | 0 | chr1 | −1 | 45316450 | 45452282 | 218488_at | 45148672 | 45196876 |
| DGAT2 | 61730 | 7425 | 418080 | 0 | 0.009217032 | 92 | 0 | chr11 | 1 | 75479778 | 75512579 | 226064_s_at | 75388873 | 75418048 |
| ZNF643 | 10028 | 110698 | 1567 | 643 | 0.009236976 | 0 | 0 | chr1 | 1 | 40916716 | 40929390 | 207219_at | 40897051 | 40906688 |
| KCNMB4 | 5674 | 73672 | 1007196 | 0 | 0.009239329 | 4 | 0 | chr12 | 1 | 70760062 | 70824978 | 222857_s_at | 70765736 | 70916353 |
| MSLN | 0 | 52594 | 14376 | 14083 | 0.009240689 | 75 | 8 | chr16 | 1 | 812594 | 818865 | 204885_s_at | 795707 | 837324 |
| MARCKS | 8384 | 254767 | 483895 | 1194 | 0.009288164 | 100 | 100 | chr6 | 1 | 114178541 | 114184648 | 225897_at | 114154848 | 114170157 |
| PRR15 | 40581 | 0 | 3694 | 98 | 0.009293264 | 100 | 100 | chr7 | 1 | 29603427 | 29606911 | 226961_at | 29644008 | 29680839 |
| FAM127B | 0 | 0 | 814642 | 0 | 0.009297598 | 4 | 4 | chrX | −1 | 134184962 | 134186205 | 217948_at | 134185573 | 134232424 |
| LPL | 7052 | 0 | 0 | 560 | 0.009299221 | 50 | 0 | chr8 | 1 | 19796284 | 19824769 | 203549_s_at | 19803336 | 20054515 |
| BRCA2 | 96 | 447610 | 224177 | 0 | 0.00933262 | 29 | 0 | chr13 | 1 | 32889611 | 32973347 | 214727_at | 32605926 | 32889515 |
| NR3C2 | 7568 | 0 | 4869 | 0 | 0.00933262 | 100 | 100 | chr4 | −1 | 148999913 | 149365850 | 205259_at | 149373418 | 149550514 |
| SSX2IP | 7856 | 291185 | 201941 | 0 | 0.00933262 | 8 | 0 | chr1 | −1 | 85109390 | 85156228 | 203019_x_at | 85164084 | 85353693 |
| HOMEZ | 37722 | 74852 | 65659 | 0 | 0.00933262 | 0 | 0 | chr14 | −1 | 23742844 | 23755309 | 231868_at | 23653907 | 23717587 |
| TEAD2 | 3186 | 22475 | 21505 | 23 | 0.009338709 | 38 | 0 | chr19 | −1 | 49843857 | 49865714 | 238323_at | 49868900 | 49924222 |

TABLE 15-continued

Genes with higher gene expression variability in cancer compared to normal.

| gene | dist2block | dist2PMD | dist2DMR | dist2CGI | p-value | Cancer % On | Normal % On | chr | strand | txStart | txEnd | affyid | blockStart | blockEnd |
|---|---|---|---|---|---|---|---|---|---|---|---|---|---|---|
| CHEK1 | 59968 | 69755 | 129286 | 198 | 0.009347576 | 96 | 12 | chr11 | 1 | 125495036 | 125525640 | 205393_s_at | 125555004 | 125751240 |
| BUD31 | 98399 | 265801 | 14782 | 0 | 0.009352247 | 100 | 100 | chr7 | 1 | 99006264 | 99017239 | 205690_s_at | 98821222 | 98907865 |
| SLFN13 | 6244 | 0 | 2263 | 2596 | 0.00937768 | 17 | 0 | chr17 | −1 | 33762115 | 33772699 | 1558217_at | 33713350 | 33766455 |
| STOX1 | 7417 | 422697 | 72450 | 0 | 0.009414804 | 4 | 0 | chr10 | 1 | 70587298 | 70655188 | 1553202_at | 70566017 | 70579881 |
| SIAE | 21625 | 41028 | 870 | 0 | 0.00948285 | 100 | 100 | chr11 | −1 | 124505694 | 124543763 | 224391_s_at | 124565388 | 124588053 |
| MET | 2461 | 699681 | 950 | 0 | 0.009492357 | 71 | 0 | chr7 | 1 | 116312446 | 116438440 | 213816_s_at | 116166755 | 116309985 |
| MS4A12 | 0 | 0 | 236324 | 22533 | 0.009502226 | 79 | 100 | chr11 | 1 | 60260251 | 60274893 | 220834_at | 59880038 | 60600316 |
| DLAT | 113522 | 379253 | 152426 | 39 | 0.009536442 | 100 | 100 | chr11 | 1 | 111895538 | 111935114 | 213149_at | 111755267 | 111782016 |
| FAM40B | 56026 | 281522 | 56894 | 0 | 0.009560713 | 0 | 0 | chr7 | 1 | 129074287 | 129123472 | 1555292_at | 128993853 | 129018261 |
| FMR1 | 20272 | 0 | 588298 | 0 | 0.009585581 | 92 | 100 | chrX | 1 | 146993481 | 147031835 | 215245_x_at | 146295424 | 146973209 |
| APOLD1 | 19918 | 539869 | 29956 | 0 | 0.009618491 | 46 | 0 | chr12 | 1 | 12878865 | 12944316 | 221031_s_at | 12898783 | 12939687 |
| | 29690 | 216356 | 25972 | 162 | 0.009660567 | 0 | 0 | chr6 | −1 | 30667584 | 30685666 | 203062_s_at | 30715356 | 30743413 |
| CYB5D1 | 63338 | 131788 | 132670 | 0 | 0.009681533 | 0 | 0 | chr17 | 1 | 7761064 | 7765598 | 1552711_a_at | 7664688 | 7697726 |
| APOA2 | 4596 | 19959 | 34699 | 21161 | 0.009693688 | 0 | 0 | chr1 | −1 | 161192082 | 161193418 | 219465_at | 161198014 | 161219016 |
| SPATA6 | 12169 | 29569 | 303884 | 161 | 0.009695896 | 8 | 0 | chr1 | −1 | 48761044 | 48937845 | 220299_at | 48950014 | 49242359 |
| C3orf39 | 398 | 7566 | 560 | 0 | 0.009727032 | 0 | 0 | chr3 | −1 | 43120724 | 43147431 | 225689_at | 43147829 | 43320434 |
| WFS1 | 3411 | 2476 | 1841 | 0 | 0.009751162 | 54 | 0 | chr4 | 1 | 6271576 | 6304610 | 202908_at | 6225827 | 6268165 |
| ALDH1B1 | 5946 | 7340 | 31117 | 0 | 0.009763351 | 100 | 58 | chr9 | 1 | 38392661 | 38398658 | 209645_s_at | 38398607 | 38421365 |
| SLCO3A1 | 4664 | 7928 | 61741 | 0 | 0.009763351 | 17 | 0 | chr15 | 1 | 92396925 | 92709133 | 227367_at | 92090952 | 92392261 |
| FCAR | 0 | 0 | 212242 | 65087 | 0.009797727 | 0 | 0 | chr19 | 1 | 55385736 | 55401838 | 207674_at | 55372699 | 55550348 |
| NPHP1 | 24 | 159907 | 90713 | 0 | 0.009808754 | 12 | 0 | chr2 | −1 | 110879888 | 110962619 | 238844_s_at | 110962643 | 110969823 |
| NAPEPLD | 309 | 93086 | 618 | 0 | 0.009834565 | 100 | 100 | chr7 | −1 | 102740223 | 102789679 | 226041_at | 102769130 | 102789370 |
| FOLH1 | 15944 | 0 | 0 | 181 | 0.009852821 | 0 | 0 | chr11 | −1 | 49168190 | 49230222 | 205860_x_at | 48849695 | 49214278 |
| THBS2 | 0 | 266063 | 0 | 5091 | 0.009852821 | 4 | 0 | chr6 | −1 | 169615875 | 169654139 | 203083_at | 169616680 | 169952489 |
| HELLS | 73972 | 84437 | 1367 | 0 | 0.00985699 | 92 | 4 | chr10 | 1 | 96305574 | 96361856 | 223556_at | 96379546 | 96939818 |
| RP9 | 522 | 645526 | 344222 | 0 | 0.00989954 | 0 | 0 | chr7 | −1 | 33134409 | 33149002 | 227035_x_at | 33149524 | 33168630 |
| TREX2 | 6242 | 29238 | 46893 | 0 | 0.009901824 | 67 | 0 | chrX | −1 | 152710178 | 152736045 | 207891_s_at | 152742287 | 152756534 |
| | 41518 | 191660 | 281725 | 37766 | 0.009960756 | 4 | 0 | chr8 | −1 | 95444175 | 95449165 | 220549_at | 95490683 | 95496265 |

TABLE 16

Partial listing of regions with cancer-specific differential methylation (C-DMRs) at a FDR of 5%.

| | chr | start | end | delta M | colon. tumor | colon. normal | fdr | state | name | annotation | region | distance | island | distToIsla |
|---|---|---|---|---|---|---|---|---|---|---|---|---|---|---|
| 2325 | chr10 | 5774977 | 5775480 | 0.884039577 | 1.262918606 | 0.420204198 | 0 | Some methylation | ASB13 | NM_024701 | upstream | 26431 | Far | −7274 |
| 3576 | chr11 | 117907224 | 117907958 | 1.001570264 | 1.129919936 | 0.236686302 | 0 | Some methylation | TMEM25 | NM_032780 | inside | 3800 | Shore | 0 |
| 6904 | chr11 | 65947037 | 65948698 | −0.882029631 | 0.824501834 | 1.694138469 | 0 | Less methylation | NPAS4 | NM_178864 | inside | 2054 | Shore | −1064 |
| 13834 | chr13 | 113615559 | 113616275 | −0.913827499 | 1.138092601 | 1.910209397 | 0 | Less methylation | FAM70B | NM_182614 | inside | 35597 | Shore | 0 |
| 18878 | chr15 | 58474576 | 58476390 | −0.805171203 | 0.407560089 | 1.181506906 | 0 | No methylation | ANXA2 | NM_001002857 | inside | 1086 | Far | 651 |
| 31523 | chr19 | 5159373 | 5160095 | −1.014437008 | 1.521337314 | 2.518715498 | 0 | Less methylation | PTPRS | NM_130854 | inside | 131718 | Far | 1469 |
| 31686 | chr19 | 5297115 | 5297780 | −0.932920958 | 0.29967316 | 1.256908951 | 0 | No methylation | PTPRS | NM_130854 | upstream | 5302 | Far | −5054 |
| 32005 | chr19 | 55631525 | 55632172 | −0.846213883 | 0.704148578 | 1.674940533 | 0 | Less methylation | MYBPC2 | NM_004533 | inside | 29216 | Shore | −4036 |
| 32467 | chr19 | 60702435 | 60703541 | −0.930609844 | 1.30766243 | 2.173488599 | 0 | Less methylation | NAT14 | NM_020378 | upstream | 11689 | Shore | 3082 |
| 33832 | chr20 | 33650044 | 33650445 | 0.88180542 | 1.935235972 | 1.053430552 | 0 | More methylation | SPAG4 | NM_003116 | downstream | 21933 | Shore | 1688 |
| 37372 | chr21 | 37858818 | 37859555 | −1.163675835 | 0.490611645 | 1.65428748 | 0 | No methylation | DYRK1A | NM_001396 | upstream | 49271 | Far | −402 |
| 38130 | chr2 | 147061940 | 147063253 | −0.858337503 | 0.992346964 | 1.906435228 | 0 | Less methylation | ACVR2A | NM_001616 | downstream | 1341608 | Shore | −91 |
| 40126 | chr22 | 35335058 | 35336773 | −1.037291011 | 1.139288 | 2.182025256 | 0 | Less methylation | CACNG2 | NM_006078 | inside | 92075 | Shore | −44058 |
| 41538 | chr22 | 48414225 | 48414719 | −0.96407167 | 1.159071722 | 2.123143393 | 0 | Less methylation | C22orf34 | NM_001039473 | inside | 22470 | Far | −1806 |
| 44705 | chr3 | 193607217 | 193607552 | −0.935728144 | 0.885876325 | 1.898131578 | 0 | Less methylation | FGF12 | NM_021032 | inside | 1153 | Far | 960 |
| 45816 | chr3 | 82629728 | 82630444 | −0.837733539 | 0.977708408 | 1.768733642 | 0 | Less methylation | GBE1 | NM_000158 | upstream | 736294 | Shore | 309227 |
| 47784 | chr4 | 62618513 | 62619190 | −0.87266859 | 1.84179962 | 2.691995246 | 0 | Less methylation | LPHN3 | NM_015236 | inside | 1571 | Far | −552670 |
| 49706 | chr5 | 1718578 | 1720081 | −1.006675313 | 1.152316522 | 2.178490529 | 0 | Less methylation | MRPL36 | NM_032479 | downstream | 132864 | Shore | 106 |
| 54115 | chr6 | 52637426 | 52638797 | −0.887556038 | 0.387977123 | 1.292585668 | 0 | No methylation | TMEM14A | NM_014051 | downstream | 20544 | Shore | 0 |
| 56085 | chr7 | 153219537 | 153220325 | −1.02673515 | 0.690401085 | 1.588873129 | 0 | Less methylation | DPP6 | NM_001039350 | inside | 1096601 | Shore | −2938 |
| 57345 | chr7 | 27106893 | 27108170 | 0.882121475 | 1.490759927 | 0.681905484 | 0 | More methylation | HOXA2 | NM_006735 | inside | 748 | Far | 1536 |
| 61903 | chr8 | 819298 | 820365 | −0.874467186 | 0.96711901 | 1.87443307 | 0 | Less methylation | ERICH1 | NM_207332 | upstream | 148073 | Far | 1879 |
| 64837 | chr9 | 94989150 | 94990319 | 0.845241759 | 1.311616403 | 0.49341257 | 0 | Some methylation | WNK2 | NM_006648 | inside | 132354 | Shore | −1494 |
| 65721 | chrX | 135941512 | 135943110 | 0.904877352 | 0.842032974 | −0.068886929 | 0 | Some methylation | GPR101 | NM_054021 | promoter | 14 | Shore | 0 |
| 14300 | chr13 | 24843229 | 24844191 | 0.835162395 | 1.564834811 | 0.706498375 | 2.95E−12 | More methylation | ATP8A2 | NM_016529 | downstream | 649227 | Shore | 0 |
| 60198 | chr8 | 144543158 | 144544935 | −0.796122139 | 0.657035363 | 1.656096515 | 3.04E−12 | Less methylation | RHPN1 | NM_052924 | upstream | 7196 | Shore | −9061 |
| 33157 | chr20 | 15408602 | 15408931 | −0.877118107 | 0.624232323 | 1.538178033 | 5.30E−12 | Less methylation | C20orf133 | NM_001033087 | inside | 572907 | Shore | 1092905 |
| 30814 | chr19 | 43436599 | 43438474 | 0.828947084 | 1.841118609 | 1.065766155 | 6.70E−12 | More methylation | PPP1R14A | NM_033256 | inside | 537 | Shore | 4 |
| 57366 | chr7 | 27121979 | 27122917 | 0.793013224 | 1.329883346 | 0.487838224 | 1.34E−11 | Some methylation | HOXA3 | NM_030661 | inside | 2821 | Far | −28 |
| 980 | chr10 | 129973472 | 129974329 | −0.791044282 | 1.191324369 | 1.95202271 | 1.92E−11 | Less methylation | MKI67 | NM_002417 | upstream | 158828 | Far | −19204 |
| 55445 | chr7 | 129912736 | 129913242 | −0.824647723 | 0.572058383 | 1.347853705 | 2.24E−11 | Less methylation | MEST | NM_177524 | downstream | 20122 | Shore | 11 |
| 19785 | chr15 | 90735153 | 90735977 | −0.780988544 | 0.805516346 | 1.521399712 | 4.62E−11 | Less methylation | ST8SIA2 | NM_006011 | downstream | 76982 | Shore | 1704 |
| 40200 | chr22 | 36145002 | 36145832 | 0.778035539 | 1.115864323 | 0.401317933 | 5.64E−11 | Some methylation | LRRC62 | NM_052906 | upstream | 43478 | Shore | 0 |
| 49841 | chr5 | 175019374 | 175020506 | −0.773226995 | 0.814882726 | 1.578348104 | 7.72E−11 | Less methylation | HRH2 | NM_022304 | downstream | 23655 | Far | −1012 |
| 59441 | chr8 | 118032313 | 118033443 | −0.769581485 | 0.797225434 | 1.573042397 | 8.22E−11 | Less methylation | LOC441376 | NM_001025357 | upstream | 7911 | Shore | −12173 |
| 57396 | chr7 | 27151643 | 27153628 | 0.720370124 | 1.475288315 | 0.751826211 | 8.57E−11 | More methylation | HOXA6 | NM_024014 | inside | 264 | Shore | 0 |
| 8775 | chr12 | 108883476 | 108884015 | −0.79920787 | 1.742699258 | 2.498324416 | 8.98E−11 | Less methylation | GIT2 | NM_139201 | inside | 34467 | Far | 34165 |
| 57951 | chr7 | 4865828 | 4866751 | −0.752290368 | 0.579969952 | 1.276474622 | 1.80E−10 | Less methylation | PAPOLB | NM_020144 | inside | 1399 | Far | 1111 |

TABLE 16-continued

Partial listing of regions with cancer-specific differential methylation (C-DMRs) at a FDR of 5%.

| | chr | start | end | delta M | colon. tumor | colon. normal | fdr | state | name | annotation | region | distance | island | distToIsla |
|---|---|---|---|---|---|---|---|---|---|---|---|---|---|---|
| 19143 | chr15 | 70198422 | 70199761 | −0.756651884 | 0.328158957 | 1.123706438 | 2.30E−10 | No methylation | SENP8 | NM_145204 | inside | 20595 | Far | −366 |
| 32707 | chr19 | 63146186 | 63149953 | −0.693139257 | 1.2067458 | 2.101579723 | 2.31E−10 | Less methylation | ZNF256 | NM_005773 | inside | 935 | Far | 545 |
| 9574 | chr12 | 128898887 | 128900474 | −0.720321969 | 0.291118321 | 0.863809773 | 3.16E−10 | No methylation | TMEM132D | NM_133448 | inside | 53691 | Shore | 5162 |
| 5439 | chr1 | 14092469 | 14093393 | 0.743518354 | 1.950039432 | 1.157238839 | 3.74E−10 | More methylation | PRDM2 | NM_012231 | upstream | 68308 | Far | −145 |
| 34856 | chr20 | 56858718 | 56860946 | 0.682356929 | 1.097259392 | 0.353022441 | 3.76E−10 | Some methylation | GNAS | NM_016592 | inside | 58697 | Island | 0 |
| 54056 | chr6 | 50873235 | 50873811 | −0.772772257 | 0.71134484 | 1.293278883 | 3.81E−10 | Less methylation | TFAP2B | NM_003221 | downstream | 45822 | Shore | 21434 |
| 62237 | chr9 | 101171244 | 101172098 | −0.742206353 | 1.451503765 | 2.162847317 | 4.84E−10 | Less methylation | SEC61B | NM_006808 | upstream | 138524 | Far | −72210 |
| 55753 | chr7 | 145026589 | 145027407 | −0.738007248 | 0.853276734 | 1.545617074 | 7.53E−10 | Less methylation | CNTNAP2 | NM_014141 | downstream | 2721611 | Shore | 416556 |
| 7404 | chr11 | 73980533 | 73981178 | −0.784853788 | 0.605105525 | 1.389959312 | 8.52E−10 | Less methylation | POLD3 | NM_006591 | downstream | 50234 | Shore | 0 |
| 49578 | chr5 | 16236219 | 16237106 | −0.727976294 | 0.319286099 | 1.034134495 | 1.00E−09 | No methylation | FBXL7 | NM_012304 | upstream | 243320 | Far | −2799 |
| 63454 | chr9 | 137437549 | 137438193 | −0.745855742 | 0.943703974 | 1.666021652 | 1.27E−09 | Less methylation | KIAA0649 | NM_014811 | downstream | 82366 | Shore | 6096 |
| 60504 | chr8 | 17060922 | 17062917 | −0.684418678 | 0.524740457 | 1.214365839 | 1.34E−09 | Less methylation | ZDHHC2 | NM_016353 | inside | 61694 | Far | −1761 |
| 63300 | chr9 | 136758751 | 136759638 | −0.721949494 | 1.187281075 | 1.831695978 | 1.46E−09 | Less methylation | COL5A1 | NM_000093 | inside | 116868 | Shore | 40696 |
| 28167 | chr18 | 73809395 | 73809862 | −0.761987843 | 0.712040225 | 1.397770327 | 1.78E−09 | Less methylation | GALR1 | NM_001480 | upstream | 698315 | Far | 9620 |
| 43646 | chr3 | 129687777 | 129688211 | 0.765371171 | 1.045816916 | 0.248273603 | 1.99E−09 | Some methylation | GATA2 | NM_032638 | inside | 6506 | Shore | 0 |
| 44692 | chr3 | 191521264 | 191521946 | −0.736310316 | 0.305208673 | 0.941463033 | 2.29E−09 | No methylation | CLDN1 | NM_021101 | inside | 962 | Far | 562 |
| 14770 | chr13 | 42886712 | 42887185 | −0.755363018 | 0.485004123 | 1.152369344 | 2.66E−09 | No methylation | PIG38 | NM_017993 | inside | 252469 | Shore | 370673 |
| 57384 | chr7 | 27147025 | 27148414 | 0.687423459 | 1.392236867 | 0.69627026 | 2.78E−09 | More methylation | HOXA5 | NM_019102 | overlaps 3' | 1397 | Shore | 724 |
| 42160 | chr2 | 4028054 | 4028969 | −0.716859847 | 1.030407359 | 1.739677942 | 2.80E−09 | Less methylation | ALLC | NM_199232 | upstream | 299922 | Island | 0 |
| 26127 | chr17 | 74692697 | 74693892 | −0.705530207 | 0.763221549 | 1.574707214 | 2.93E−09 | Less methylation | LOC146713 | NM_001025448 | downstream | 237673 | Far | −873 |
| 8908 | chr12 | 112557312 | 112558104 | −0.753141903 | 1.042028792 | 1.710085381 | 3.06E−09 | Less methylation | LHX5 | NM_022363 | upstream | 163053 | Far | −43177 |
| 34318 | chr20 | 44094989 | 44097868 | −0.676720601 | 0.260559817 | 0.813306387 | 3.15E−09 | No methylation | SLC12A5 | NM_020708 | inside | 24327 | Far | −634 |
| 58791 | chr7 | 92075312 | 92075873 | −0.755796746 | 0.73620026 | 1.585335161 | 3.60E−09 | Less methylation | CDK6 | NM_001259 | inside | 225274 | Shore | −17503 |
| 57976 | chr7 | 50103520 | 50103993 | −0.743374995 | 0.807983185 | 1.493863455 | 5.51E−09 | Less methylation | ZPBP | NM_007009 | promoter | 149 | Far | −53 |
| 38447 | chr2 | 172826386 | 172826961 | −0.729008517 | 0.432491545 | 1.192572807 | 5.75E−09 | No methylation | DLX2 | NM_004405 | upstream | 150663 | Shore | −18042 |
| 59135 | chr8 | 1032896 | 1034248 | −0.687184842 | 0.539672279 | 1.258802261 | 5.85E−09 | Less methylation | ERICH1 | NM_207332 | upstream | 361671 | Far | 1718 |
| 34832 | chr20 | 56841054 | 56842229 | −0.676159209 | 0.397024805 | 1.076612063 | 7.76E−09 | No methylation | GNAS | NM_016592 | downstream | 77414 | Shore | 5761 |
| 57370 | chr7 | 27129188 | 27131713 | 0.628259986 | 1.460162662 | 0.834558503 | 7.80E−09 | More methylation | HOXA3 | NM_153631 | inside | 1450 | Shore | 0 |
| 22668 | chr16 | 86201868 | 86205260 | −0.678519462 | 0.923526175 | 1.762011152 | 9.80E−09 | Less methylation | JPH3 | NM_020655 | inside | 83999 | Shore | 327 |
| 27359 | chr18 | 32022373 | 32023451 | −0.682417577 | 1.013390788 | 1.725157179 | 1.01E−08 | Less methylation | MOCOS | NM_017947 | inside | 79230 | Far | −230 |
| 20997 | chr16 | 31139986 | 31140921 | −0.701244098 | 1.041352011 | 1.764370993 | 1.03E−08 | Less methylation | TRIM72 | NM_001008274 | inside | 3089 | Shore | 2105 |
| 66376 | chrX | 23042002 | 23042577 | −0.737872027 | 0.72397743 | 1.521827355 | 1.05E−08 | Less methylation | DDX53 | NM_182699 | upstream | 111878 | Shore | 217628 |
| 10059 | chr12 | 16648817 | 16649638 | 0.693702713 | 0.965838459 | 0.240165199 | 1.13E−08 | Some methylation | LMO3 | NM_018640 | inside | 1059 | Far | −693016 |
| 4628 | chr11 | 2190993 | 2192468 | −0.654016557 | 0.728706953 | 1.344128093 | 1.36E−08 | Less methylation | TH | NM_000360 | upstream | 41383 | Shore | −46172 |
| 52759 | chr6 | 168586102 | 168588777 | 0.621864525 | 1.229549259 | 0.709159744 | 1.36E−08 | More methylation | SMOC2 | NM_022138 | inside | 221818 | Shore | −153 |
| 46821 | chr4 | 172202321 | 172202941 | −0.710142653 | 1.176641595 | 1.899312607 | 1.39E−08 | Less methylation | GALNT17 | NM_001034845 | downstream | 1996342 | Shore | 767368 |
| 33981 | chr20 | 3603786 | 3604568 | −0.692611023 | 0.436419597 | 1.130207665 | 1.43E−08 | No methylation | ADAM33 | NM_025220 | inside | 6169 | Shore | −1013 |
| 55137 | chr7 | 1182527 | 1183550 | −0.701093724 | 0.584832729 | 1.240497677 | 1.53E−08 | Less methylation | ZFAND2A | NM_182491 | upstream | 16204 | Far | −15857 |
| 41004 | chr2 | 242632926 | 242634574 | −0.699239495 | 1.216656053 | 1.917461412 | 2.62E−08 | Less methylation | FLJ33590 | NM_173821 | upstream | 168280 | Shore | 1740 |
| 17867 | chr14 | 95577239 | 95578925 | −0.646974007 | 0.433930917 | 0.991416457 | 3.05E−08 | No methylation | C14orf132 | NM_020215 | inside | 50960 | Shore | −1084 |

TABLE 16-continued

Partial listing of regions with cancer-specific differential methylation (C-DMRs) at a FDR of 5%.

| | chr | start | end | delta M | colon. tumor | colon. normal | fdr | state | name | annotation | region | distance | island | distToIsla |
|---|---|---|---|---|---|---|---|---|---|---|---|---|---|---|
| 62117 | chr8 | 966339 | 968282 | −0.625531408 | 1.036720214 | 1.662365404 | 3.25E−08 | Less methylation | ERICH1 | NM_207332 | upstream | 295114 | Shore | −581 |
| 65865 | chrX | 142544143 | 142544508 | −0.728714637 | 0.713998945 | 1.304872981 | 3.62E−08 | Less methylation | SLITRK4 | NM_173078 | inside | 6176 | Far | 4568 |
| 57988 | chr7 | 50436454 | 50438081 | −0.637817371 | 0.612478628 | 1.510098644 | 3.80E−08 | Less methylation | IKZF1 | NM_006060 | overlaps 5' | 0 | Shore | −560 |
| 15376 | chr13 | 87123702 | 87125149 | 0.640539634 | 0.720765875 | 0.169112114 | 3.98E−08 | Some methylation | SLITRK5 | NM_015567 | inside | 4719 | Shore | 0 |
| 12514 | chr12 | 88272781 | 88274261 | −0.65038077 | 0.929225424 | 1.579606194 | 4.42E−08 | Less methylation | DUSP6 | NM_001946 | upstream | 2355 | Far | −506 |
| 13142 | chr13 | 112142200 | 112143003 | −0.678295439 | 0.658334617 | 1.327603281 | 4.68E−08 | Less methylation | C13orf28 | NM_145248 | upstream | 5199 | Far | 11335 |
| 58570 | chr7 | 80386676 | 80389252 | −0.601910229 | 0.476007171 | 1.05329169 | 4.84E−08 | No methylation | SEMA3C | NM_006379 | promoter | 74 | Shore | −14 |
| 58751 | chr7 | 90064351 | 90065062 | 0.677011457 | 0.690804337 | 0.05018534 | 5.06E−08 | Some methylation | PFTK1 | NM_012395 | downstream | 612777 | Far | −51 |
| 59080 | chr8 | 100031456 | 100033208 | 0.618925139 | 0.940654534 | 0.235287751 | 5.12E−08 | Some methylation | OSR2 | NM_053001 | inside | 291 | Far | −842 |
| 12935 | chr13 | 110126686 | 110127336 | 0.682652476 | 1.946777838 | 1.27856897 | 5.44E−08 | More methylation | FLJ12118 | NM_024537 | inside | 29127 | Shore | 1831 |
| 61933 | chr8 | 846979 | 849372 | −0.596646108 | 0.55360301 | 1.131506643 | 5.47E−08 | Less methylation | ERICH1 | NM_207332 | upstream | 175754 | Far | −6574 |
| 3269 | chr11 | 103540808 | 103541706 | −0.672096716 | 0.914417143 | 1.675406973 | 5.56E−08 | Less methylation | PDGFD | NM_025208 | upstream | 572 | Shore | −540 |
| 44954 | chr3 | 28591265 | 28591843 | 0.687620751 | 0.820959578 | 0.117410558 | 6.39E−08 | Some methylation | ZCWPW2 | NM_001040432 | upstream | 49632 | Shore | 0 |
| 62175 | chr8 | 98356982 | 98358151 | −0.641614569 | 1.081648716 | 1.732896661 | 6.46E−08 | Less methylation | TSPYL5 | NM_033512 | inside | 1200 | Shore | 629 |
| 50428 | chr5 | 3586182 | 3587073 | −0.706076627 | 0.832023199 | 1.552694773 | 6.57E−08 | Less methylation | IRX1 | NM_024337 | downstream | 67442 | Far | 1557 |
| 34521 | chr20 | 4928754 | 4929383 | 0.695670621 | 0.737084605 | 0.05345522 | 6.64E−08 | Some methylation | SLC23A2 | NM_005116 | inside | 761 | Shore | 111977 |
| 9576 | chr12 | 128900526 | 128905070 | −0.566798145 | 0.601192264 | 1.087718526 | 8.89E−08 | Less methylation | TMEM132D | NM_133448 | inside | 49095 | Far | 566 |
| 51194 | chr5 | 7900127 | 7901201 | −0.656770027 | 0.625665717 | 1.352285824 | 9.34E−08 | Less methylation | FASTKD3 | NM_024091 | downstream | 20913 | Far | 1744 |
| 30182 | chr19 | 35406489 | 35408138 | 0.619251049 | 0.697131292 | 0.07706136 | 9.87E−08 | Some methylation | ZNF536 | NM_014717 | downstream | 332666 | Island | 0 |
| 57697 | chr7 | 3984090 | 3985861 | −0.619295823 | 0.657262411 | 1.441495463 | 9.87E−08 | Less methylation | SDK1 | NM_152744 | inside | 285898 | Shore | 134310 |
| 28407 | chr18 | 75366596 | 75367142 | −0.770077524 | 1.031079534 | 1.801157059 | 1.07E−07 | Less methylation | NFATC1 | NM_172389 | inside | 23167 | Shore | 4639 |
| 48611 | chr5 | 11954677 | 11955633 | −0.645408794 | 1.247918641 | 1.825251349 | 1.12E−07 | Less methylation | CTNND2 | NM_001332 | inside | 1476 | Far | 917 |
| 4640 | chr11 | 2243719 | 2244678 | −0.641643739 | 0.897753903 | 1.618595497 | 1.20E−07 | Less methylation | ASCL2 | NM_005170 | downstream | 4079 | Shore | 2002 |
| 63374 | chr9 | 137111474 | 137112189 | −0.659852348 | 0.896213837 | 1.550180764 | 1.32E−07 | Less methylation | OLFM1 | NM_006334 | inside | 17578 | Far | −3926 |
| 57568 | chr7 | 32076356 | 32076691 | 0.709312665 | 0.683771808 | 0.032096544 | 1.58E−07 | Some methylation | PDE1C | NM_005020 | inside | 824 | Shore | 0 |

TABLE 17

Regions with consistent cancer-specific differential methylation (C-DMRs) at a FDR of 5%. DeltaM is cancer minus normal. FDR is false discovery rate. Columns are chromo some, start, end, delta M, fdr, gene, relation to gene, distance to TSS, relation to CGI, distance to CGI

| chr | start | end | deltaM | fdr | gene name | relation | TSS distance | CGI | distToCGI |
|---|---|---|---|---|---|---|---|---|---|
| chr7 | 153219537 | 153220325 | −1.02673515 | 1.31E−06 | DPP6 | inside | 1096601 | Far | −2938 |
| chr21 | 37858785 | 37859555 | −1.084012454 | 1.64E−06 | DYRK1A | upstream | 49238 | Shore | −369 |
| chr11 | 117907224 | 117907958 | 1.001570264 | 3.28E−06 | TMEM25 | inside | 3800 | Shore | 0 |
| chr19 | 5159412 | 5160095 | −1.022283546 | 6.28E−06 | PTPRS | inside | 131718 | Shore | 1469 |
| chr11 | 65947037 | 65948698 | −0.882029631 | 6.38E−06 | NPAS4 | inside | 2054 | Shore | −1064 |
| chr22 | 35335058 | 35337265 | −0.871428279 | 6.65E−06 | CACNG2 | inside | 91583 | Far | −44058 |
| chr19 | 60702504 | 60703541 | −0.941226599 | 8.92E−06 | NAT14 | upstream | 11758 | Far | 3082 |
| chrX | 135941512 | 135943110 | 0.904877352 | 9.30E−06 | GPR101 | promoter | 14 | Island | 0 |
| chr6 | 52637426 | 52638797 | −0.887556038 | 1.30E−05 | TMEM14A | downstream | 20544 | Shore | 0 |
| chr7 | 27106893 | 27108203 | 0.870705583 | 1.56E−05 | HOXA2 | inside | 715 | Shore | 1503 |
| chr5 | 1718233 | 1720117 | −0.859031092 | 2.05E−05 | MRPL36 | downstream | 132828 | Shore | 70 |
| chr19 | 5297115 | 5297780 | −0.932920958 | 2.26E−05 | PTPRS | upstream | 5302 | Far | −5054 |
| chr2 | 147061970 | 147063253 | −0.860149055 | 2.29E−05 | ACVR2A | downstream | 1341608 | Shore | −121 |
| chr8 | 819298 | 820365 | −0.874467186 | 2.43E−05 | ERICH1 | upstream | 148073 | Shore | 1879 |
| chr22 | 48414225 | 48414719 | −0.96407167 | 2.49E−05 | C22orf34 | inside | 22470 | Shore | −1806 |
| chr13 | 113615559 | 113616275 | −0.913827499 | 2.70E−05 | FAM70B | inside | 35597 | cover | 0 |
| chr15 | 58474612 | 58476390 | −0.81855457 | 3.99E−05 | ANXA2 | inside | 1086 | Shore | 651 |
| chr7 | 3984567 | 3985861 | −0.840761885 | 6.63E−05 | SDK1 | inside | 285898 | Far | 134310 |
| chr20 | 33650044 | 33650409 | 0.94650255 | 6.95E−05 | SPAG4 | downstream | 21969 | Shore | 1724 |
| chr13 | 24843229 | 24844069 | 0.886018997 | 7.38E−05 | ATP8A2 | downstream | 649349 | Shore | 0 |
| chr4 | 62618513 | 62619190 | −0.87266859 | 7.61E−05 | LPHN3 | inside | 1571 | Far | −552670 |
| chr3 | 193607217 | 193607552 | −0.935728144 | 0.000111597 | FGF12 | inside | 1153 | Shore | 960 |
| chr10 | 5774977 | 5775480 | 0.884039577 | 0.000120662 | ASB13 | upstream | 26431 | Far | −7274 |
| chr3 | 82629728 | 82630444 | −0.837733539 | 0.000141351 | GBE1 | upstream | 736294 | Far | 309227 |
| chr15 | 70198455 | 70199761 | −0.825003332 | 0.000148319 | SENP8 | inside | 20595 | Shore | −399 |
| chr8 | 144543158 | 144544971 | −0.770400642 | 0.000172289 | RHPN1 | upstream | 7196 | Far | −9061 |
| chr19 | 63146186 | 63149398 | −0.700896124 | 0.000209459 | ZNF256 | inside | 1490 | Shore | 1100 |
| chr7 | 27121979 | 27122917 | 0.793013224 | 0.000214766 | HOXA3 | inside | 2821 | Shore | −28 |
| chr10 | 129973472 | 129974329 | −0.791044282 | 0.000243982 | MKI67 | upstream | 158828 | Far | −19204 |
| chr5 | 175019374 | 175020470 | −0.786575281 | 0.000320566 | HRH2 | downstream | 23691 | Shore | −1012 |
| chr15 | 90735153 | 90736013 | −0.774643272 | 0.000336501 | ST8SIA2 | downstream | 76946 | Shore | 1668 |
| chr20 | 15408602 | 15408931 | −0.877118107 | 0.00036397 | C20orf133 | inside | 572907 | Far | 1092905 |
| chr12 | 128898887 | 128900474 | −0.720321969 | 0.000387656 | TMEM132D | inside | 53691 | Far | 5162 |
| chr20 | 56858718 | 56860982 | 0.659681384 | 0.000397048 | GNAS | inside | 58661 | cover | 0 |
| chr8 | 118032349 | 118033443 | −0.770523086 | 0.000399429 | LOC441376 | upstream | 7947 | Far | −12209 |
| chr19 | 55631492 | 55632172 | −0.789979406 | 0.000409085 | MYBPC2 | inside | 29216 | Far | −4003 |
| chr7 | 27151538 | 27154015 | 0.661580605 | 0.000409085 | HOXA6 | covers | 0 | Shore | 0 |
| chr22 | 36144969 | 36145868 | 0.759848671 | 0.000411532 | LRRC62 | upstream | 43445 | Shore | 0 |
| chr20 | 16499527 | 16500276 | −0.775760202 | 0.000435467 | C20orf23 | inside | 1801 | Shore | 1560 |
| chr7 | 4865828 | 4866751 | −0.752290368 | 0.00043806 | PAPOLB | inside | 1399 | Shore | 1111 |
| chr8 | 17060922 | 17062917 | −0.684418678 | 0.000513695 | ZDHHC2 | inside | 61694 | Shore | −1761 |
| chr12 | 108883476 | 108884015 | −0.79920787 | 0.000559116 | GIT2 | inside | 34467 | Far | 34165 |
| chr1 | 14092469 | 14093393 | 0.743518354 | 0.000560746 | PRDM2 | upstream | 68308 | Shore | −145 |
| chr9 | 101171277 | 101172098 | −0.751851067 | 0.000568963 | SEC61B | upstream | 138557 | Far | −72243 |
| chr7 | 27129188 | 27131713 | 0.628259986 | 0.00063513 | HOXA3 | inside | 1450 | cover | 0 |
| chr9 | 94987821 | 94990808 | 0.598842709 | 0.000698251 | WNK2 | inside | 131865 | Shore | −165 |
| chr7 | 145026589 | 145027407 | −0.738007248 | 0.00073506 | CNTNAP2 | downstream | 2721611 | Far | 416556 |
| chr5 | 16236219 | 16237106 | −0.727976294 | 0.000747719 | FBXL7 | upstream | 243320 | Far | −2799 |
| chr6 | 168586102 | 168588777 | 0.621864525 | 0.000780248 | SMOC2 | inside | 221818 | Shore | −153 |
| chr7 | 27147025 | 27148381 | 0.688088459 | 0.000795867 | HOXA5 | overlaps 3' | 1430 | Shore | 757 |
| chr6 | 50873235 | 50873811 | −0.772772257 | 0.000800382 | TFAP2B | downstream | 45822 | Far | 21434 |
| chr9 | 136758751 | 136759638 | −0.721949494 | 0.000834999 | COL5A1 | inside | 116868 | Far | 40696 |
| chr17 | 74692733 | 74693892 | −0.716568667 | 0.000851618 | LOC146713 | downstream | 237673 | Shore | −909 |
| chr20 | 44094989 | 44097479 | −0.683544424 | 0.000863673 | SLC12A5 | inside | 24716 | Shore | −634 |
| chr12 | 128900559 | 128905004 | −0.581538135 | 0.000893245 | TMEM132D | inside | 49161 | Shore | 632 |
| chr9 | 137437549 | 137438193 | −0.745855742 | 0.001032389 | KIAA0649 | downstream | 82366 | Far | 6096 |
| chr8 | 1032932 | 1034329 | −0.687184842 | 0.001090973 | ERICH1 | upstream | 361707 | Shore | 1637 |
| chr20 | 56841054 | 56842229 | −0.676159209 | 0.001106085 | GNAS | downstream | 77414 | Far | 5761 |
| chr11 | 2190993 | 2192468 | −0.654016557 | 0.001130661 | TH | upstream | 41383 | Far | −46172 |
| chr7 | 80386676 | 80389252 | −0.601910229 | 0.001187784 | SEMA3C | promoter | 74 | Shore | −14 |
| chr8 | 846979 | 849372 | −0.596646108 | 0.001191034 | ERICH1 | upstream | 175754 | Far | −6574 |
| chr3 | 191521264 | 191521946 | −0.736310316 | 0.001220642 | CLDN1 | inside | 962 | Shore | 562 |
| chr3 | 193338227 | 193339771 | −0.673047389 | 0.001237379 | FGF12 | downstream | 268934 | Far | 268741 |
| chr16 | 86201868 | 86205260 | −0.678519462 | 0.00127148 | JPH3 | inside | 83999 | Shore | 327 |
| chr22 | 48392638 | 48393144 | −0.760715735 | 0.001285358 | C22orf34 | downstream | 44045 | Shore | 1818 |
| chr8 | 966339 | 968246 | −0.626496123 | 0.001295856 | ERICH1 | upstream | 295114 | Shore | −581 |
| chr11 | 73980533 | 73981178 | −0.784853788 | 0.001331416 | POLD3 | downstream | 50234 | Shore | 0 |
| chr18 | 32022373 | 32023451 | −0.682417577 | 0.001353174 | MOCOS | inside | 79230 | Shore | −230 |
| chr18 | 73809395 | 73809862 | −0.761987843 | 0.001443472 | GALR1 | upstream | 698315 | Far | 9620 |
| chr13 | 113548528 | 113549312 | 0.709469821 | 0.001455135 | GAS6 | inside | 41083 | Shore | −393 |
| chr3 | 129687744 | 129688211 | 0.759314875 | 0.001514741 | GATA2 | inside | 6506 | Shore | 0 |
| chr14 | 95577239 | 95578964 | −0.645499663 | 0.001518792 | C14orf132 | inside | 50921 | Shore | −1084 |
| chr7 | 92075312 | 92075740 | −0.777130862 | 0.001522853 | CDK6 | inside | 225407 | Far | −17503 |

TABLE 17-continued

Regions with consistent cancer-specific differential methylation (C-DMRs) at a FDR of 5%. DeltaM is cancer minus normal. FDR is false discovery rate. Columns are chromo some, start, end, delta M, fdr, gene, relation to gene, distance to TSS, relation to CGI, distance to CGI

| chr | start | end | deltaM | fdr | gene name | relation | TSS distance | CGI | distToCGI |
|---|---|---|---|---|---|---|---|---|---|
| chr12 | 16648850 | 16649638 | 0.700736708 | 0.001551557 | LMO3 | inside | 1059 | Far | −693049 |
| chr19 | 43436533 | 43438474 | 0.714930008 | 0.001597653 | PPP1R14A | inside | 537 | Shore | 4 |
| chr7 | 50436490 | 50438081 | −0.639172776 | 0.001610437 | IKZF1 | overlaps 5' | 0 | Shore | −596 |
| chr13 | 42886712 | 42887185 | −0.755363018 | 0.001619012 | PIG38 | inside | 252469 | Far | 370673 |
| chr8 | 100031420 | 100033208 | 0.611013818 | 0.001627628 | OSR2 | inside | 291 | Shore | −806 |
| chr16 | 31139986 | 31140921 | −0.701244098 | 0.001675759 | TRIM72 | inside | 3089 | Far | 2105 |
| chr13 | 87123702 | 87125116 | 0.642126998 | 0.001693577 | SLITRK5 | inside | 4752 | cover | 0 |
| chr2 | 172826386 | 172826961 | −0.729008517 | 0.001729729 | DLX2 | upstream | 150663 | Far | −18042 |
| chr12 | 88272781 | 88274261 | −0.65038077 | 0.001936245 | DUSP6 | promoter | 2355 | Shore | −506 |
| chr7 | 50103520 | 50103993 | −0.743374995 | 0.001982182 | ZPBP | promoter | 149 | Shore | −53 |
| chr7 | 1182527 | 1183550 | −0.701093724 | 0.002018587 | ZFAND2A | upstream | 16204 | Far | −15857 |
| chrX | 23042002 | 23042541 | −0.759184452 | 0.002060928 | DDX53 | upstream | 111878 | Far | 217664 |
| chr8 | 98356982 | 98358151 | −0.641614569 | 0.00212045 | TSPYL5 | inside | 1200 | Shore | 629 |
| chr11 | 132451645 | 132454794 | −0.551863416 | 0.002125937 | OPCML | inside | 452818 | Far | 2108 |
| chr4 | 172202321 | 172202941 | −0.710142653 | 0.002125937 | GALNT17 | downstream | 1996342 | Far | 767368 |
| chr11 | 133791126 | 133793856 | −0.564608575 | 0.002244148 | B3GAT1 | upstream | 4105 | Far | −2997 |
| chr7 | 129912706 | 129913314 | −0.698922372 | 0.002556137 | MEST | overlaps 3' | 20050 | Shore | 0 |
| chr12 | 38783104 | 38784488 | 0.607732473 | 0.002601858 | SLC2A13 | inside | 1439 | Shore | 741 |
| chr13 | 112142200 | 112143003 | −0.678295439 | 0.00268194 | C13orf28 | upstream | 5199 | Far | 11335 |
| chr7 | 90064351 | 90065026 | 0.683927774 | 0.00268194 | PFTK1 | downstream | 612813 | Shore | −51 |
| chr11 | 103540808 | 103541706 | −0.672096716 | 0.002722801 | PDGFD | promoter | 572 | Shore | −540 |
| chr21 | 42057698 | 42059424 | −0.588799731 | 0.002743438 | RIPK4 | inside | 893 | Shore | 0 |
| chr2 | 4028568 | 4028969 | −0.739275995 | 0.002855883 | ALLC | upstream | 300436 | Island | 0 |
| chr11 | 2243752 | 2244711 | −0.641643739 | 0.002863045 | ASCL2 | downstream | 4046 | Shore | 1969 |
| chr5 | 11954677 | 11955633 | −0.645408794 | 0.002877417 | CTNND2 | inside | 1476 | Shore | 917 |
| chr5 | 7900127 | 7901165 | −0.662624905 | 0.002920922 | FASTKD3 | downstream | 20949 | Shore | 1780 |
| chr13 | 109229281 | 109231903 | −0.549669563 | 0.003032257 | IRS2 | inside | 5011 | Shore | 564 |
| chr13 | 110126656 | 110127336 | 0.674417006 | 0.003124028 | FLJ12118 | inside | 29127 | Shore | 1831 |
| chr20 | 48778557 | 48780262 | −0.595456871 | 0.00331501 | PARD6B | downstream | 23421 | Shore | 510 |
| chr14 | 100997052 | 100997806 | −0.669615597 | 0.003372632 | DIO3 | downstream | 101733 | Shore | −1304 |
| chr3 | 28591265 | 28591843 | 0.687620751 | 0.003405956 | ZCWPW2 | upstream | 49632 | Shore | 0 |
| chr11 | 133445524 | 133446466 | −0.659812073 | 0.003603295 | JAM3 | inside | 80392 | Shore | −633 |
| chr5 | 132392 | 134453 | −0.575968981 | 0.003647512 | KIAA1909 | downstream | 108624 | Shore | 1975 |
| chrX | 142544143 | 142544478 | −0.743808544 | 0.003755595 | SLITRK4 | inside | 6206 | Far | 4598 |
| chr20 | 4928754 | 4929383 | 0.695670621 | 0.003773881 | SLC23A2 | inside | 761 | Far | 111977 |
| chr12 | 112557273 | 112558104 | −0.692536013 | 0.00396112 | LHX5 | upstream | 163014 | Far | −43138 |
| chr16 | 85092993 | 85096638 | 0.4875436 | 0.003989902 | FOXF1 | downstream | 8931 | Shore | 0 |
| chr10 | 1437553 | 1439129 | −0.58556974 | 0.00404802 | ADARB2 | inside | 330540 | Far | −7539 |
| chr2 | 242632887 | 242634574 | −0.663580398 | 0.004057778 | FLJ33590 | upstream | 168241 | Shore | 1740 |
| chr2 | 4028054 | 4028513 | −0.727374572 | 0.004067558 | ALLC | upstream | 299922 | Shore | 11 |
| chr19 | 35406489 | 35407329 | 0.646090813 | 0.004106883 | ZNF536 | downstream | 333475 | Shore | 60 |
| chr7 | 42233455 | 42234204 | 0.645603687 | 0.004136596 | GLI3 | upstream | 4036 | Shore | 0 |
| chr3 | 174341049 | 174341237 | −0.801112836 | 0.00415651 | SPATA16 | inside | 457 | Far | 254724 |
| chr5 | 3586182 | 3587073 | −0.706076627 | 0.00415651 | IRX1 | downstream | 67442 | Shore | 1557 |
| chr8 | 22469866 | 22470840 | −0.625728011 | 0.004206665 | SORBS3 | inside | 18110 | Far | −4286 |
| chr6 | 10501022 | 10502013 | 0.65421633 | 0.004288023 | TFAP2A | downstream | 18579 | Shore | −1938 |
| chr11 | 31966319 | 31967492 | −0.637486731 | 0.004339572 | RCN1 | downstream | 116160 | Shore | −699 |
| chr1 | 206062462 | 206063805 | 0.576184672 | 0.004476158 | LOC148696 | overlaps 5' | 0 | Far | 44680 |
| chr22 | 47267034 | 47267870 | −0.630643807 | 0.004476158 | FAM19A5 | downstream | 265877 | Shore | −1327 |
| chr6 | 80711271 | 80712497 | −0.594390766 | 0.004508209 | ELOVL4 | inside | 1443 | Shore | 966 |
| chr22 | 47455137 | 47456387 | −0.584007269 | 0.004551258 | FAM19A5 | inside | 77360 | Far | −4801 |
| chr11 | 134186796 | 134187368 | −0.666896255 | 0.004693669 | B3GAT1 | upstream | 399775 | Far | −48599 |
| chr19 | 13474169 | 13475470 | −0.622911411 | 0.004693669 | CACNA1A | inside | 2846 | Far | 2282 |
| chr16 | 25608094 | 25609031 | −0.617716356 | 0.004749475 | HS3ST4 | downstream | 447477 | Shore | 1425 |
| chr8 | 117611158 | 117611838 | −0.647479337 | 0.004749475 | EIF3S3 | downstream | 225404 | Far | 225273 |
| chr20 | 3603573 | 3604604 | −0.598667161 | 0.004966877 | ADAM33 | inside | 6133 | Shore | −800 |
| chr20 | 59905352 | 59906092 | −0.676814042 | 0.005037317 | CDH4 | inside | 39601 | Shore | −1622 |
| chr14 | 52326048 | 52327382 | −0.59636953 | 0.005144616 | GNPNAT1 | inside | 750 | Shore | 32 |
| chr22 | 46984389 | 46985561 | −0.585617065 | 0.005144616 | LOC388915 | upstream | 66632 | Shore | −218 |
| chr7 | 152249022 | 152250754 | −0.636478846 | 0.00515666 | ACTR3B | upstream | 65627 | Far | 2095 |
| chr7 | 27108458 | 27111260 | 0.508492851 | 0.00515666 | HOXA2 | overlaps 5' | 0 | cover | 0 |
| chr5 | 158465126 | 158466712 | 0.54868809 | 0.00532789 | EBF1 | upstream | 5780 | cover | 0 |
| chr7 | 149667109 | 149668386 | 0.570024092 | 0.005365221 | RARRES2 | inside | 1252 | Shore | 6 |
| chr10 | 3499370 | 3500060 | −0.644793235 | 0.00540278 | PITRM1 | upstream | 294368 | Far | −8794 |
| chr11 | 31780765 | 31782111 | 0.582076146 | 0.005427947 | PAX6 | inside | 7322 | Shore | 208 |
| chr7 | 139121471 | 139122253 | 0.621563749 | 0.005529639 | TBXAS1 | downstream | 244217 | Shore | 1622 |
| chr17 | 14831980 | 14832519 | −0.662742648 | 0.00555532 | FLJ45831 | upstream | 207736 | Far | 272136 |
| chr3 | 148446946 | 148448043 | −0.61085168 | 0.005632988 | ZIC4 | downstream | 159053 | Far | 111759 |
| chr18 | 11140361 | 11141025 | −0.641611395 | 0.005672176 | FAM38B | upstream | 452548 | Shore | −425 |
| chr19 | 4505154 | 4505834 | −0.635384318 | 0.005698433 | SEMA6B | inside | 3668 | Shore | 1102 |
| chr4 | 81341228 | 81342411 | 0.593057633 | 0.005724795 | PRDM8 | inside | 2092 | Shore | 121 |
| chr13 | 100427954 | 100428562 | −0.659465205 | 0.005831309 | VGCNL1 | downstream | 438251 | Far | −302230 |
| chr1 | 221053963 | 221054618 | −0.658163166 | 0.005953193 | FLJ43505 | upstream | 63194 | Shore | 249 |

TABLE 17-continued

Regions with consistent cancer-specific differential methylation (C-DMRs) at a FDR of 5%.
DeltaM is cancer minus normal. FDR is false discovery rate.
Columns are chromo some, start, end, delta M, fdr, gene, relation to gene, distance to TSS, relation to CGI, distance to CGI

| chr | start | end | deltaM | fdr | gene name | relation | TSS distance | CGI | distToCGI |
|---|---|---|---|---|---|---|---|---|---|
| chr9 | 97304533 | 97306772 | 0.538529057 | 0.005980578 | PTCH1 | inside | 3879 | Shore | 1524 |
| chr10 | 134597978 | 134600218 | −0.585261073 | 0.006063388 | C10orf93 | inside | 5835 | Far | 5435 |
| chr10 | 24025367 | 24026498 | −0.60528892 | 0.006119146 | C10orf67 | upstream | 351590 | Shore | −383 |
| chr19 | 50669649 | 50670313 | 0.642613368 | 0.006119146 | FOSB | overlaps 5' | 0 | Shore | −1547 |
| chr18 | 491107 | 491721 | 0.648047368 | 0.006231999 | COLEC12 | promoter | 423 | Shore | −385 |
| chr17 | 41333049 | 41334735 | −0.548189858 | 0.006260492 | MAPT | inside | 126808 | Far | −2213 |
| chr12 | 52430235 | 52431320 | 0.598152778 | 0.006361111 | CALCOCO1 | upstream | 22750 | Island | 0 |
| chr13 | 67580738 | 67581346 | −0.639592071 | 0.006404661 | PCDH9 | upstream | 878275 | Far | 875559 |
| chr5 | 134553843 | 134554689 | 0.606657045 | 0.006419235 | H2AFY | downstream | 208137 | Shore | 137 |
| chr12 | 122813965 | 122816002 | −0.550995205 | 0.006522058 | ATP6V0A2 | upstream | 3575 | Shore | −758 |
| chr20 | 24399131 | 24400197 | 0.576626292 | 0.006522058 | C20orf39 | inside | 194969 | Island | 0 |
| chr2 | 100303439 | 100304155 | 0.619440354 | 0.006641312 | LONRF2 | upstream | 11041 | Shore | 56 |
| chr13 | 21140646 | 21141533 | 0.594077102 | 0.006747202 | FGF9 | downstream | 32650 | Shore | 0 |
| chr8 | 132984463 | 132985363 | −0.623396903 | 0.006793028 | KIAA0143 | downstream | 109587 | Shore | 141 |
| chr11 | 1861791 | 1862726 | −0.59253943 | 0.006901003 | LSP1 | inside | 7341 | Shore | −1881 |
| chr10 | 101273278 | 101274941 | 0.562231173 | 0.006916548 | NKX2-3 | downstream | 11326 | Shore | −348 |
| chr13 | 113850844 | 113851732 | 0.592061228 | 0.006947729 | RASA3 | inside | 64464 | Far | 2436 |
| chr7 | 32076356 | 32076652 | 0.715435355 | 0.006994728 | PDE1C | inside | 863 | Shore | 0 |
| chr11 | 45645190 | 45645996 | −0.605303898 | 0.007010455 | CHST1 | promoter | 1443 | Shore | −1119 |
| chr19 | 16876450 | 16876750 | −0.746371667 | 0.007010455 | CPAMD8 | inside | 121718 | Far | −6593 |
| chr8 | 53636408 | 53637226 | −0.600422547 | 0.007026213 | UNQ9433 | inside | 3338 | Far | 2871 |
| chr15 | 24571127 | 24572559 | −0.554446179 | 0.00705782 | GABRB3 | promoter | 1108 | Shore | −1091 |
| chr6 | 133605067 | 133606789 | 0.529371985 | 0.00708955 | EYA4 | inside | 287568 | Shore | 0 |
| chr12 | 88266873 | 88268978 | −0.496208684 | 0.0072177 | DUSP6 | inside | 1448 | Shore | 321 |
| chr17 | 782607 | 784014 | −0.562507428 | 0.007233859 | NXN | inside | 45745 | Far | 12943 |
| chr19 | 36535076 | 36535822 | 0.607202133 | 0.007347841 | TSHZ3 | upstream | 73062 | Shore | 0 |
| chr13 | 20184925 | 20186542 | −0.533916441 | 0.007413666 | IL17D | inside | 8693 | Far | 7069 |
| chr17 | 22902924 | 22903499 | −0.634066178 | 0.007631109 | KSR1 | inside | 71344 | Far | 53125 |
| chr1 | 32992405 | 32992989 | 0.632485647 | 0.00780208 | KIAA1522 | inside | 20168 | Shore | 0 |
| chr15 | 32835765 | 32836849 | −0.563189738 | 0.007923707 | CX36 | promoter | 1785 | Shore | −993 |
| chr12 | 130718351 | 130718755 | −0.681706414 | 0.008011574 | SFRS8 | downstream | 131479 | Far | −5588 |
| chr13 | 36392772 | 36394298 | 0.523296289 | 0.008011574 | ALG5 | downstream | 77178 | Shore | −20 |
| chr20 | 61186047 | 61186916 | −0.586579264 | 0.008011574 | BHLHB4 | upstream | 77261 | Shore | 1296 |
| chr11 | 19323912 | 19324590 | 0.644908853 | 0.008029248 | E2F8 | upstream | 104830 | inside | 0 |
| chr12 | 111302662 | 111303588 | 0.576207223 | 0.008207826 | RPL6 | downstream | 28237 | Island | 0 |
| chr15 | 97011564 | 97012941 | 0.531506065 | 0.008280203 | IGF1R | inside | 306092 | Shore | 0 |
| chr16 | 49141667 | 49142498 | −0.597924762 | 0.008371442 | NKD1 | inside | 83643 | Shore | −701 |
| chr14 | 57669356 | 57669957 | −0.633107389 | 0.008537837 | C14orf37 | inside | 18642 | Far | 18087 |
| chr8 | 144372893 | 144373912 | −0.591419915 | 0.008556499 | LOC338328 | promoter | 2476 | Far | 9171 |
| chr9 | 124022303 | 124023189 | 0.590922099 | 0.008612692 | LHX6 | inside | 7615 | Shore | 0 |
| chr19 | 3240846 | 3241458 | −0.618423464 | 0.008669201 | BRUNOL5 | inside | 6612 | Far | 2809 |
| chr16 | 4101996 | 4102769 | 0.59406133 | 0.008840627 | ADCY9 | inside | 3417 | Far | 2040 |
| chr12 | 4889938 | 4890628 | 0.610450142 | 0.008898408 | KCNA1 | close to 3' | 1662 | inside | 0 |
| chr3 | 151719593 | 151721472 | −0.528810826 | 0.00895651 | SERP1 | downstream | 25645 | Far | 24824 |
| chr19 | 41058856 | 41059386 | −0.636595945 | 0.009034481 | APLP1 | inside | 3151 | Shore | −1192 |
| chr7 | 71437052 | 71438143 | −0.553874961 | 0.009034481 | CALN1 | inside | 1752 | Shore | 550 |
| chr9 | 37023001 | 37023958 | 0.572428385 | 0.009192158 | PAX5 | inside | 517 | Shore | 177 |
| chr20 | 33336228 | 33337040 | −0.586120135 | 0.009212032 | FAM83C | overlaps 3' | 6598 | Shore | −75 |
| chr7 | 5360426 | 5361424 | 0.575877608 | 0.009311946 | SLC29A4 | upstream | 50199 | Shore | 974 |
| chr18 | 75366596 | 75367142 | −0.770077524 | 0.009352169 | NFATC1 | inside | 23167 | Far | 4639 |
| chr6 | 7413675 | 7414250 | −0.619224954 | 0.00939254 | RIOK1 | upstream | 50409 | Far | 72267 |
| chr11 | 64244495 | 64245421 | −0.57059158 | 0.009433058 | NRXN2 | inside | 1814 | Shore | 1648 |
| chr16 | 7291114 | 7292175 | −0.557798462 | 0.009494114 | A2BP1 | inside | 408671 | Far | 2159 |
| chr8 | 3257254 | 3257862 | −0.611993878 | 0.009494114 | CSMD1 | inside | 1581873 | Far | −389899 |
| chr5 | 88221043 | 88221995 | 0.573950547 | 0.009555505 | MEF2C | upstream | 6264 | Island | 0 |
| chr13 | 99440030 | 99441015 | 0.573722467 | 0.009596619 | ZIC2 | upstream | 3012 | Shore | 0 |
| chr10 | 102811316 | 102812341 | −0.552736003 | 0.009658572 | KAZALD1 | overlaps 3' | 2996 | inside | 0 |
| chr17 | 71291527 | 71292204 | −0.596863212 | 0.009888639 | H3F3B | upstream | 4073 | Shore | 237 |
| chr10 | 112248574 | 112249464 | 0.566330793 | 0.00999474 | DUSP5 | inside | 11825 | Shore | 0 |

This application claims priority under 35 USC § 119(e) to U.S. Provisional Application Ser. No. 61/518,892, the entire content of which is incorporated by reference.

Although the invention has been described with reference to the above example, it will be understood that modifications and variations are encompassed within the spirit and scope of the invention. Accordingly, the invention is limited only by the following claims.

What is claimed is:

1. A method comprising:

a) identifying an anti-profile in a sample from a subject comprising:

i) determining the methylation status of a plurality of differentially methylated regions of genomic nucleic acid sequences from a non-cancerous biological sample and corresponding plurality of differentially methylated regions of genomic nucleic acid sequences in a test sample from the subject, wherein determining methylation status comprises detecting methylated and unmethylated nucleic acids in the differentially methylated regions, and utilizing an algorithm configured to quantile normalize raw intensity data from methylated and unmethylated nucleic acids and calculate methylation status as a ratio of methylated nucleic acid intensity over a sum of methylated and unmethylated nucleic acid intensity; and ii) performing statistical analysis to determine a methylation variance score for the non-cancerous sample and a methylation variance score for the test sample, and detecting increased stochastic variation in the methylation status of the test sample as compared to the non-cancerous sample, wherein at least 25 nucleic acids are analyzed;

b) detecting expression of MMP3, MMP7, MMP10, or a combination thereof, in the sample;

c) diagnosing the subject as having or at risk of having cancer, wherein the sample from the subject has increased stochastic variation in methylation status as compared to the non-cancerous sample; and d) administering a chemotherapeutic to the subject.

2. The method of claim 1, wherein the plurality of differentially methylated regions of genomic nucleic acid sequences are small differentially methylated regions (sDMRs) as set forth in Table 7.

3. The method of claim 2 comprising detecting, in a plurality of the sDMRs from the test sample, a loss of methylation boundary wherein the loss comprises an increase of methylation in a CpG island of the sDMR and a decrease of methylation in a nucleic acid sequence up to about 2 kb in distance from the CpG island as compared to methylation of a corresponding region in the non-cancerous biological sample.

4. The method of claim 2 comprising detecting, in a plurality of the sDMRs from the test sample, a shift of methylation boundary comprising a similar level of methylation as compared to that of a corresponding region in the non-cancerous biological sample.

5. The method of claim 2 comprising detecting, in a plurality of the sDMRs from the test sample, an increased level of methylation as compared to that of a corresponding region in the non-cancerous biological sample.

6. The method of claim 1, wherein determining a methylation variance score comprises performing principal component analysis, a statistical F-test, or combination thereof.

7. The method of claim 1, wherein the plurality of differentially methylated regions of genomic nucleic acid sequences are located outside of a promoter region of a gene and/or outside of a CpG island.

8. The method of claim 1, wherein the method further comprises detecting a shift or loss of methylation boundary in one or more of the plurality of differentially methylated regions of genomic nucleic acid sequences from the test sample as compared to that of the corresponding plurality of differentially methylated regions of genomic nucleic acid sequences in the non-cancerous biological sample.

9. The method of claim 1, wherein the cancer is selected from the group consisting of colorectal cancer, esophageal cancer, stomach cancer, leukemia/lymphoma, lung cancer, prostate cancer, uterine cancer, breast cancer, skin cancer, endocrine cancer, urinary cancer, liver cancer, thyroid cancer, kidney cancer, pancreas cancer, other gastrointestinal cancer, ovarian cancer, cervical cancer, head cancer, neck cancer, and adenomas.

10. The method of claim 1, further comprising detecting expression of one or more additional genes selected from the group consisting of genes as set forth in FIG. 16A, FIG. 16B, Table 14 and Table 15.

* * * * *